United States Patent
Ichikawa et al.

(10) Patent No.: US 9,346,750 B2
(45) Date of Patent: May 24, 2016

(54) SALT AND PHOTORESIST COMPOSITION CONTAINING THE SAME

(75) Inventors: Koji Ichikawa, Toyonaka (JP);
Mitsuyoshi Ochiai, Ibaraki (JP);
Masako Sugihara, Nishinomiya (JP)

(73) Assignee: SUMITOMO CHEMICAL COMPANY, LIMITED, TOKYO (JP)

( * ) Notice: Subject to any disclaimer, the term of this patent is extended or adjusted under 35 U.S.C. 154(b) by 1214 days.

(21) Appl. No.: 12/947,349

(22) Filed: Nov. 16, 2010

(65) Prior Publication Data

US 2011/0117495 A1    May 19, 2011

(30) Foreign Application Priority Data

Nov. 18, 2009  (JP) ................. 2009-262882
Nov. 18, 2009  (JP) ................. 2009-262883
Aug. 30, 2010  (JP) ................. 2010-191872
Aug. 30, 2010  (JP) ................. 2010-191873

(51) Int. Cl.
| | |
|---|---|
| C07C 309/19 | (2006.01) |
| C07C 309/17 | (2006.01) |
| C07C 381/12 | (2006.01) |
| C07D 307/33 | (2006.01) |
| C07D 307/93 | (2006.01) |
| C07D 327/06 | (2006.01) |
| C07D 333/08 | (2006.01) |
| G03F 7/004 | (2006.01) |
| G03F 7/039 | (2006.01) |
| G03F 7/20 | (2006.01) |

(52) U.S. Cl.
CPC ............ *C07C 309/17* (2013.01); *C07C 381/12* (2013.01); *C07D 307/33* (2013.01); *C07D 307/93* (2013.01); *C07D 327/06* (2013.01); *C07D 333/08* (2013.01); *G03F 7/0045* (2013.01); *G03F 7/0397* (2013.01); *C07C 2103/74* (2013.01); *G03F 7/0046* (2013.01); *G03F 7/2041* (2013.01)

(58) Field of Classification Search
CPC .................................................... C07C 309/19
USPC .......................................................... 558/52
See application file for complete search history.

(56) References Cited

U.S. PATENT DOCUMENTS

| | | |
|---|---|---|
| 7,304,175 B2 | 12/2007 | Harada et al. |
| 7,439,006 B2 | 10/2008 | Yoshida et al. |
| 2006/0194982 A1 | 8/2006 | Harada et al. |

(Continued)

FOREIGN PATENT DOCUMENTS

JP    2008-74843 A    4/2008

OTHER PUBLICATIONS

The Notice of Reasons for the Rejection, dated Jul. 22, 2014, issued in the corresponding Japanese Patent Application No. 2010-252600.

(Continued)

*Primary Examiner* — Yong Chu
*Assistant Examiner* — Sonya Wright
(74) *Attorney, Agent, or Firm* — Birch, Stewart, Kolasch & Birch, LLP

(57) ABSTRACT

A salt represented by the formula (X):

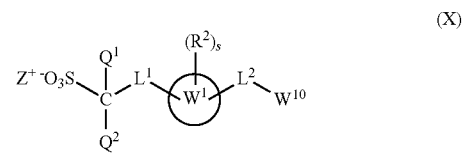

wherein $Q^1$ and $Q^2$ each independently represent a fluorine atom etc., $L^1$ and $L^2$ independently each represent a C1-C17 divalent saturated hydrocarbon group, ring $W^1$ represents a C3-C36 saturated hydrocarbon ring, $R^2$ is independently in each occurrence a hydroxyl group etc., s represents an integer of 0 to 2, $Z^+$ represents an organic counter ion, and $W^{10}$ represents a group represented by the formula (X-1):

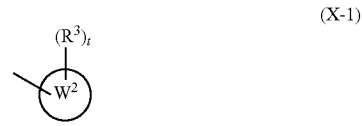

wherein ring $W^2$ represents a C4-C36 saturated hydrocarbon ring in which one or more —$CH_2$— can be replaced by —O— or —CO—, with the proviso that at least one —$CH_2$— in the C4-C36 saturated hydrocarbon ring is replaced by —CO—, $R^3$ is independently in each occurrence a C1-C6 alkyl group etc., and t represents an integer of 0 to 2, or a group represented by the formula (X-2):

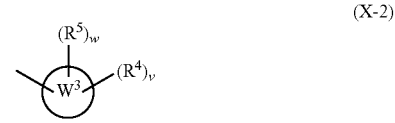

wherein ring $W^3$ represents a C3-C36 saturated hydrocarbon ring, $R^4$ is independently in each occurrence a hydroxyl group etc., $R^5$ is independently in each occurrence a C1-C6 alkyl group etc., v represents an integer of 1 to 3, and w represents an integer of 0 to 2.

12 Claims, No Drawings

(56) References Cited

U.S. PATENT DOCUMENTS

2007/0027336 A1  2/2007  Yoshida et al.
2007/0078269 A1  4/2007  Harada et al.
2007/0122750 A1  5/2007  Yamaguchi et al.
2008/0076063 A1  3/2008  Yoshida et al.
2008/0081925 A1  4/2008  Sakamoto et al.
2008/0086014 A1*  4/2008  Shigematsu et al. ............ 558/52
2009/0208871 A1  8/2009  Kawaue et al.

OTHER PUBLICATIONS

The Examination Report (including an English translation), dated Sep. 9, 2014, issued in the corresponding Taiwanese Patent Application No. 099139162.

* cited by examiner

SALT AND PHOTORESIST COMPOSITION CONTAINING THE SAME

This nonprovisional application claims priority under 35 U.S.C. §119(a) on Patent Applications Nos. 2009-262882 filed in JAPAN on Nov. 18, 2009, 2009-262883 filed in JAPAN on Nov. 18, 2009, 2010-191872 filed in JAPAN on Aug. 30, 2010, and 2010-191873 filed in JAPAN on Aug. 30, 2010, the entire contents of which are hereby incorporated by reference.

FIELD OF THE INVENTION

The present invention relates to a salt and a photoresist composition containing the same.

BACKGROUND OF THE INVENTION

A chemically amplified positive photoresist composition used for semiconductor microfabrication employing a lithography process contains an acid generator comprising a compound generating an acid by irradiation.

US 2008/0076063 A1 discloses a salt represented by the following formula:

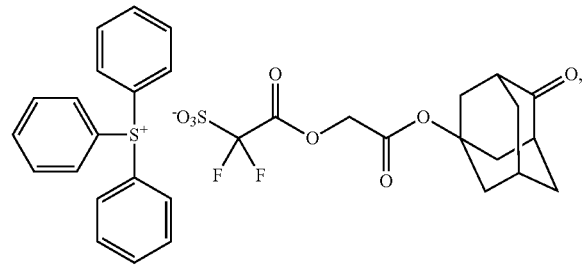

and a photoresist composition containing the same as an acid generator.

US 2007/0122750 A1 discloses a salt represented by the following formula:

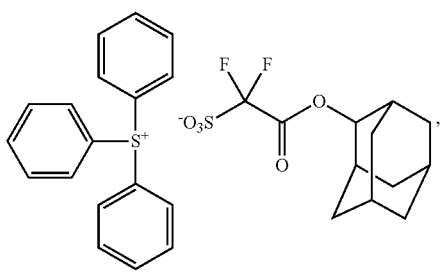

and a photoresist composition containing the same as an acid generator.

SUMMARY OF THE INVENTION

An object of the present invention is to provide a novel salt and a photoresist composition containing the same.

The present invention relates to the followings:
<1> A salt represented by the formula (X):

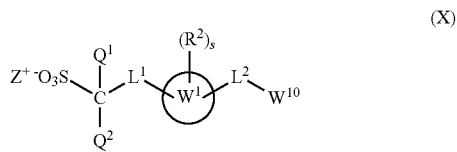

wherein $Q^1$ and $Q^2$ each independently represent a fluorine atom or a C1-C6 perfluoroalkyl group, $L^1$ and $L^2$ independently each represent a C1-C17 divalent saturated hydrocarbon group in which one or more —$CH_2$— can be replaced by —O— or —CO—, ring $W^1$ represents a C3-C36 saturated hydrocarbon ring, $R^2$ is independently in each occurrence a hydroxyl group, a C1-C6 alkyl group or a C1-C6 alkoxy group, s represents an integer of 0 to 2, $Z^+$ represents an organic counter ion, and $W^{10}$ represents a group represented by the formula (X-1):

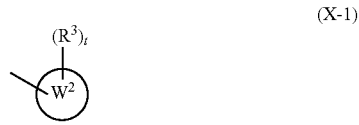

wherein ring $W^2$ represents a C4-C36 saturated hydrocarbon ring in which one or more —$CH_2$— can be replaced by —O— or —CO—, with the proviso that at least one —$CH_2$— in the C4-C36 saturated hydrocarbon ring is replaced by —CO—, $R^3$ is independently in each occurrence a C1-C6 alkyl group, a C1-C6 alkoxy group or a C1-C6 alkoxycarbonyl group, and t represents an integer of 0 to 2, or a group represented by the formula (X-2):

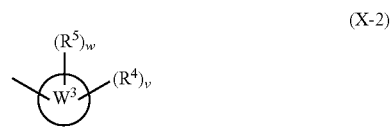

wherein ring $W^3$ represents a C3-C36 saturated hydrocarbon ring, $R^4$ is independently in each occurrence a hydroxyl group, a C1-C6 hydroxyalkyl group which can have one or more halogen atoms or a C1-C6 hydroxyalkoxy group which can have one or more halogen atoms, $R^5$ is independently in each occurrence a C1-C6 alkyl group or a C1-C6 alkoxy group, v represents an integer of 1 to 3, and w represents an integer of 0 to 2;

<2> The salt according to <1>, wherein $W^{10}$ is the group represented by the formula (X-1);
<3> The salt according to <1>, wherein $W^{10}$ is the group represented by the formula (X-2);
<4> The salt according to <1>, wherein the salt represented by the formula (X) is a salt represented by the formula (I-1):

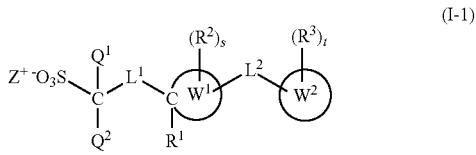

wherein $Q^1$, $Q^2$, $L^1$, $L^2$, $W^1$, $W^2$, $R^2$, $R^3$, $Z^+$, s and t are the same as defined in <1>, and $R^1$ represents a hydrogen atom or a C1-C6 alkyl group, or $R^1$ are bonded to a carbon atom in ring $W^1$ to form a ring;

<5> The salt according to <1>, wherein the salt represented by the formula (X) is a salt represented by the formula (I-2):

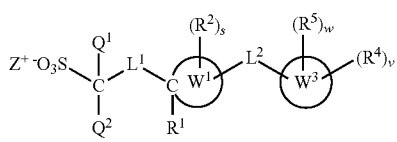

(I-2)

wherein $Q^1$, $Q^2$, $L^1$, $L^2$, $W^1$, $W^3$, $R^2$, $R^4$, $R^5$, $Z^+$, s, v and w are the same as defined in <1>, and $R^1$ represents a hydrogen atom or a C1-C6 alkyl group, or $R^1$ are bonded to a carbon atom in ring $W^3$ to form a ring;

<6> The salt according to any one of <1> to <5>, wherein $L^1$ is *—CO—O-$L^3$-, *—CO—O-$L^4$-O—, *-$L^5$-O—CO— or *—CO—O-$L^6$-CO—O— wherein $L^1$ is represents a single bond or a C1-C6 alkylene group, $L^4$, $L^5$ and $L^6$ independently each represent a C1-C6 alkylene group and * represents a binding position to —C($Q^1$)($Q^2$)-;

<7> The salt according to any one of <1> to <5>, wherein $L^1$ is *—CO—O-$L^3$-, *—CO—O-$L^4$-O— or *-$L^5$-O—CO— wherein $L^3$, $L^4$, $L^5$ and * are the same as defined in <6>;

<8> The salt according to any one of <1> to <7>, wherein $L^2$ is *—O-$L^7$-CO—O—, *—O-$L^8$-CO—O-$L^9$-O—, *—CO—O-$L^{10}$-CO—O—, *—O—CO-$L^{11}$-O— or *—O-$L^{12}$-O— wherein $L^7$, $L^8$, $L^9$, $L^{10}$, $L^{11}$ and $L^{12}$ independently each represent a C1-C6 alkylene group and * represents a binding position to ring $W^1$;

<9> The salt according to any one of <1> to <8>, wherein ring $W^1$ is an adamantane ring;

<10> The salt according to any one of <1> to <9>, wherein ring $W^2$ is a ring represented by the formula (I-Ba) or (I-Bb);

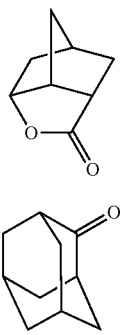

(I-Ba)

(I-Bb)

<11> The salt according to any one of <1> to <9>, wherein ring $W^3$ is an adamantane ring;
<12> The salt according to any one of <1> to <11>, wherein $Z^+$ is a triarylsulfonium cation;
<13> An acid generator comprising the salt according to any one of <1> to <12>;
<14> A photoresist composition comprising the acid generator according to <13> and a resin comprising a structural unit having an acid-labile group, being insoluble or poorly soluble in an aqueous alkali solution but becoming soluble in an aqueous alkali solution by the action of an acid;
<15> The photoresist composition according to <14>, which further contains a basic compound;
<16> A process for producing a photoresist pattern comprising the following steps (1) to (5):
(1) a step of applying the photoresist composition according to <14> or <15> on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

DESCRIPTION OF PREFERRED EMBODIMENTS

The salt of the present invention is represented by the formula (X):

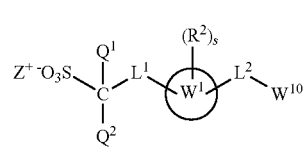

(X)

wherein $Q^1$ and $Q^2$ each independently represent a fluorine atom or a C1-C6 perfluoroalkyl group, $L^1$ and $L^2$ independently each represent a C1-C17 divalent saturated hydrocarbon group in which one or more —$CH_2$— can be replaced by —O— or —CO—, ring $W^1$ represents a C3-C36 saturated hydrocarbon ring, $R^2$ is independently in each occurrence a hydroxyl group, a C1-C6 alkyl group or a C1-C6 alkoxy group, s represents an integer of 0 to 2, $Z^+$ represents an organic counter ion, and $W^{10}$ represents a group represented by the formula (X-1):

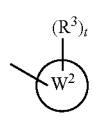

(X-1)

wherein ring $W^2$ represents a C4-C36 saturated hydrocarbon ring in which one or more —$CH_2$— can be replaced by —O— or —CO—, with the proviso that at least one —$CH_2$— in the C4-C36 saturated hydrocarbon ring is replaced by —CO—, $R^3$ is independently in each occurrence a C1-C6 alkyl group, a C1-C6 alkoxy group or a C1-C6 alkoxycarbonyl group, and t represents an integer of 0 to 2, or a group represented by the formula (X-2):

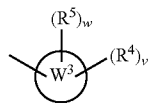

(X-2)

wherein ring $W^3$ represents a C3-C36 saturated hydrocarbon ring, $R^4$ is independently in each occurrence a hydroxyl group, a C1-C6 hydroxyalkyl group which can have one or more halogen atoms or a C1-C6 hydroxyalkoxy group which can have one or more halogen atoms, $R^5$ is independently in each occurrence a C1-C6 alkyl group or a C1-C6 alkoxy group, v represents an integer of 1 to 3, and w represents an integer of 0 to 2 (hereinafter, simply referred to as SALT (X)).

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

$L^1$ is preferably *—CO—O-$L^3$-, *—CO—O-$L^4$-O—, *-$L^5$-O—CO— or *—CO—O-$L^6$-CO—O— wherein $L^3$ represents a single bond or a C1-C6 alkylene group, $L^4$, $L^5$ and $L^6$ independently each represent a C1-C6 alkylene group and * represents a binding position to —C($Q^1$) ($Q^2$)-.

When the group represented by the formula (X) the group represented by the formula (X-1), $L^1$ is more preferably *—CO—O-$L^3$-, *—CO—O-$L^4$-O— or *-$L^5$-O—CO—, and is much more preferably *—CO—O-$L^3$- or *—CO—O-$L^4$-O—, and is especially preferably *—CO—O—, *—CO—O—$CH_2$— or *—CO—O—$CH_2CH_2$—O—. Among them, preferred is *—CO—O—. When the group represented by the formula (X) the group represented by the formula (X-2), $L^1$ is more preferably *—CO—O-$L^3$-, *—CO—O-$L^4$-O— or *-$L^5$-O—CO—, and is much more preferably *—CO—O-$L^3$- or *—CO—O-$L^4$-O—, and is especially preferably *—CO—O—, *—CO—O—$CH_2$— or *—CO—O—$CH_2CH_2$—O—. Among them, preferred is *—CO—O—.

$L^2$ is preferably *—O-$L^7$-CO—O—, *—O-$L^8$-CO—O-$L^9$-O—, *—CO—O-$L^{10}$-CO—O—, *—O—CO-$L^{11}$-O— or *—O-$L^{12}$-O— wherein $L^7$, $L^8$, $L^9$, $L^{10}$, $L^{11}$ and $L^{12}$ independently each represent a C1-C6 alkylene group and * represents a binding position to ring $W^1$, and is more preferably *—O-$L^7$-CO—O— or *—CO—O-$L^{10}$-CO—O—, and much more preferably *—O—$CH_2$—CO—O— *—CO—O—$CH_2$—CO—O—.

SALT (X) is preferably a salt represented by the formula (I-1):

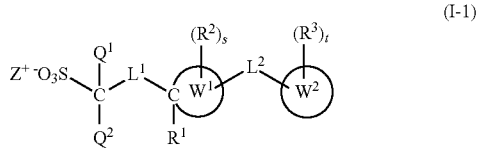

wherein $Q^1$, $Q^2$, $L^1$, $L^2$, $W^1$, $W^2$, $R^2$, $R^3$, $Z^+$, s and t are the same as defined above, and $R^1$ represents a hydrogen atom or a C1-C6 alkyl group, or $R^1$ is bonded to a carbon atom in ring $W^1$ to form a ring or a salt represented by the formula (I-2):

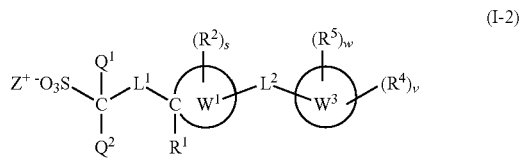

wherein $Q^1$, $Q^2$, $L^1$, $L^2$, $W^1$, $W^3$, $R^2$, $R^4$, $R^5$, $Z^+$, s, v and w are the same as defined above, and $R^1$ represents a hydrogen atom or a C1-C6 alkyl group, or $R^1$ is bonded to a carbon atom in ring $W^3$ to form a ring.

The group represented by the formula (I-A):

wherein $W^1$, $R^1$, $R^2$ and s are the same as defined above in the formulae (I-1) and (I-2) and * represents a binding position to —C($Q^1$) ($Q^2$)-, will be illustrated.

Ring $W^1$ represents a C3-C36 saturated hydrocarbon ring, and "saturated hydrocarbon ring" means a ring having no unsaturated bond and consisting of carbon atoms and hydrogen atoms. Examples of the saturated hydrocarbon ring include a cyclohexane ring and an adamantane ring, and an adamantane ring is preferable.

Examples of the C1-C6 alkyl group represented by $R^1$ include a methyl group, an ethyl group, a propyl group, an isopropyl group, a butyl group, a sec-butyl group, a tert-butyl group, a pentyl group and a hexyl group.

Examples of the group represented by the formula (I-A) wherein $R^1$ is a C1-C6 alkyl group include the followings:

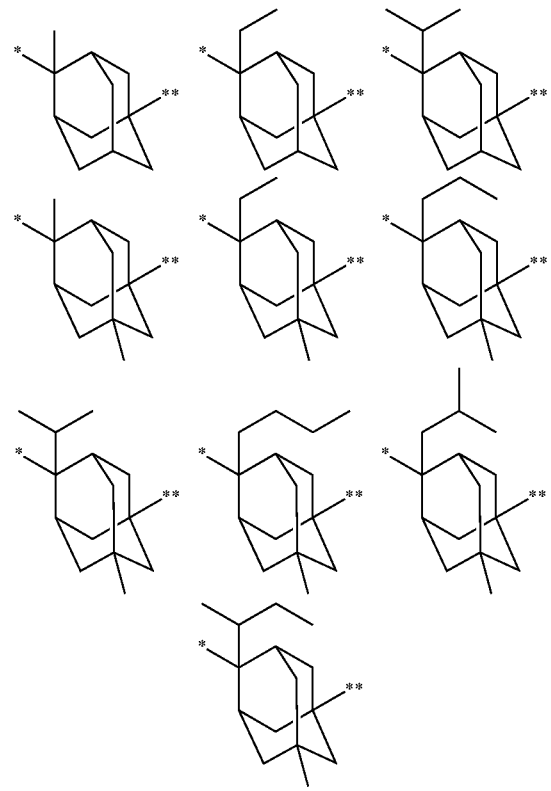

wherein * represents a binding position to —C($Q^1$) ($Q^2$)- and ** represents a binding position to $L^2$.

Examples of the group represented by the formula (I-A) wherein $R^1$ is a hydrogen atom include the followings:

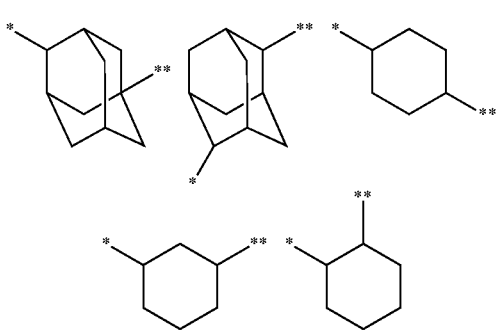

wherein * represents a binding position to —C(Q¹) (Q²)- and ** represents a binding position to L².

Examples of the group represented by the formula (I-A) wherein $R^1$ is a hydrogen atom include the followings:

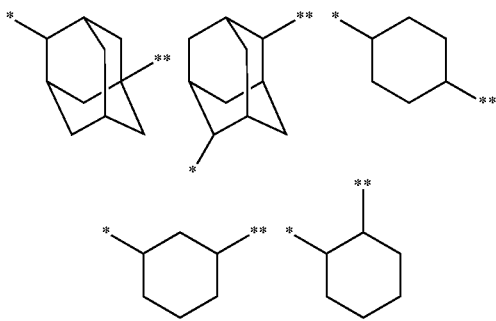

wherein * represents a binding position to —C(Q¹) (Q²)- and ** represents a binding position to L².

Examples of the group represented by the formula (I-A) wherein $R^1$ is bonded to a carbon atom in ring $W^1$ to form a ring include the followings:

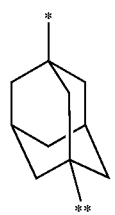

wherein * represents a binding position to —C(Q¹) (Q²)- and ** represents a binding position to L².

When the group represented by the formula (X) the group represented by the formula (X-1), the followings:

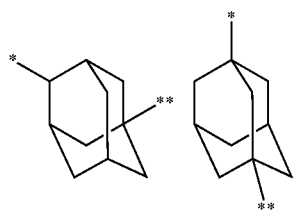

wherein represents a binding position to —C(Q¹) (Q²)- and ** represents a binding position to L², are preferable as the group represented by the formula (I-A). When the group represented by the formula (X) the group represented by the formula (X-2), the following group:

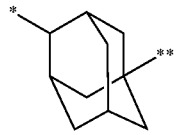

wherein * represents a binding position to —C(Q¹)(Q²)- and ** represents a binding position to L², is more preferable as the group represented by the formula (I-A).

$R^2$ is independently in each occurrence a hydroxyl group, a C1-C6 alkyl group or a C1-C6 alkoxy group. Examples of the C1-C6 alkyl group include a methyl group, an ethyl group, a propyl group, an isopropyl group, a butyl group, a sec-butyl group, a tert-butyl group, a pentyl group and a hexyl group, and a C1-C4 alkyl group is preferable, and a C1-C2 alkyl group is more preferable, and a methyl group is especially preferable. Examples of the C1-C6 alkoxy group include a methoxy group, an ethoxy group, a propoxy group, an isopropoxy group, a butoxy group, a sec-butoxy group, a tert-butoxy group, a pentyloxy group and a hexyloxy group, and a C1-C4 alkoxy group is preferable, and a C1-C2 alkoxy group is more preferable, and a methoxy group is especially preferable. When SALT (X) is the salt represented by the formula (X-2), it is preferred that $R^2$ is independently in each occurrence a C1-C6 alkyl group or a C1-C6 alkoxy group.

The group represented by the formula (X-1):

(X-1)

wherein ring $W^2$, $R^3$ and t are the same as defined above, will be illustrated.

Examples of the saturated hydrocarbon ring include an adamantane ring and a cyclohexane ring, and an adamantane ring is preferable.

Examples of ring $W^2$ include the followings:

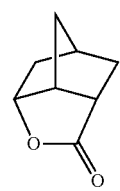

(I-Ba)

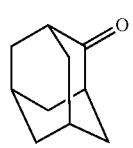

(I-Bb)

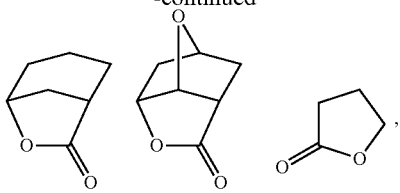

and the ring represented by the formula (I-Ba) or (I-Bb) is preferable. Examples of the group represented by the formula (X-1) include the following groups:

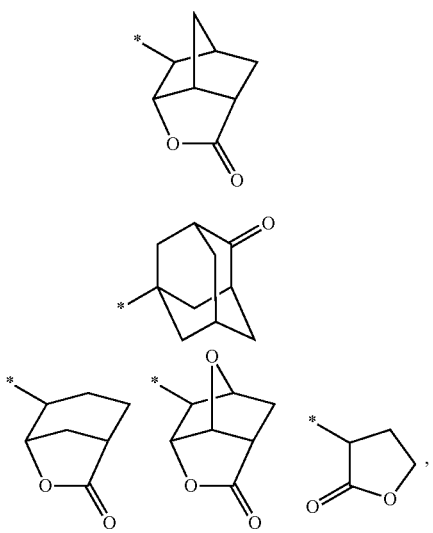

and the group represented by the formula (I-B1) or (I-B2) is preferable.

$R^3$ is independently in each occurrence a C1-C6 alkyl group, a C1-C6 alkoxy group or a C1-C6 alkoxycarbonyl group. "C1-C6 alkoxycarbonyl group" means a group combining a C1-C6 alkoxy group with a carbonyl group. Examples of the C1-C6 alkyl group include a methyl group, an ethyl group, a propyl group, an isopropyl group, a butyl group, a sec-butyl group, a tert-butyl group, a pentyl group and a hexyl group, and a C1-C4 alkyl group is preferable, and a C1-C2 alkyl group is more preferable, and a methyl group is especially preferable. Examples of the C1-C6 alkoxy group include a methoxy group, an ethoxy group, a propoxy group, an isopropoxy group, a butoxy group, a sec-butoxy group, a tert-butoxy group, a pentyloxy group and a hexyloxy group, and a C1-C4 alkoxy group is preferable, and a C1-C2 alkoxy group is more preferable, and a methoxy group is especially preferable. Examples of the C1-C6 alkoxycarbonyl group include a methoxycarbonyl group, an ethoxycarbonyl group, a propoxycarbonyl group, an isopropoxycarbonyl group, a butoxycarbonyl group, sec-butoxycarbonyl group, a tert-butoxycarbonyl group, a pentyloxycarbonyl group and a hexyloxycarbonyl group, and a C4-C6 alkoxycarbonyl group is preferable, and a C4-C5 alkoxycarbonyl group is more preferable, and a tert-butoxycarbonyl group is especially preferable.

The group represented by the formula (X-2):

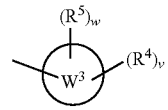

wherein ring $W^3$, $R^4$, $R^5$, v and w are the same as defined above, will be illustrated.

Examples of the saturated hydrocarbon ring include an adamantane ring and a cyclohexane ring, and an adamantane ring is preferable.

Examples of the group represented by the formula (X-2) include the following groups:

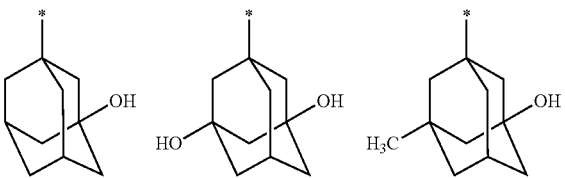

$R^4$ is independently in each occurrence a hydroxyl group, a C1-C6 hydroxyalkyl group which can have one or more halogen atoms or a C1-C6 hydroxyalkoxy group which can have one or more halogen atoms. Examples of the hydroxyalkyl group include the groups formed by replacing a hydrogen atom in the above-mentioned alkyl groups by a hydroxyl group, and examples of the hydroxyalkoxy group include the groups formed by replacing a hydrogen atom in the above-mentioned alkoxy groups by a hydroxyl group. Specific examples of $R^4$ include the followings.

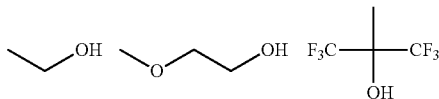

$R^5$ is independently in each occurrence a C1-C6 alkyl group or a C1-C6 alkoxy group, and examples of the C1-C6 alkyl group and the C1-C6 alkoxy group include the same as described above.

Examples of SALT (X) include the followings.
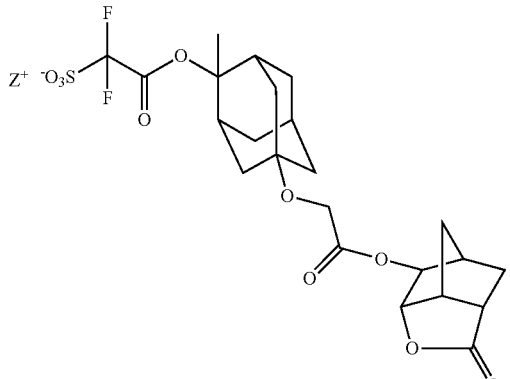
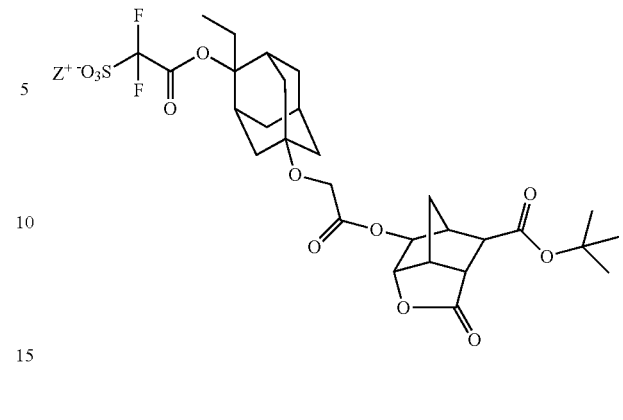
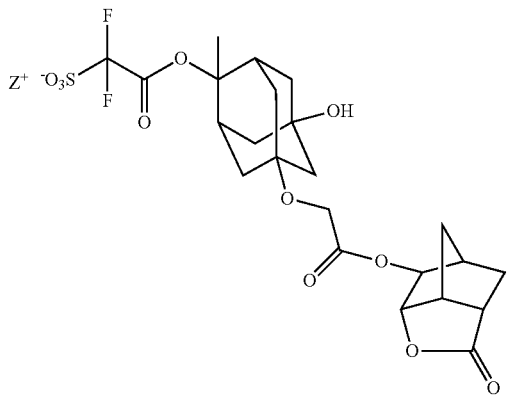
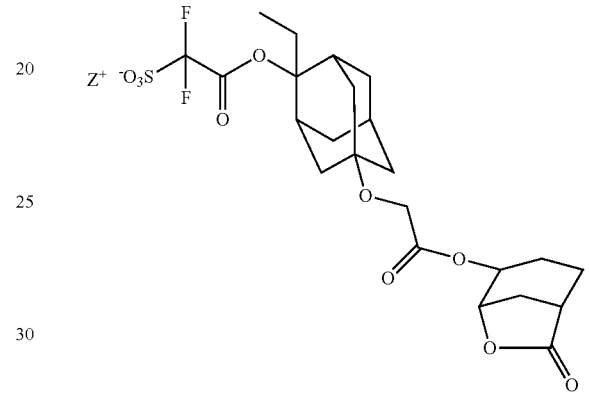
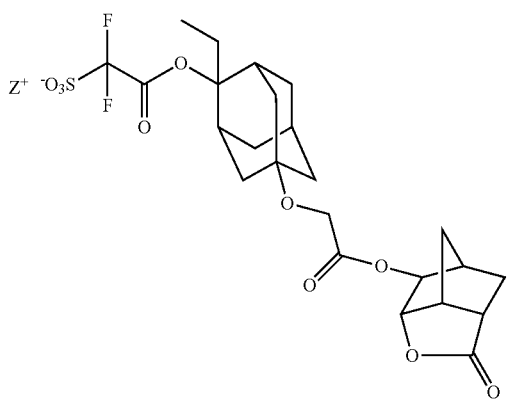
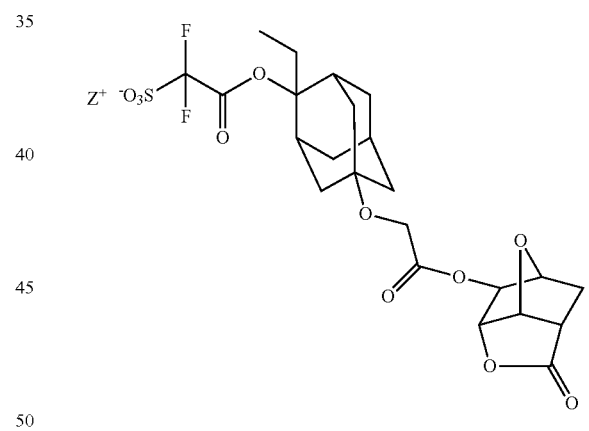
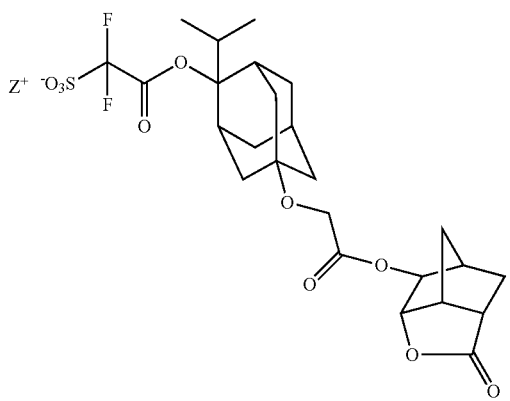
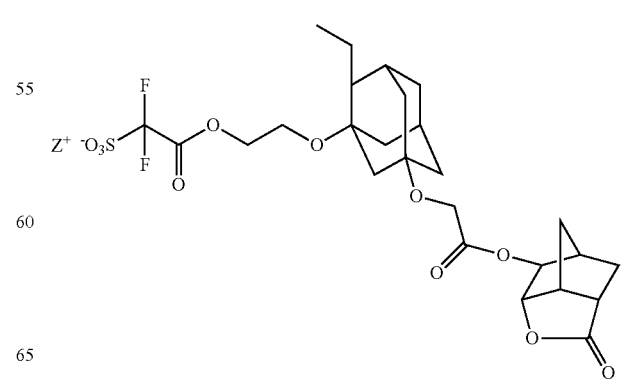

13
-continued
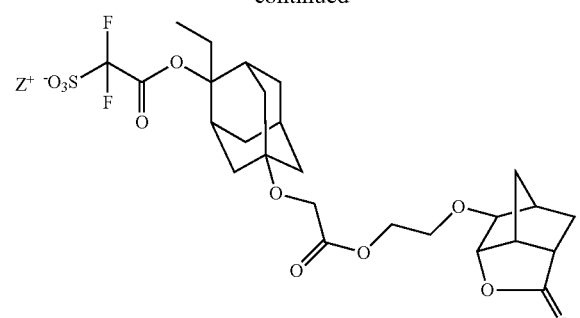
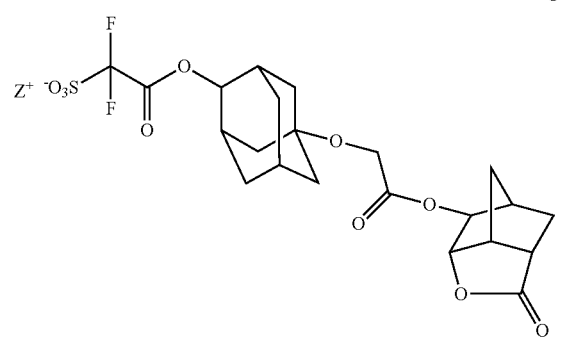
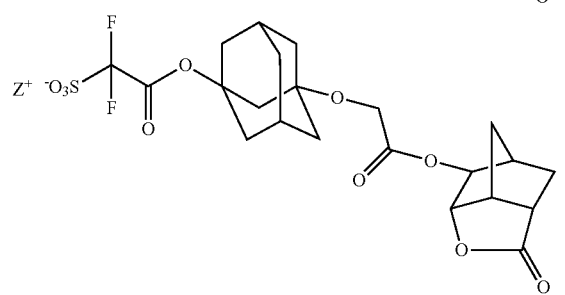
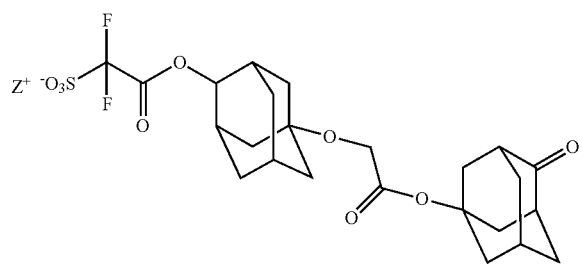
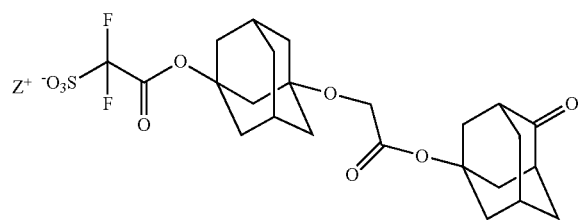
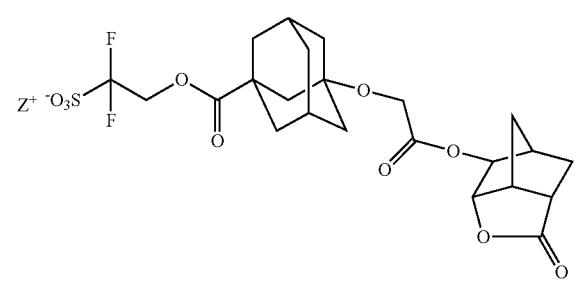
14
-continued
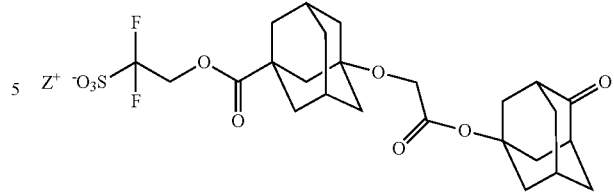
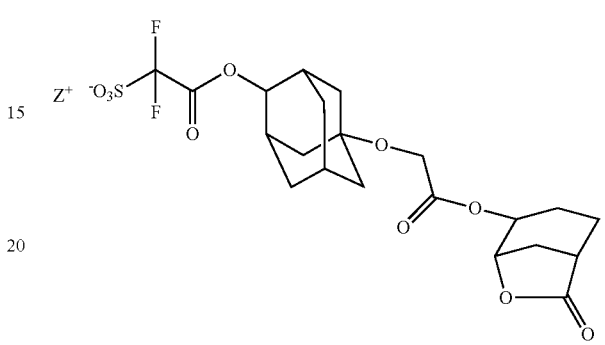
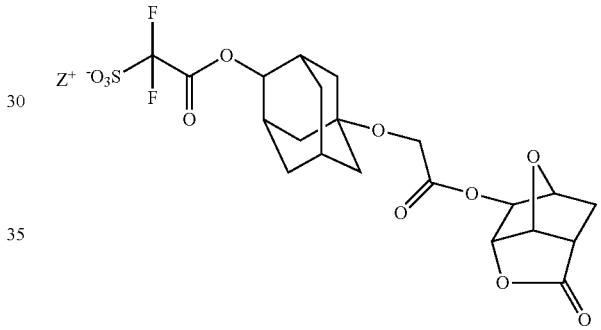
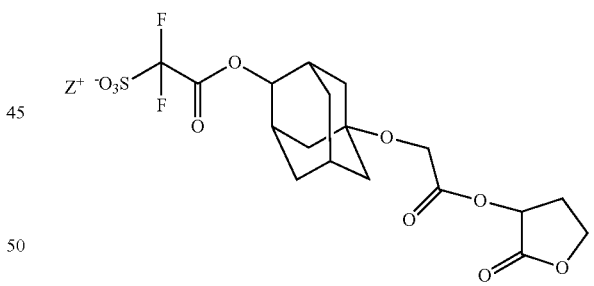
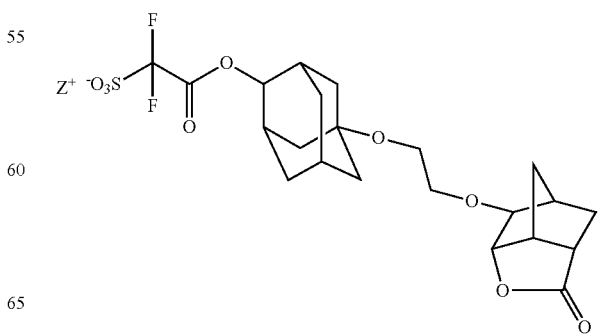

15
-continued
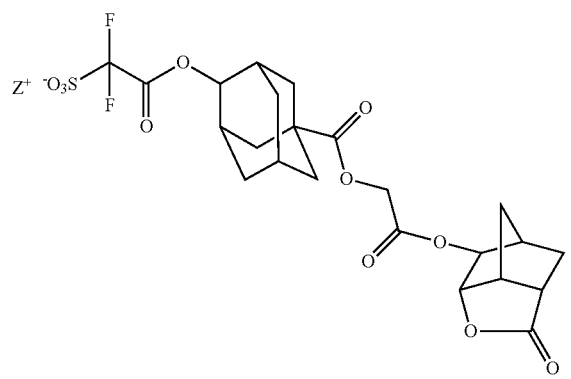
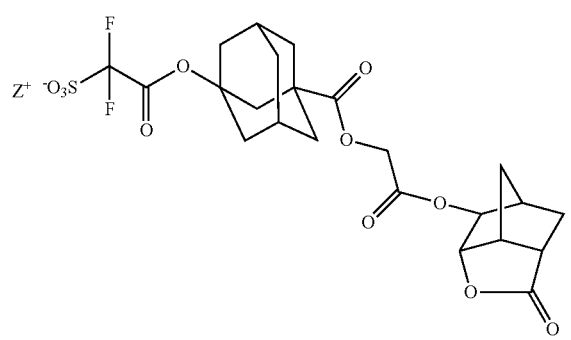
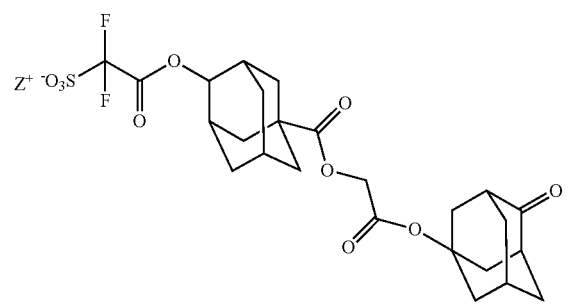
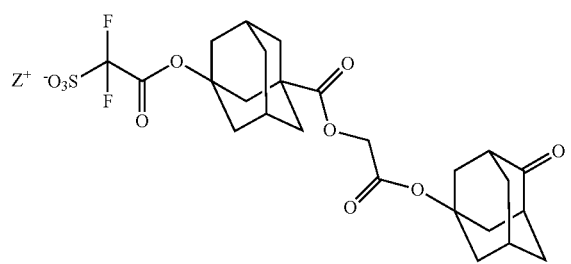
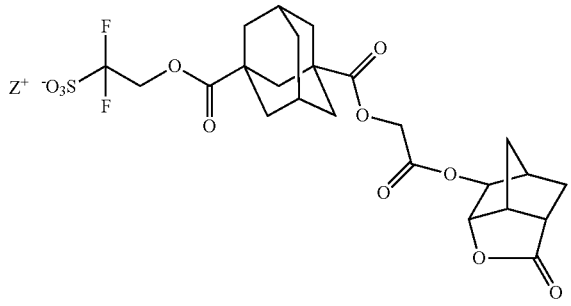
16
-continued
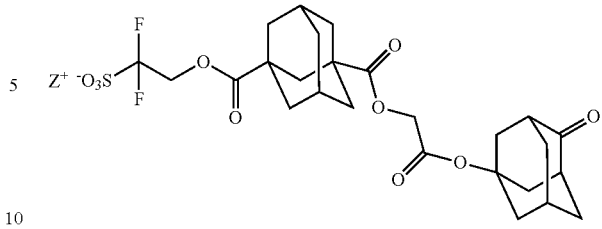
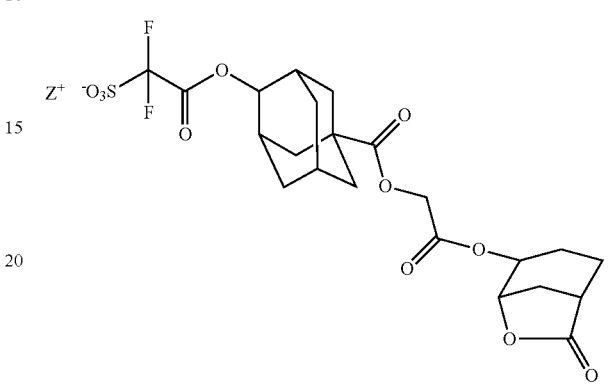
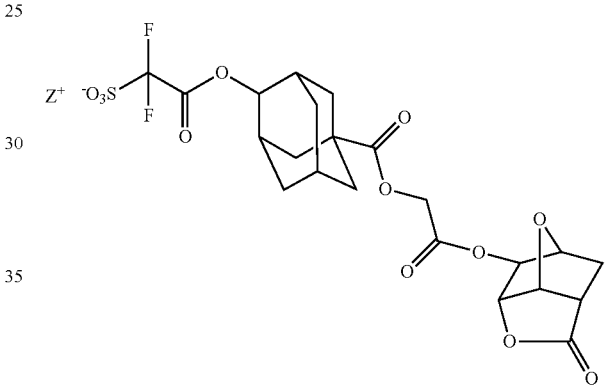
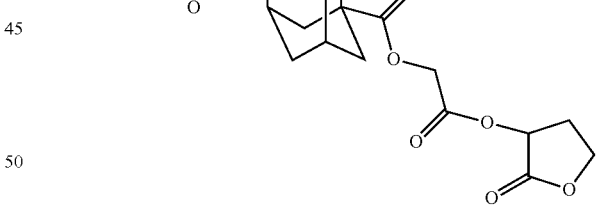
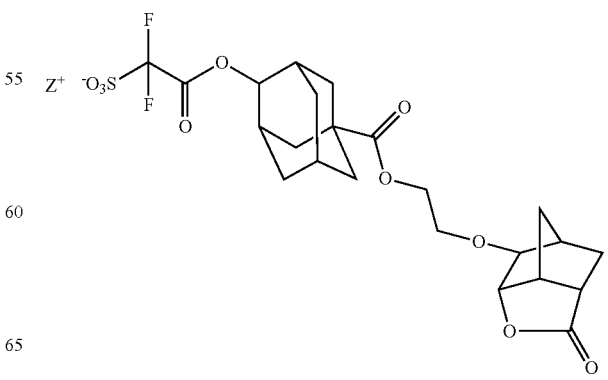

17
-continued
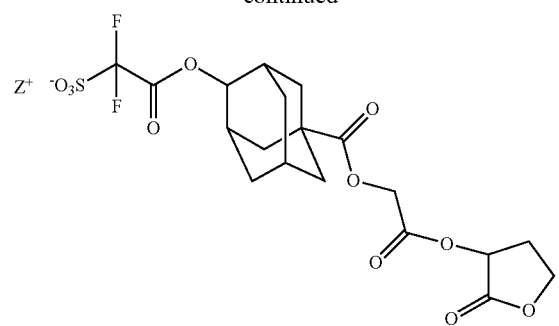
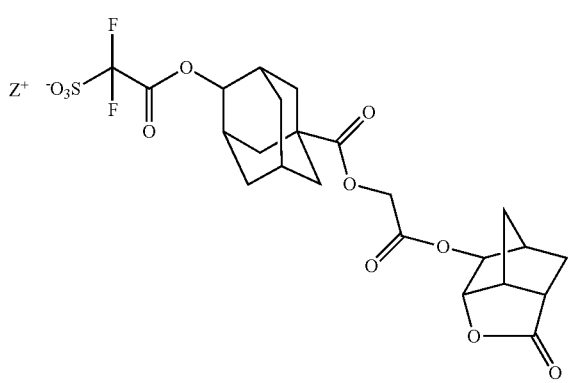
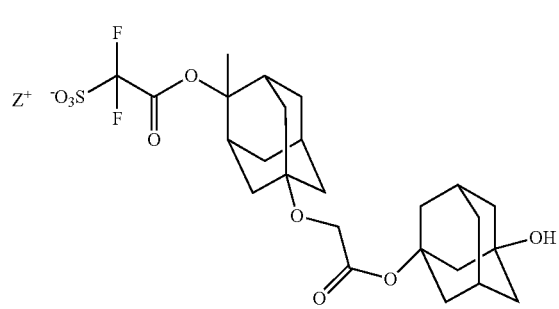
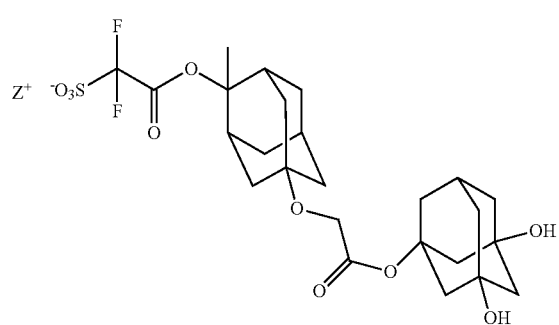
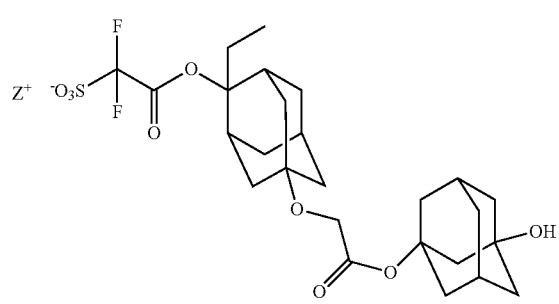
18
-continued
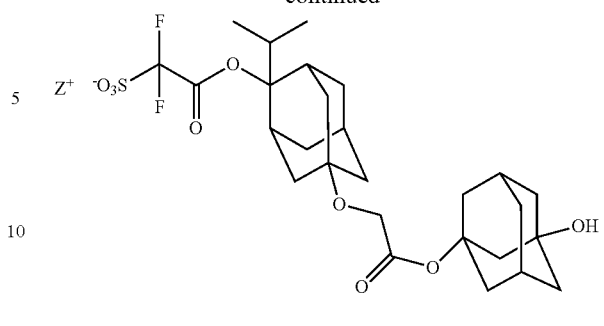
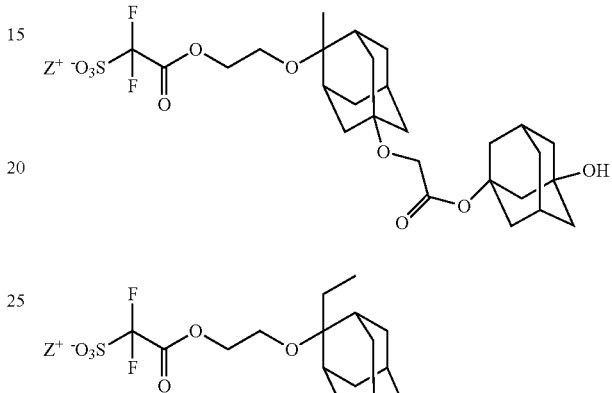
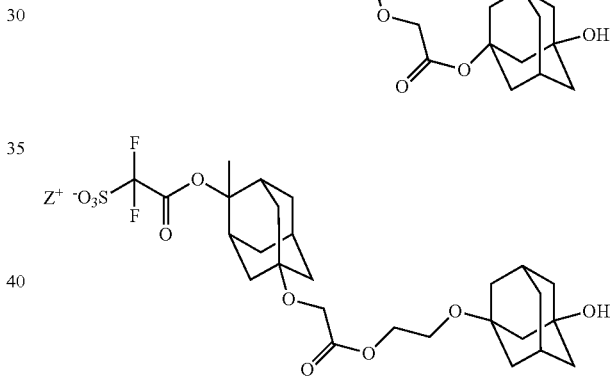
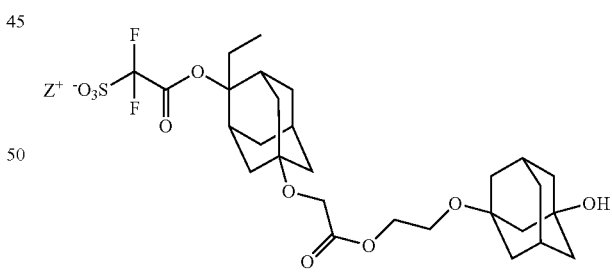
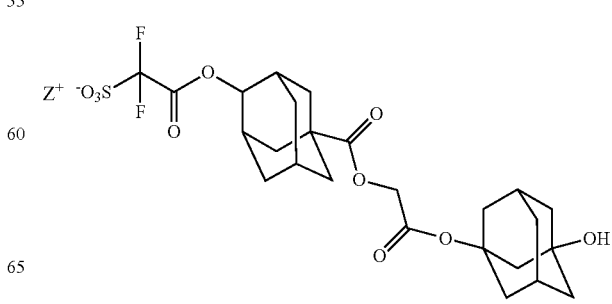

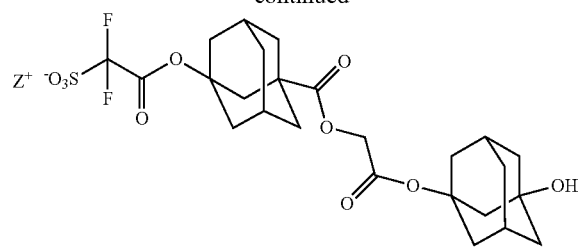

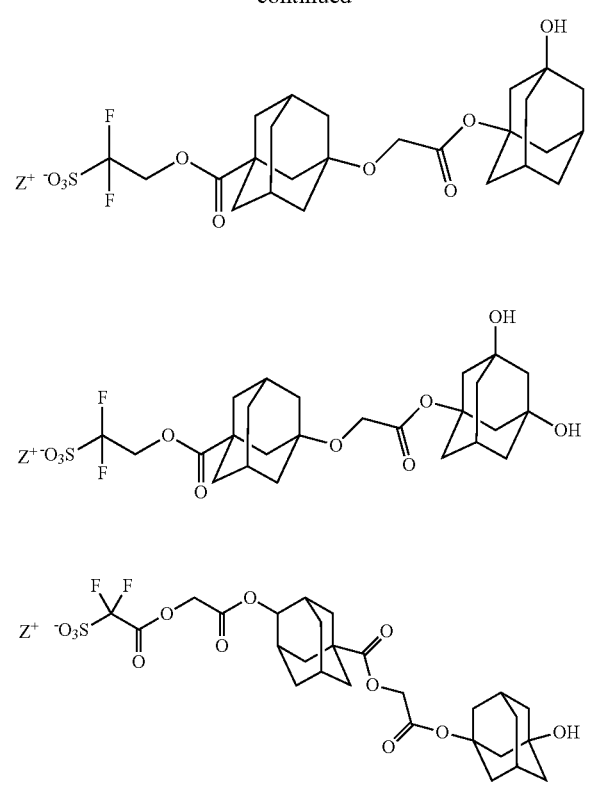

Examples of the counter ion represented by $Z^+$ include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable, and triarylsulfonium cation is especially preferable.

Preferable examples of the cation part represented by $Z^+$ include the cations represented by the formulae (b2-1) to (b2-4):

(b2-1)

(b2-2)

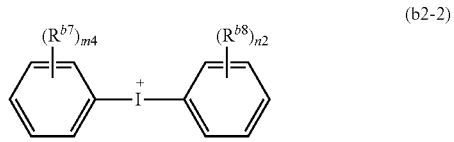

(b2-3)

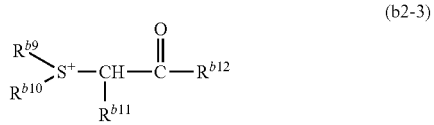

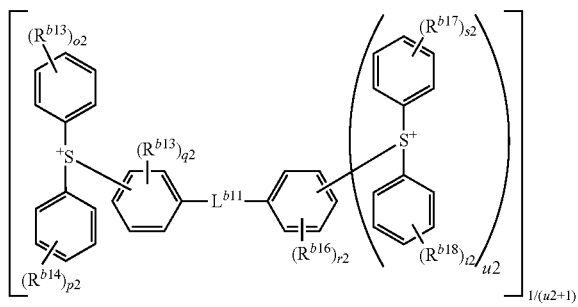

(b2-4)

wherein $R^{b4}$, $R^{b5}$ and $R^{b6}$ each independently represent a C1-C30 aliphatic hydrocarbon group which can have one or more substituents selected from the group consisting of a hydroxyl group, a C1-C12 alkoxy group and a C6-C18 aromatic hydrocarbon group, a C3-C36 saturated cyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C36 aliphatic hydrocarbon group, a C3-C36 saturated cyclic hydrocarbon group or a C1-C12 alkoxy group, $R^{b7}$ and $R^{b8}$ are independently in each occurrence a hydroxyl group, a C1-C12 aliphatic hydrocarbon group or a C1-C12 alkoxy group, m4 and n2 independently represents an integer of 0 to 5, $R^{b9}$ and $R^{b10}$ each independently represent a C1-C36 aliphatic hydrocarbon group or a C3-C36 saturated cyclic hydrocarbon group, or $R^{b9}$ and $R^{b10}$ are bonded to form a C2-C11 divalent acyclic hydrocarbon group which forms a ring together with the adjacent and one or more —CH$_2$— in the divalent acyclic hydrocarbon group may be replaced by —CO—, —O— or —S—, and $R^{b11}$ represents a hydrogen atom, a C1-C36 aliphatic hydrocarbon group, a C3-C36 saturated cyclic hydrocarbon group or a C6-C18 aromatic hydrocarbon group, $R^{b12}$ represents a C1-C12 aliphatic hydrocarbon group, a C6-C18 saturated cyclic hydrocarbon group or a C6-C18 aromatic hydrocarbon group and the aromatic hydrocarbon group can have one or more substituents selected from the group consisting of a C1-C12 aliphatic hydrocarbon group, a C1-C12 alkoxy group, a C3-C18 saturated cyclic hydrocarbon group and an C2-C13 acyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —CH$_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ each independently represent a hydroxyl group, a C1-C12 aliphatic hydrocarbon group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The aliphatic hydrocarbon group represented by $R^{b9}$ to $R^{b11}$ has preferably 1 to 12 carbon atoms. The saturated cyclic hydrocarbon group represented by $R^{b9}$ to $R^{b11}$ has preferably 3 to 18 carbon atoms and more preferably 4 to 12 carbon atoms.

Examples of the aliphatic hydrocarbon group, the saturated cyclic hydrocarbon group and the aromatic hydrocarbon group include the same as described above. Preferable examples of the aliphatic hydrocarbon group include a methyl group, an ethyl group, a propyl group, an isopropyl group, a butyl group, a sec-butyl group, a tert-butyl group, a pentyl group, a hexyl group, an octyl group and a 2-ethylhexyl group. Preferable examples of the saturated cyclic hydrocarbon group include a cyclopropyl group, a cyclobutyl group, a cyclopentyl group, a cyclohexyl group, a cycloheptyl group, a cyclodecyl group, a 2-alkyl-2-adamantyl group, a 1-(1-adamantyl)-1-alkyl group and an isobornyl group. Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the aliphatic hydrocarbon group having an aromatic hydrocarbon group include a benzyl group. Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent S$^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

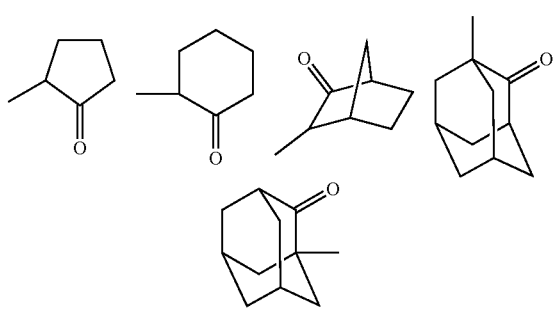

Among the above-mentioned cations, preferred is the cation represented by the formula (b2-1), and more preferred is the cation represented by the formula (b2-1-1), and especially preferred is a triphenylsulfonium cation.

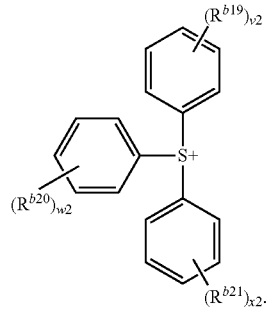

(b2-1-1)

wherein $R^{b19}$, $R^{b20}$ and $R^{b21}$ are independently in each occurrence a hydroxyl group, a C1-C36 aliphatic hydrocarbon group, a C3-C36 saturated cyclic hydrocarbon group or a C1-C12 alkoxy group, and one or more hydrogen atoms in the aliphatic hydrocarbon group can be replaced by a hydroxyl group, a C1-C12 alkoxy group or a C6-C18 aromatic hydrocarbon group, one or more hydrogen atoms of the saturated cyclic hydrocarbon group can be replaced by a halogen atom, a C2-C4 acyl group or a glycidyloxy group, and v2, w2 and x2 independently each represent an integer of 0 to 5. The aliphatic hydrocarbon group preferably has 1 to 12 carbon atoms, and the saturated cyclic hydrocarbon group preferably has 4 to 36 carbon atoms, and it is preferred that v2, w2 and x2 independently each represent 0 or 1. It is preferred that $R^{b19}$, $R^{b20}$ and $R^{b21}$ are independently halogen atom (preferably a fluorine atom), a hydroxyl group, a C1-C12 alkyl group or a C1-C12 alkoxy group.

Examples of the cation represented by the formula (b2-1) include the followings.

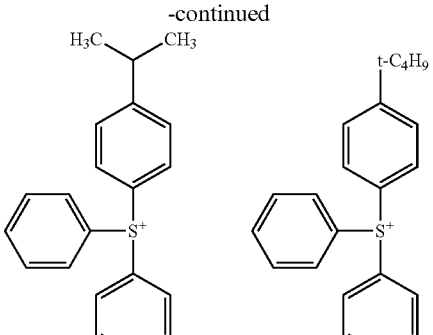

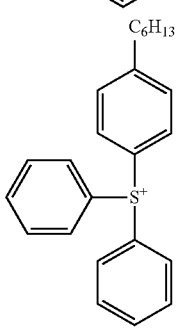 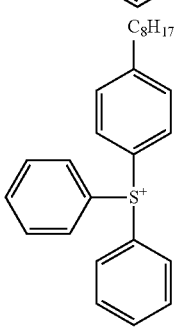

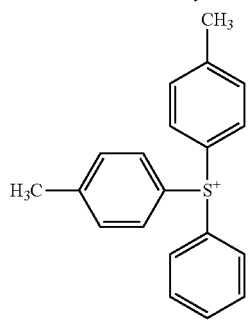 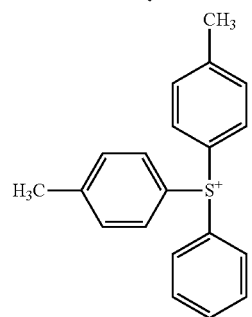

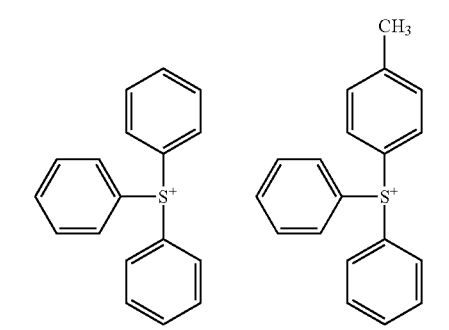

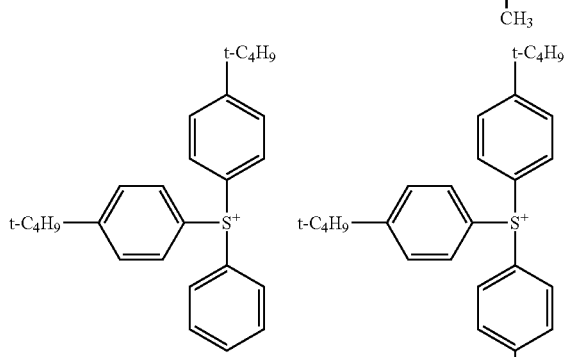

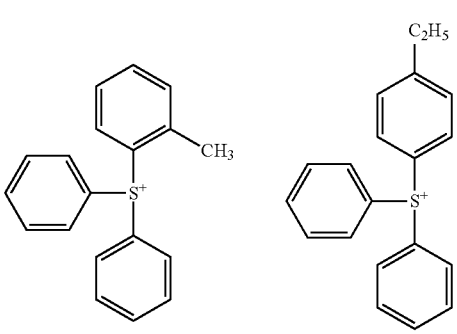

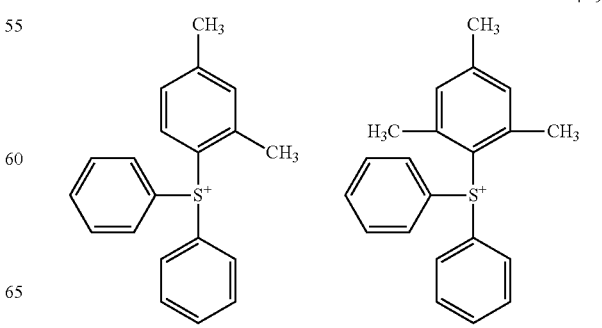

-continued
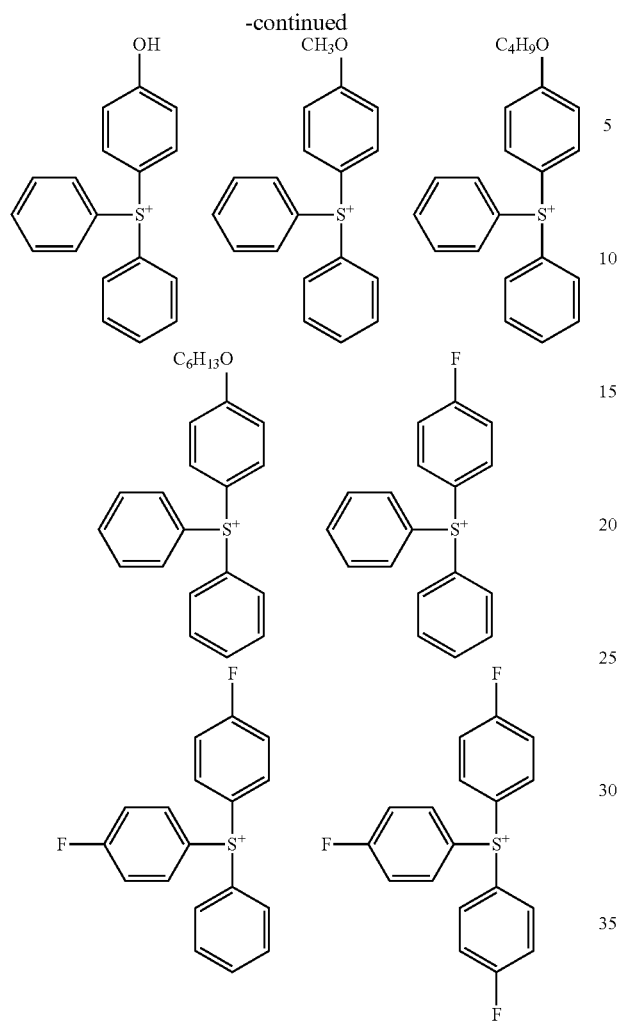
Examples of the cation represented by the formula (b2-2) include the followings.
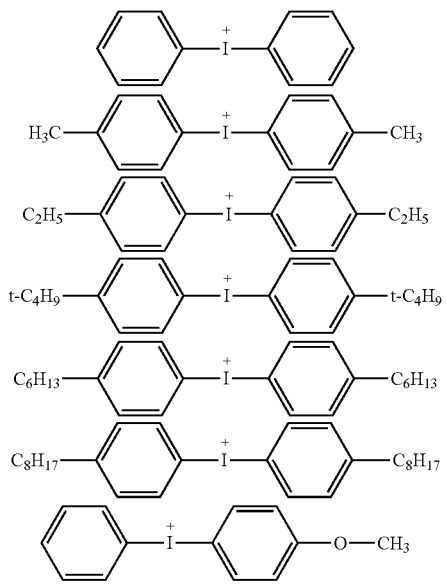
-continued
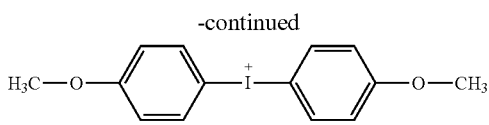
Examples of the cation represented by the formula (b2-3) include the followings.
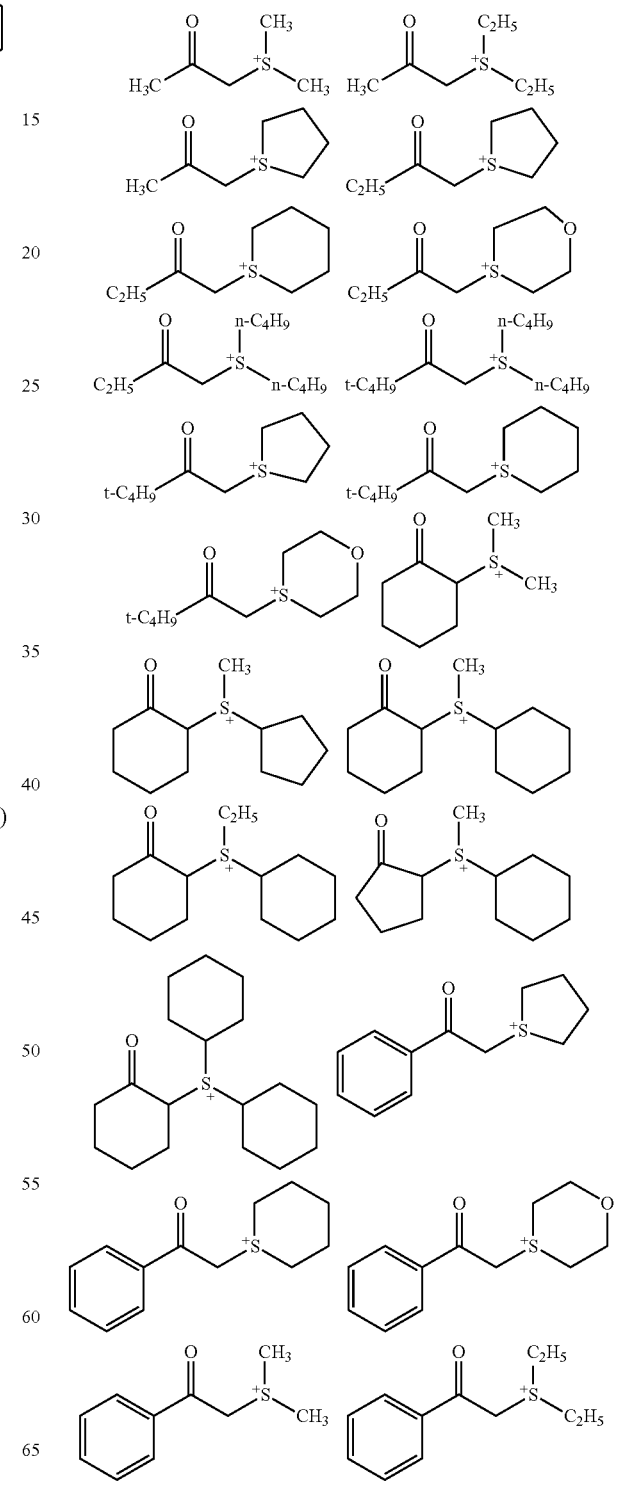

Examples of the cation represented by the formula (b2-4) include the followings.

-continued
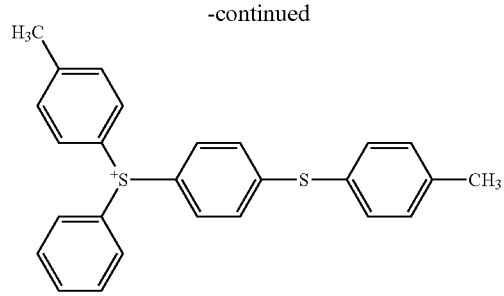
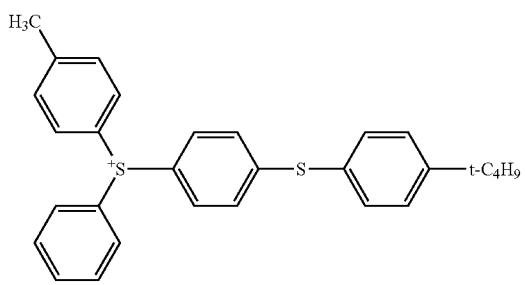
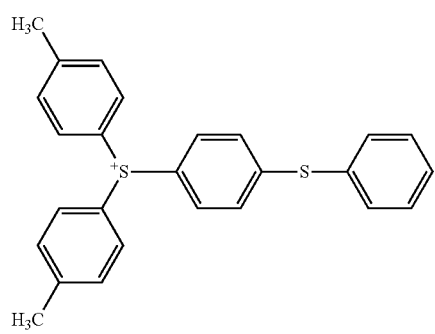
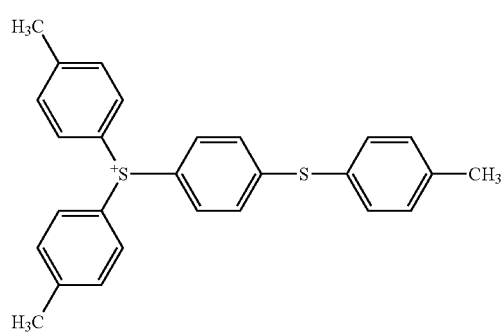
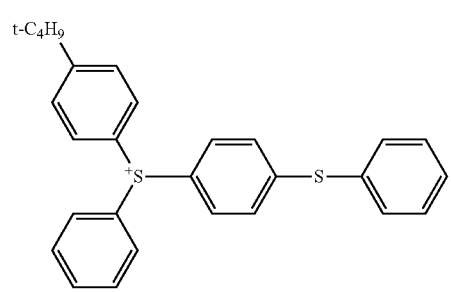
-continued
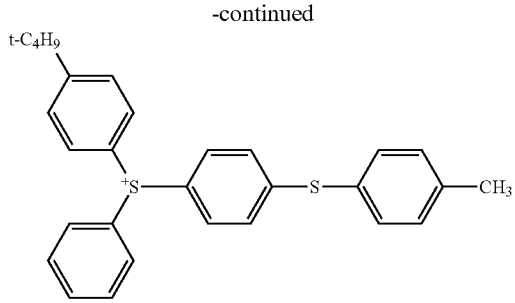
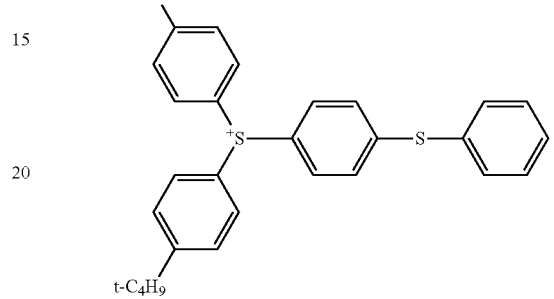
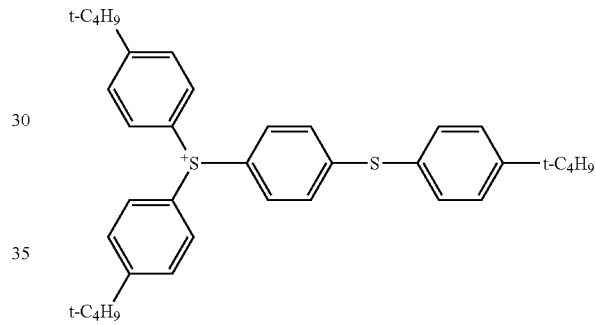
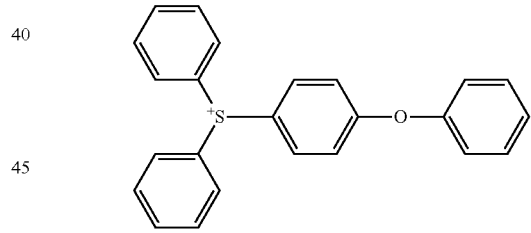
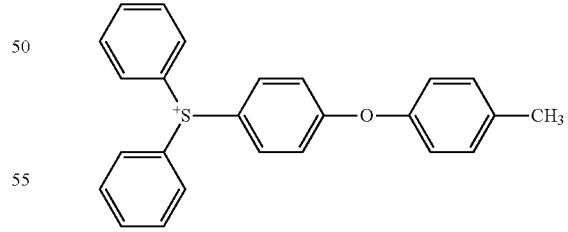
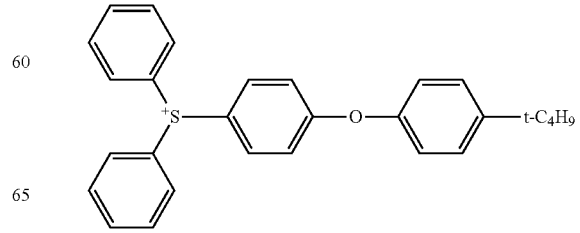

31
-continued
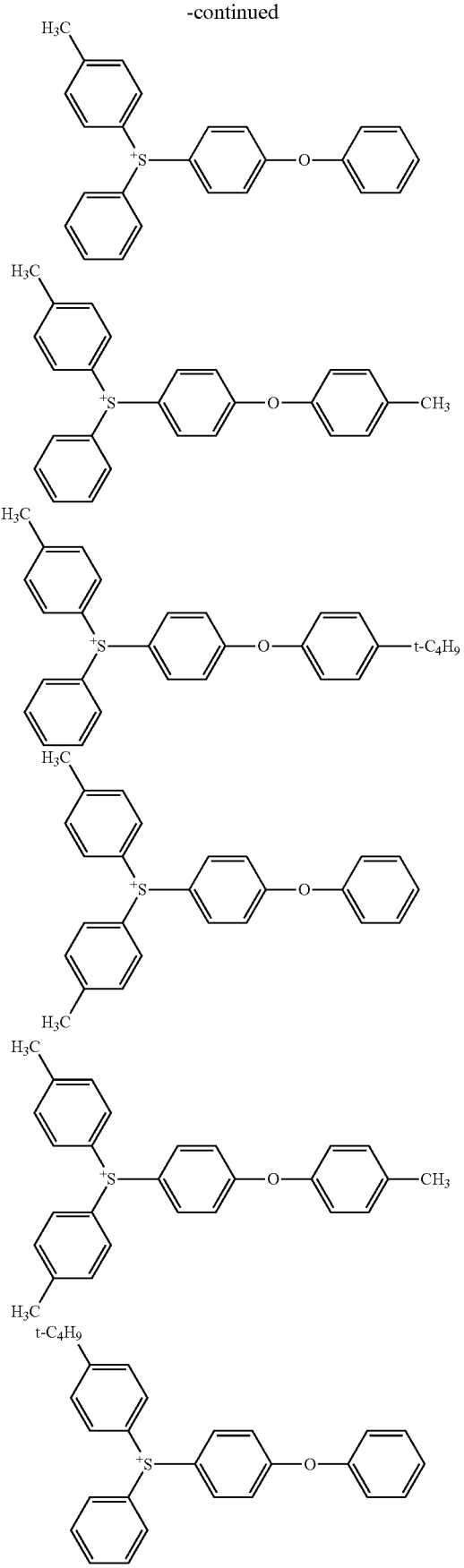
32
-continued
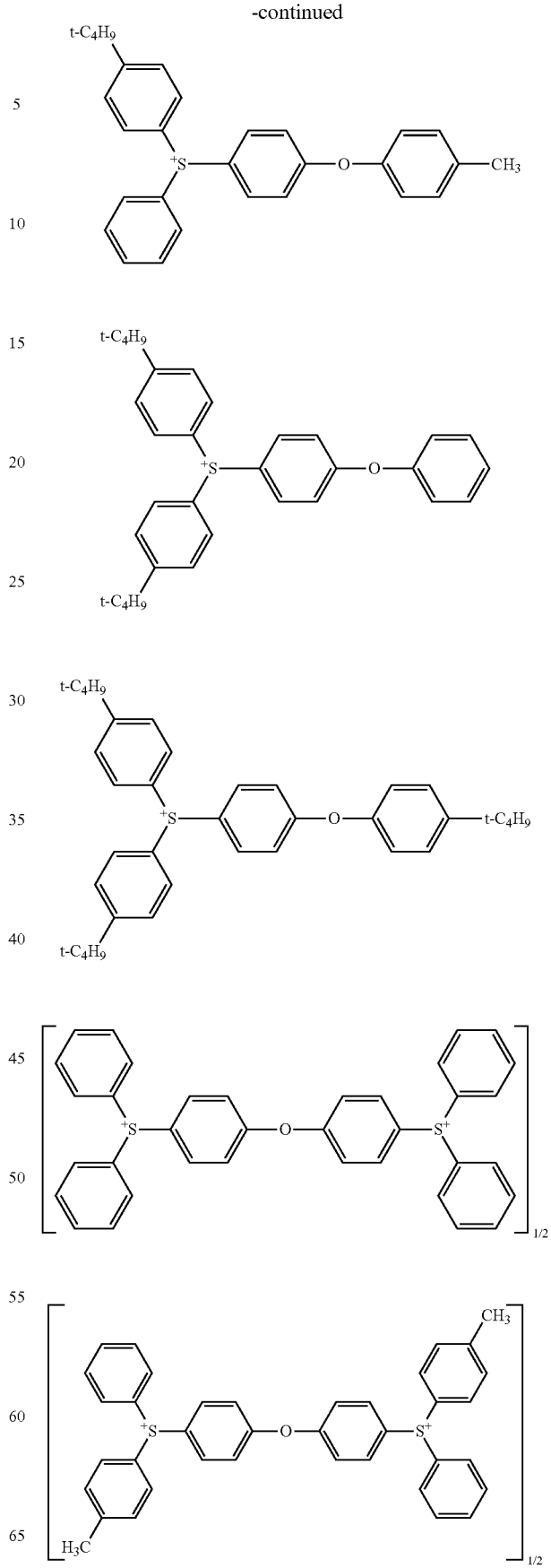

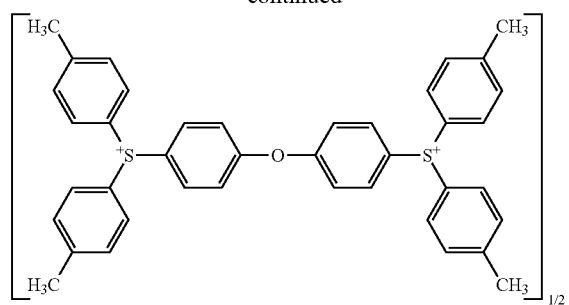
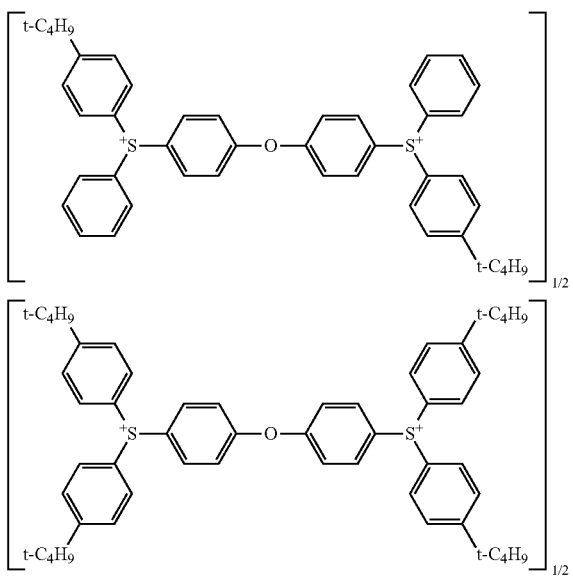
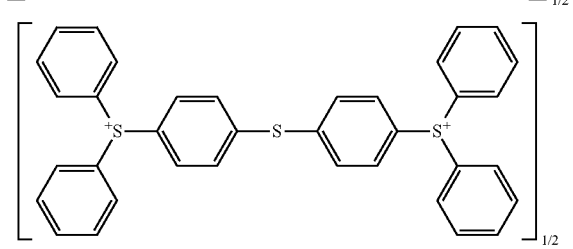
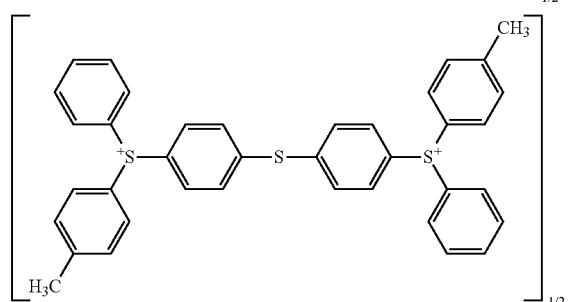
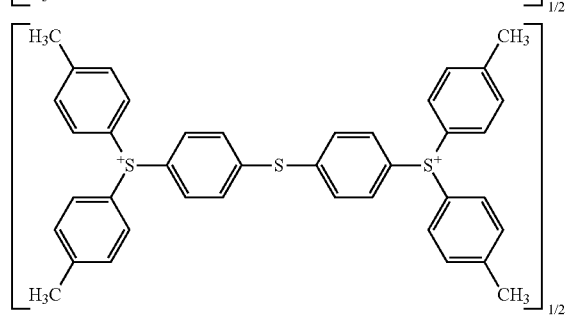
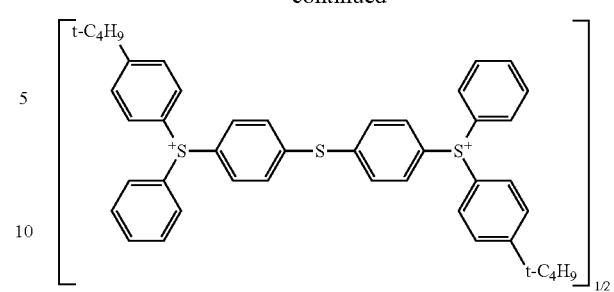
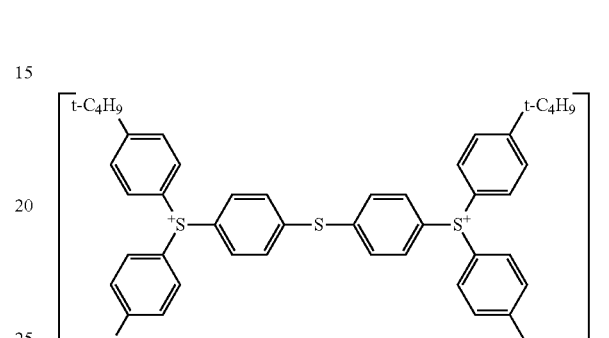
Specific examples of SALT (X) include the followings.
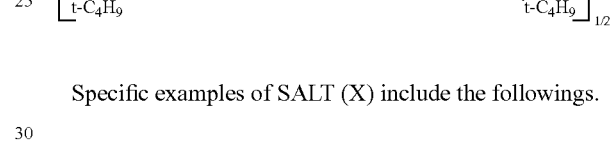
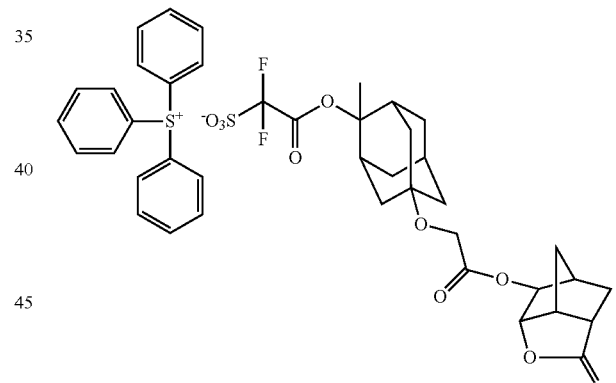
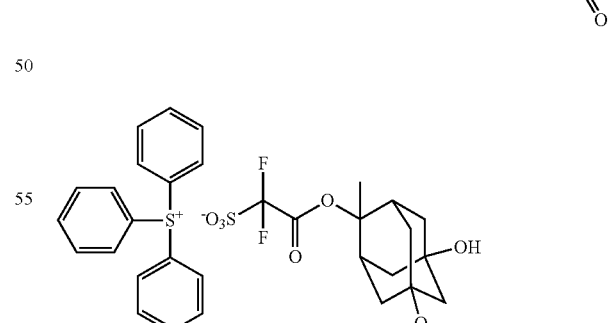

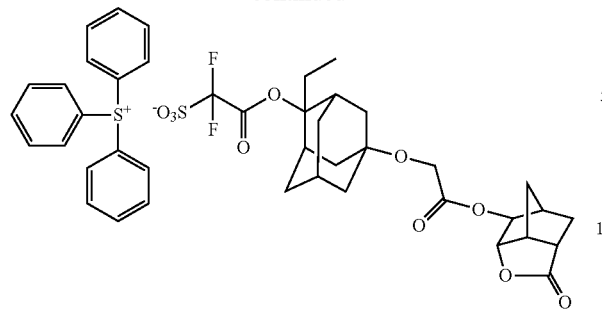
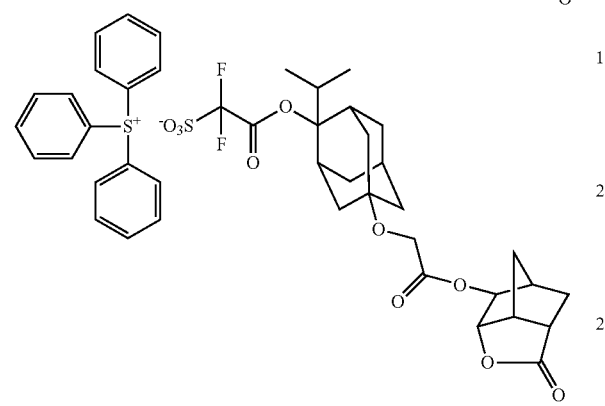
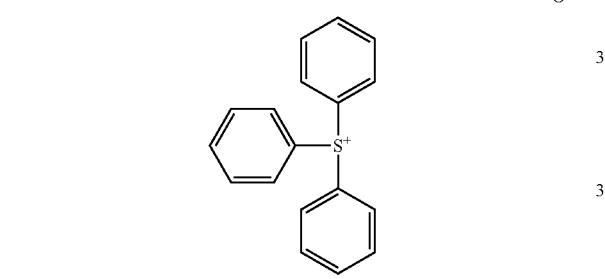
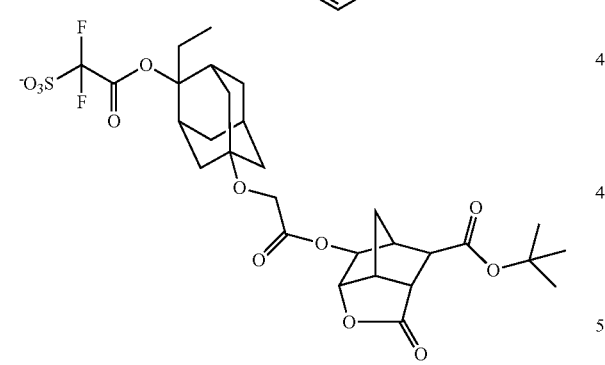
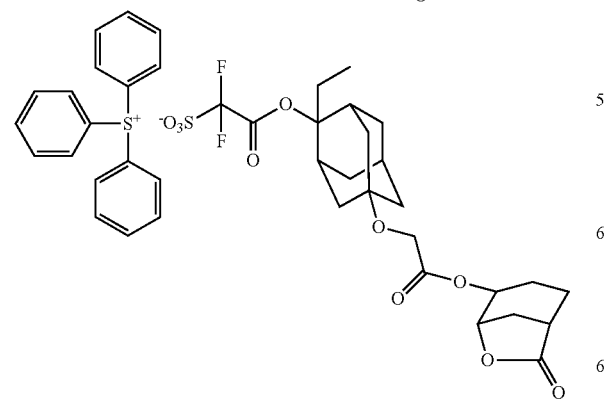
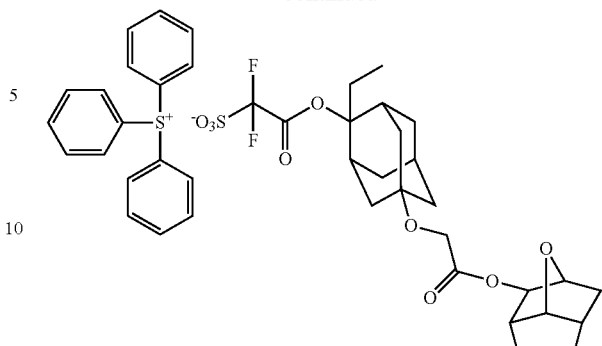
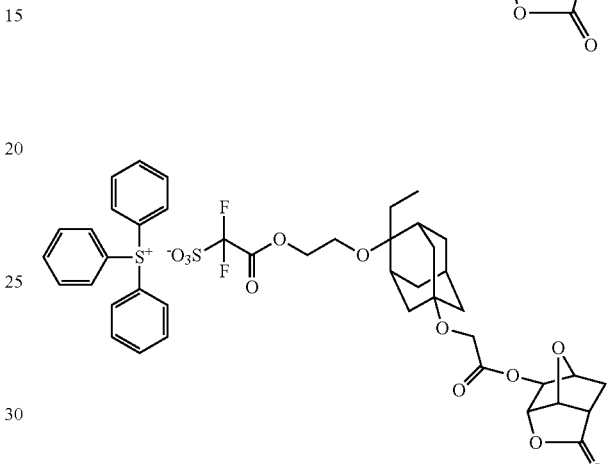
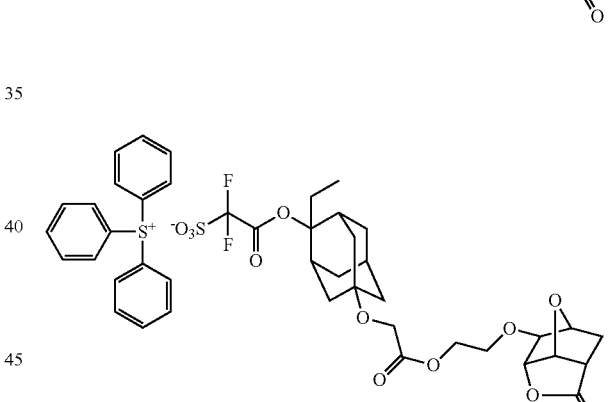
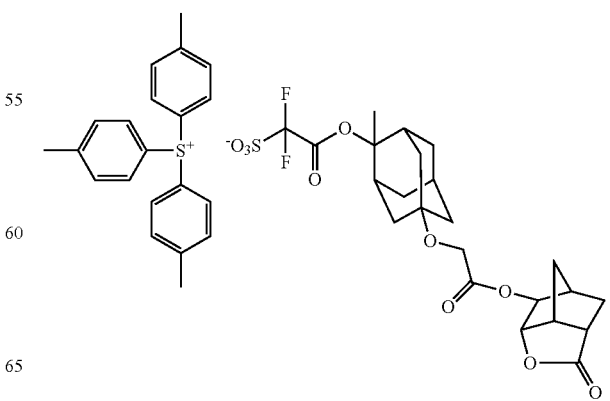

37
-continued
38
-continued
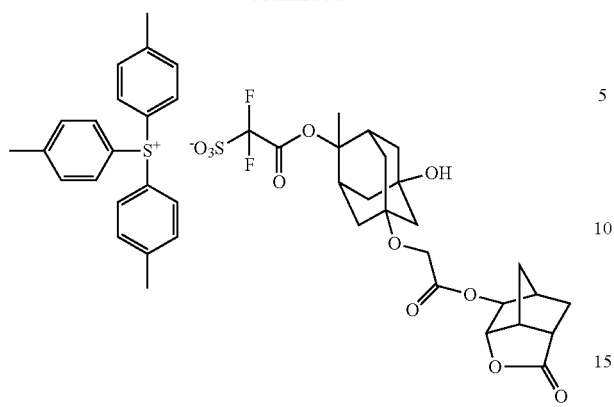
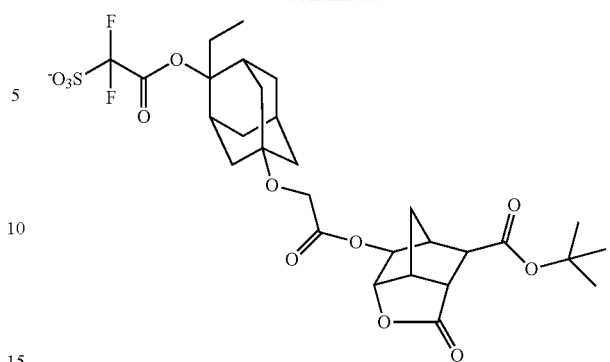
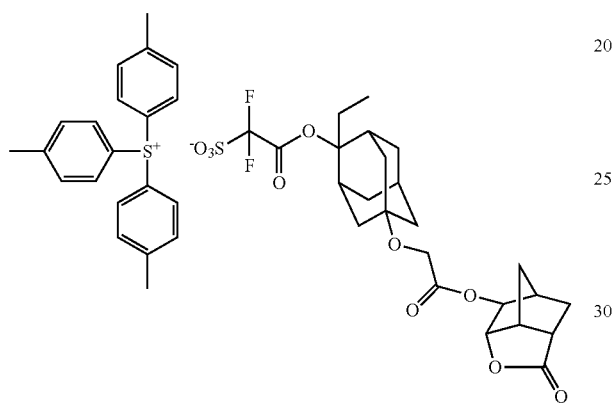
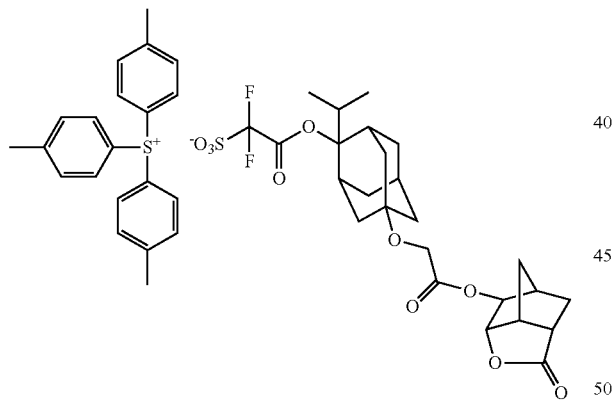
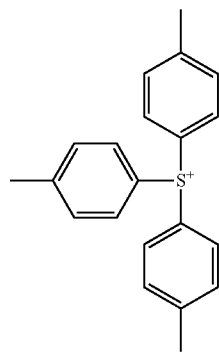
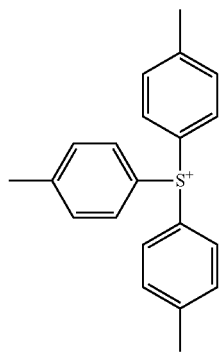

39
-continued
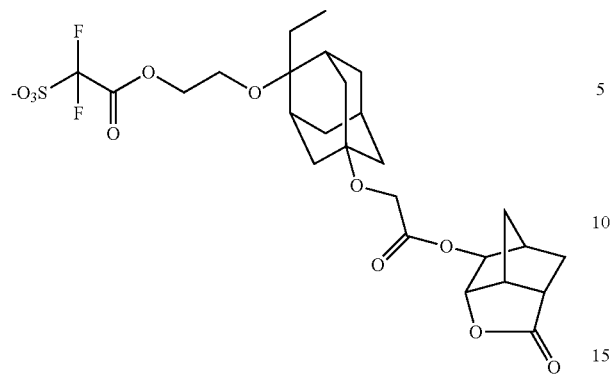
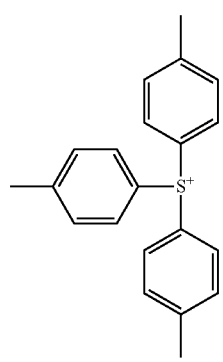
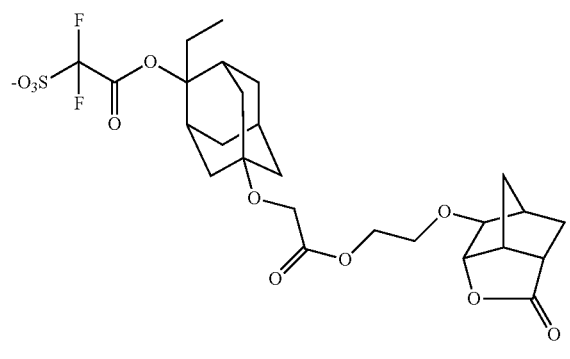
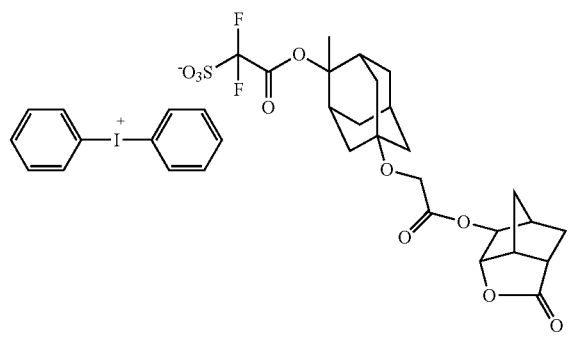
40
-continued
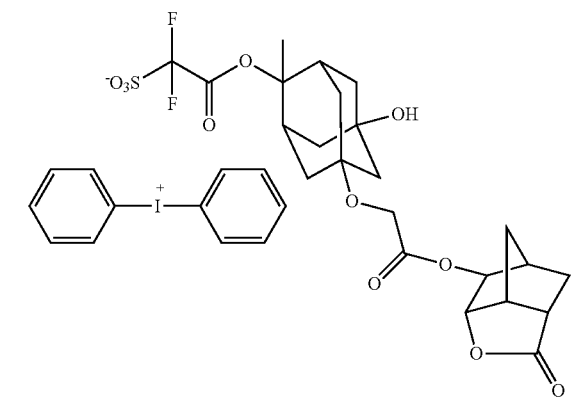
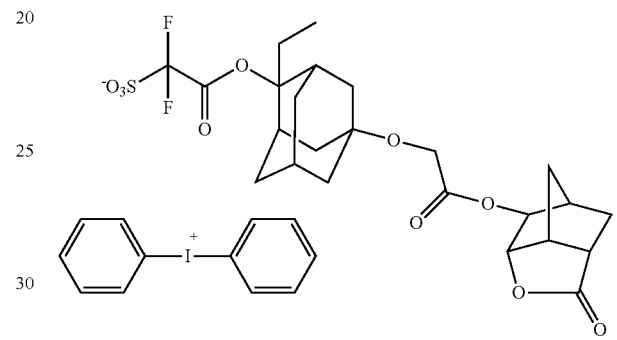
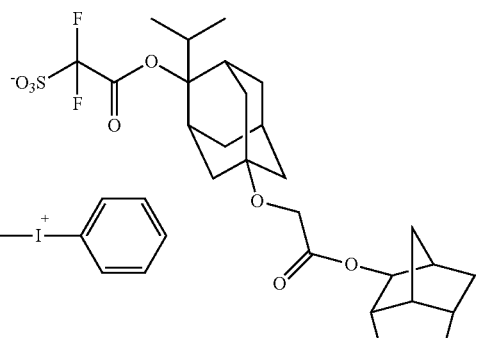
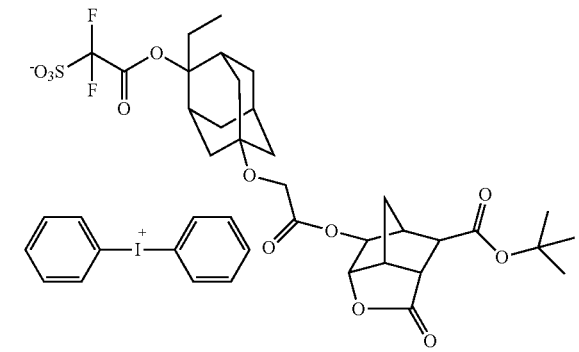

41
-continued
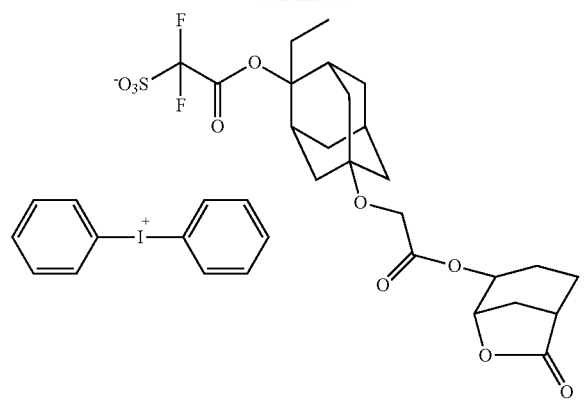
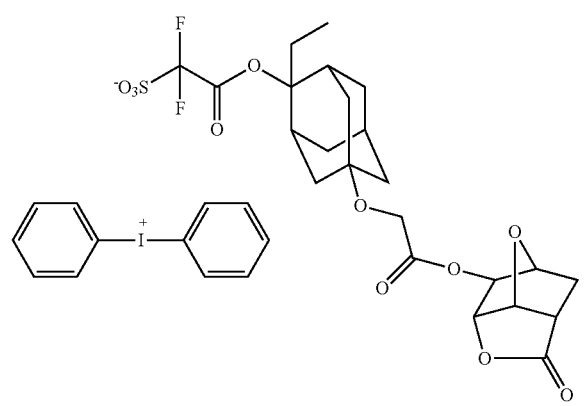
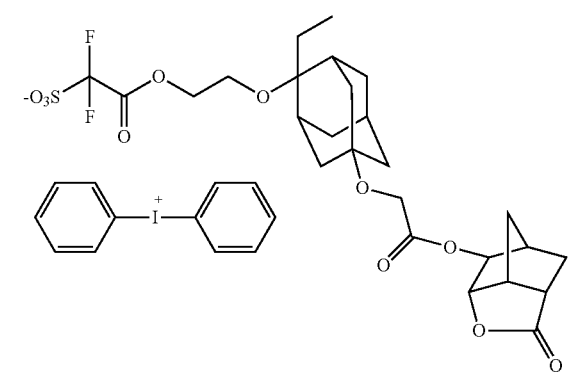
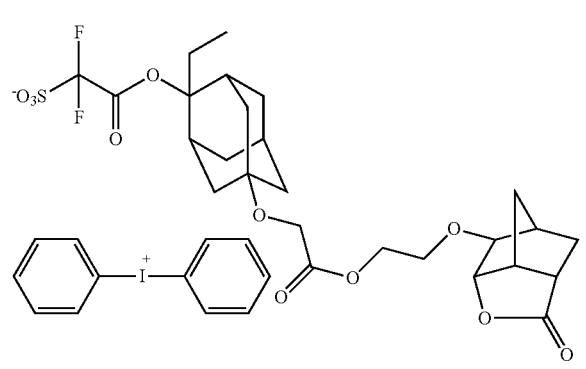
42
-continued
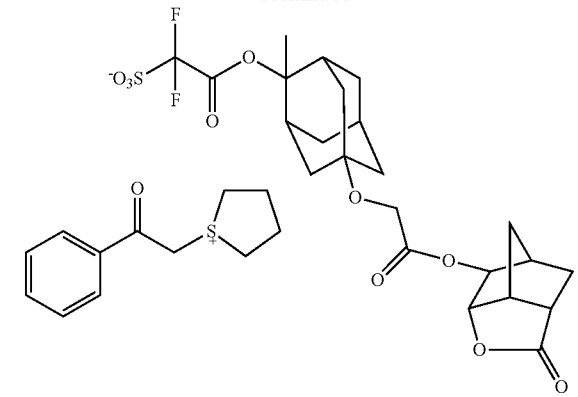
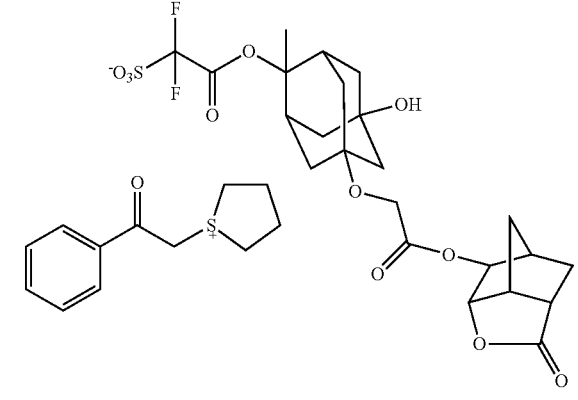
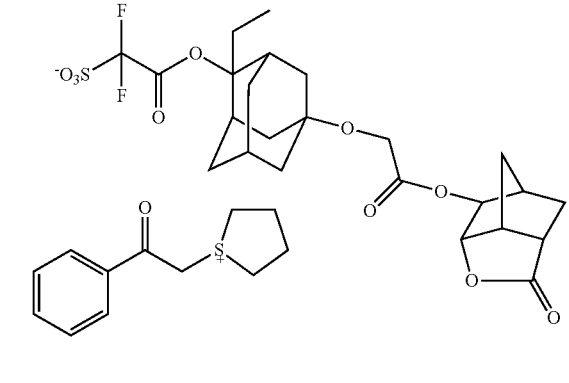
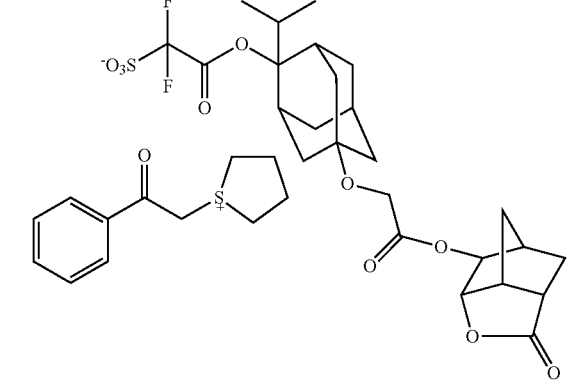

43
-continued
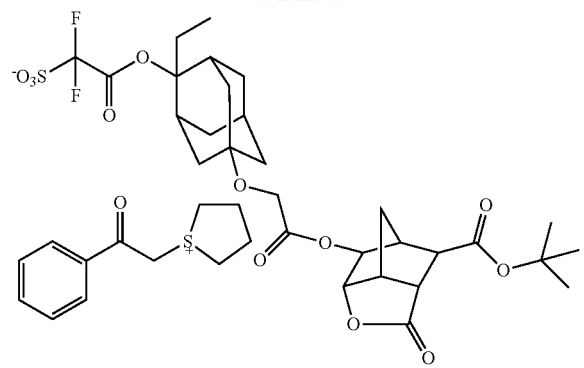
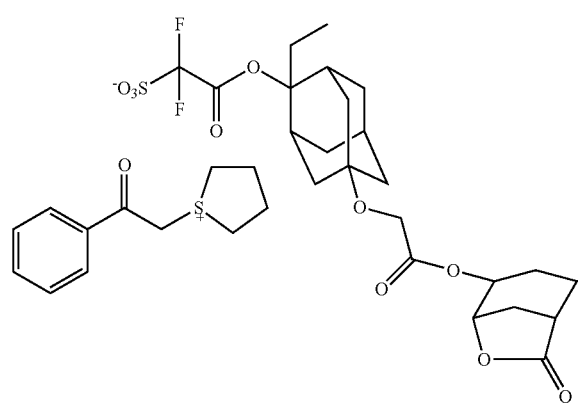
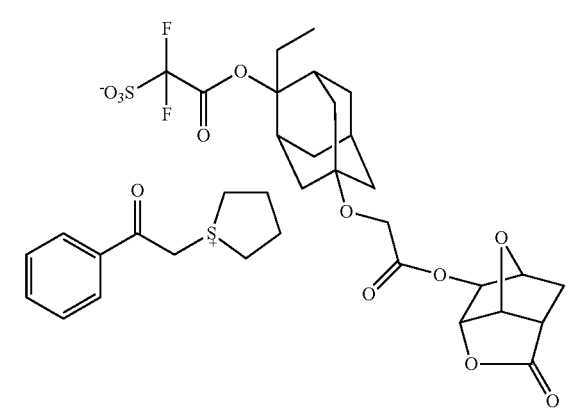
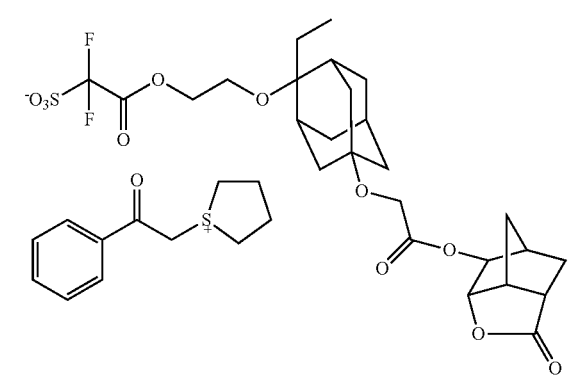
44
-continued
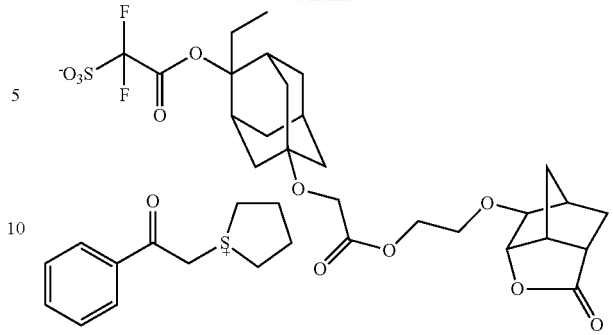
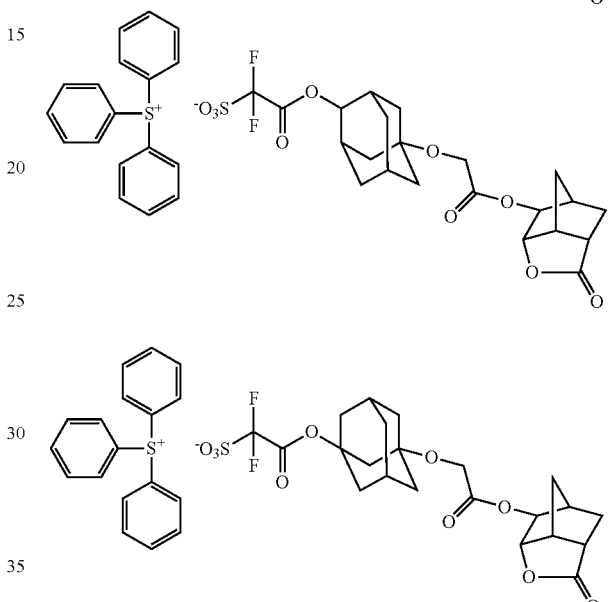
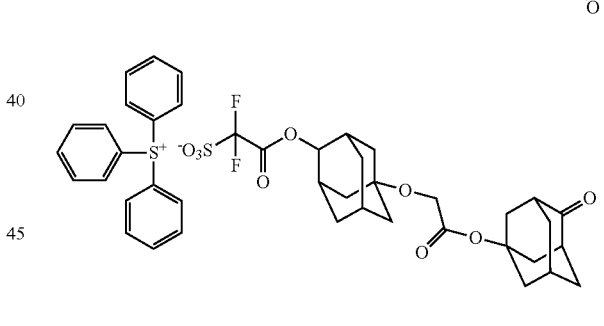
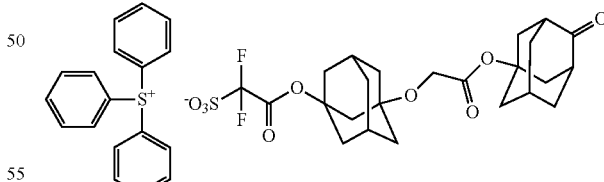
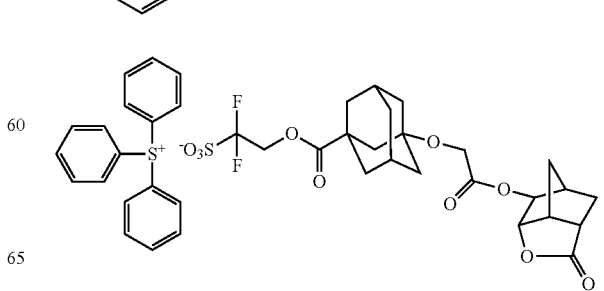

45
-continued
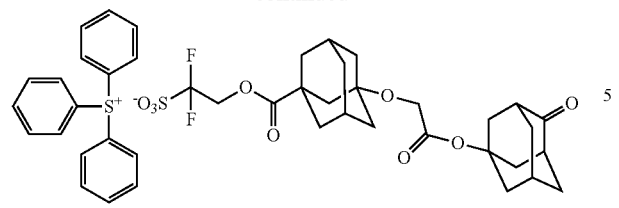
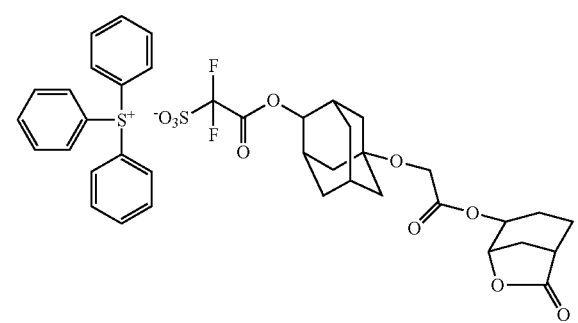
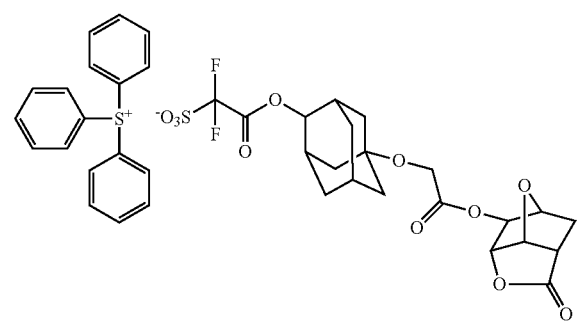
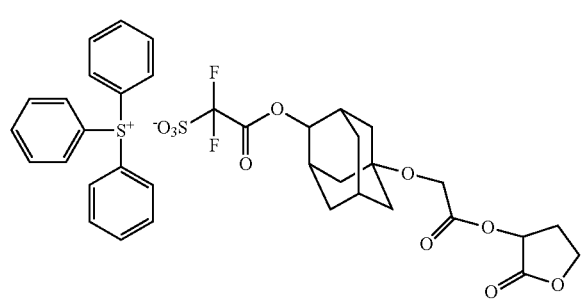
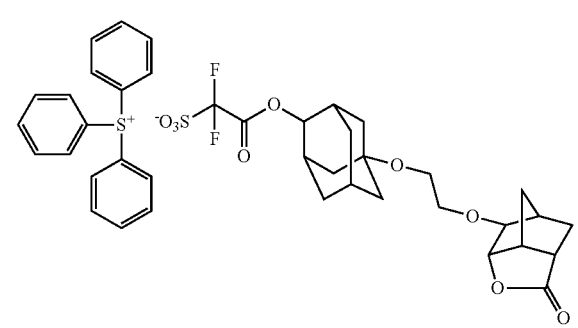
46
-continued
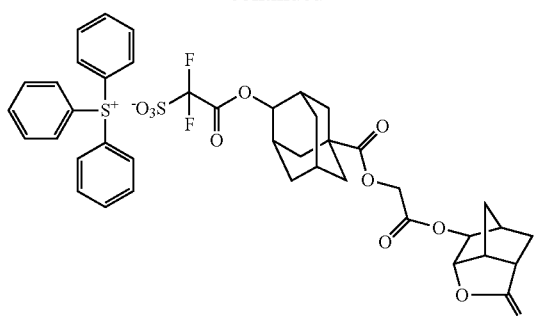
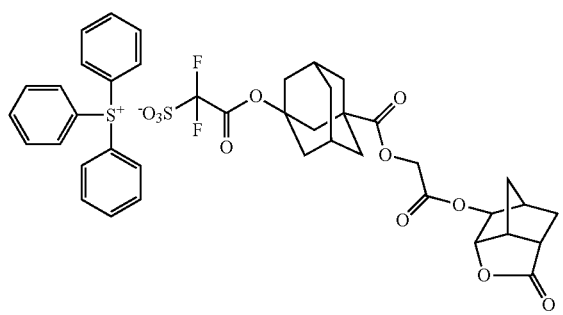
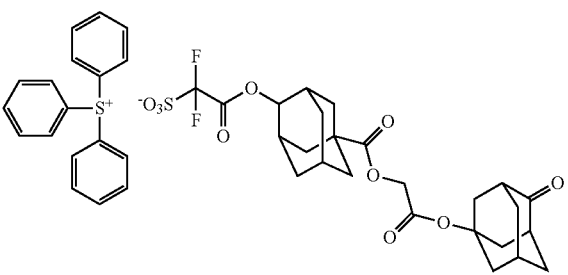
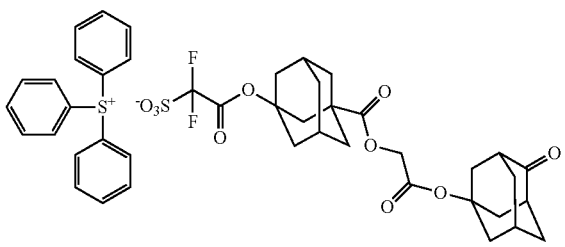
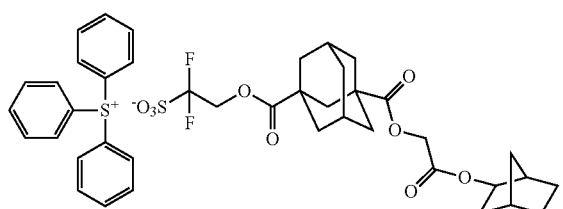
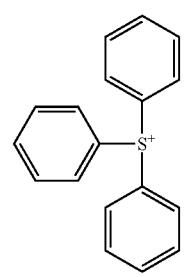

47
-continued
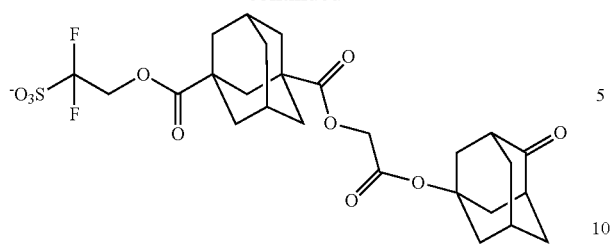
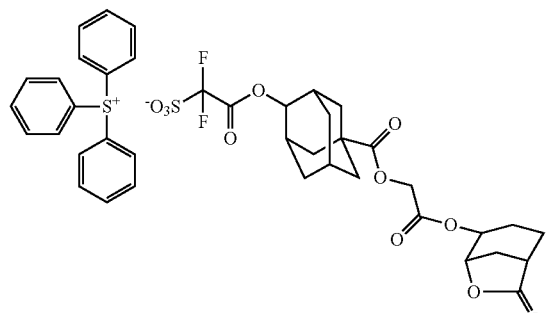
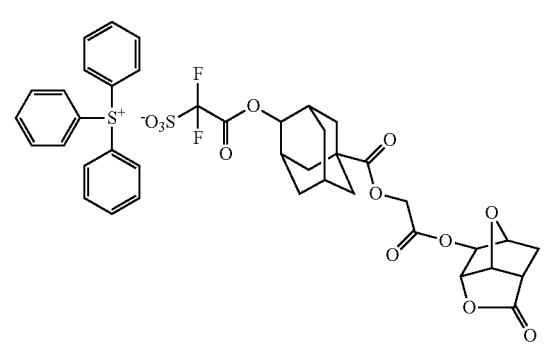
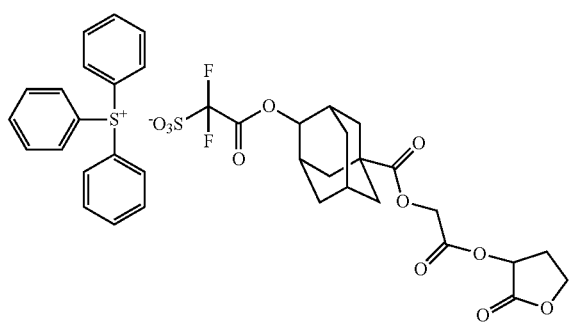
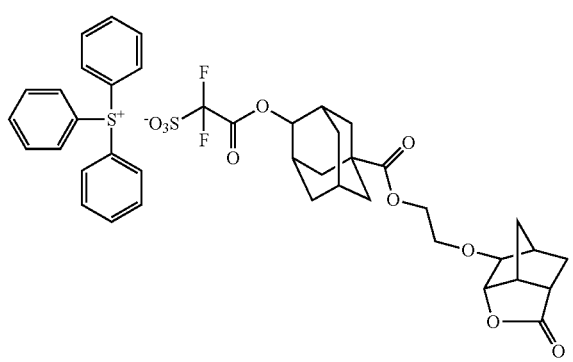
48
-continued
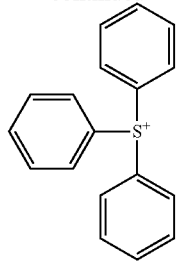
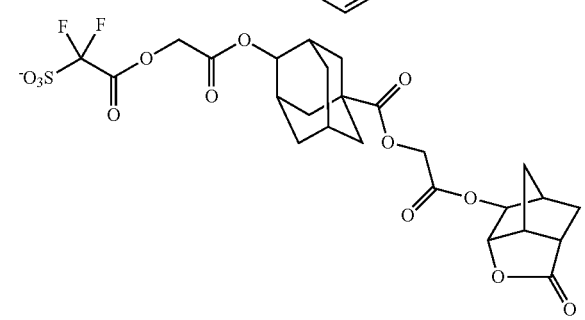
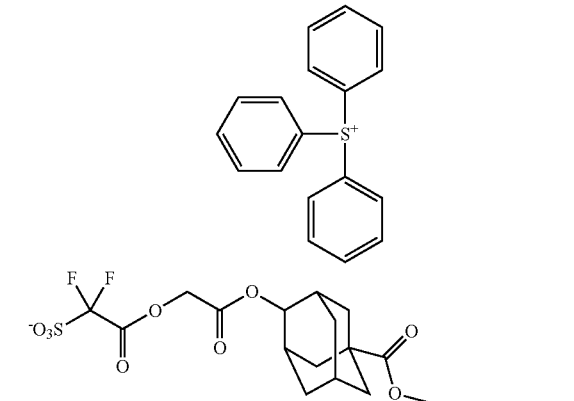
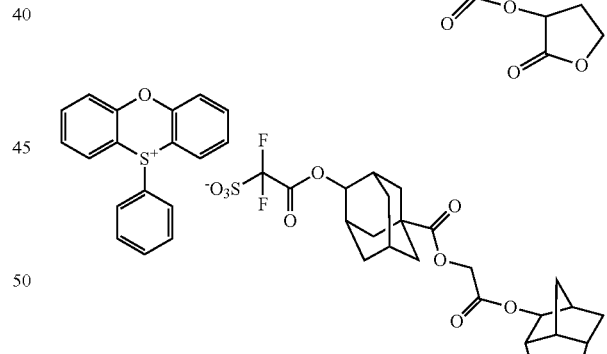
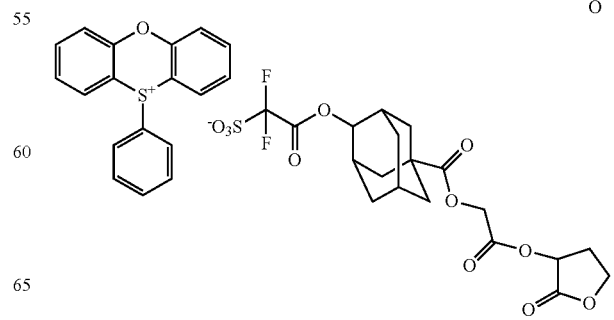

49
-continued
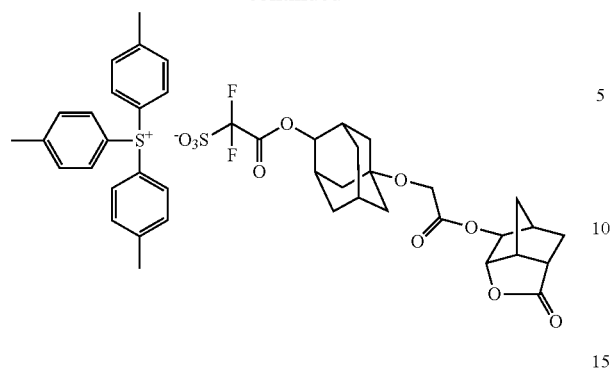
50
-continued
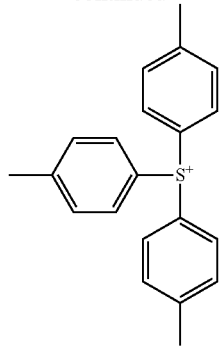
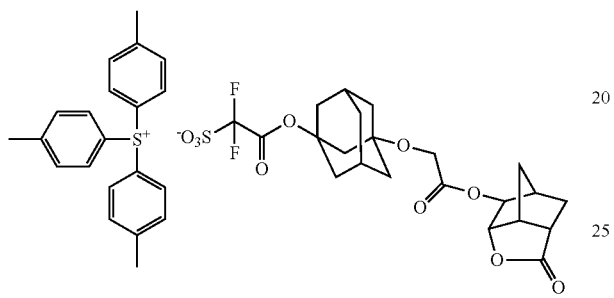
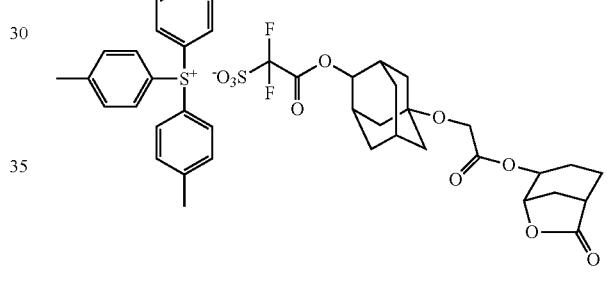
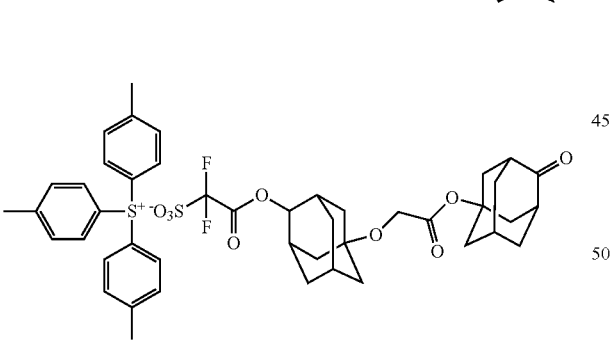
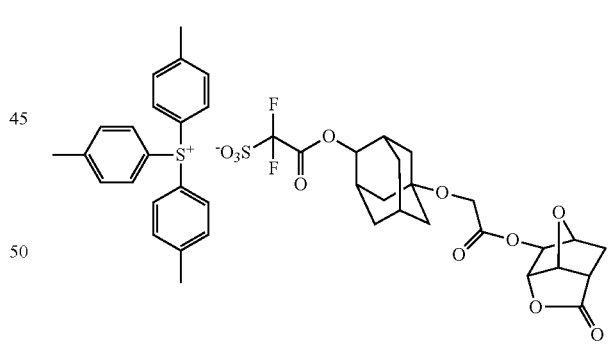
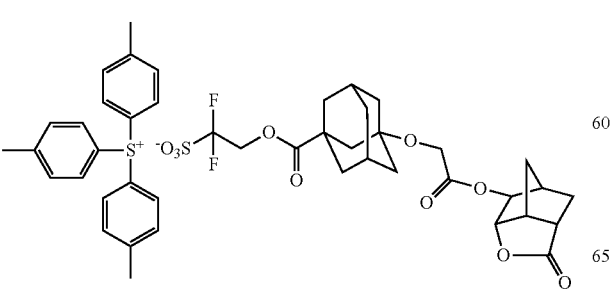
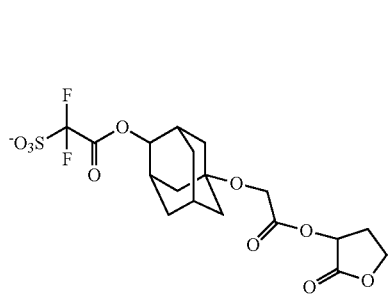

51
-continued
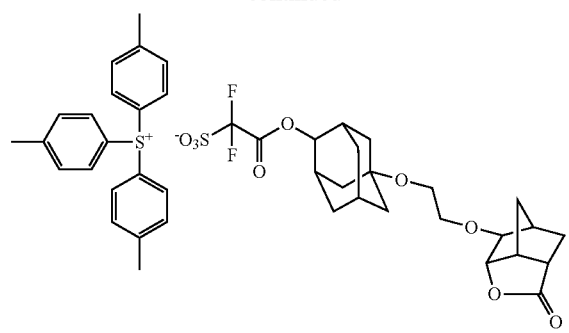
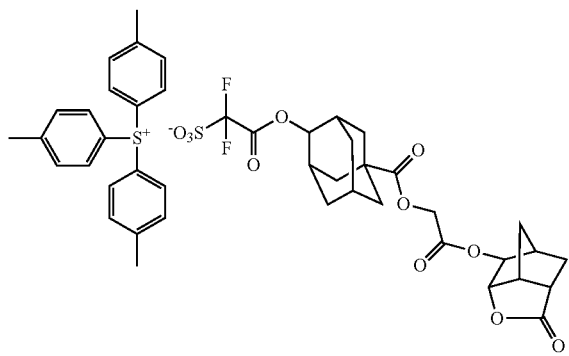
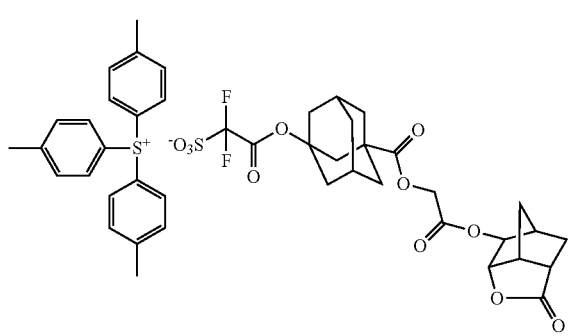
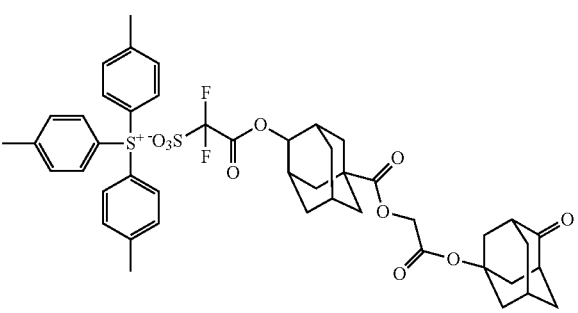
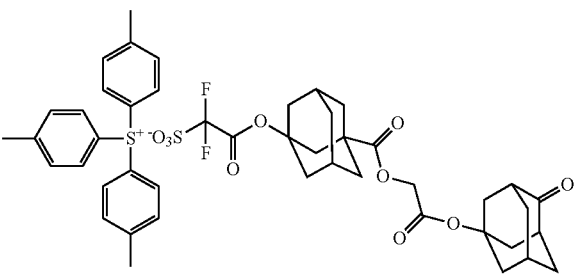
52
-continued
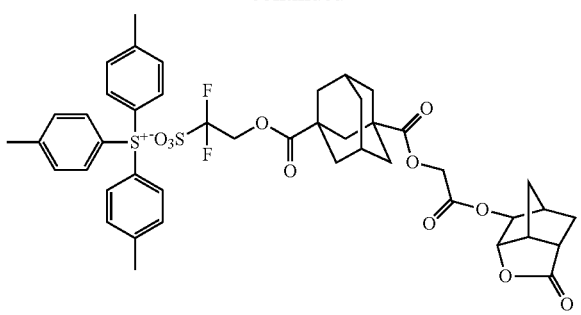
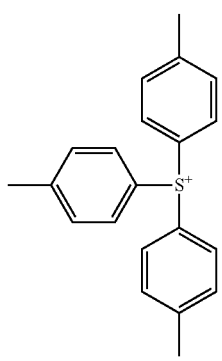
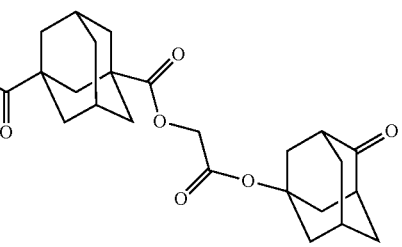
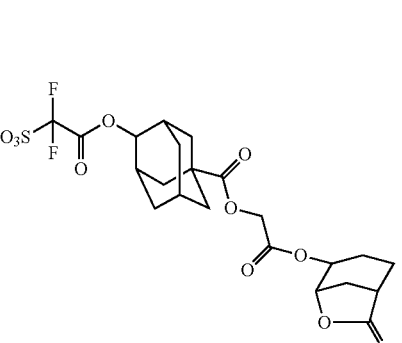
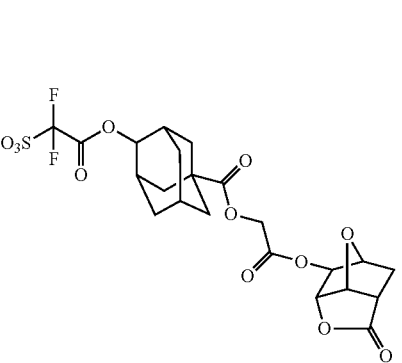

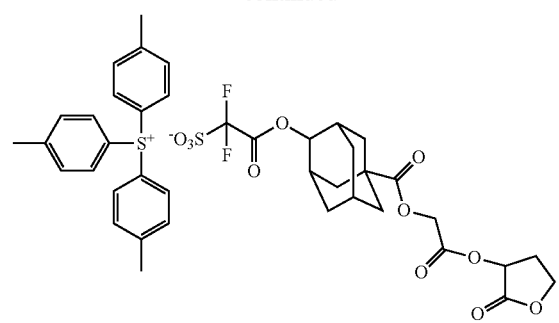
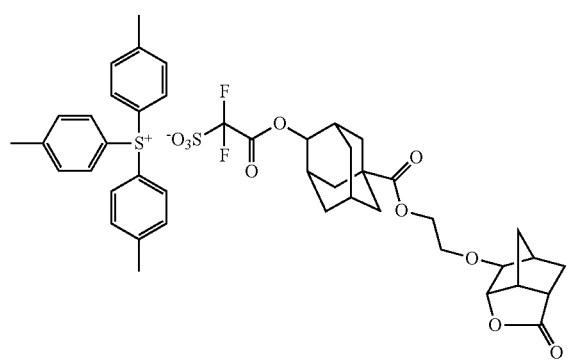
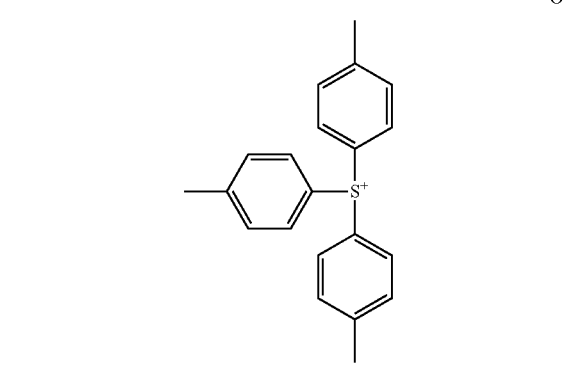
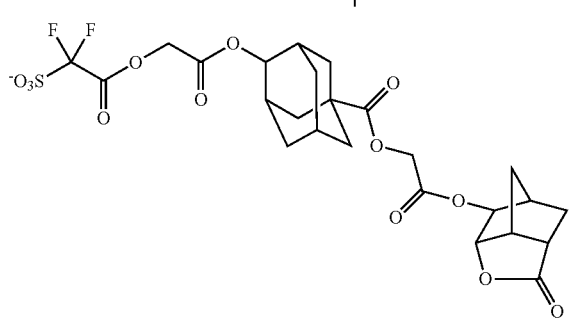
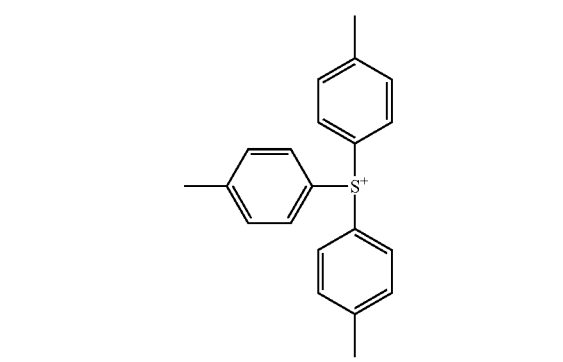
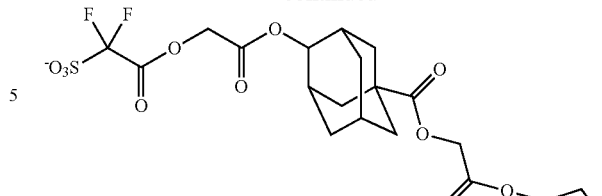
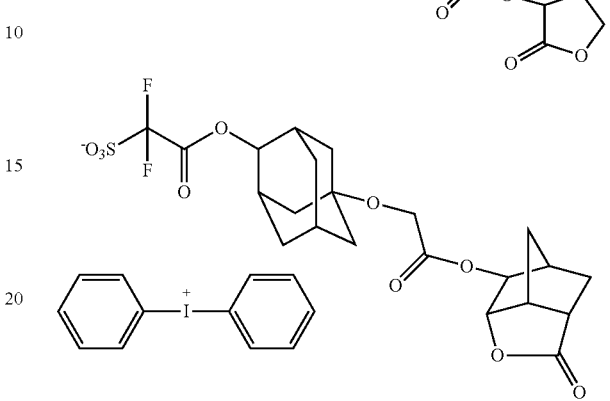
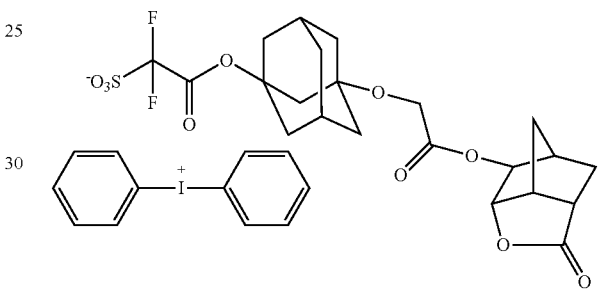
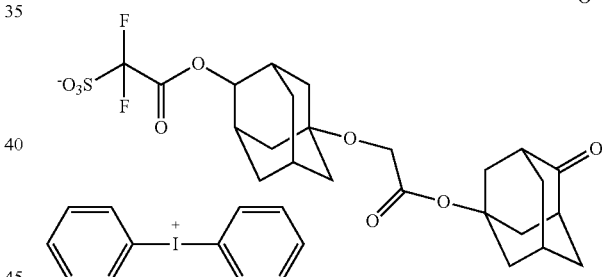
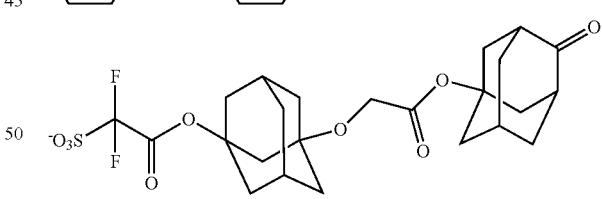
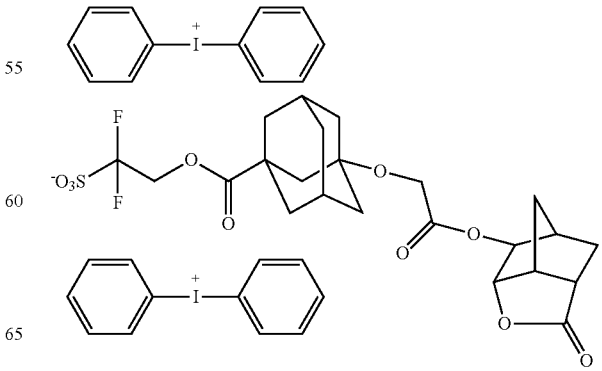

55
-continued
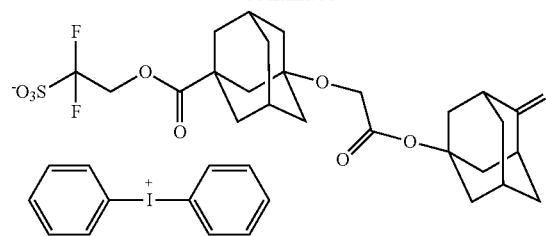
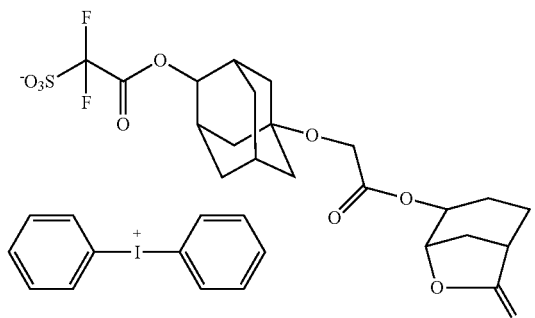
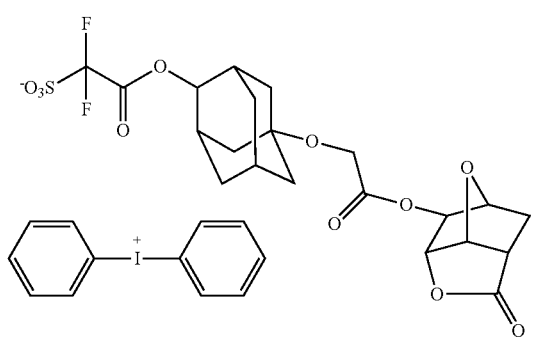
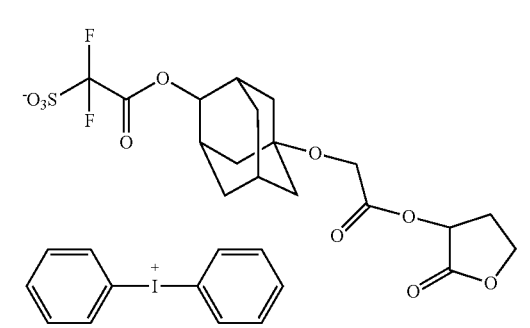
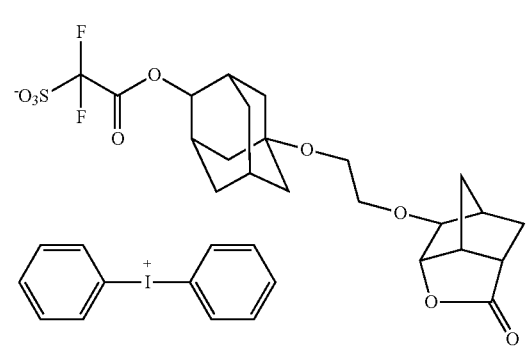
56
-continued
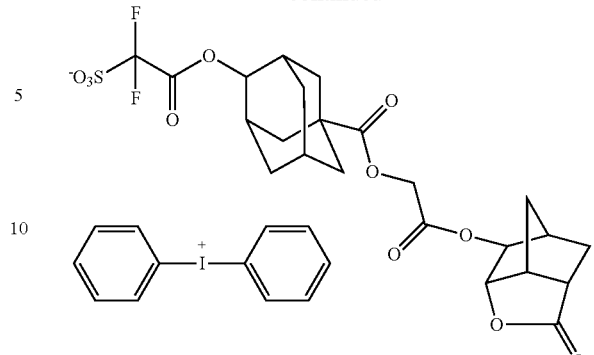
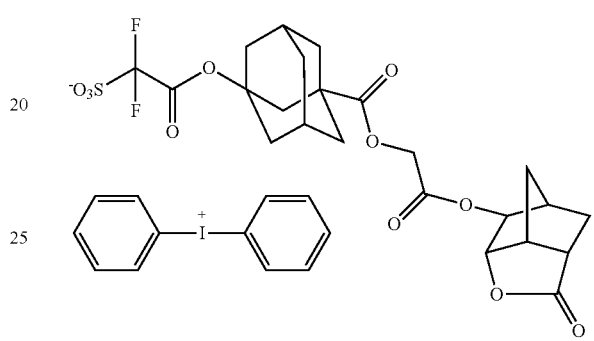
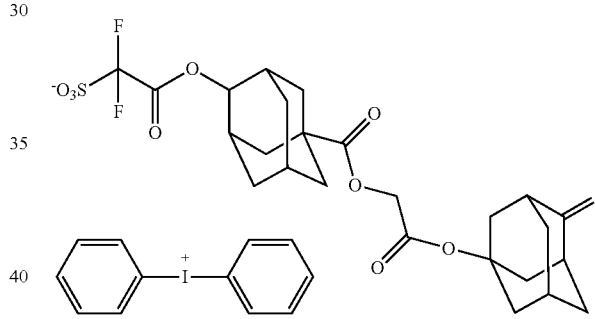
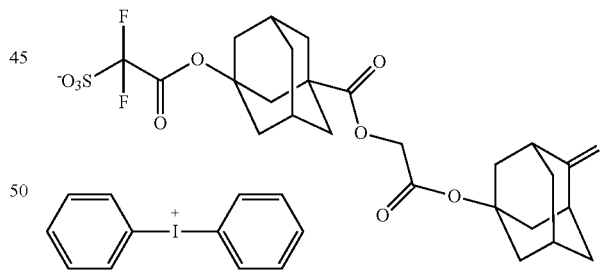
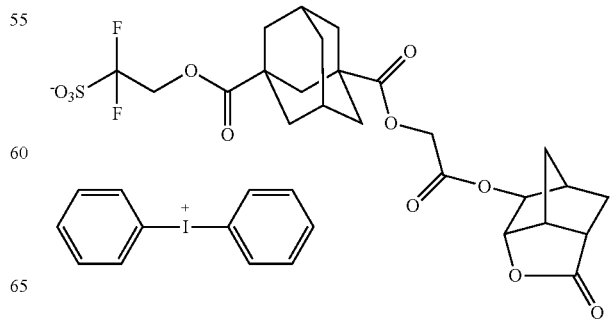

57
-continued
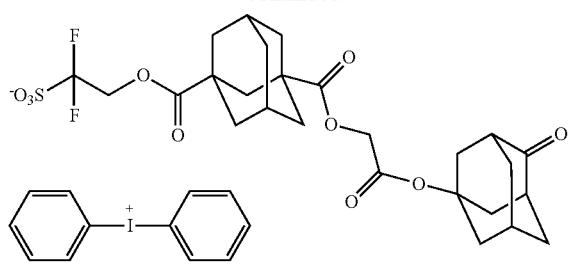
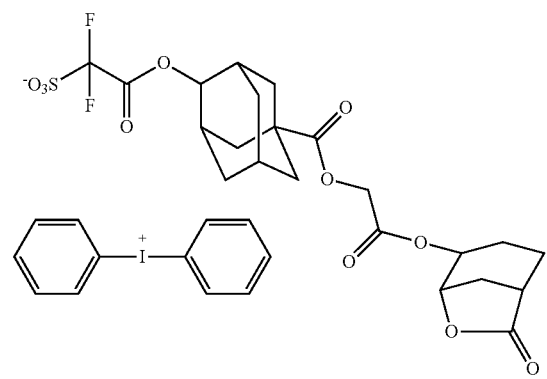
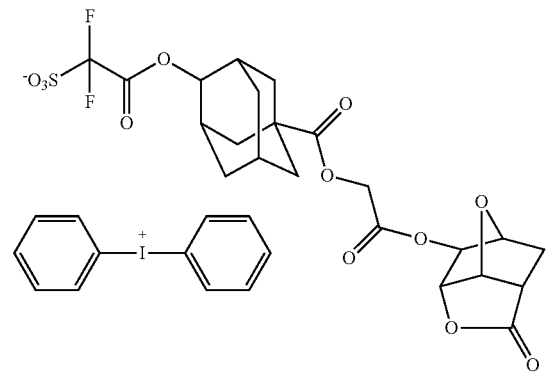
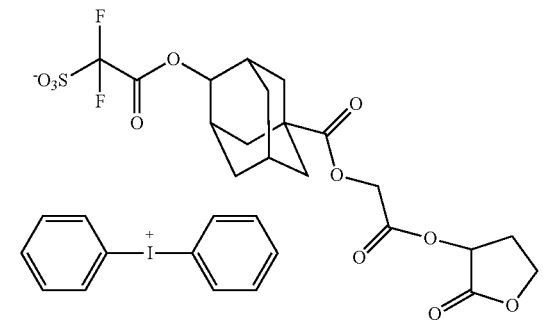
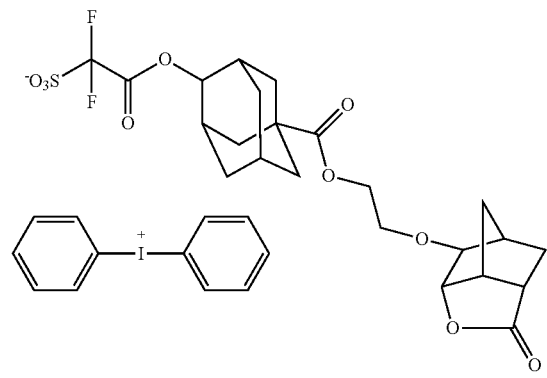
58
-continued
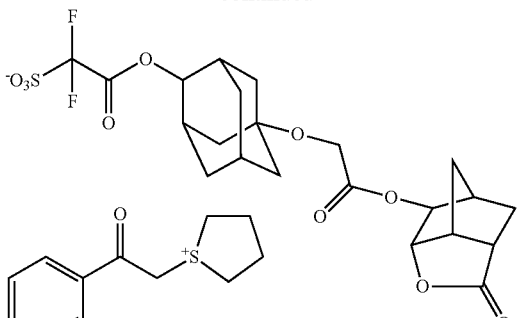
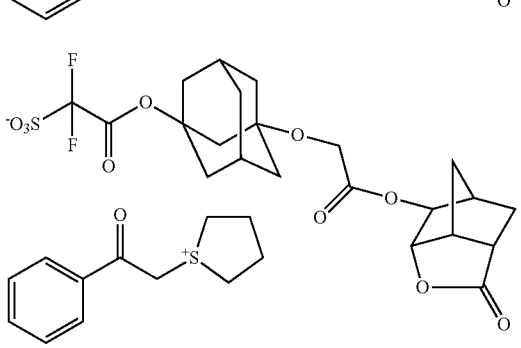
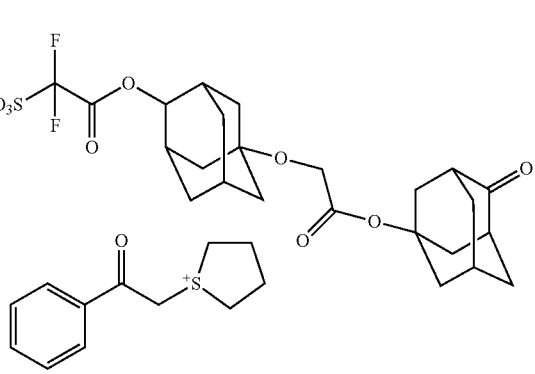
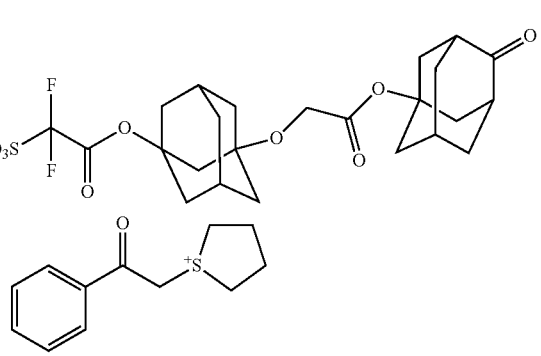
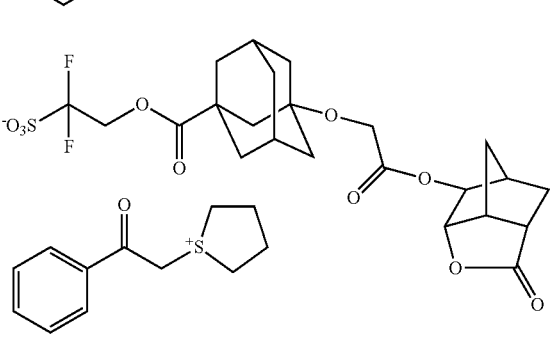

59
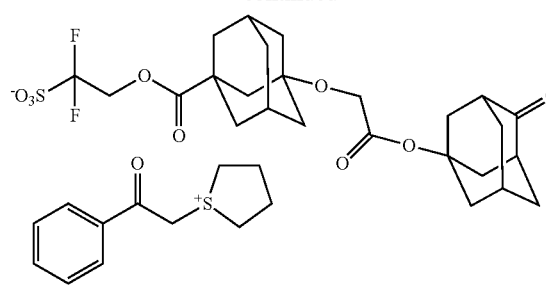
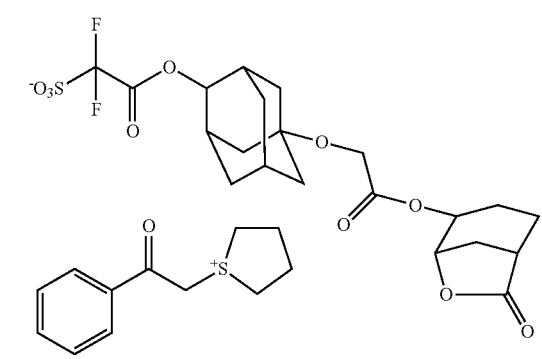
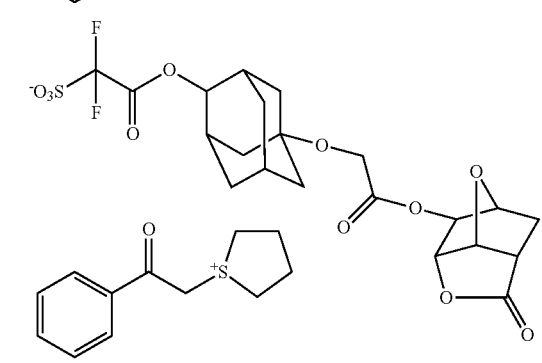
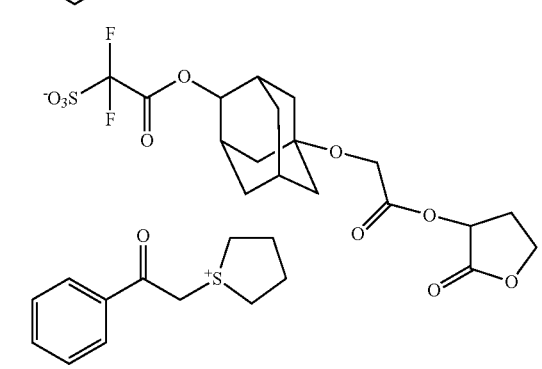
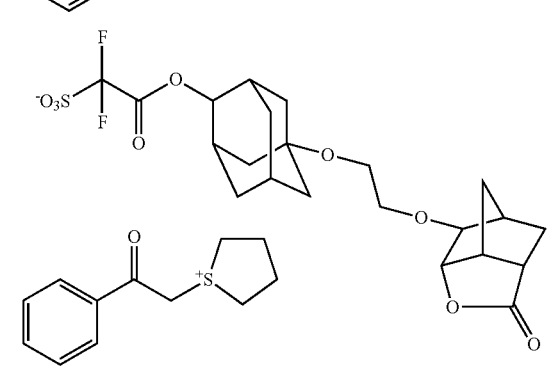
60
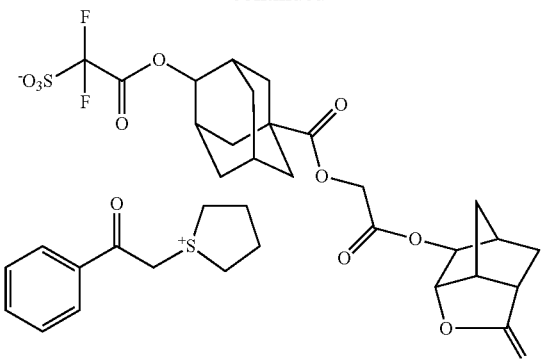
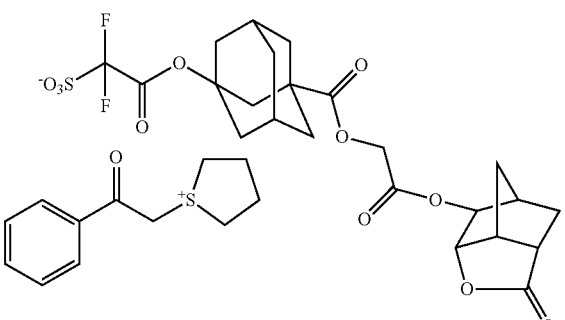
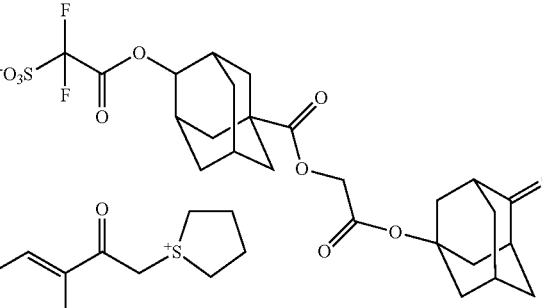
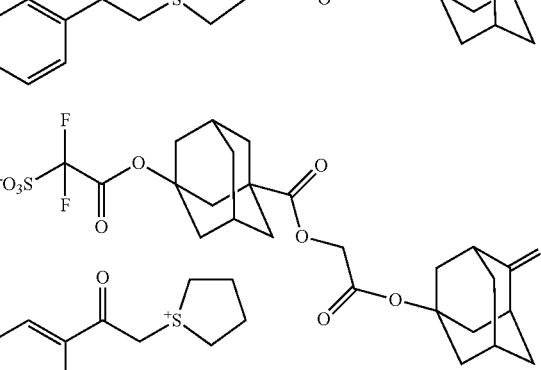
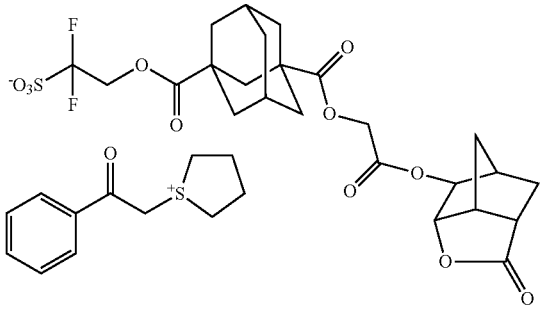

61
-continued
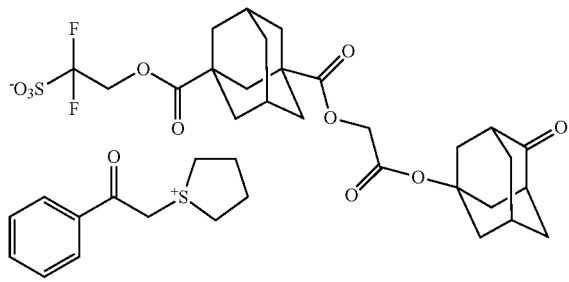
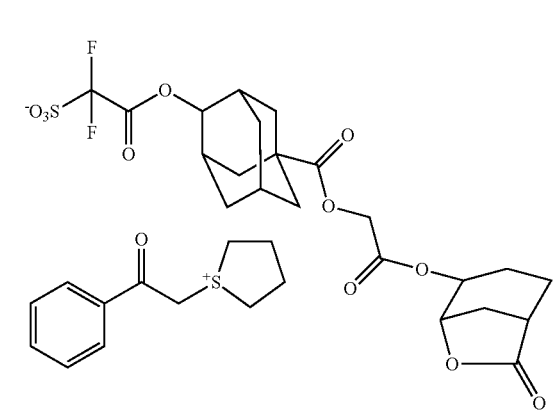
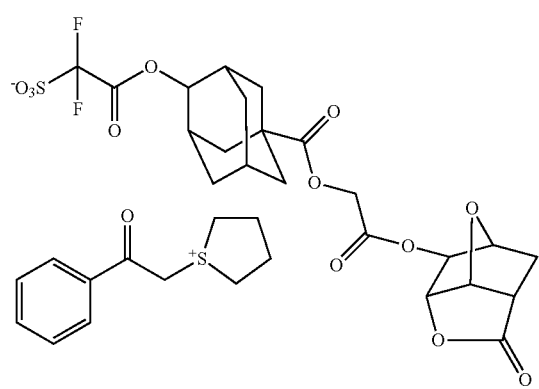
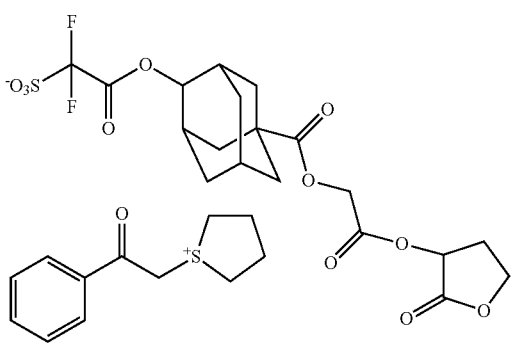
62
-continued
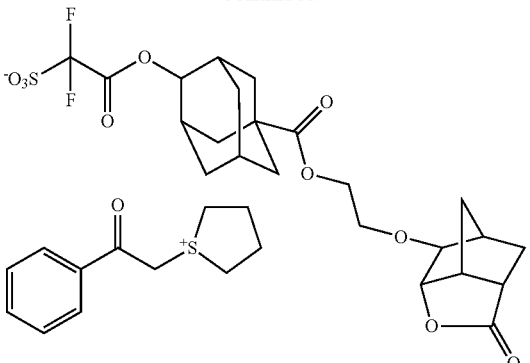
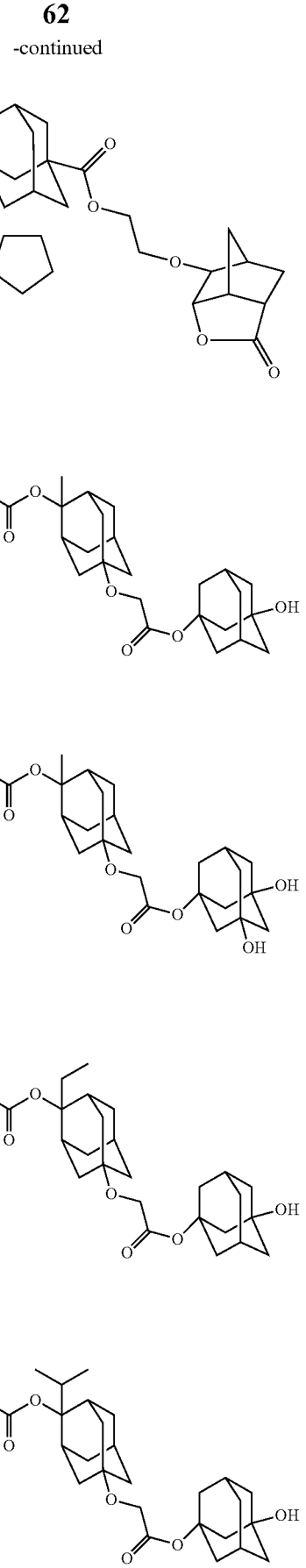

63
-continued
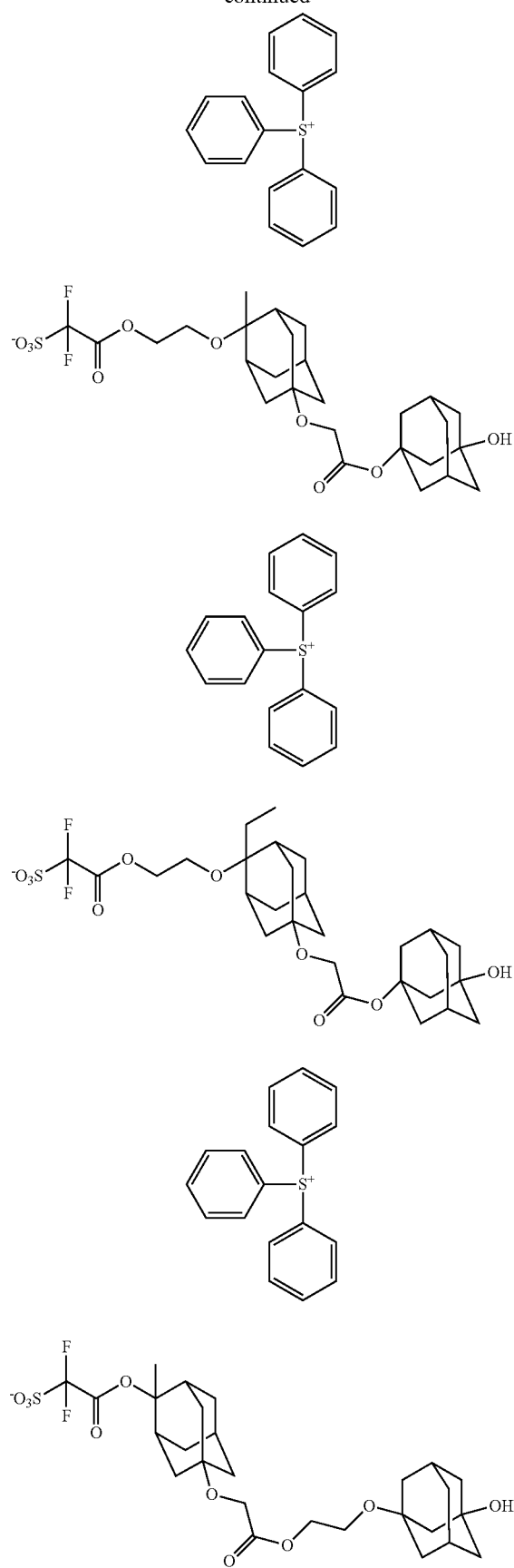
64
-continued
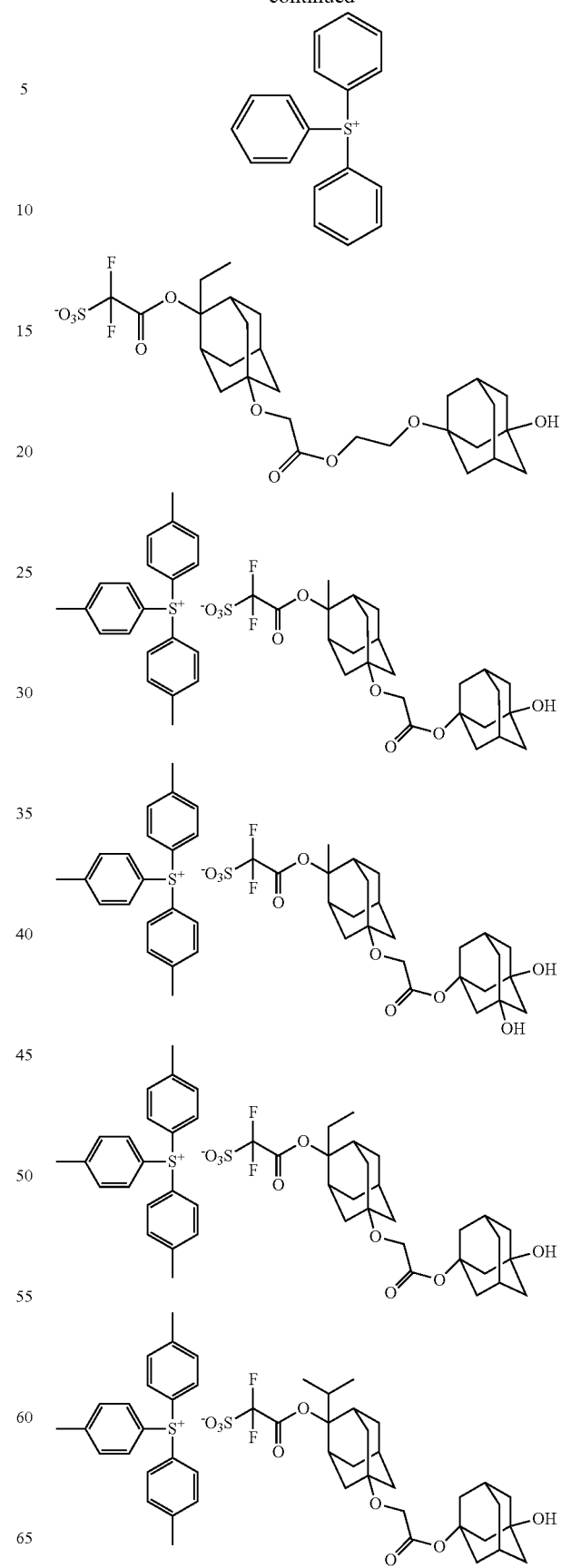

65
-continued
66
-continued
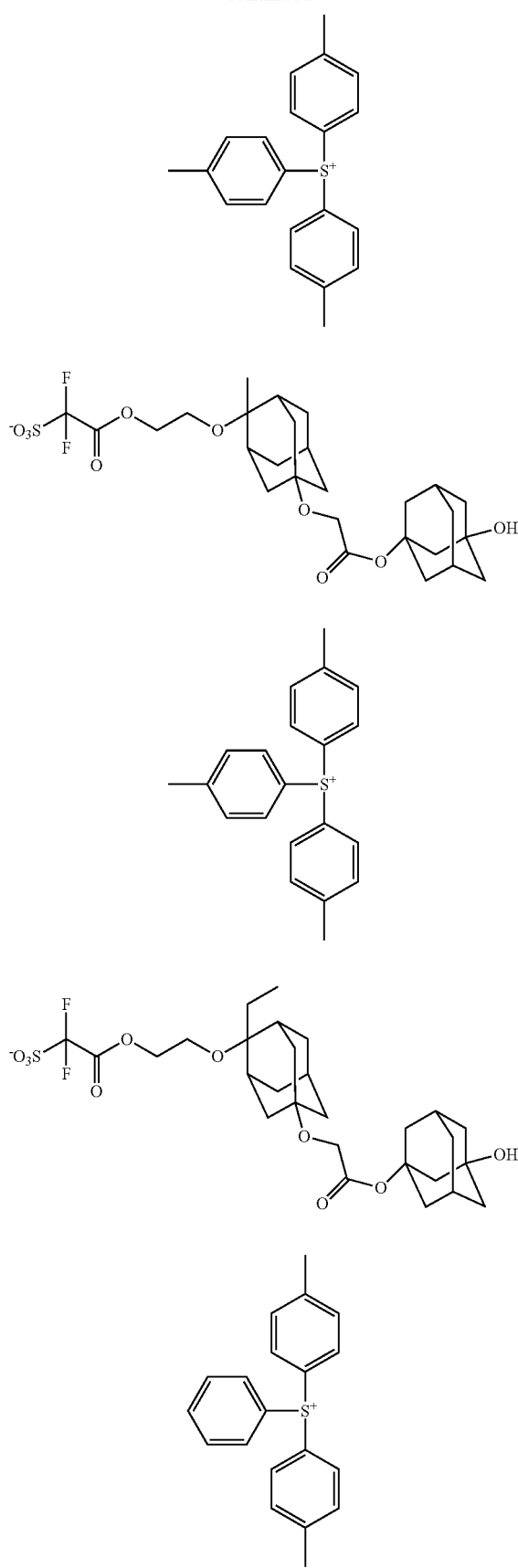
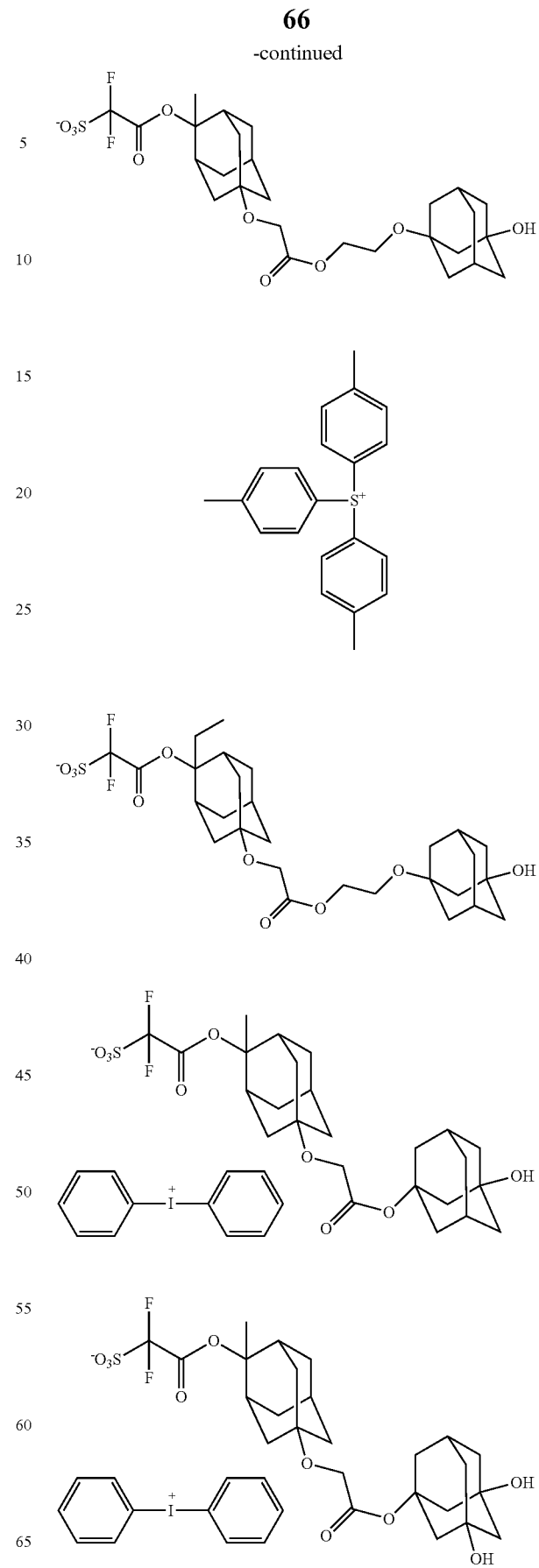

-continued
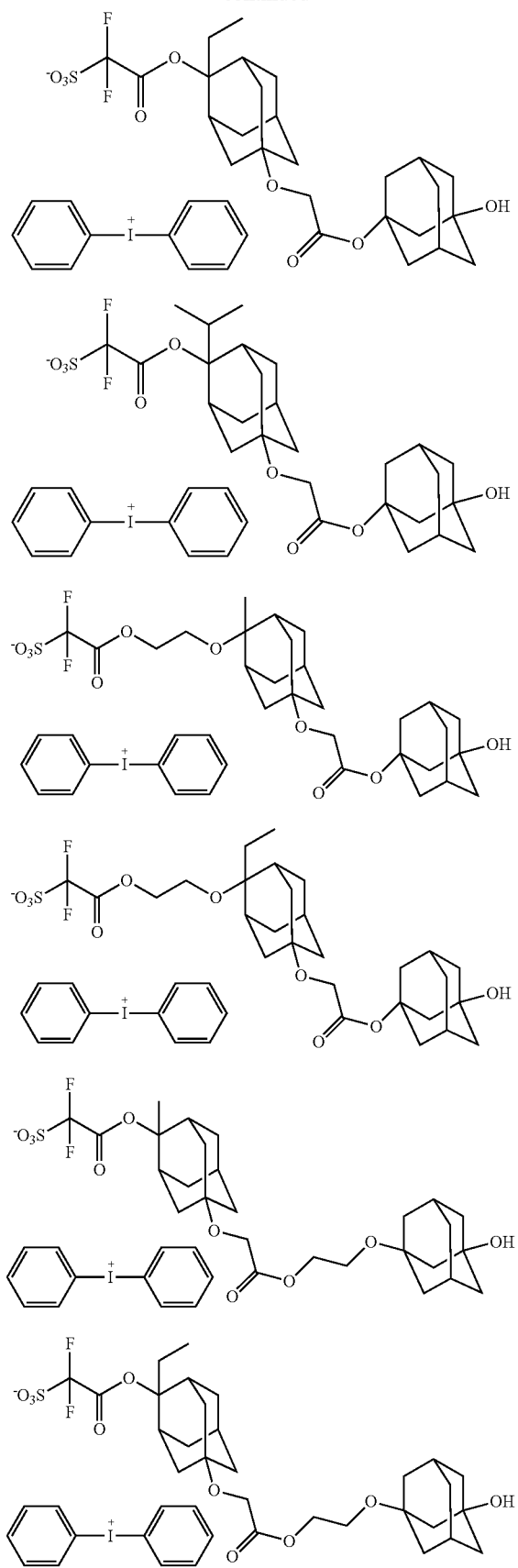
-continued
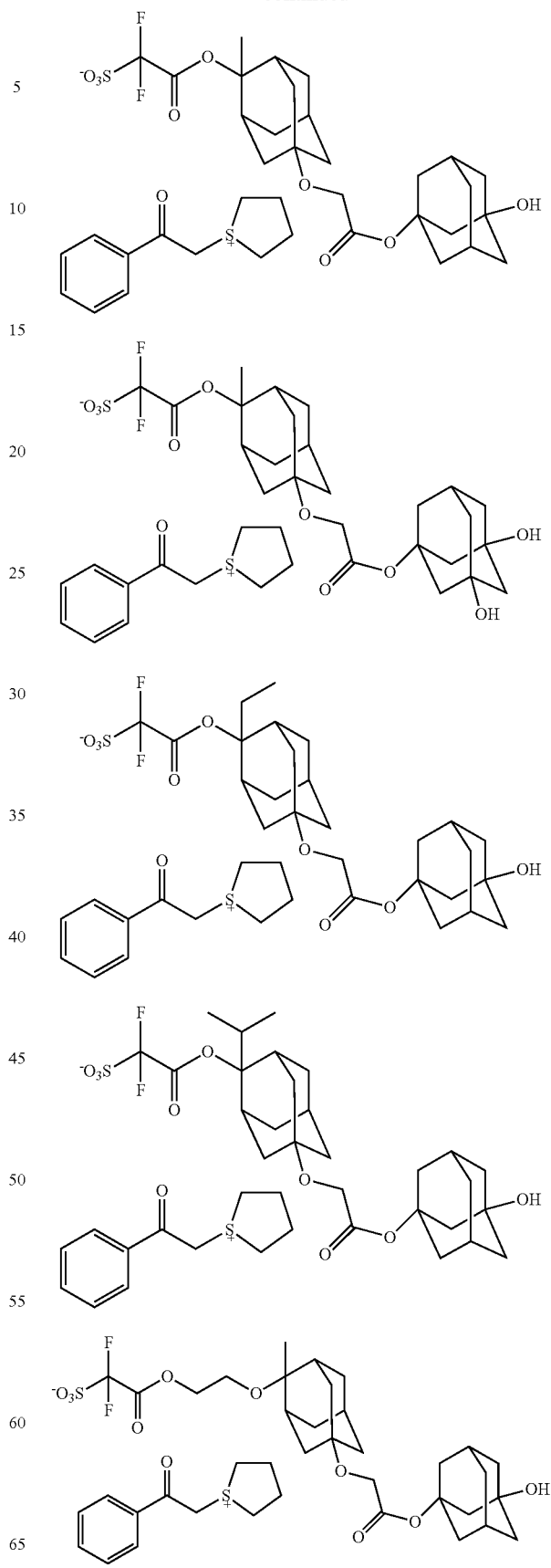

69
-continued
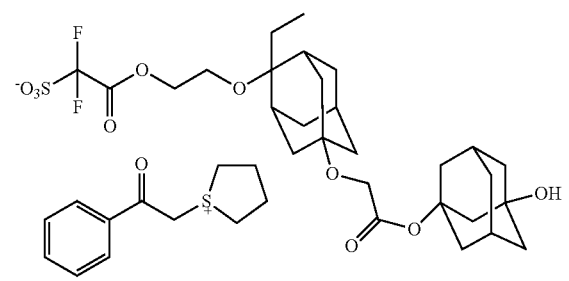
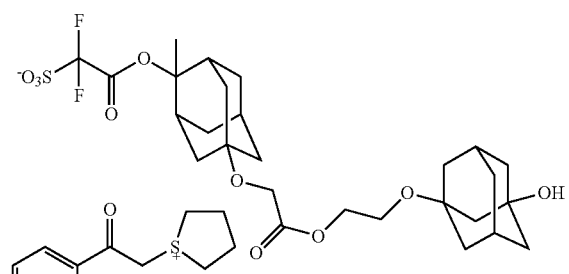
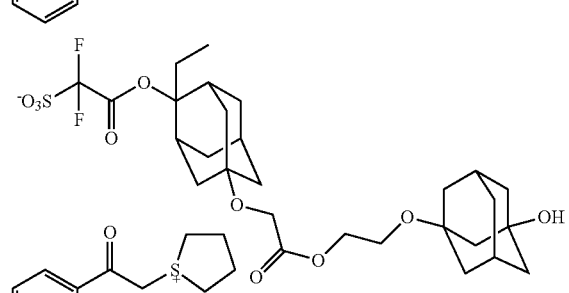
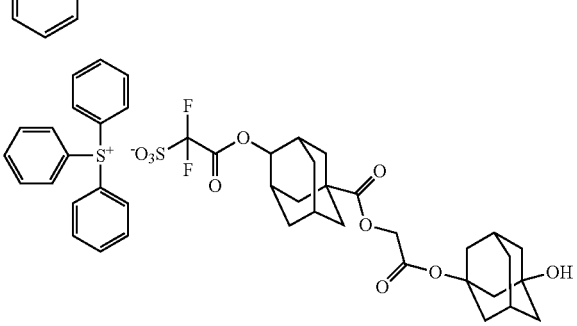
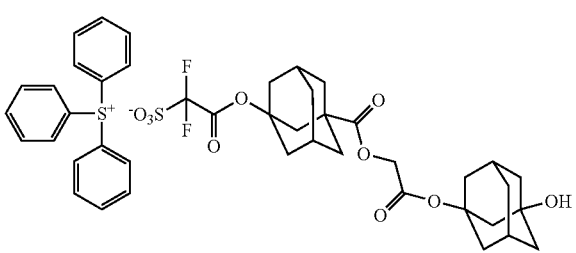
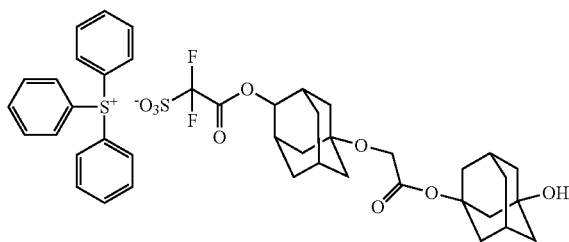
70
-continued
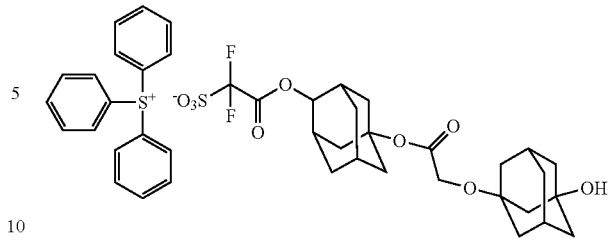
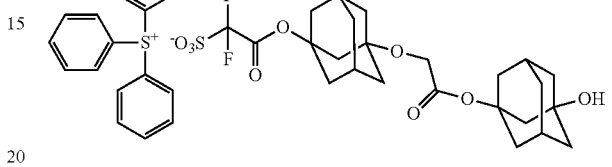
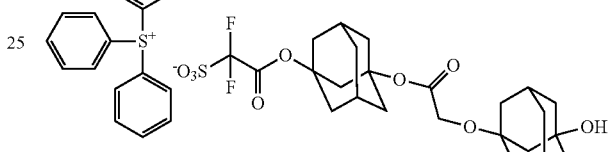
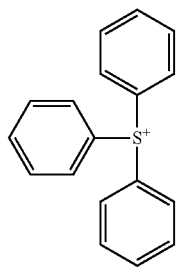
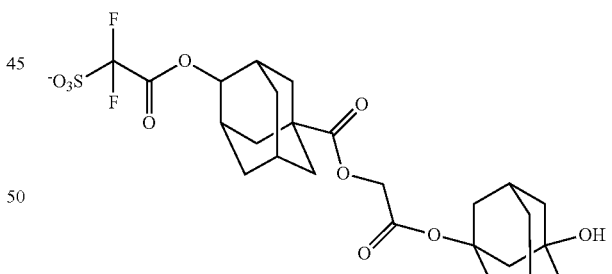
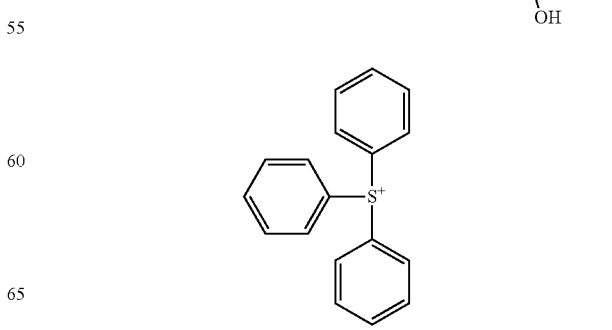

71
-continued
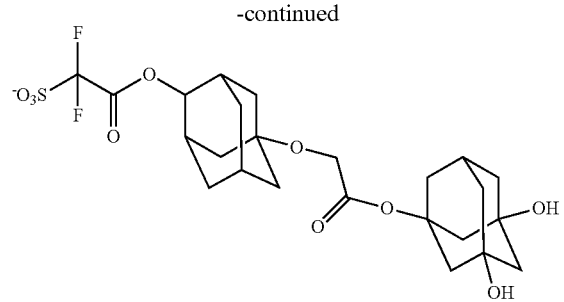
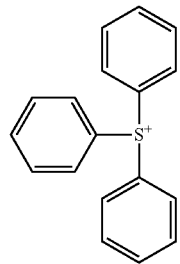
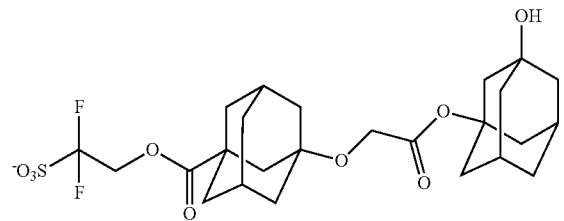
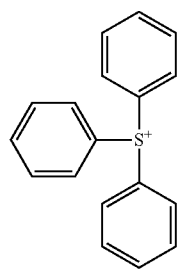
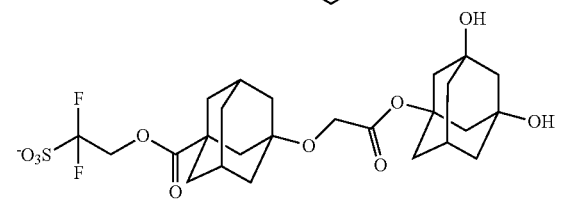
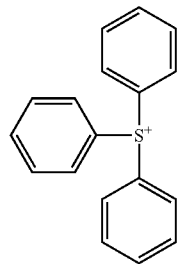
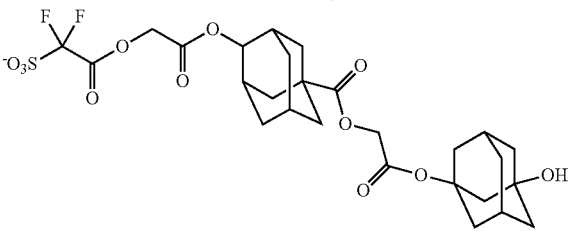
72
-continued
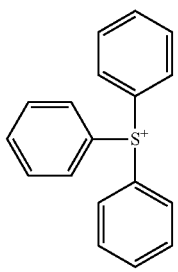
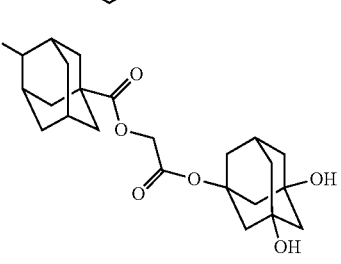
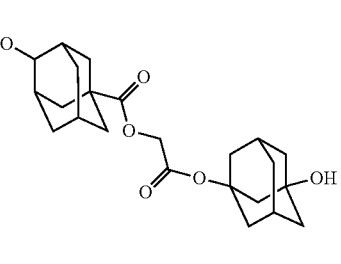
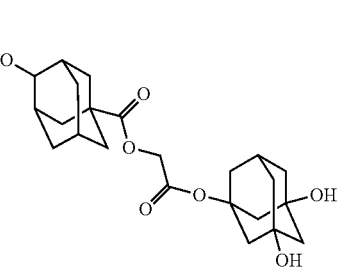
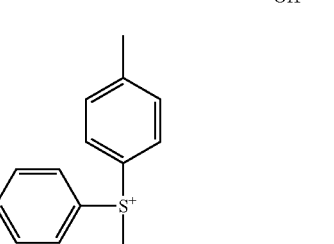
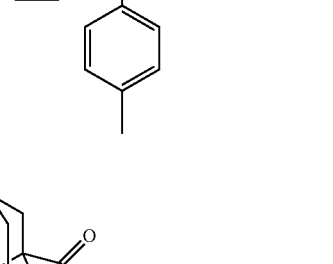
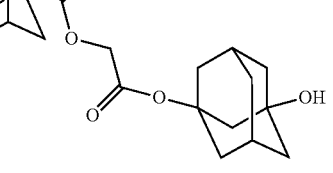

73
-continued
74
-continued
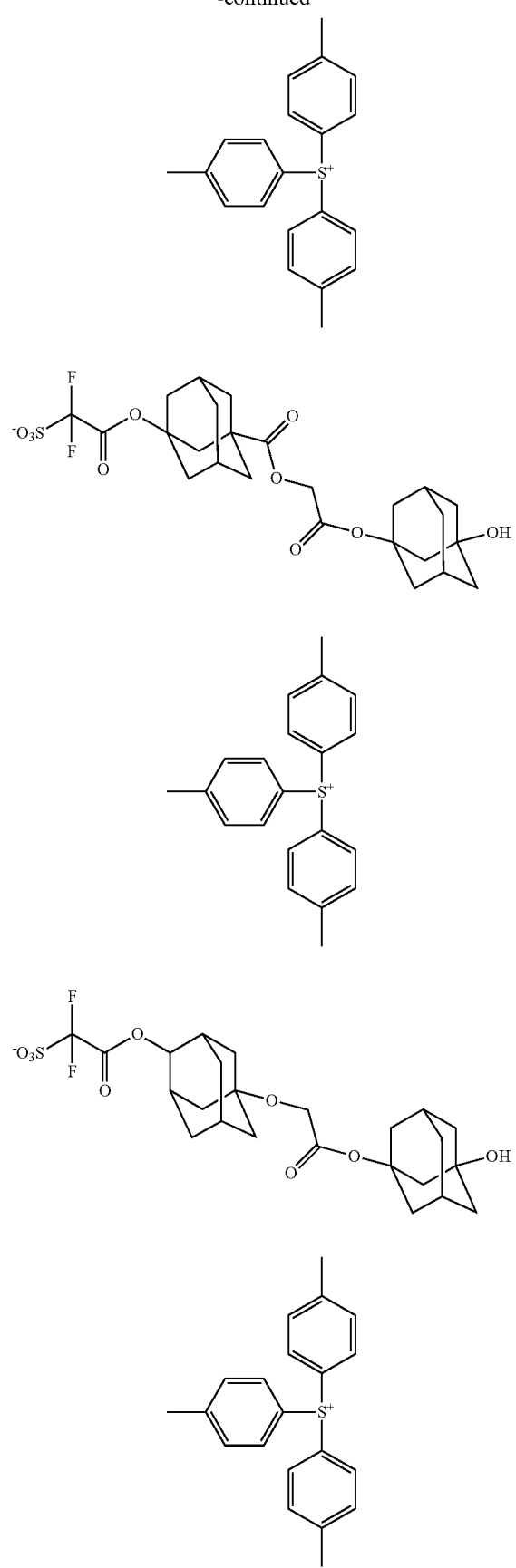
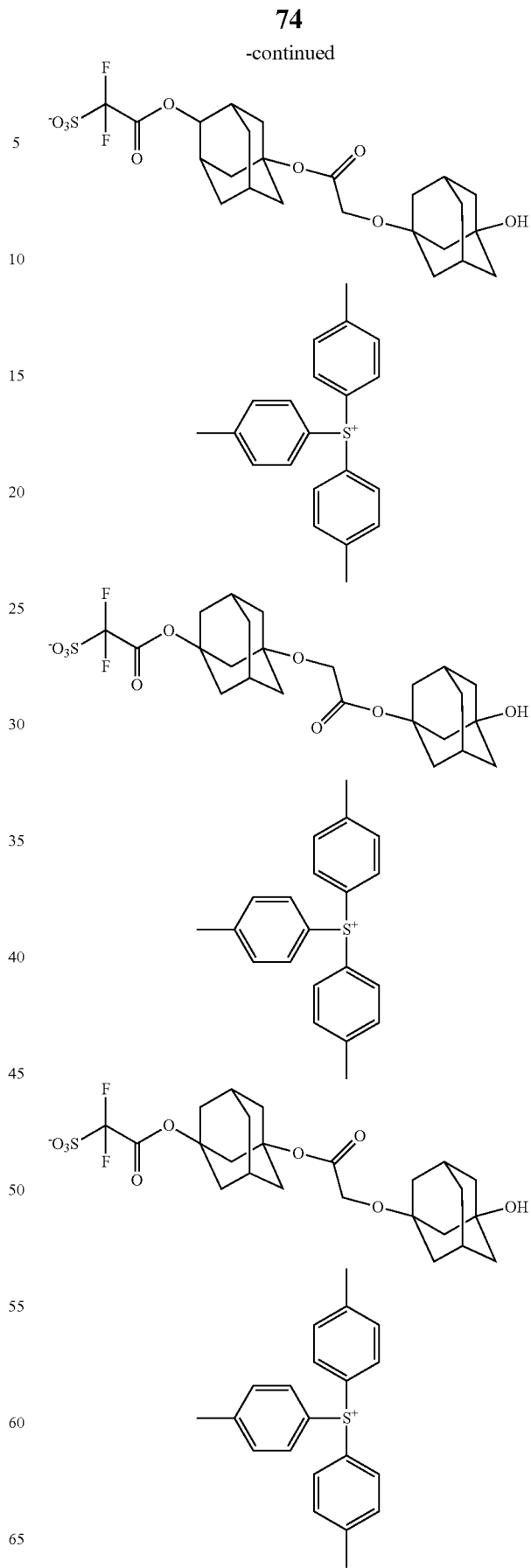

75
-continued
76
-continued
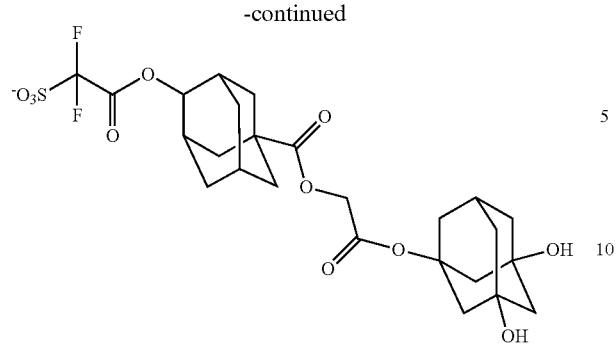
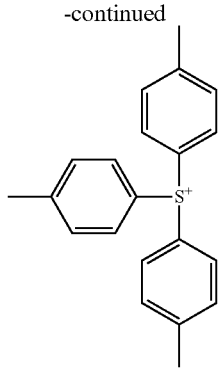
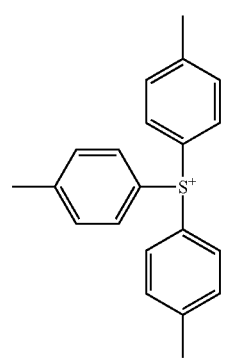
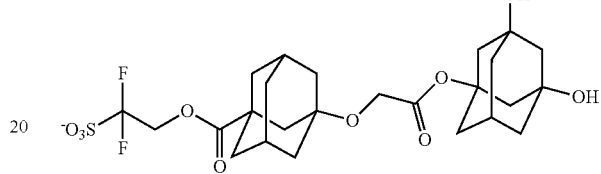
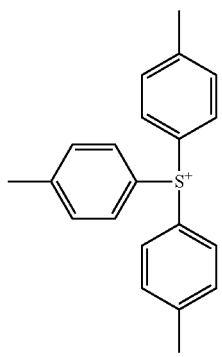
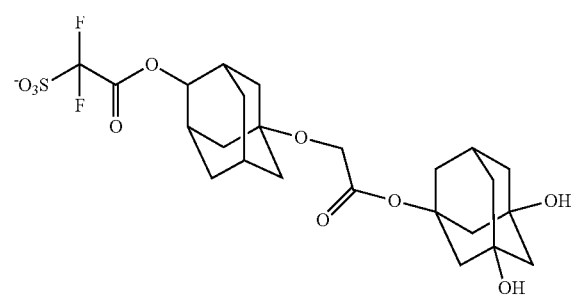
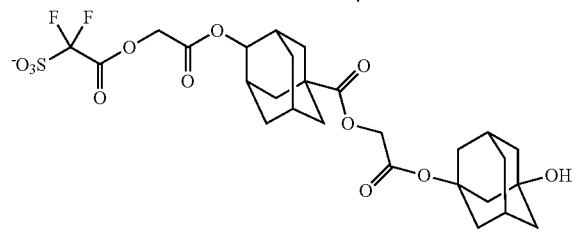
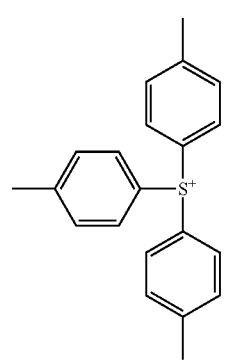
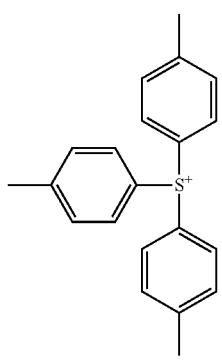
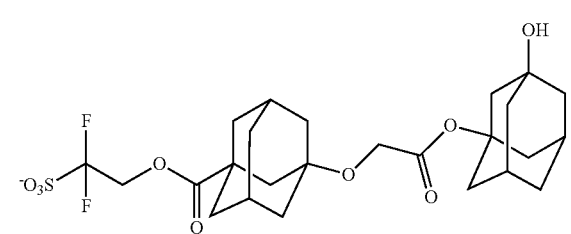
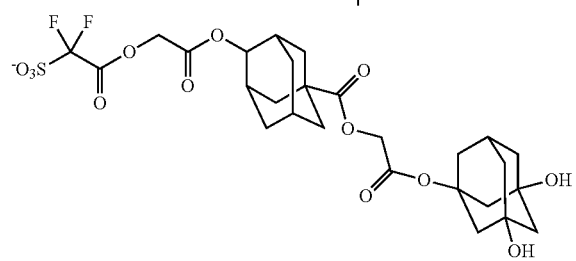

77
-continued
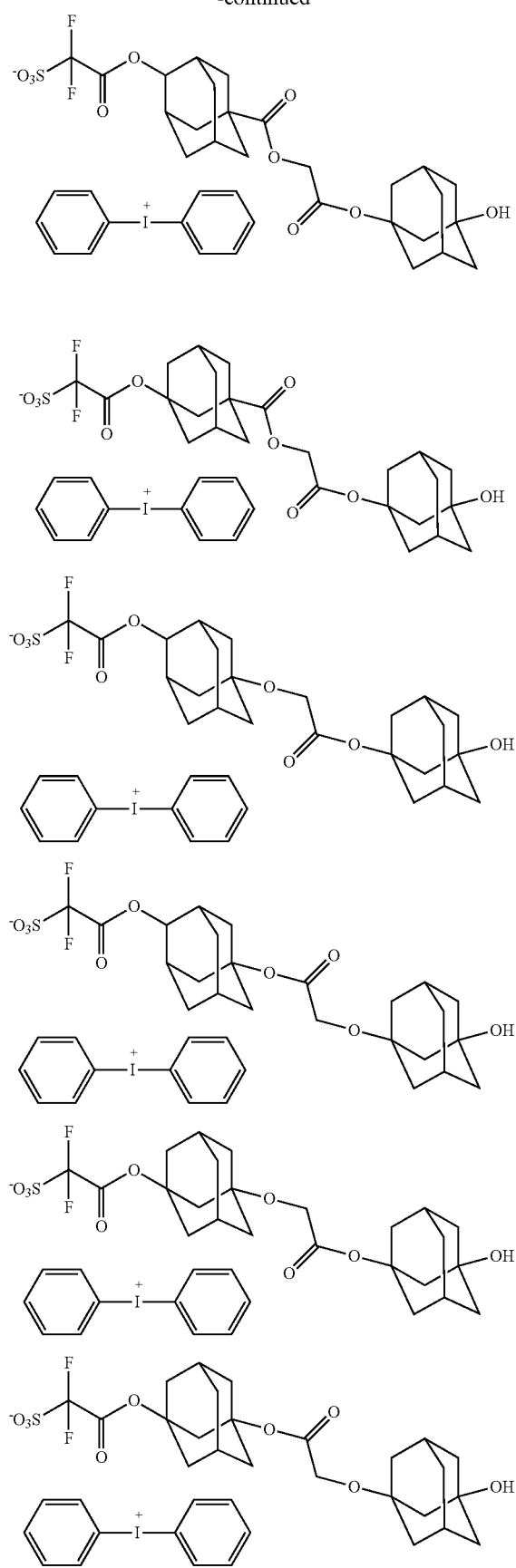
78
-continued
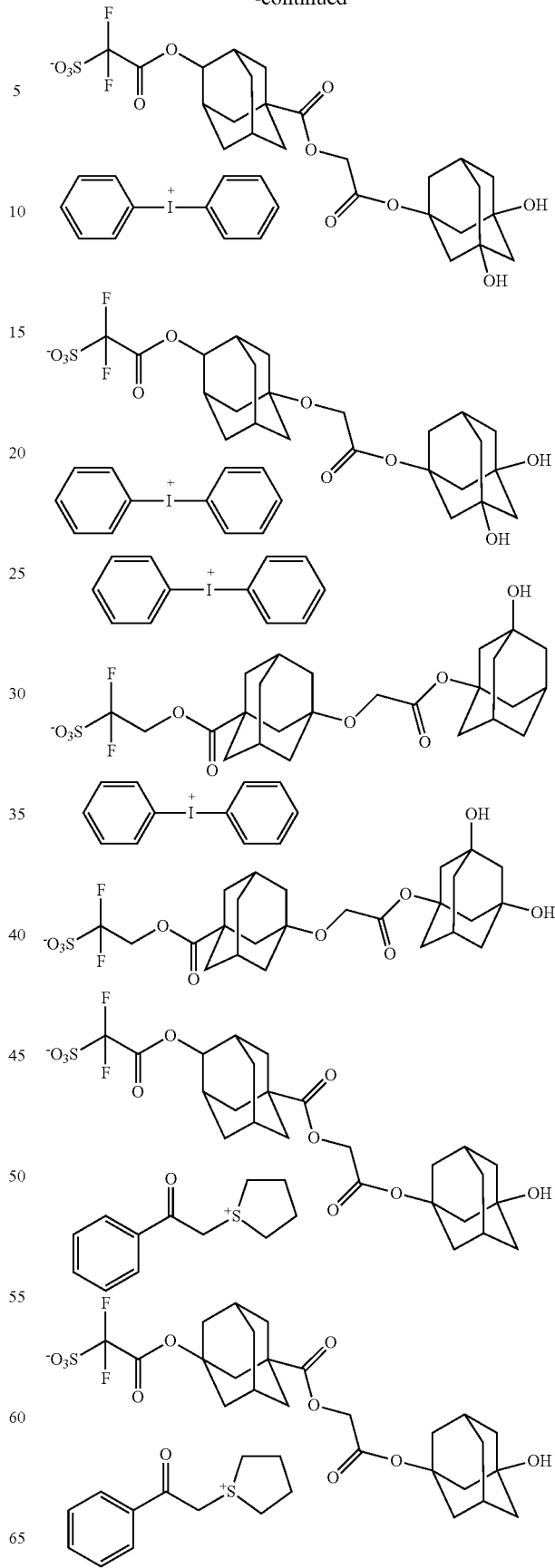

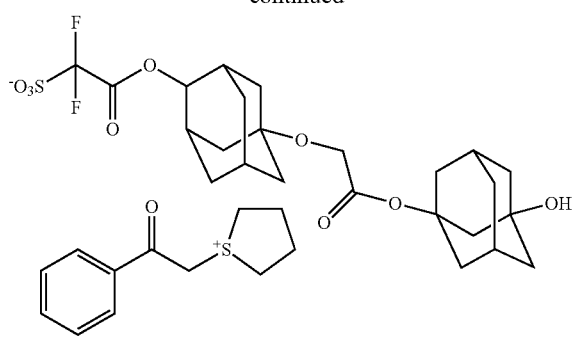
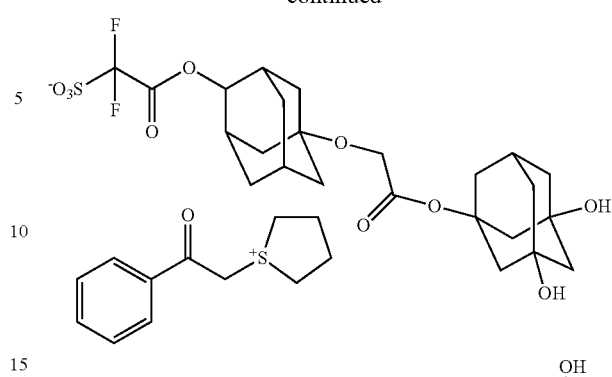
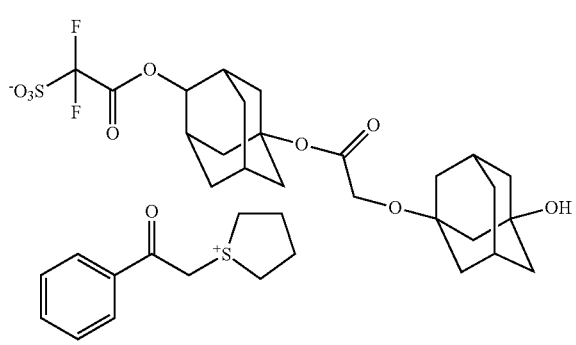
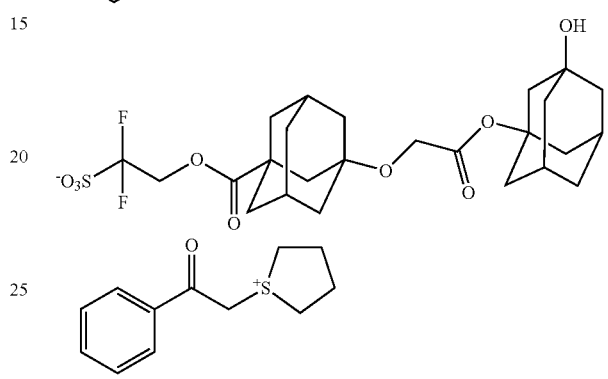
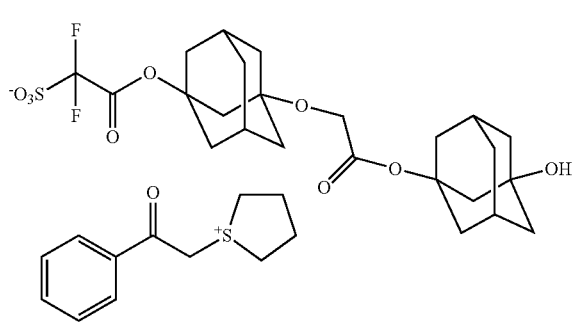
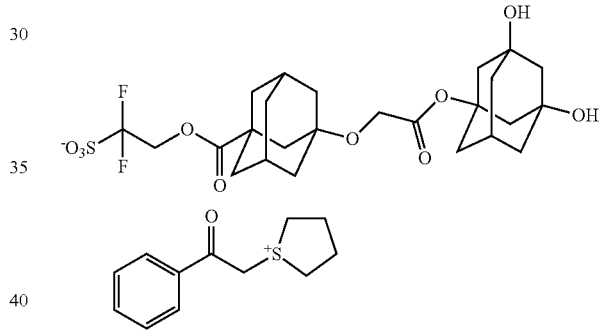
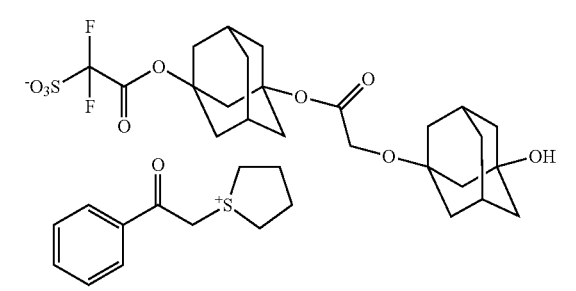
The process for producing SALT (X) will be illustrated. For example, a salt represented by the formula (b1):
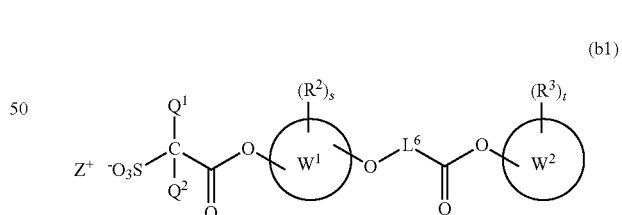
can be produced as Scheme 1 described below.
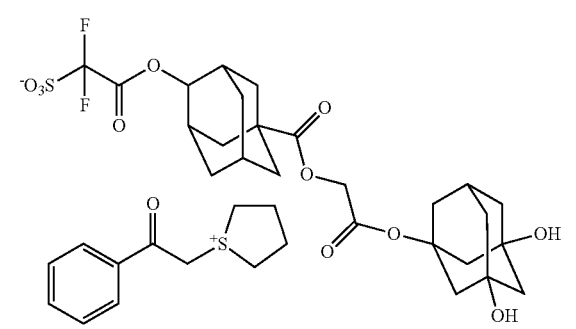
Scheme 1
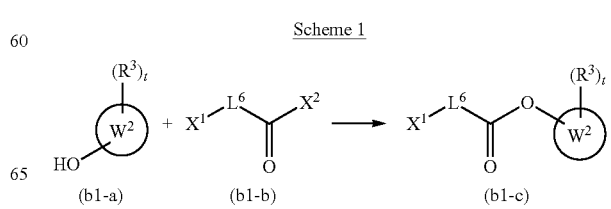

-continued

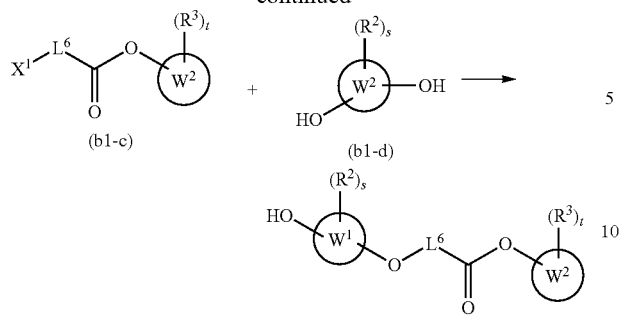

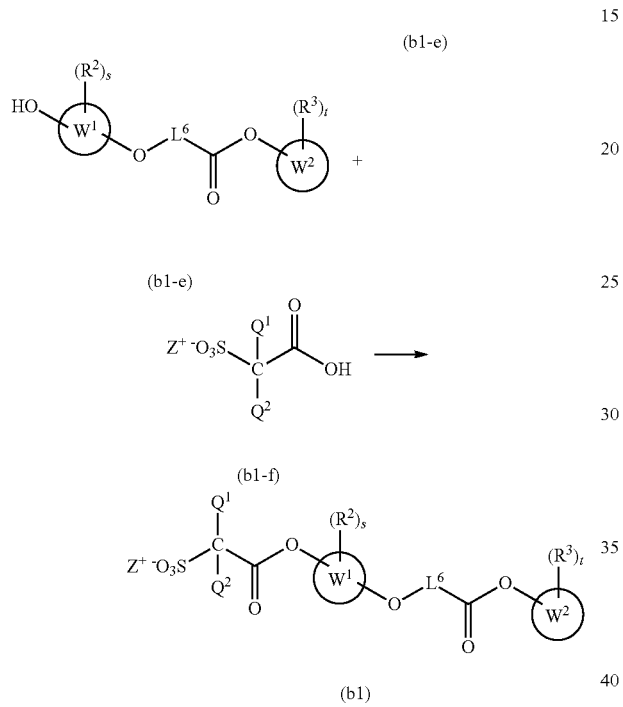

wherein $Z^+$, $Q^1$, $Q^2$, $W^1$, $R^2$, $L^6$, $W^2$, $R^3$, s and t are the same as defined above, and $X^1$ and $X^2$ independently represent a halogen atom.

Examples of the halogen atom include a fluorine atom, a chlorine atom, a bromine atom and an iodine atom, and a chlorine atom is preferable.

The compound represented by the formula (b1-c) can be produced by reacting the compound represented by the formula (b1-a) with the compound represented by the formula (b1-b) in the presence of a basic catalyst such as pyridine in a solvent such as tetrahydrofuran. The compound represented by the formula (b1-e) can be produced by reacting the compound represented by the formula (b1-c) with the compound represented by the formula (b1-d) in the presence of a catalyst such as potassium carbonate and potassium iodide in a solvent such as N,N-dimethylformamide. The compound represented by the formula (b1) can be produced by reacting the compound represented by the formula (b1-e) with the compound represented by the formula (b1-f) in the presence of a basic catalyst such as sulfuric acid in a solvent such as monochlorobenzene. The compound represented by the formula (b1-f) can be produced according to the method described in JP 2008-127367 A1.

A salt represented by the formula (b2):

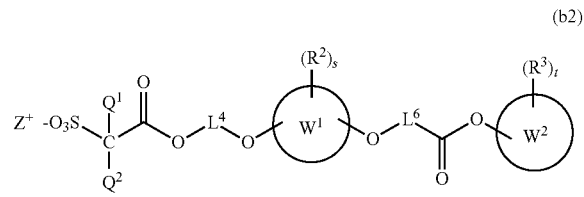

can be produced as Scheme 2 described below.

Scheme 2

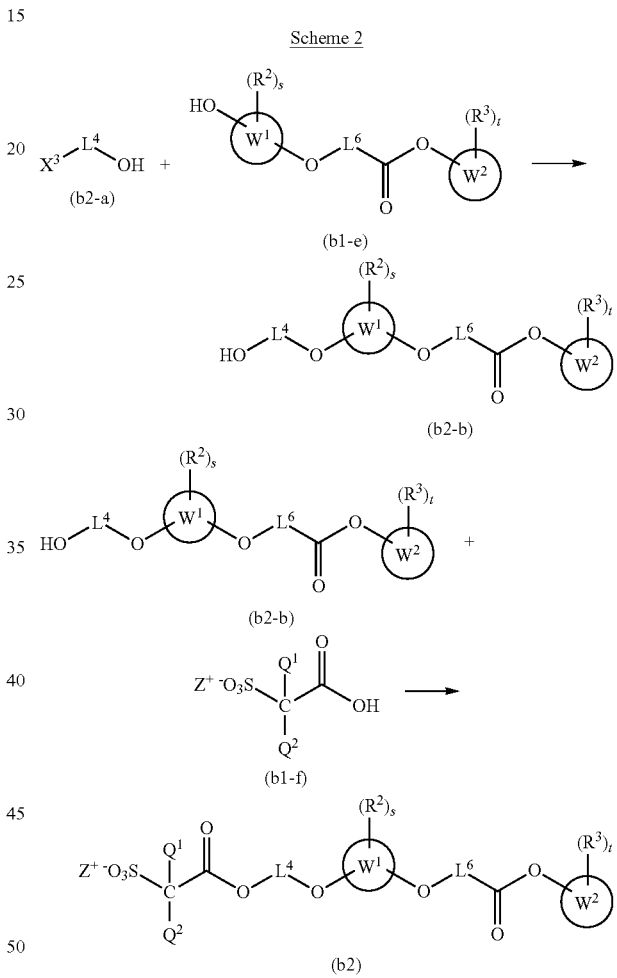

wherein $Z^+$, $Q^1$, $Q^2$, $W^1$, $R^2$, $L^4$, $L^6$, $W^2$, $R^3$, s and t are the same as defined above, and $X^3$ represents a halogen atom.

Examples of the halogen atom include a fluorine atom, a chlorine atom, a bromine atom and an iodine atom, and a bromine atom is preferable.

The compound represented by the formula (b2-b) can be produced by reacting the compound represented by the formula (b2-a) with the compound represented by the formula (b1-e) in the presence of a basic catalyst such as pyridine in a solvent such as tetrahydrofuran. The compound represented by the formula (b2) can be produced by reacting the compound represented by the formula (b2-b) with the compound represented by the formula (b1-f) in the presence of a catalyst such as sulfuric acid in a solvent such as monochlorobenzene.

A salt represented by the formula (b3):

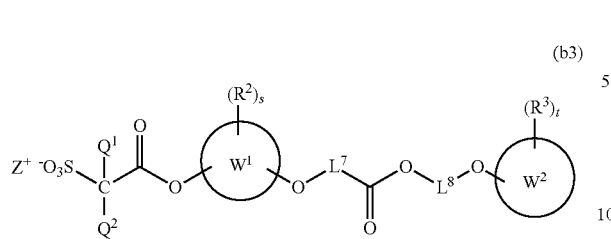

can be produced as Scheme 3 described below.

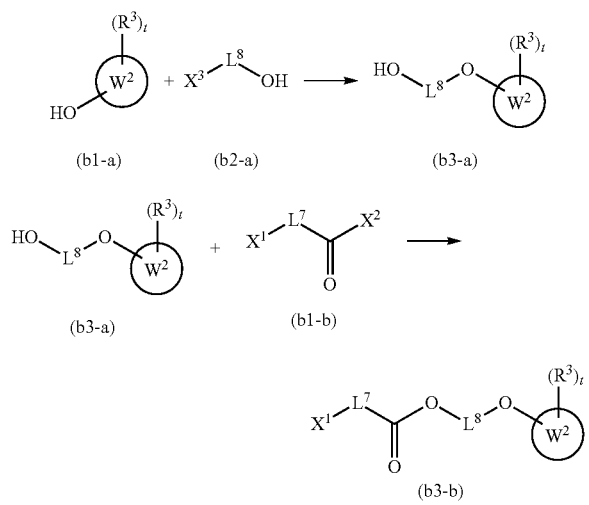

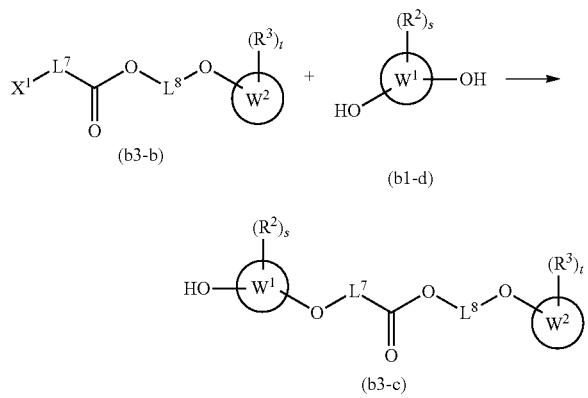

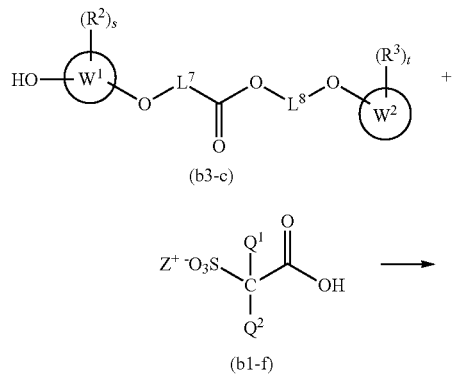

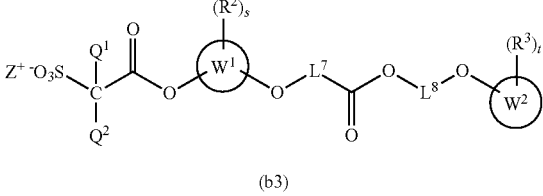

wherein $Z^+$, $Q^1$, $Q^2$, $W^1$, $R^2$, $L^7$, $L^8$, $W^2$, $R^3$, s and t are the same as defined above, and $X^1$, $X^2$ and $X^3$ independently each represent a halogen atom.

Examples of the halogen atom include a fluorine atom, a chlorine atom, a bromine atom and an iodine atom, and a bromine atom is preferable.

The compound represented by the formula (b3-a) can be produced by reacting the compound represented by the formula (b1-a) with the compound represented by the formula (b2-a) in the presence of a basic catalyst such as pyridine in a solvent such as tetrahydrofuran. The compound represented by the formula (b3-b) can be produced by reacting the compound represented by the formula (b3-a) with the compound represented by the formula (b1-b) in the presence of a catalyst such as potassium carbonate and potassium iodide in a solvent such as N,N-dimethylformamide. The compound represented by the formula (b3-c) can be produced by reacting the compound represented by the formula (b3-b) with the compound represented by the formula (b1-d) in the presence of a catalyst such as potassium carbonate and potassium iodide in a solvent such as N,N-dimethylformamide. The compound represented by the formula (b3) can be produced by reacting the compound represented by the formula (b3-c) with the compound represented by the formula (b1-f) in the presence of a catalyst such as sulfuric acid in a solvent such as monochlorobenzene.

A salt represented by the formula (b4):

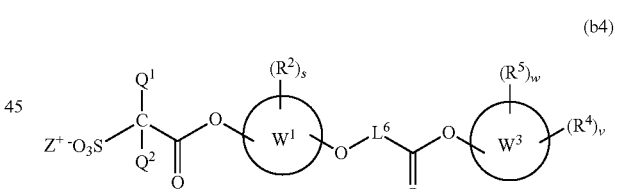

can be produced as Scheme 4 described below.

Scheme 4

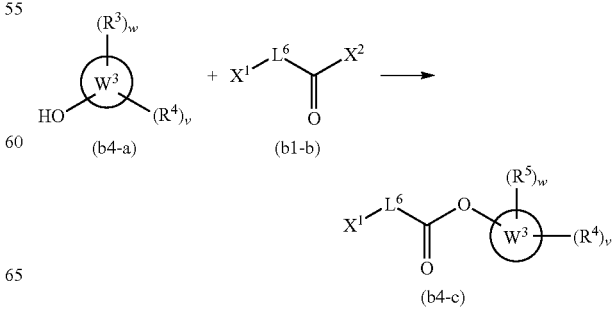

-continued

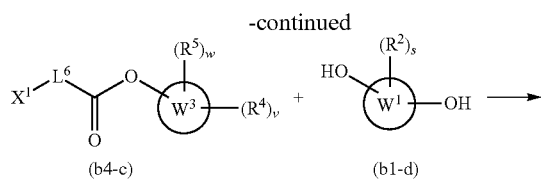

(b4-c)    (b1-d)

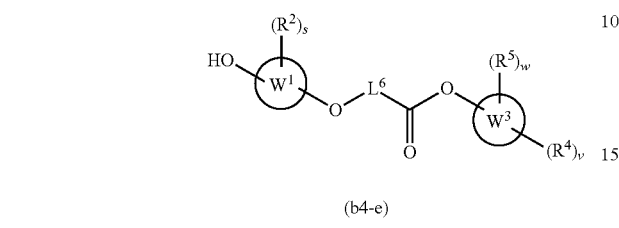

(b4-e)

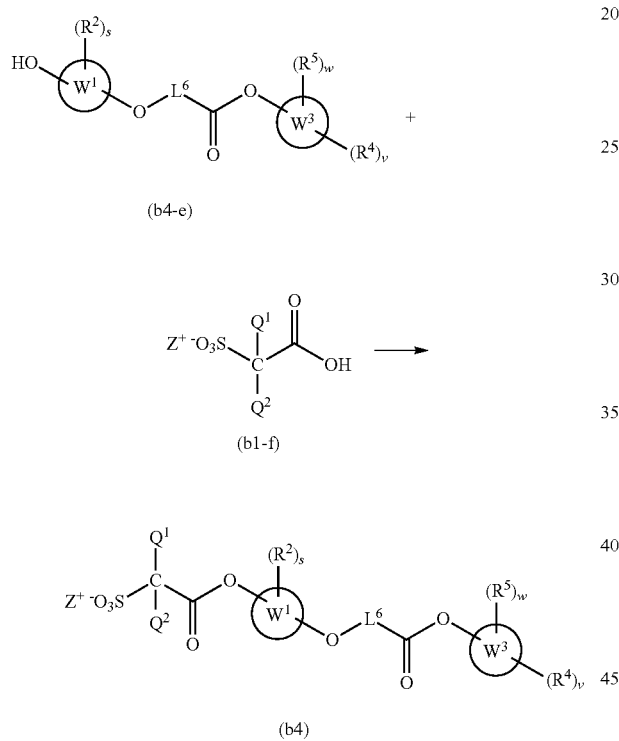

wherein $Z^+$, $Q^1$, $Q^2$, $W^1$, $R^2$, $L^6$, $W^3$, $R^4$, $R^5$, s, v, w and $X^1$ are the same as defined above.

The compound represented by the formula (b4-c) can be produced by reacting the compound represented by the formula (b4-a) with the compound represented by the formula (b1-b) in the presence of a basic catalyst such as pyridine in a solvent such as tetrahydrofuran. The compound represented by the formula (b4-e) can be produced by reacting the compound represented by the formula (b4-c) with the compound represented by the formula (b1-d) in the presence of a catalyst such as potassium carbonate and potassium iodide in a solvent such as N,N-dimethylformamide. The compound represented by the formula (b4) can be produced by reacting the compound represented by the formula (b4-e) with the compound represented by the formula (b1-f) in the presence of a catalyst such as sulfuric acid in a solvent such as monochlorobenzene.

A salt represented by the formula (b5):

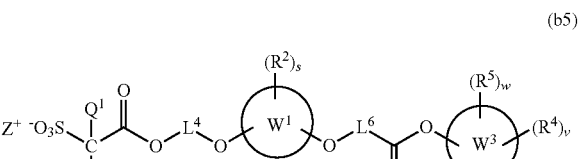

can be produced as Scheme 5 described below.

Scheme 5

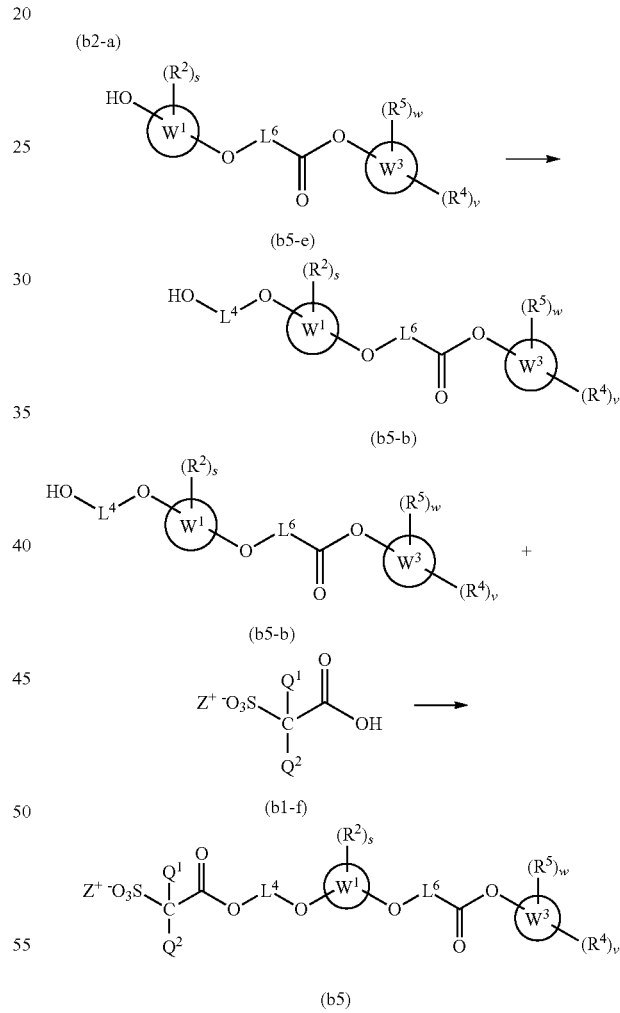

wherein $Z^+$, $Q^1$, $Q^2$, $W^1$, $R^2$, $L^4$, $L^6$, $W^3$, $R^4$, $R^5$, s, v, w and $X^3$ are the same as defined above.

The compound represented by the formula (b5-b) can be produced by reacting the compound represented by the formula (b2-a) with the compound represented by the formula (b5-e) in the presence of a basic catalyst such as pyridine in a solvent such as tetrahydrofuran. The compound represented by the formula (b5) can be produced by reacting the compound represented by the formula (b5-b) with the compound represented by the formula (b1-f) in the presence of a catalyst such as sulfuric acid in a solvent such as monochlorobenzene.

A salt represented by the formula (b6):

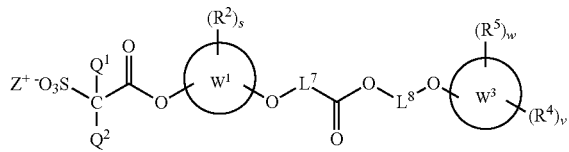

(b6)

can be produced as Scheme 6 described below.

Scheme 6

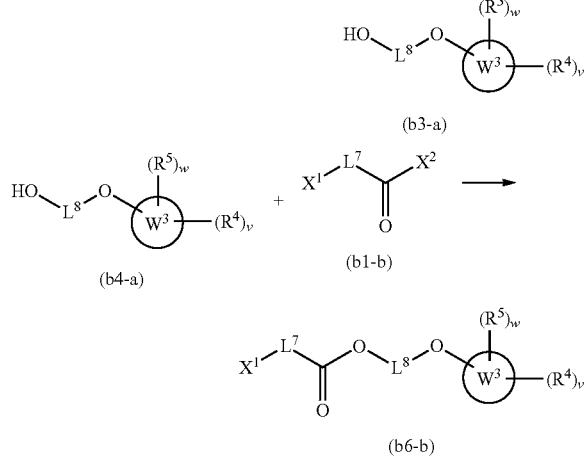

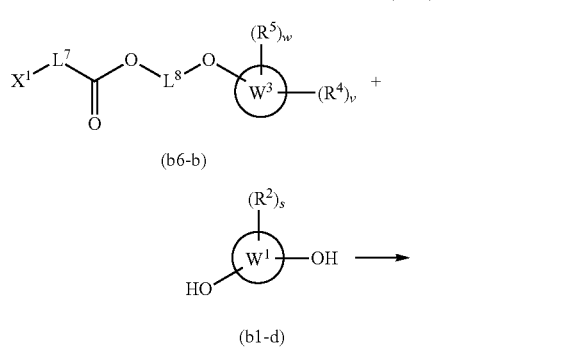

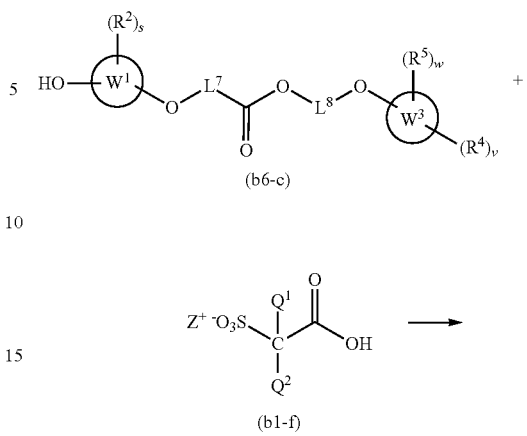

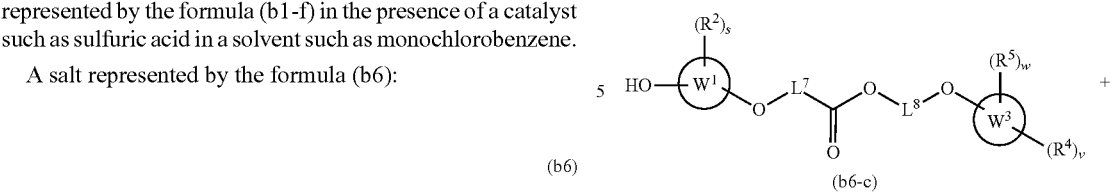

wherein $Z^+, Q^1, Q^2, W^1, R^2, L^7, L^8, W^3, R^4, R^5, s, v, w, X^1, X^2$ and $X^3$ are the same as defined above.

The compound represented by the formula (b6-a) can be produced by reacting the compound represented by the formula (b4-a) with the compound represented by the formula (b1-b) in the presence of a basic catalyst such as pyridine in a solvent such as tetrahydrofuran. The compound represented by the formula (b6-b) can be produced by reacting the compound represented by the formula (b6-a) with the compound represented by the formula (b1-b) in the presence of a basic catalyst such as pyridine in a solvent such as tetrahydrofuran. The compound represented by the formula (b6-c) can be produced by reacting the compound represented by the formula (b6-b) with the compound represented by the formula (b1-d) in the presence of a catalyst such as potassium carbonate and potassium iodide in a solvent such as N,N-dimethylformamide. The compound represented by the formula (b6) can be produced by reacting the compound represented by the formula (b6-c) with the compound represented by the formula (b1-f) in the presence of a catalyst such as sulfuric acid in a solvent such as monochlorobenzene.

A salt represented by the formula (b7):

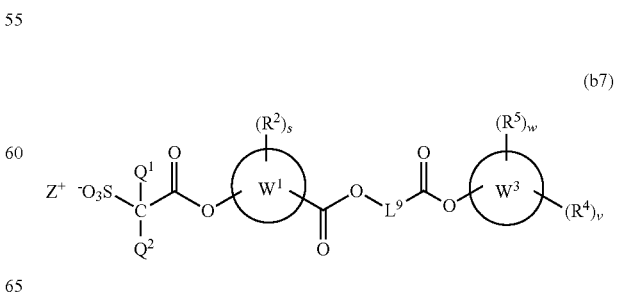

(b7)

can be produced as Scheme 7 described below.

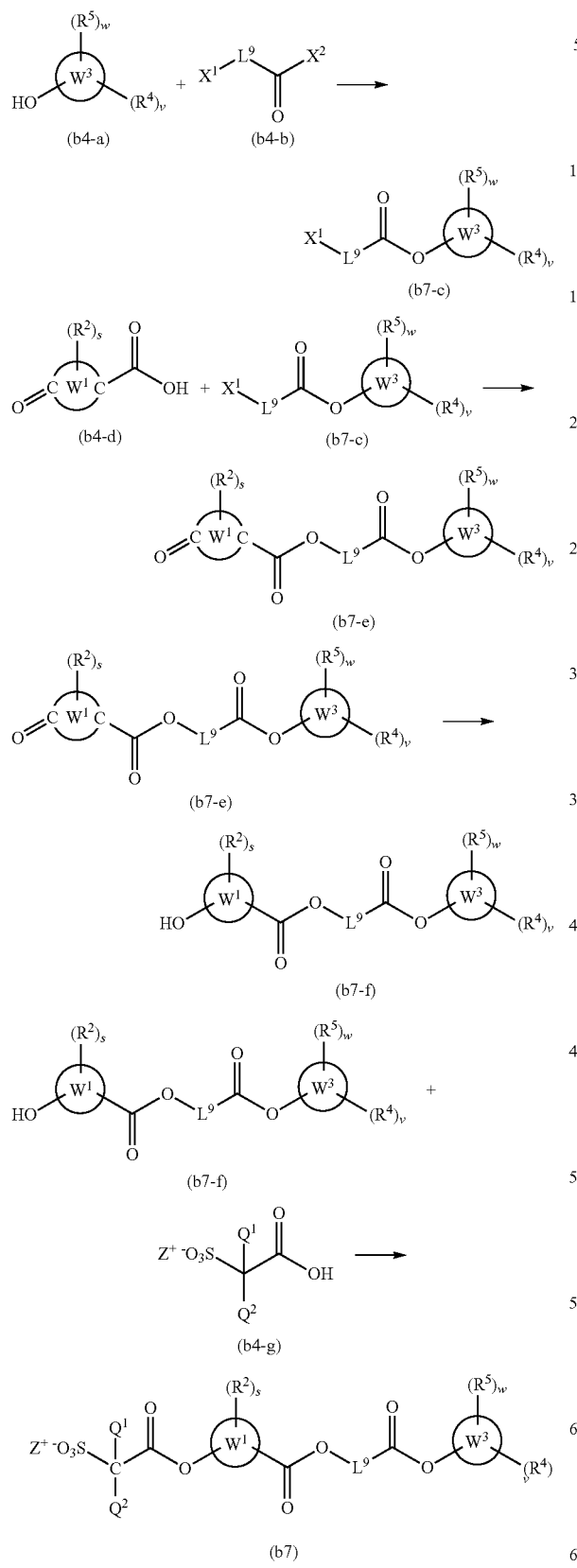

Scheme 7 wherein $Z^+$, $Q^1$, $Q^2$, $W^1$, $R^2$, $L^9$, $W^3$, $R^4$, $R^5$, s, v, w, $X^1$ and $X^2$ are the same as defined above.

The compound represented by the formula (b7-c) can be produced by reacting the compound represented by the formula (b4-a) with the compound represented by the formula (b4-b) in the presence of a catalyst such as potassium carbonate and potassium iodide in a solvent such as N,N-dimethylformamide. The compound represented by the formula (b7-e) can be produced by reacting the compound represented by the formula (b4-d) with the compound represented by the formula (b7-c) in the presence of a catalyst such as potassium carbonate and potassium iodide in a solvent such as N,N-dimethylformamide. The compound represented by the formula (b7-f) can be produced by reducing the compound represented by the formula (b7-e) with hydrogenating agent such as sodium borohydride in a solvent such as acetonitrile. The compound represented by the formula (b7) can be produced by reacting the compound represented by the formula (b7-f) with the compound represented by the formula (b4-g) in the presence of an acid catalyst such as sulfuric acid in a solvent such as monochlorobenzene. The compound represented by the formula (b4-g) can be produced according to the method described in JP 2008-13551 A1.

The acid generator of the present invention comprises SALT (X). The acid generator of the present invention can contain two or more kinds of SALT (X). The acid generator of the present invention can contain one or more known acid generators in addition to SALT (X). Examples of the known acid generator include the acid generators represented by the formulae (B1-1) to (B1-17), and the acid generator represented by the formulae (B1-1), (B1-2), (B1-6), (B1-11), (B1-12), (B1-13) and (B1-14) are preferable.

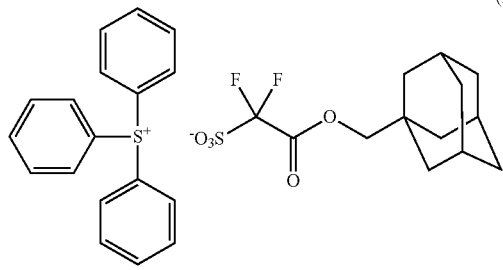

(B1-1)

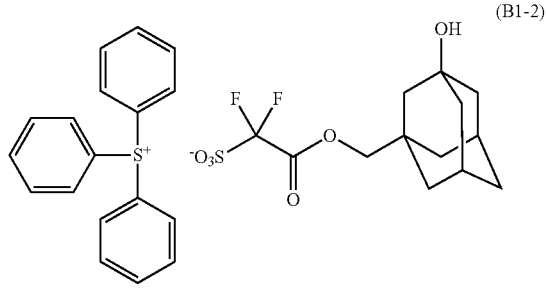

(B1-2)

-continued
(B1-3)
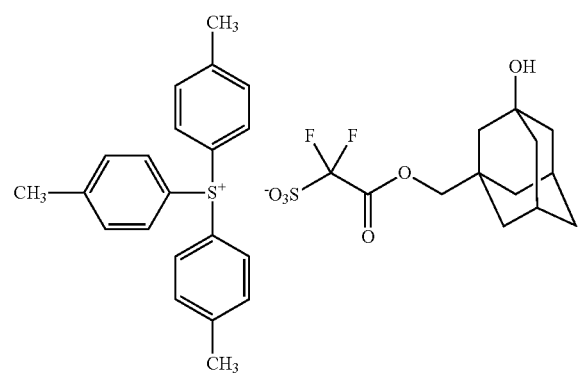
(B1-4)
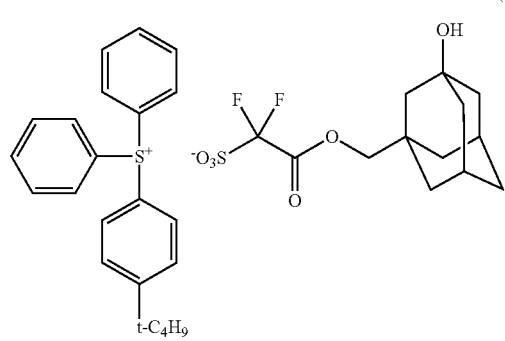
(B1-5)
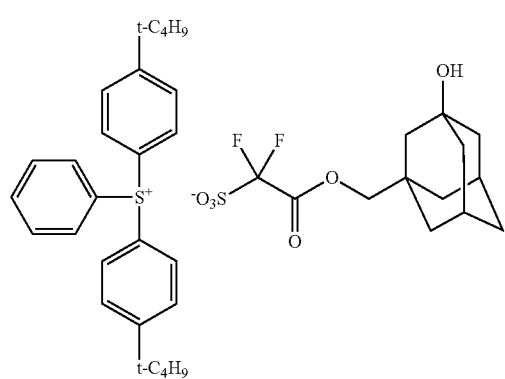
(B1-6)
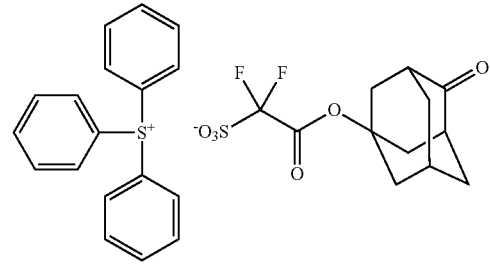
(B1-7)
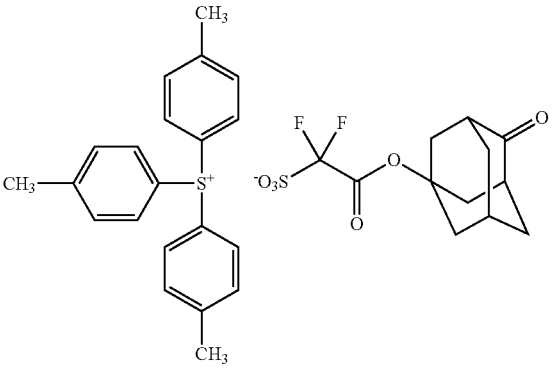
(B1-8)
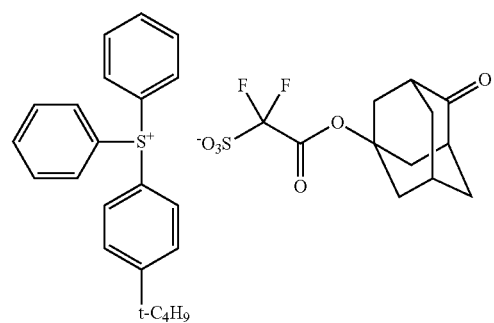
(B1-9)
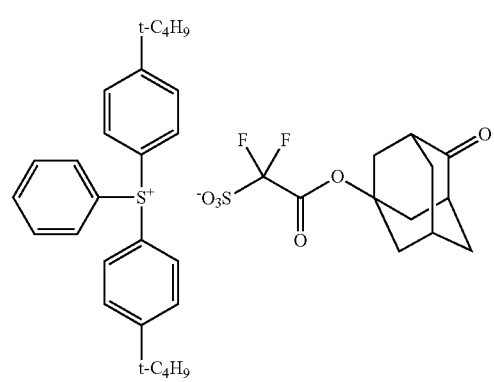
(B1-10)
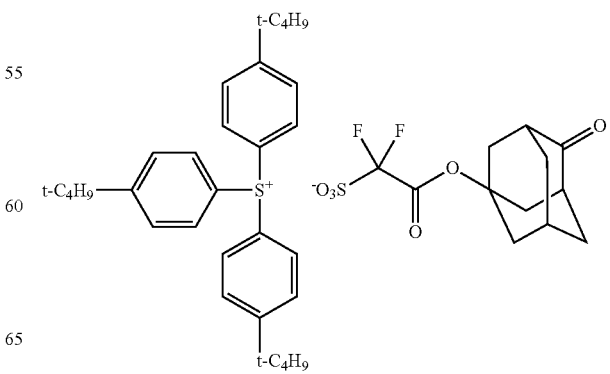

-continued (B1-11)
(B1-12)
(B1-13)
(B1-14)
(B1-15)

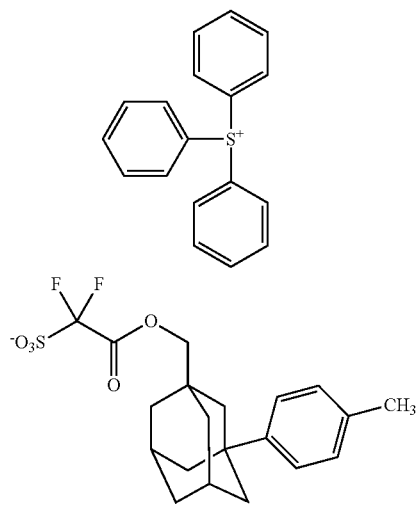

-continued (B1-16)
(B1-17)

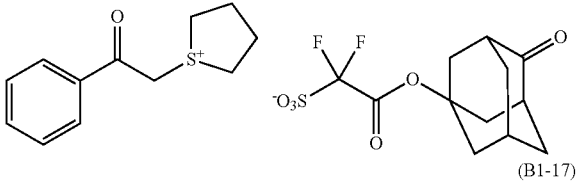
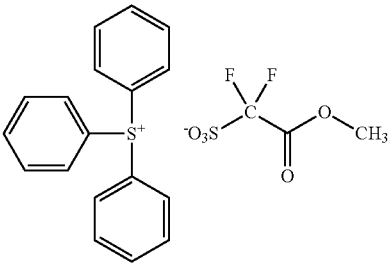
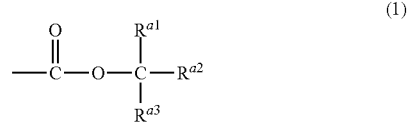

The amount of SALT (X) in the acid generator of the present invention is usually 10 parts by weight or more, and preferably 30 parts by weight or more per 100 parts by weight of the acid generator of the present invention. The amount of SALT (X) in the acid generator of the present invention is usually 90 parts by weight or less, and preferably 70 parts by weight or less per 100 parts by weight of the acid generator of the present invention.

The amount of the acid generator is usually 1 part by weight or more and preferably 3 parts by weigh or more per 100 parts by weight of the resin. The amount of the acid generator is usually 40 part by weight or less and preferably 35 parts by weigh or less per 100 parts by weight of the resin.

The resin will be illustrated below.

The resin has an acid-labile group and is insoluble or poorly soluble in an alkali aqueous solution but becomes soluble in an alkali aqueous solution by the action of an acid. The resin has a structural unit derived from a compound having an acid-labile group, and can be produced by polymerizing one or more compounds having an acid-labile group.

In this specification, "an acid-labile group" means a group capable of being eliminated by the action of an acid.

Examples of the acid-labile group include a group represented by the formula (1):

$$\begin{array}{c}\overset{O}{\underset{\|}{-C}}-O-\overset{R^{a1}}{\underset{R^{a3}}{\overset{|}{C}}}-R^{a2}\end{array} \quad (1)$$

wherein $R^{a1}$, $R^{a2}$ and $R^{a3}$ independently each represent an aliphatic hydrocarbon group or a saturated cyclic hydrocarbon group, or $R^{a1}$ and $R^{a2}$ are bonded each other to form a ring together with a carbon atom to which $R^{a1}$ and $R^{a2}$ are bonded.

Examples of the aliphatic hydrocarbon group include a C1-C8 alkyl group. Specific examples of the C1-C8 alkyl group include a methyl group, an ethyl group, a propyl group, an isopropyl group, a butyl group, a pentyl group, a hexyl group, a heptyl group and an octyl group. The saturated cyclic hydrocarbon group may be monocyclic or polycyclic, and examples thereof include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

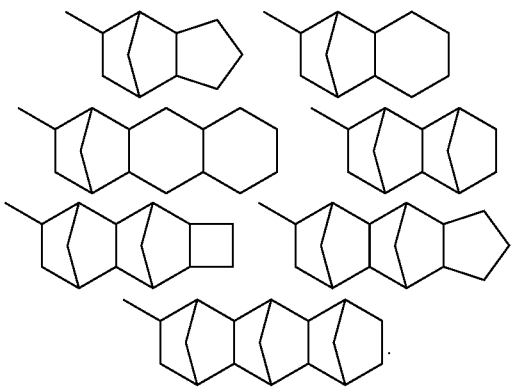

The saturated cyclic hydrocarbon group preferably has 3 to 20 carbon atoms.

Examples of the ring formed by bonding $R^{a1}$ and $R^{a2}$ each other include the following groups and the ring preferably has 3 to 20 carbon atoms, and the more preferably has 3 to 12 carbon atoms.

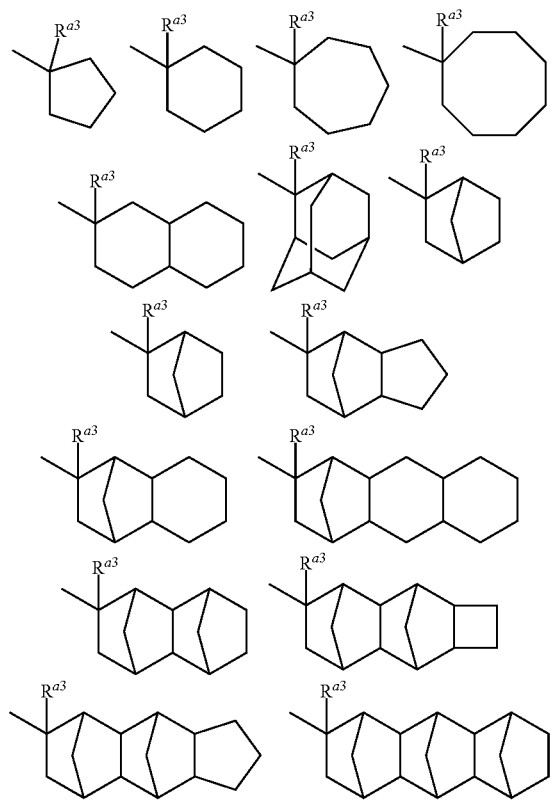

wherein $R^{a3}$ is the same as defined above.

The group represented by the formula (1) wherein $R^{a1}$, $R^{a2}$ and $R^{a3}$ independently each represent a C1-C8 alkyl group such as a tert-butyl group, the group represented by the formula (1) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (1) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

The compound having an acid-labile group is preferably an acrylate monomer having an acid-labile group in its side chain or a methacryalte monomer having an acid-labile group in its side chain.

Preferable examples of the compound having an acid-labile group include monomers represented by the formulae (a1-1) and (a1-2):

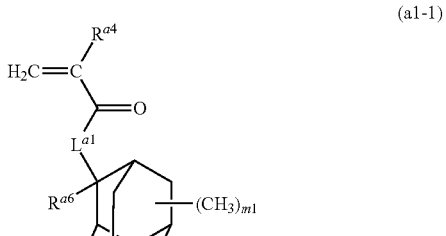

(a1-1)

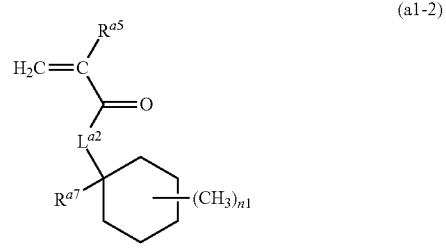

(a1-2)

wherein $R^{a4}$ and $R^{a5}$ each independently represents a hydrogen atom or a methyl group, $R^{a6}$ and $R^{a7}$ each independently represents a C1-C8 aliphatic hydrocarbon group or a C3-C10 saturated cyclic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, m1 represents an integer of 0 to 14 and n1 represents an integer of 0 to 10.

The aliphatic hydrocarbon group preferably has 1 to 6 carbon atoms, and the saturated cyclic hydrocarbon group preferably has 3 to 8 carbon atoms and more preferably 3 to 6 carbon atoms.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the saturated cyclic hydrocarbon, group include a cyclohexyl group, a methylcyclohexyl group, a dimethylcyclohexyl group, a cycloheptyl group, a methylcycloheptyl group, a norbornyl group and a methylnorbornyl group. $R^{a4}$ is preferably a methyl group, an ethyl group or an isopropyl group, and $R^{a5}$ is preferably a methyl group, an ethyl group or an isopropyl group.

$L^{a1}$ is preferably *—O— or *—O—$(CH_2)_{f1}$—CO—O— in which * represents a binding position to —CO—, and f1 represents an integer of 1 to 4, and is more preferably *—O— or *—O—CH$_2$—CO—O—, and is especially preferably *—O—. L$^{a2}$ is preferably *—O— or *—O—(CH$_2$)$_{f1}$—CO—O— in which * represents a binding position to —CO—, and f1 is the same as defined above, and is more preferably *—O— or *—O—CH$_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1.

Particularly when the photoresist composition contains a resin derived from a monomer having a bulky structure such as a saturated cyclic hydrocarbon group, the photoresist composition having excellent resolution tends to be obtained.

Examples of the monomer represented by the formula (a1-1) include the followings.

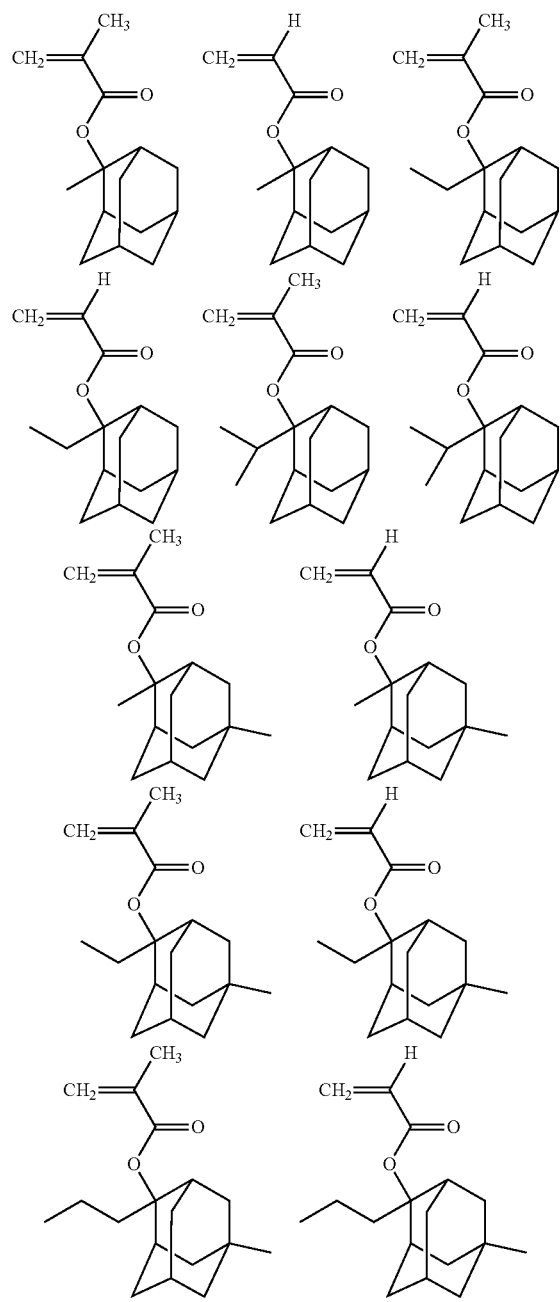

-continued

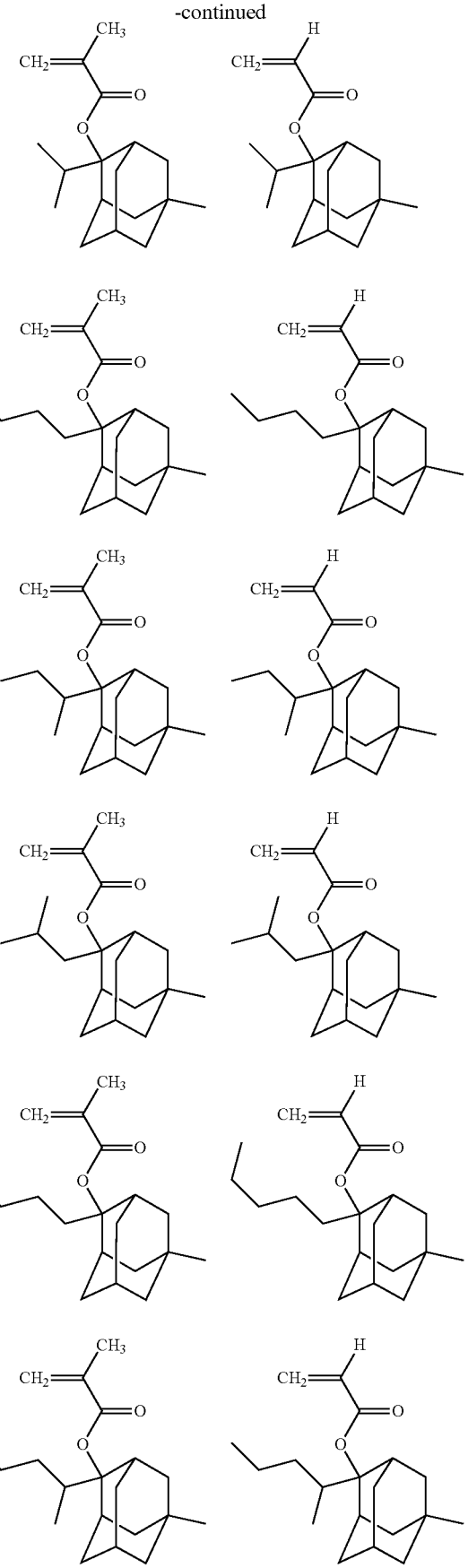

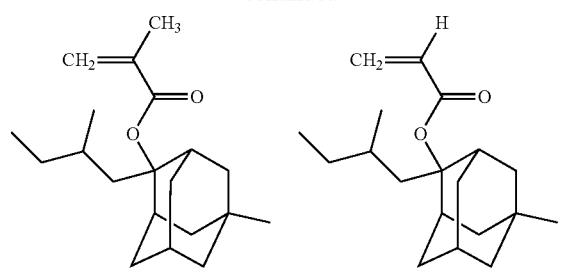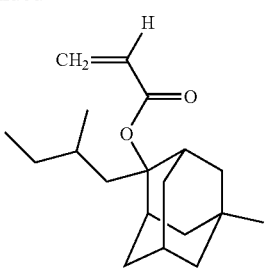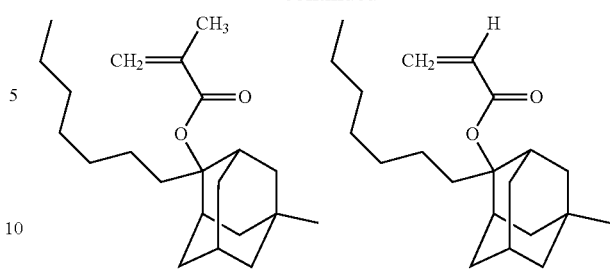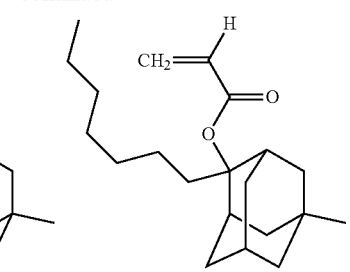
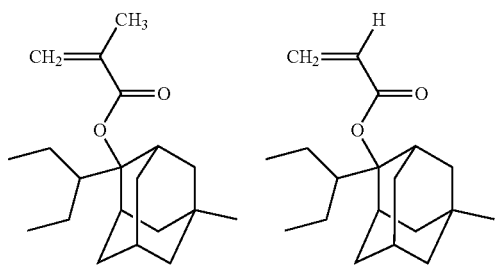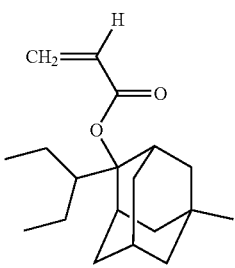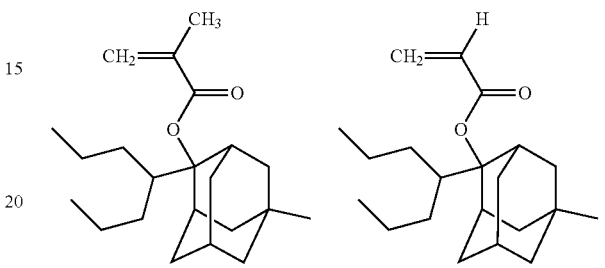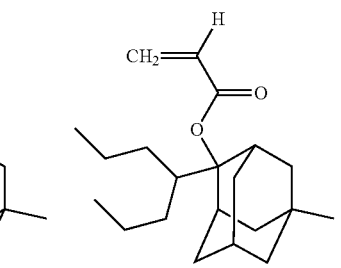
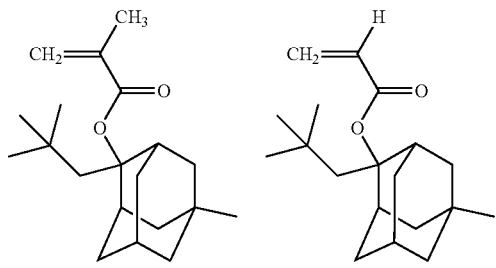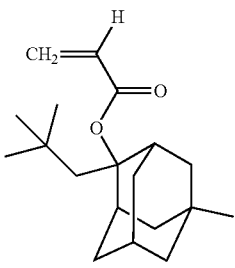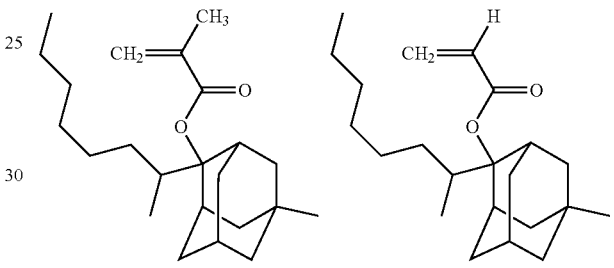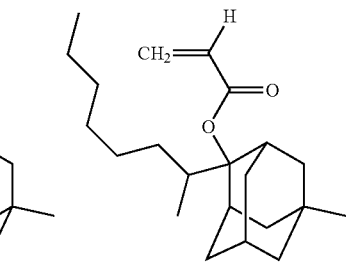
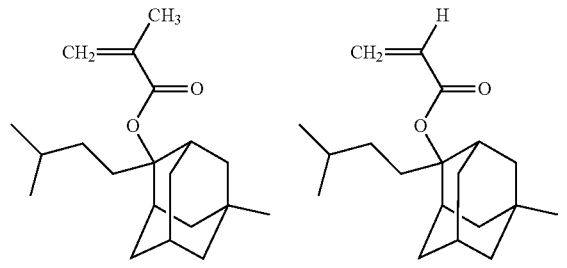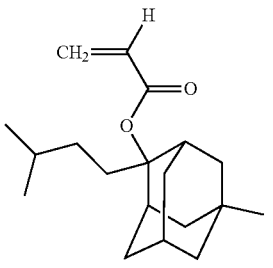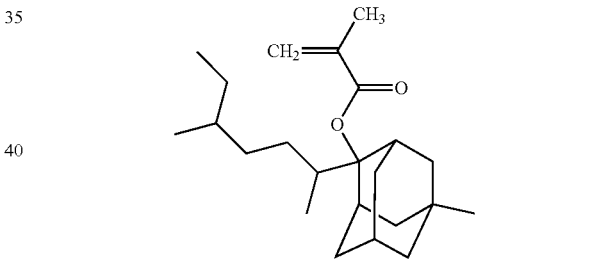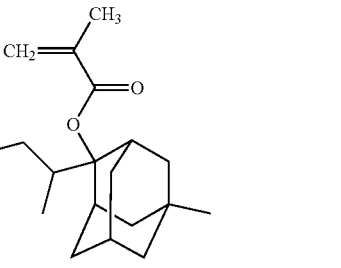
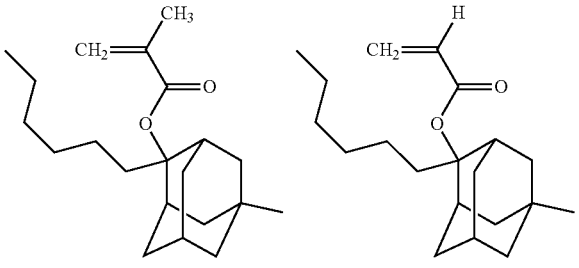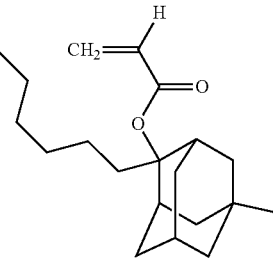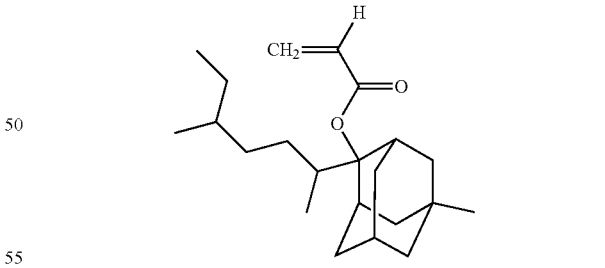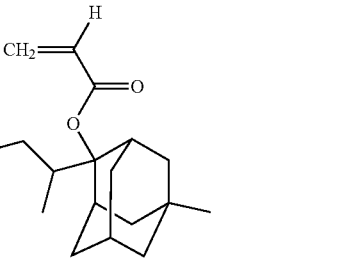
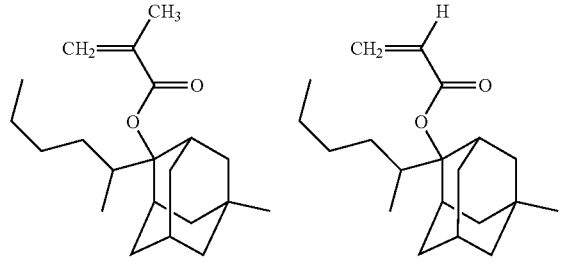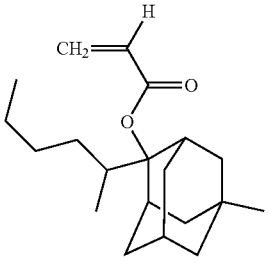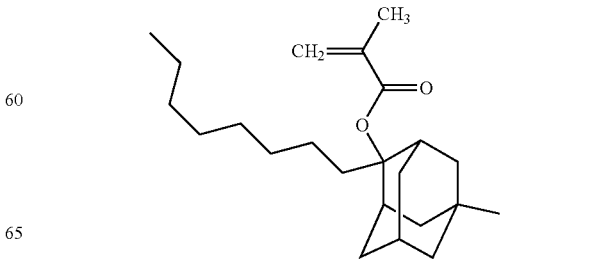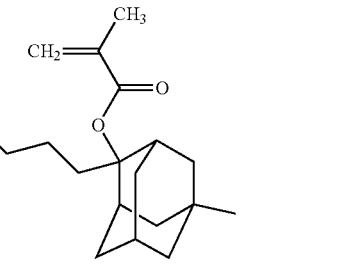

101
-continued
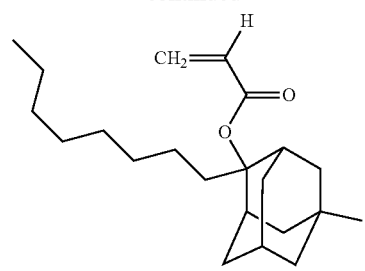
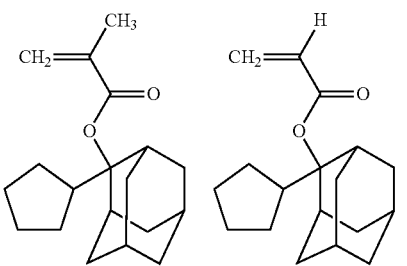
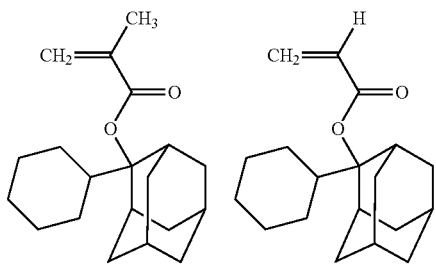
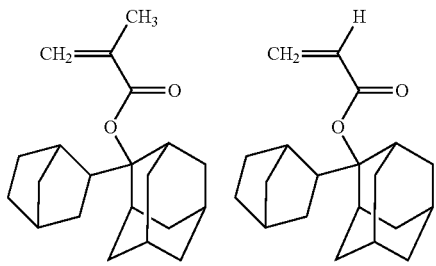
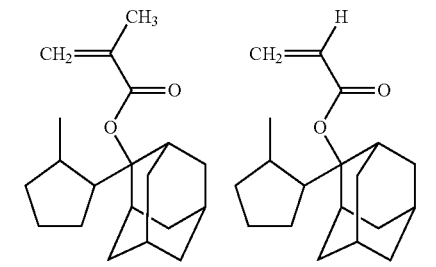
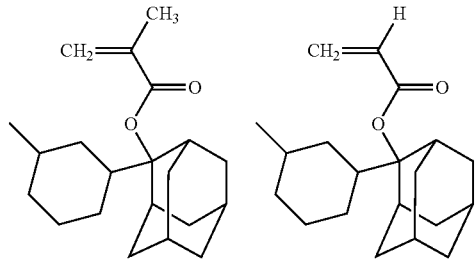
102
-continued
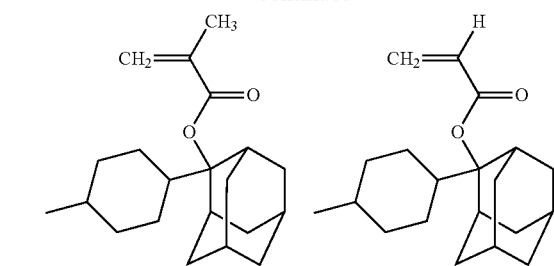
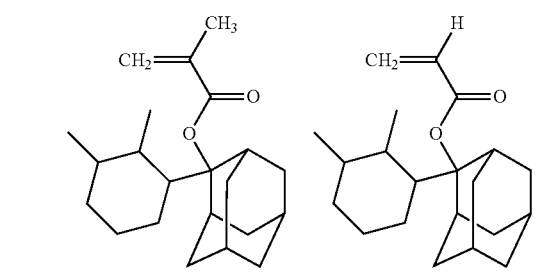
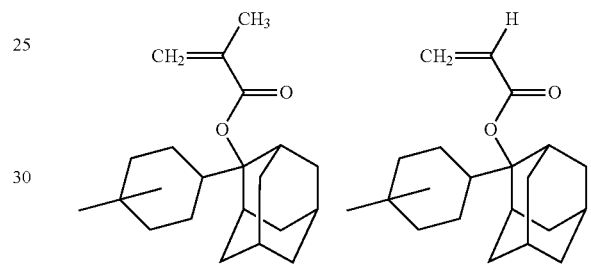
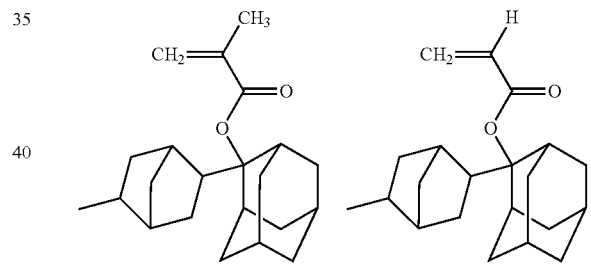
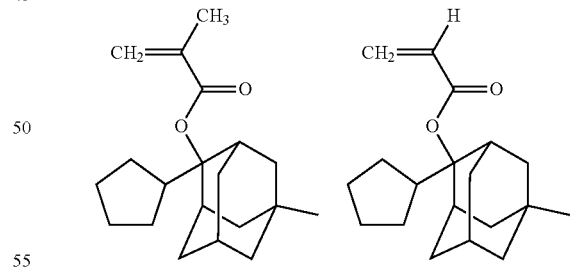
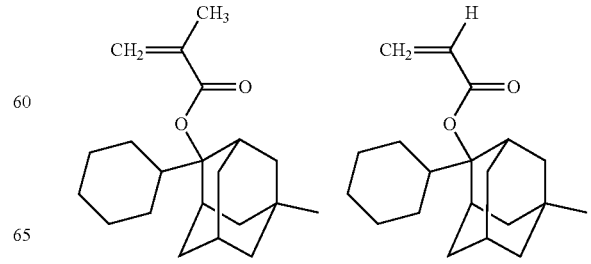

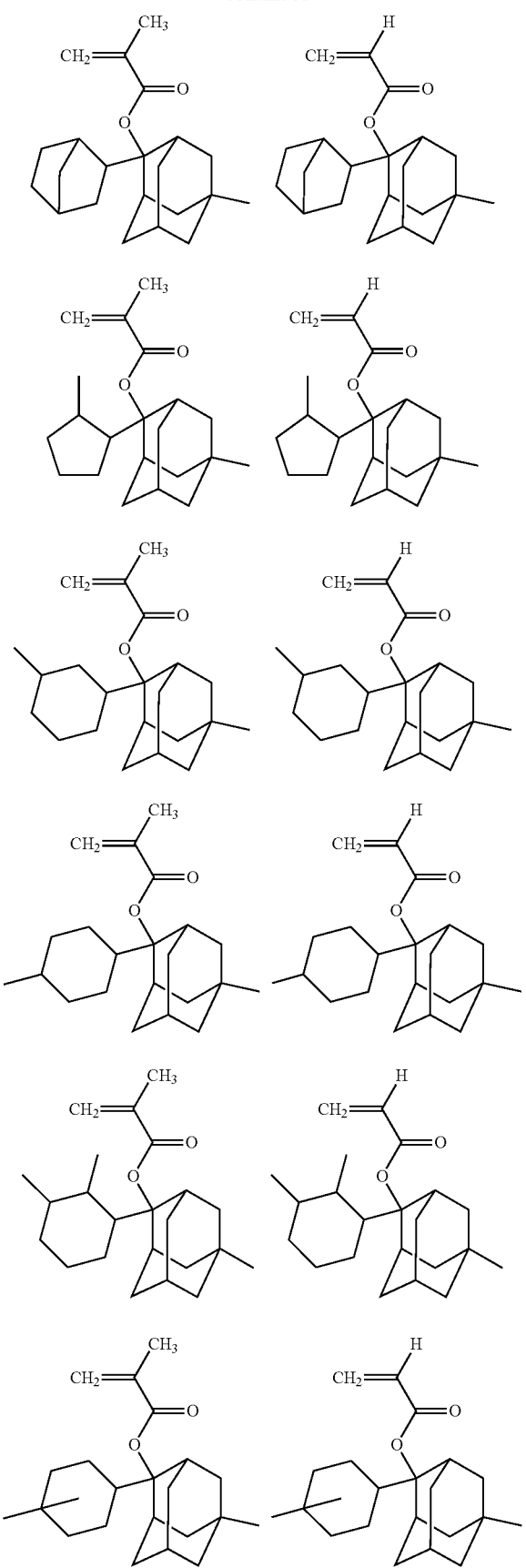
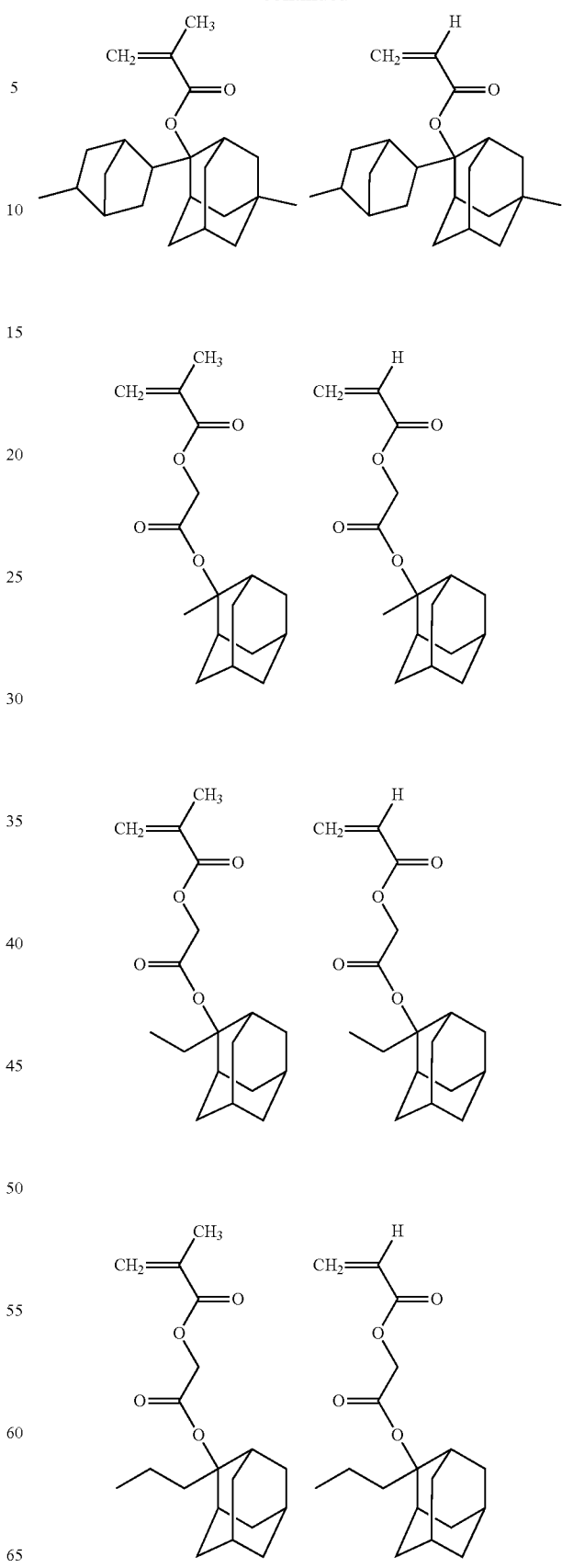

105
-continued
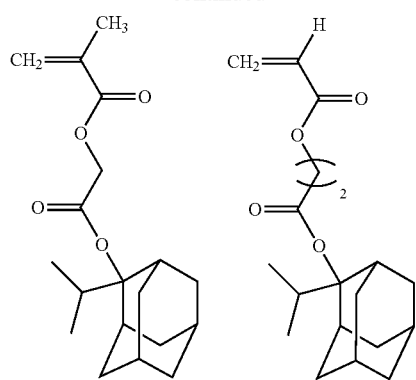
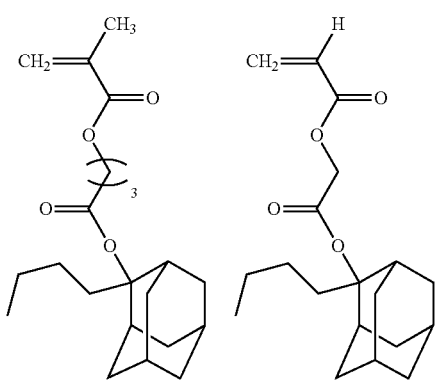
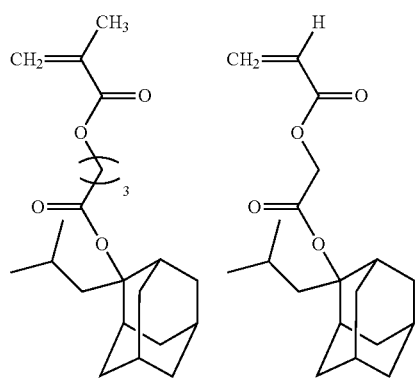
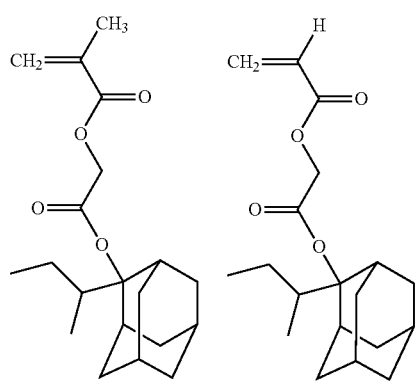
106
-continued
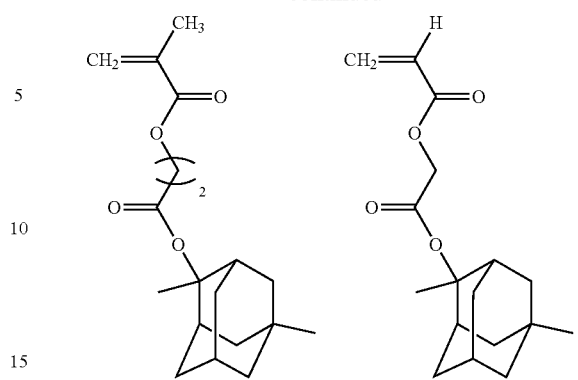
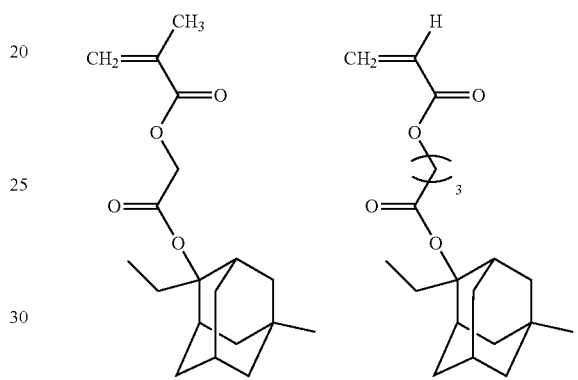
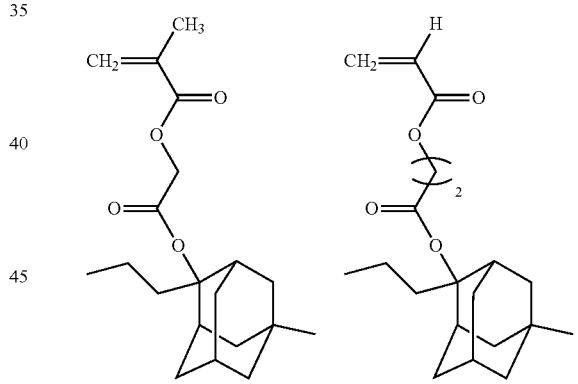
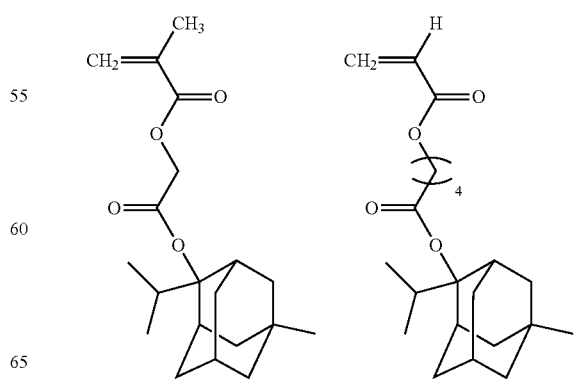

107
-continued
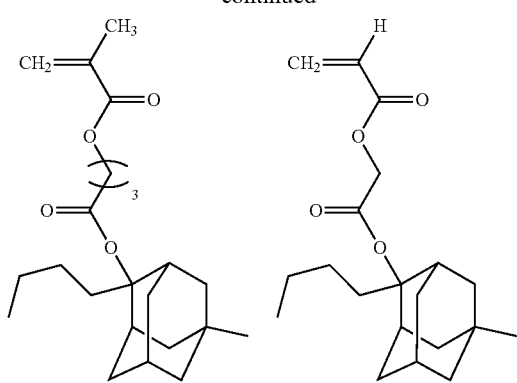
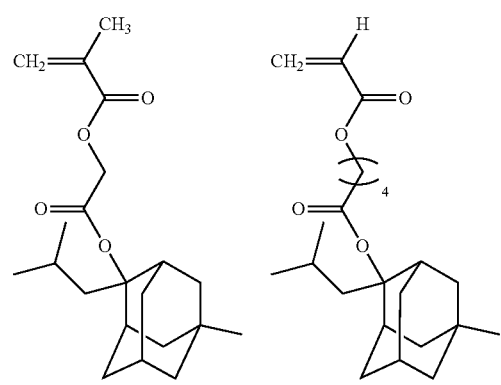
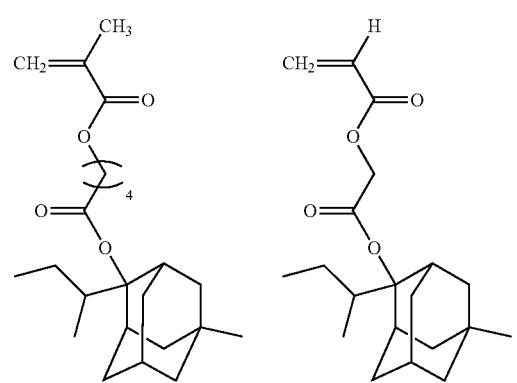
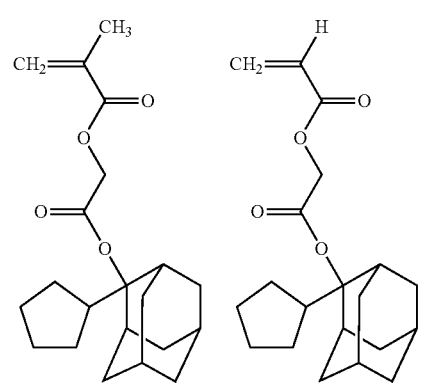
108
-continued
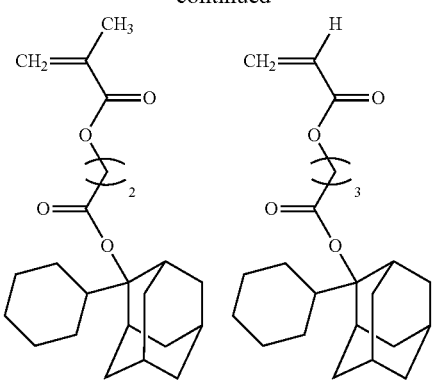
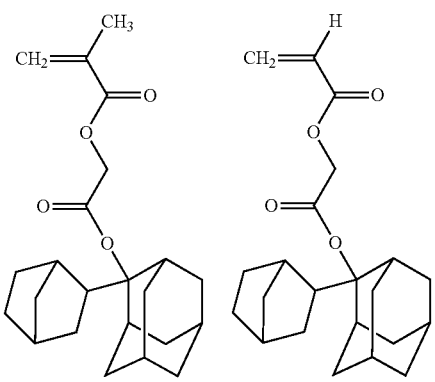
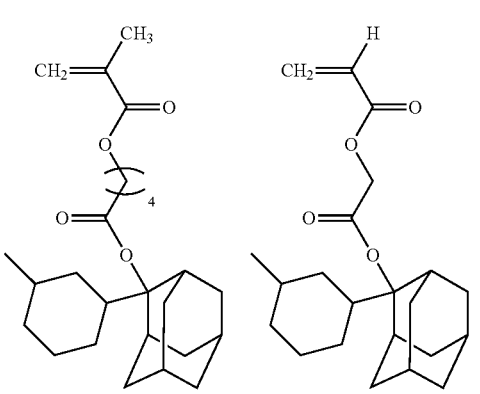
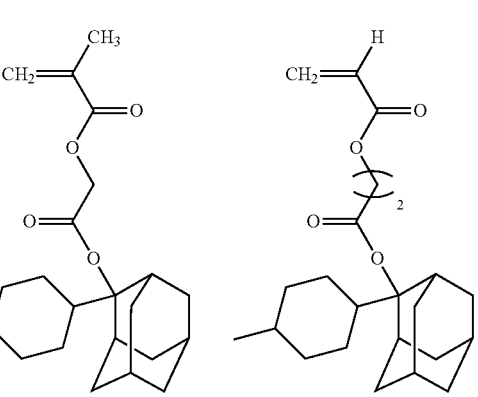

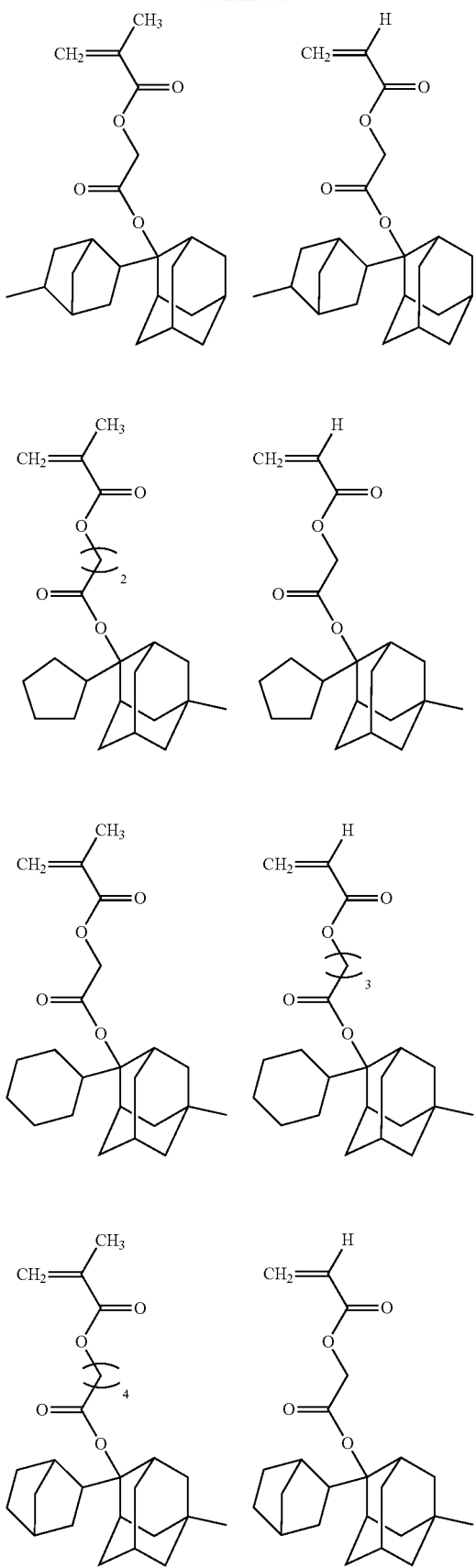
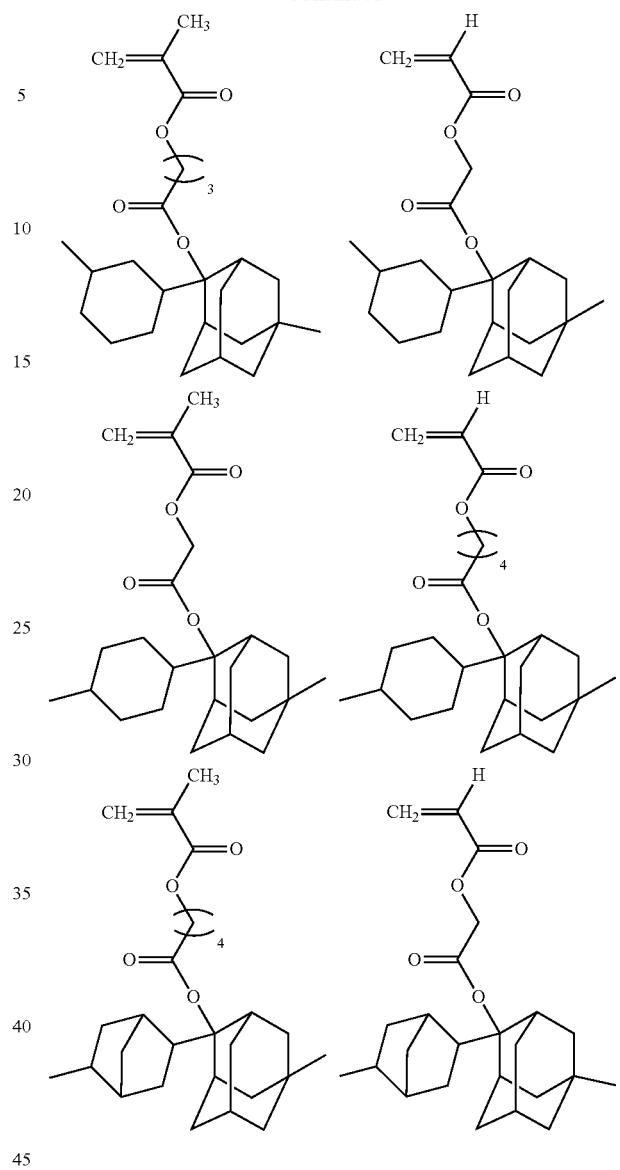

Among them, preferred are 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate and 2-isopropyl-2-adamantyl methacrylate, and more preferred are 2-methyl-2-adamantyl methacrylate, 2-ethyl-2-adamantyl methacrylate, and 2-isopropyl-2-adamantyl methacrylate.

Examples of the monomer represented by the formula (a1-2) include the followings.

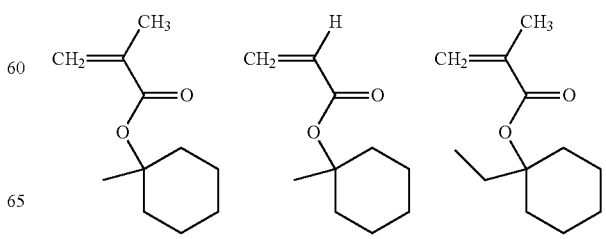

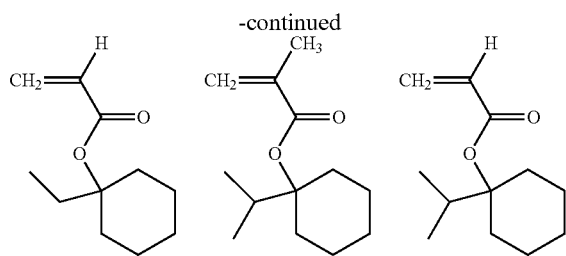

Among them, preferred are 1-ethyl-1-cyclohexyl acrylate and 1-ethyl-1-cyclohexyl methacrylate, and more preferred is 1-ethyl-1-cyclohexyl methacrylate.

The content of the structural unit derived from a compound having an acid-labile group in the resin is usually 10 to 95% by mole, preferably 15 to 90% by mole and more preferably 20 to 85% by mole based on 100% by mole of all the structural units of the resin.

Other examples of the compound having an acid-labile group include a monomer represented by the formula (a1-3):

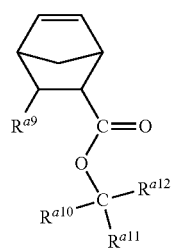

(a1-3)

wherein $R^{a9}$ represents a hydrogen atom, a C1-C3 aliphatic hydrocarbon group which can have one or more substituents, a carboxyl group, a cyano group or a —COOR$^{a13}$ group in which $R^{a13}$ represents a C1-C8 aliphatic hydrocarbon group or a C3-C8 saturated cyclic hydrocarbon group, and the C1-C8 aliphatic hydrocarbon group and the C3-C8 saturated cyclic hydrocarbon group can have one or more hydroxyl groups, and one or more —CH$_2$— in the C1-C8 aliphatic hydrocarbon group and the C3-C8 saturated cyclic hydrocarbon group can be replaced by —O— or —CO—, $R^{a10}$, $R^{a11}$ and $R^{a12}$ each independently represent a C1-C12 aliphatic hydrocarbon group or a C3-C12 saturated cyclic hydrocarbon group, and $R^{a10}$ and $R^{a11}$ can be bonded each other to form a ring together with the carbon atom to which $R^{a10}$ and $R^{a11}$ are bonded, and the C1-C12 aliphatic hydrocarbon group and the C3-C12 saturated cyclic hydrocarbon group can have one or more hydroxyl groups, and one or more —CH$_2$— in the C1-C12 aliphatic hydrocarbon group and the C3-C12 saturated cyclic hydrocarbon group can be replaced by —O— or —CO—.

Examples of the substituent include a hydroxyl group. Examples of the C1-C3 aliphatic hydrocarbon group which can have one or more substituents include a methyl group, an ethyl group, a propyl group, a hydroxymethyl group and a 2-hydroxyethyl group. Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group, and examples of the ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl) ethyl 5-norbornene-2-carboxylate and 1-(1-adamantyl)-1-methylethyl 5-norbornene-2-carboxylate.

When the resin has a structural unit derived from the monomer represented by the formula (a1-3), the photoresist composition having excellent resolution and higher dry-etching resistance tends to be obtained.

When the resin contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of the resin.

Other examples of the compound having an acid-labile group include a monomer represented by the formula (a1-4):

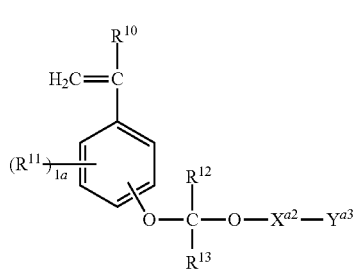

(a1-4)

wherein $R^{10}$ represents a hydrogen atom, a halogen atom, a C1-C6 alkyl group or a C1-C6 halogenated alkyl group, $R^{11}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, la represents an integer of 0 to 4, $R^{12}$ and $R^{13}$ each independently represent a hydrogen atom or a C1-C12 hydrocarbon group, $X^{a2}$ represents a single bond or a C1-C17 divalent saturated hydrocarbon group in which one or more —CH$_2$— can be replaced by —O—, —CO—, —S—, —SO$_2$— or —N(R$^c$)— wherein R$^c$ represents a hydrogen atom or a C1-C6 alkyl group, and $Y^{a3}$ represents a C1-C12 aliphatic hydrocarbon group, a C3-C18 saturated cyclic hydrocarbon group or a C6-C18 aromatic hydrocarbon group, and the C1-C12 aliphatic hydrocarbon group, the C2-C18 saturated cyclic hydrocarbon group and the C6-C18 aromatic hydrocarbon group can have one or more substituents.

Examples of the halogen atom include a fluorine atom.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 aliphatic hydrocarbon group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, and a C3-C12 saturated cyclic hydrocarbon group such as a cyclohexyl group, an adamantyl group, a 2-alkyl-2-adamantyl group, a 1-(1-adamantyl)-1-alkyl group and an isobornyl group.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 aliphatic hydrocarbon group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group. Examples of the C3-C18 saturated cyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

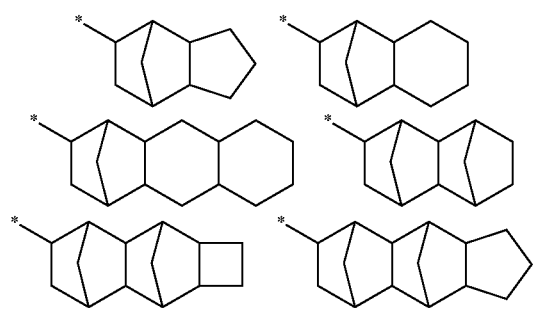

-continued

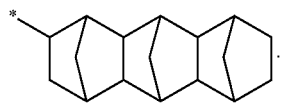

Examples of the C6-C18 aromatic hydrocarbon group include a phenyl group, a naphthyl group, an anthryl group, a p-methylphenyl group, a p-tert-butylphenyl group and a p-adamantylphenyl group.

Examples of the monomer represented by the formula (a1-4) include the followings.

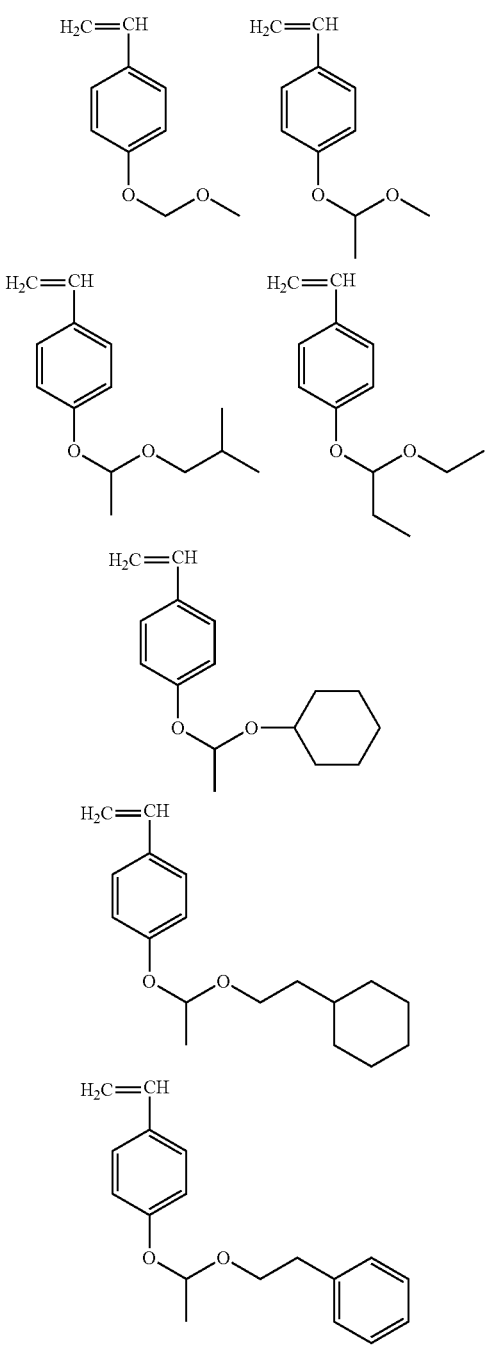

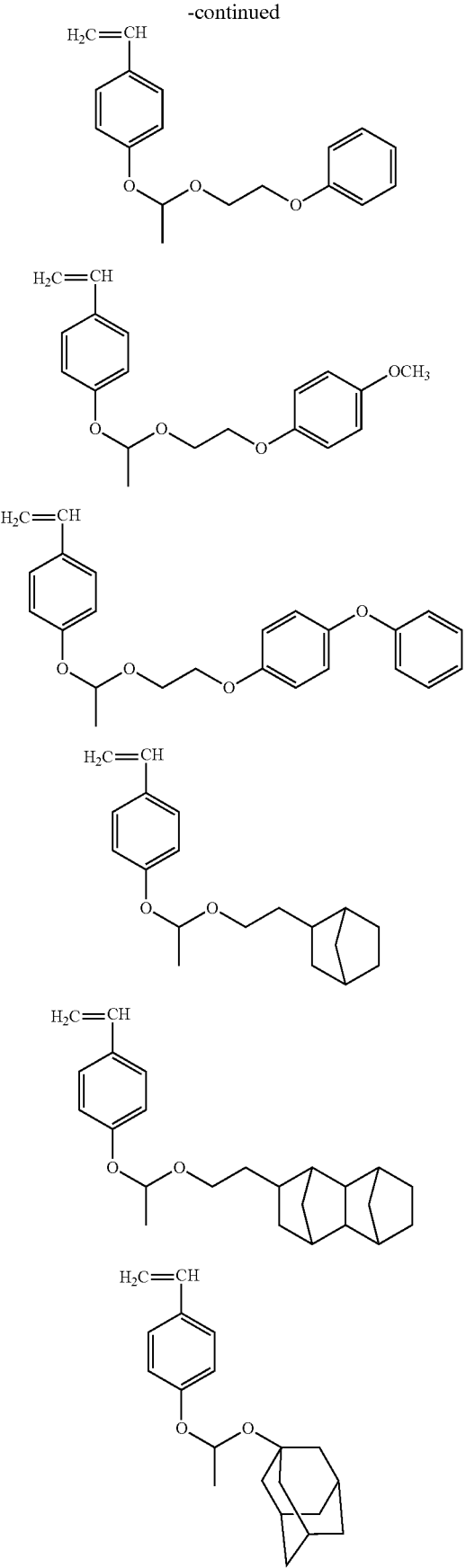
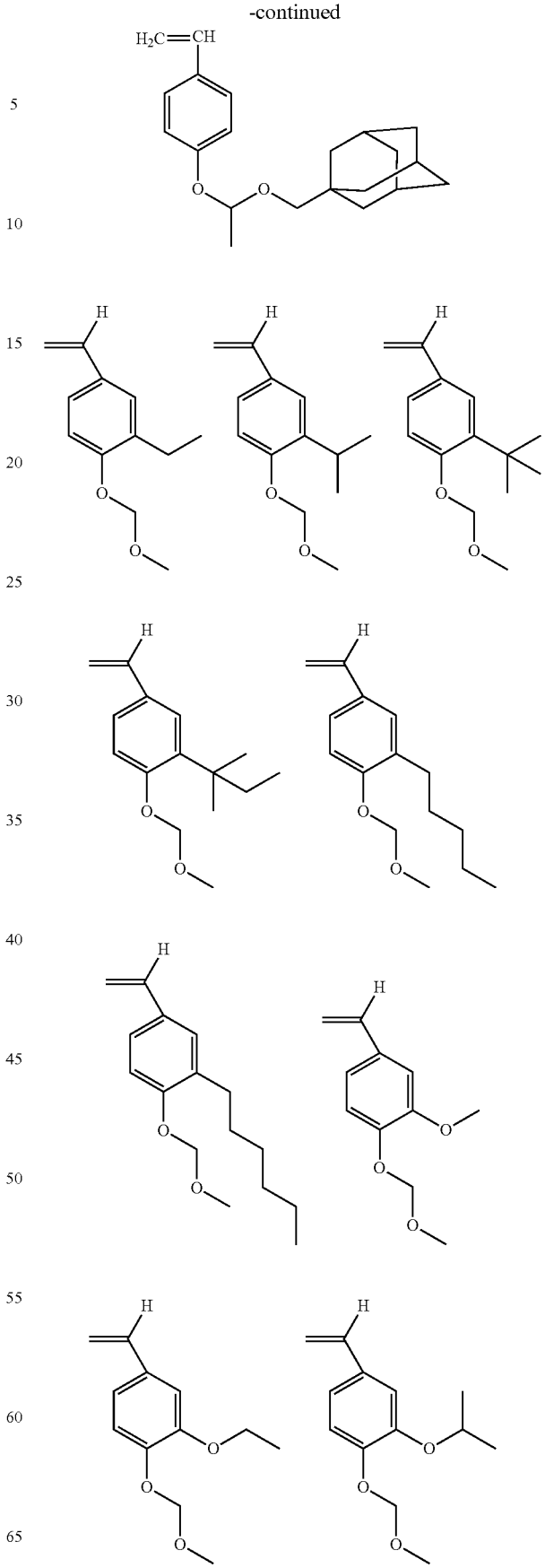

-continued

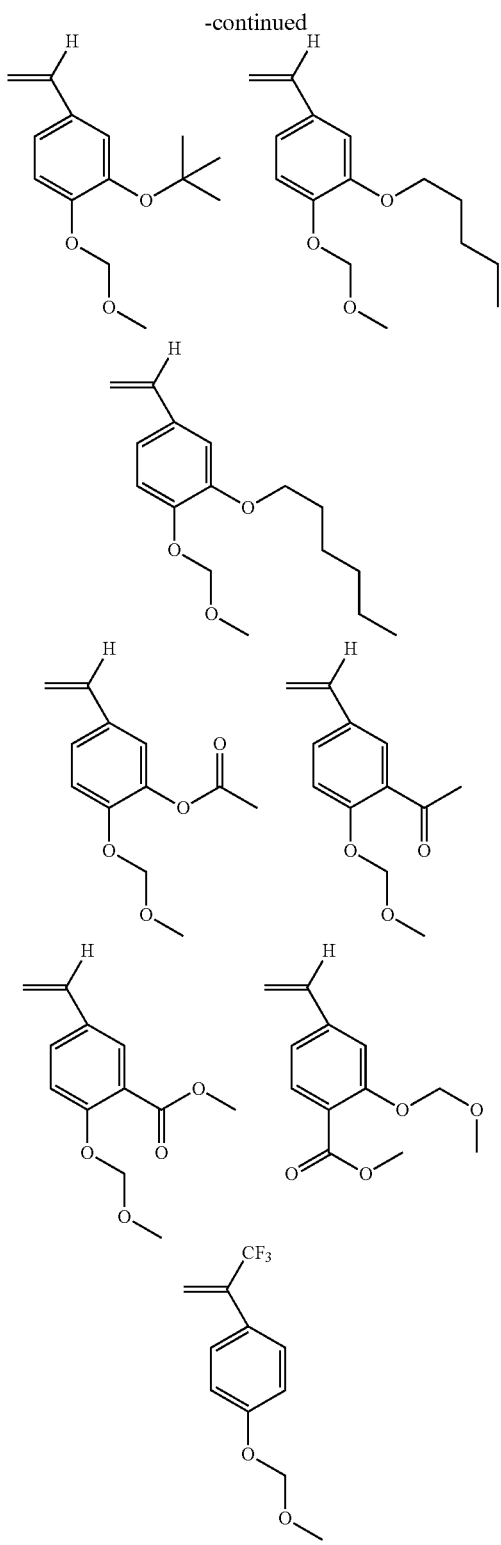

When the resin contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of the resin.

The resin can have two or more kinds of structural units derived from the compounds having an acid-labile group.

The resin preferably contains the structural unit derived from the compound having an acid-labile group and a structural unit derived from the compound having no acid-labile group. The resin can have two or more kinds of structural units derived from the compounds having no acid-labile group. When the resin contains the structural unit derived from the compound having an acid-labile group and the structural unit derived from the compound having no acid-labile group, the content of the structural unit derived from the compound having an acid-labile group is usually 10 to 80% by mole and preferably 20 to 60% by mole based on total molar of all the structural units of the resin. The content of the structural unit derived from a monomer having an adamantyl group, especially the monomer represented by the formula (a1-1) in the structural unit derived from the compound having no acid-labile group is preferably 15% by mole or more from the viewpoint of dry-etching resistance of the photoresist composition.

The compound having no acid-labile group preferably contains one or more hydroxyl groups or a lactone ring. When the resin contains the structural unit derived from the compound having no acid-labile group and having one or more hydroxyl groups or a lactone ring, a photoresist composition having good resolution and adhesiveness of photoresist to a substrate tends to be obtained.

Examples of the compound having no acid-labile group and having one or more hydroxyl groups include a monomer represented by the formula (a2-0):

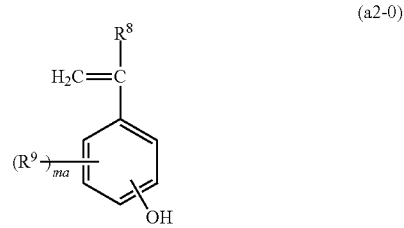

(a2-0)

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and a monomer represented by the formula (a2-1):

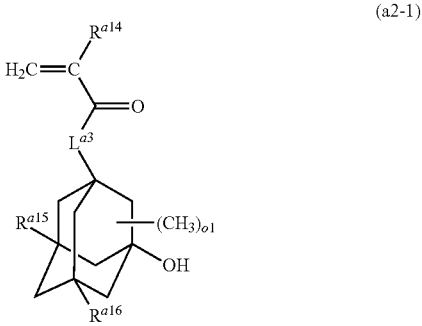

(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and of represents an integer of 0 to 10.

When KrF excimer laser (wavelength: 248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) and the structural unit derived from the compound having an acid generator can be produced, for example, by polymerizing the compound having an acid generator and a monomer obtained by protecting a hydroxyl group of the monomer represented by the formula (a2-0) with an acetyl group followed by conducting deacetylation of the obtained polymer with a base.

Examples of the monomer represented by the formula (a2-0) include the followings.

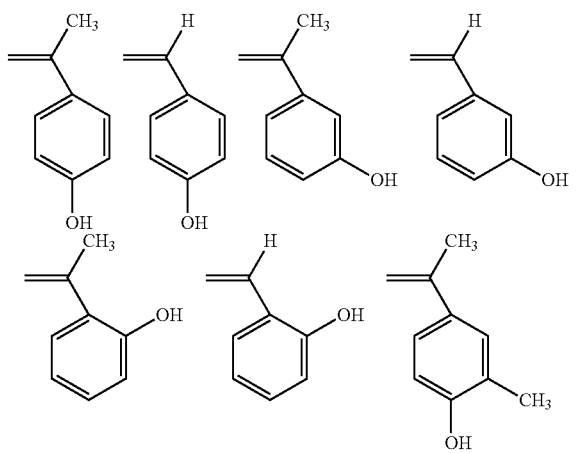

-continued

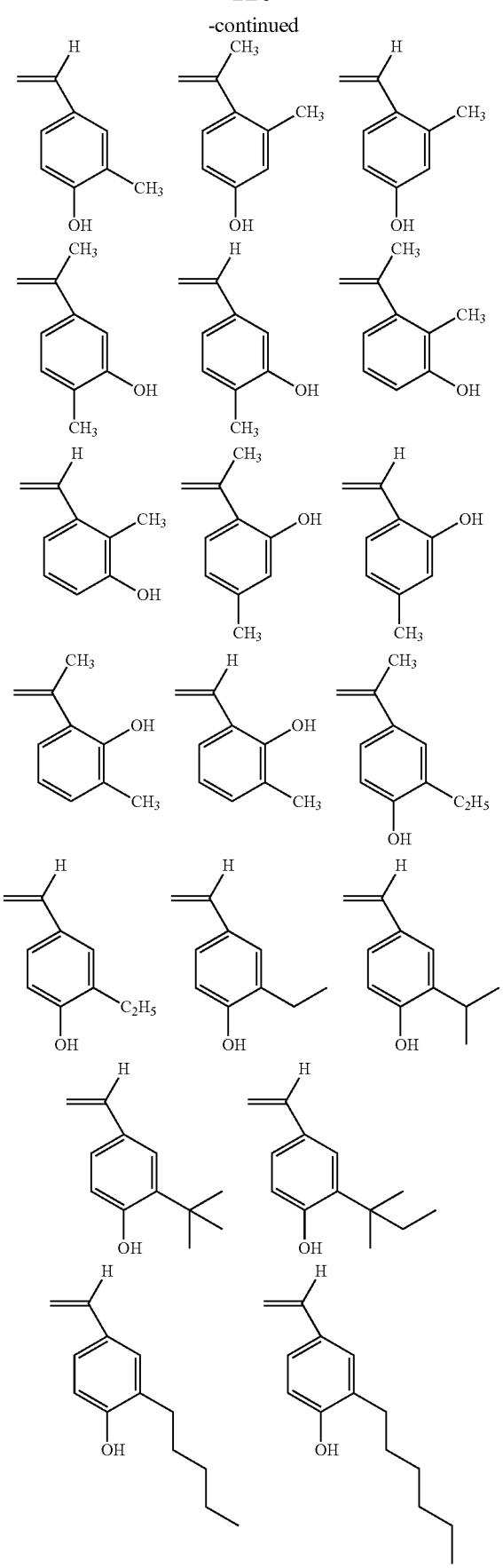

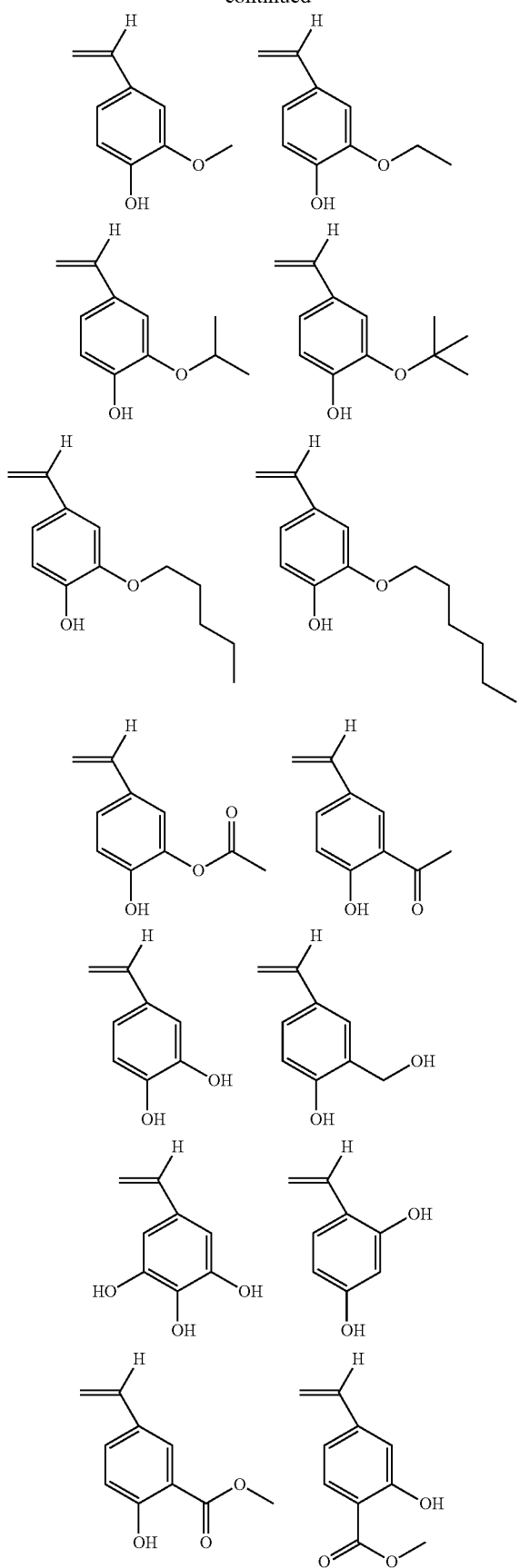

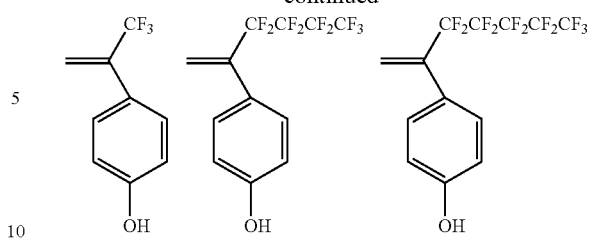

Among them, preferred are 4-hydroxystyrene and 4-hydroxy-α-methylstyrene.

When the resin contains the structural unit derived from the monomer represented by the formula (a2-0), the content of the structural unit derived from the monomer represented by the formula (a2-0) is usually 5 to 90% by mole and preferably 10 to 85% by mole and more preferably 15 to 80% by mole based on total molar of all the structural units of the resin.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O— in which * represents a binding position to —CO—, and f2 represents an integer of 1 to 4, and is more preferably *—O—, and o1 is preferably 0, 1, 2 or 3 and is more preferably 0 or 1.

Examples of the monomer represented by the formula (a2-1) include the followings, and 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 1-(3,5-dihydroxy-1-adamantyloxycarbonyl)methyl acrylate and 1-(3,5-dihydroxy-1-adamantyloxycarbonyl)methyl methacrylate are preferable, and 3-hydroxy-1-adamantyl methacrylate and 3,5-dihydroxy-1-adamantyl methacrylate are more preferable.

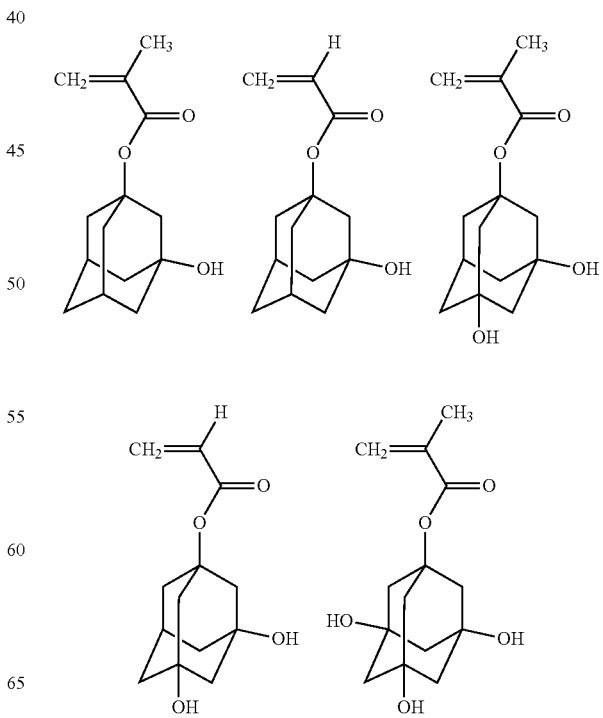

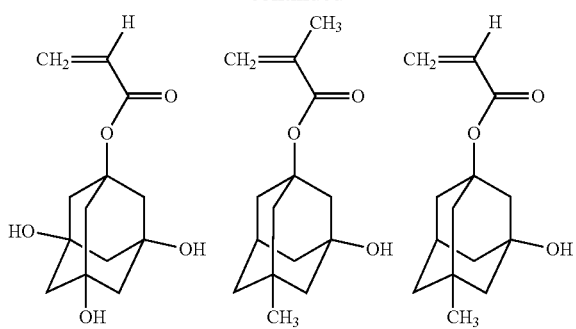
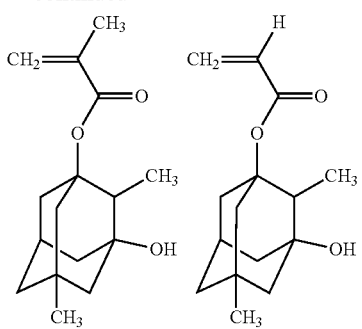

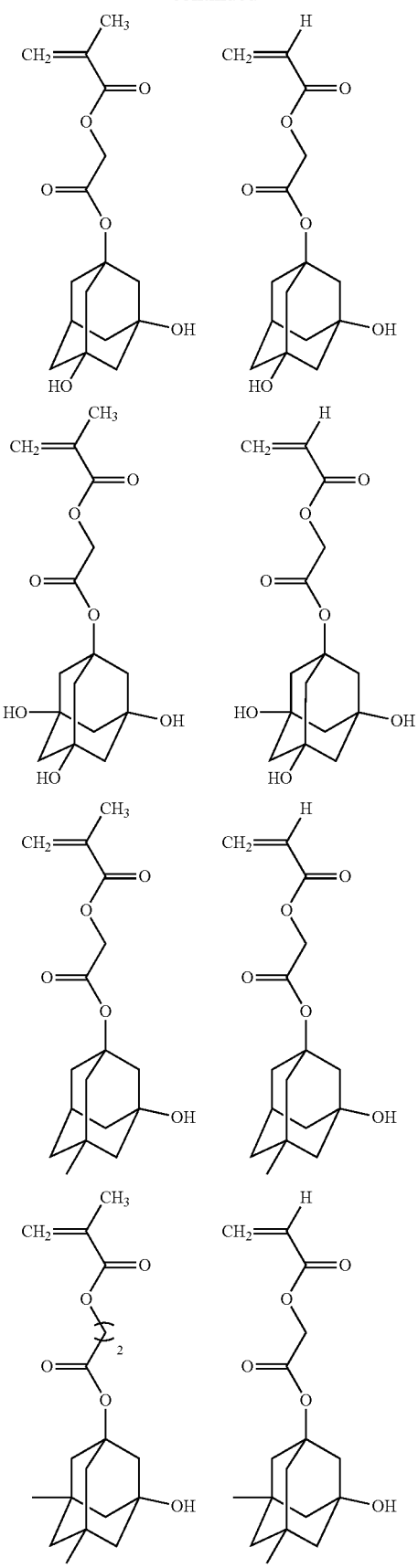
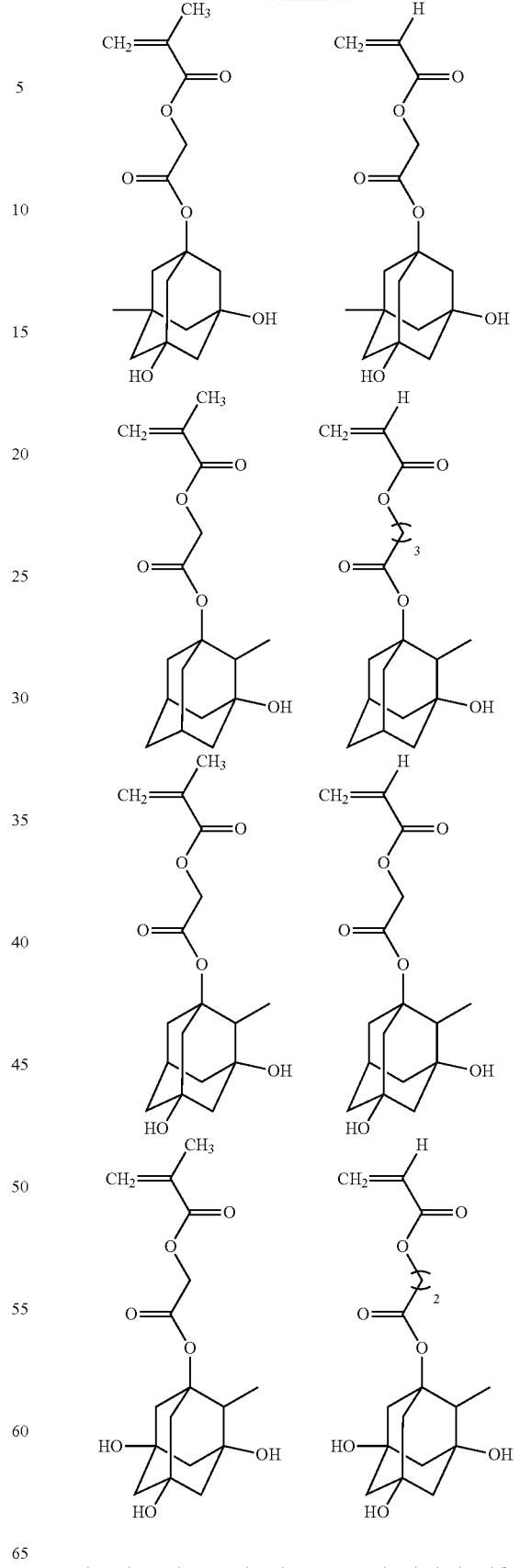
When the resin contains the structural unit derived from the monomer represented by the formula (a2-1), the content of the structural unit derived from the monomer represented by the formula (a2-1) is usually 3 to 45% by mole and preferably 5 to 40% by mole and more preferably 5 to 35% by mole based on total molar of all the structural units of the resin.

Examples of the lactone ring of the compound having no acid-labile group and having a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (a3-1), (a3-2) and (a3-3):

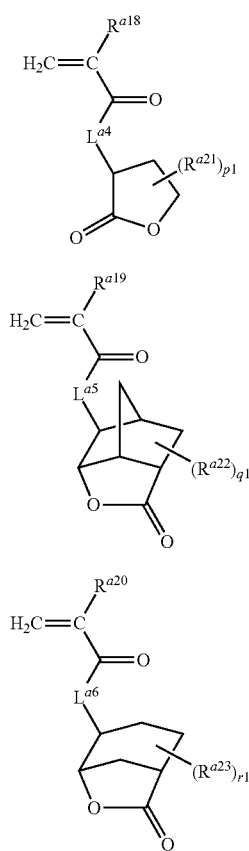

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer represented by the formula (a3-1) include the followings.

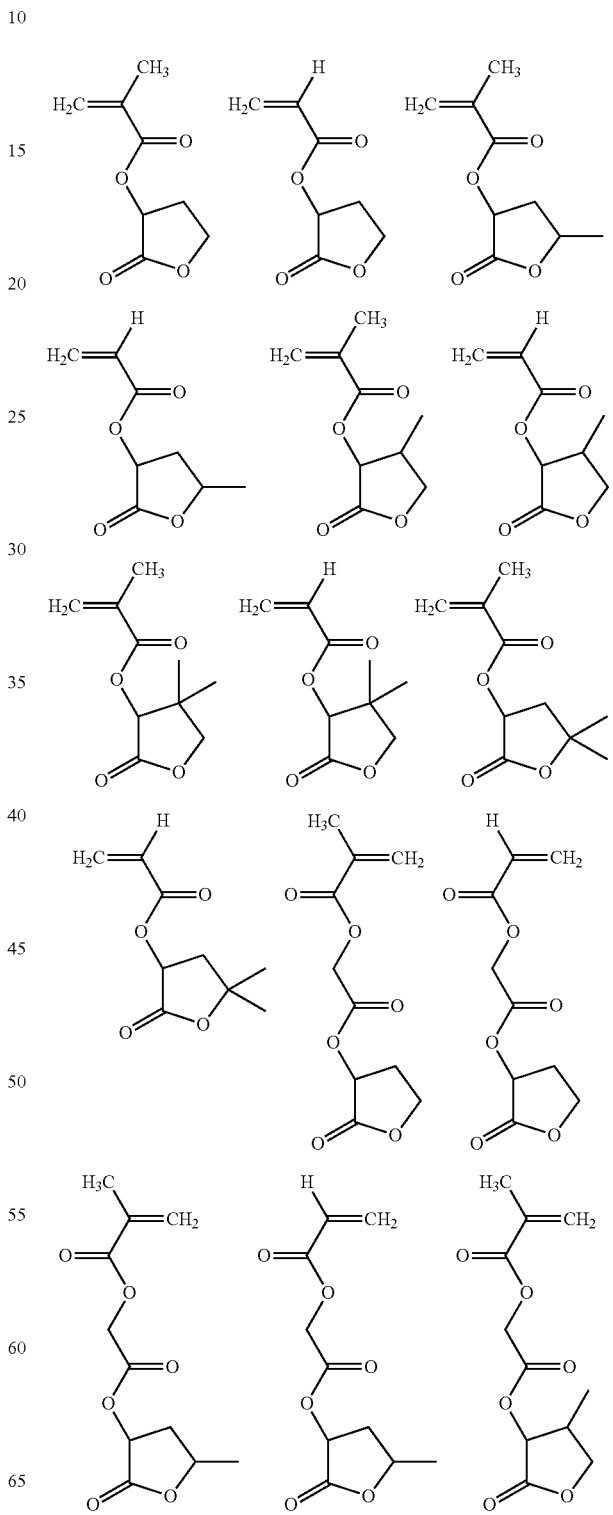

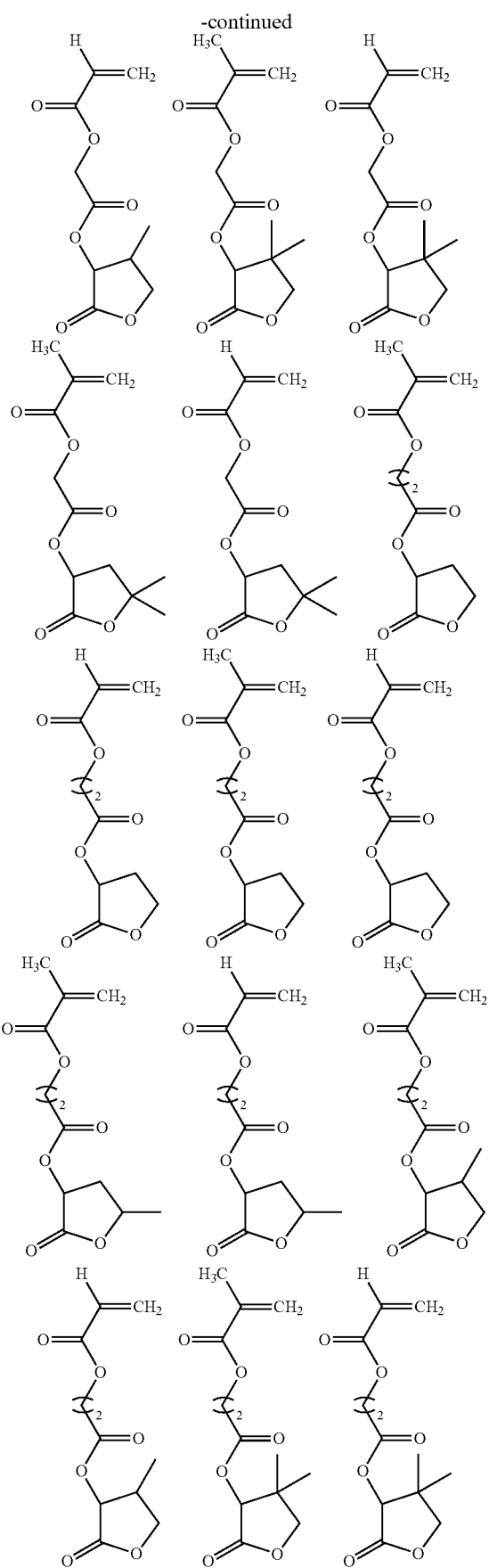
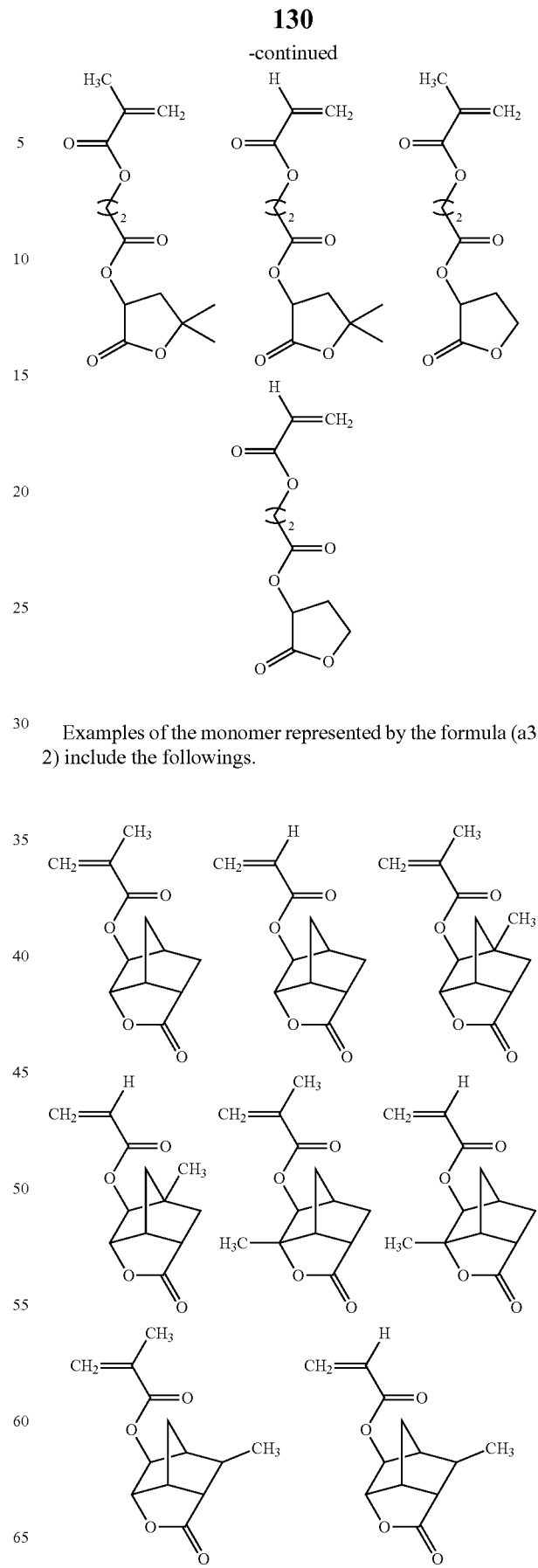
Examples of the monomer represented by the formula (a3-2) include the followings.

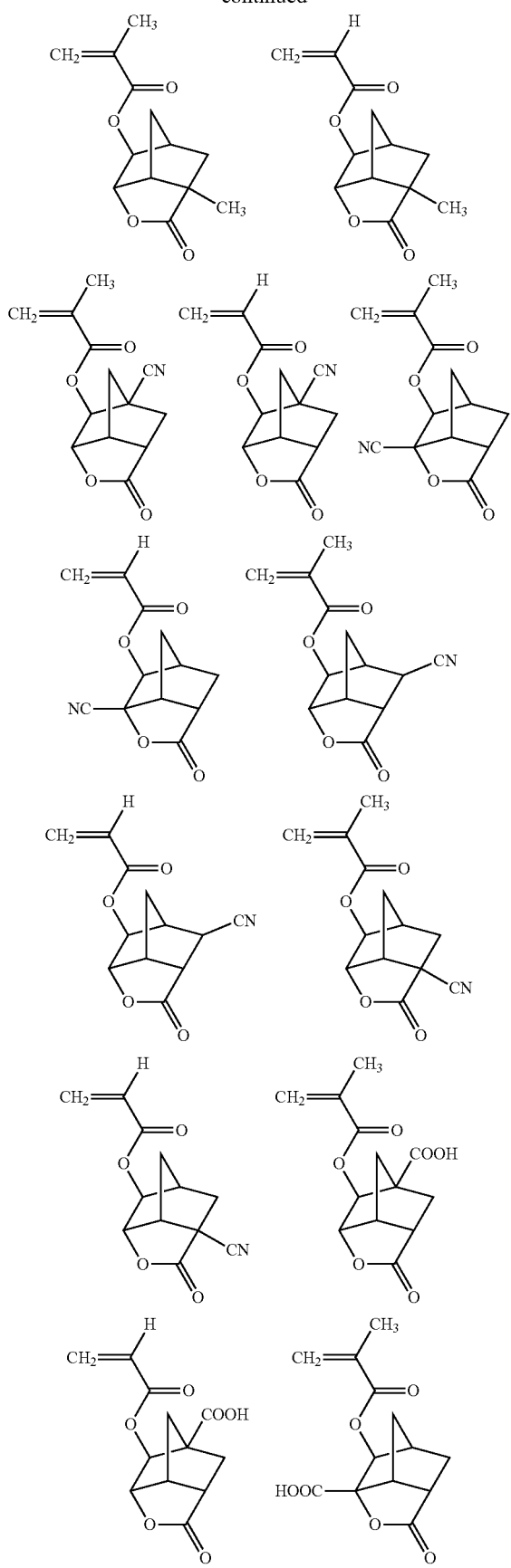
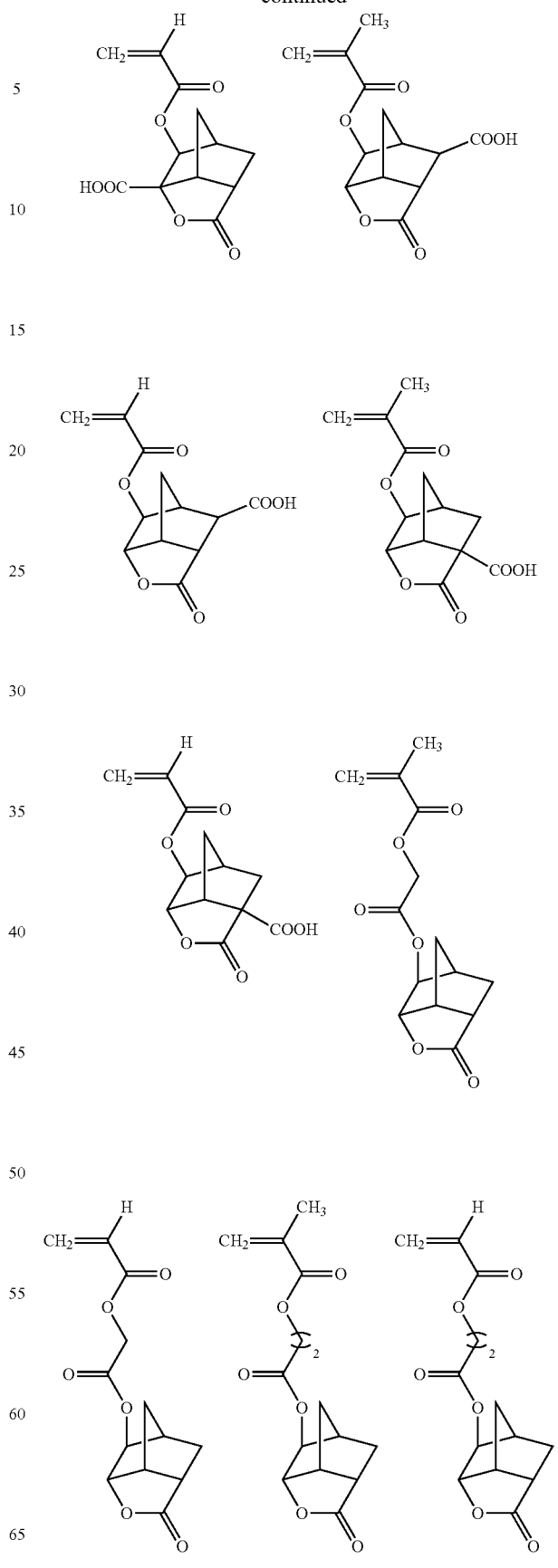

-continued
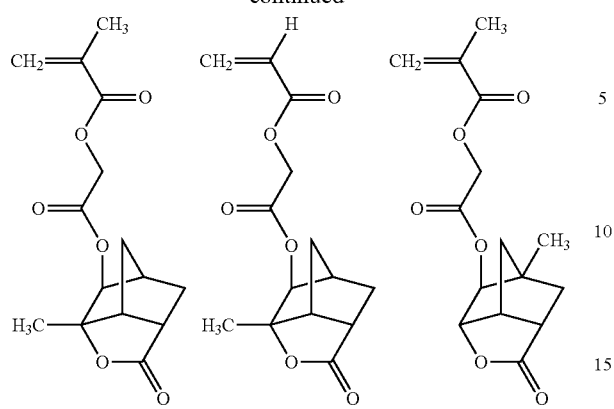
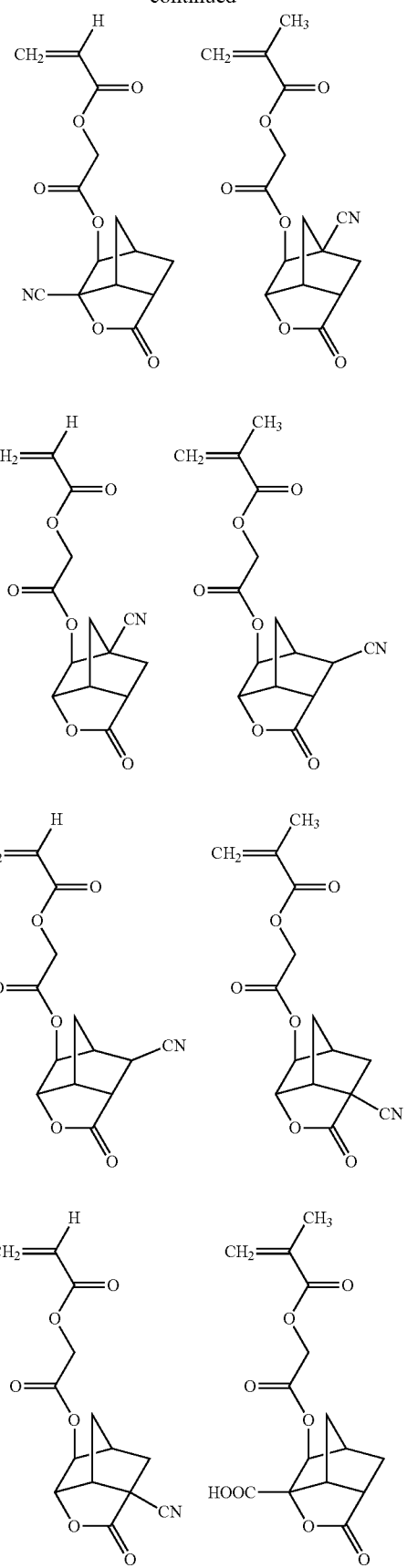

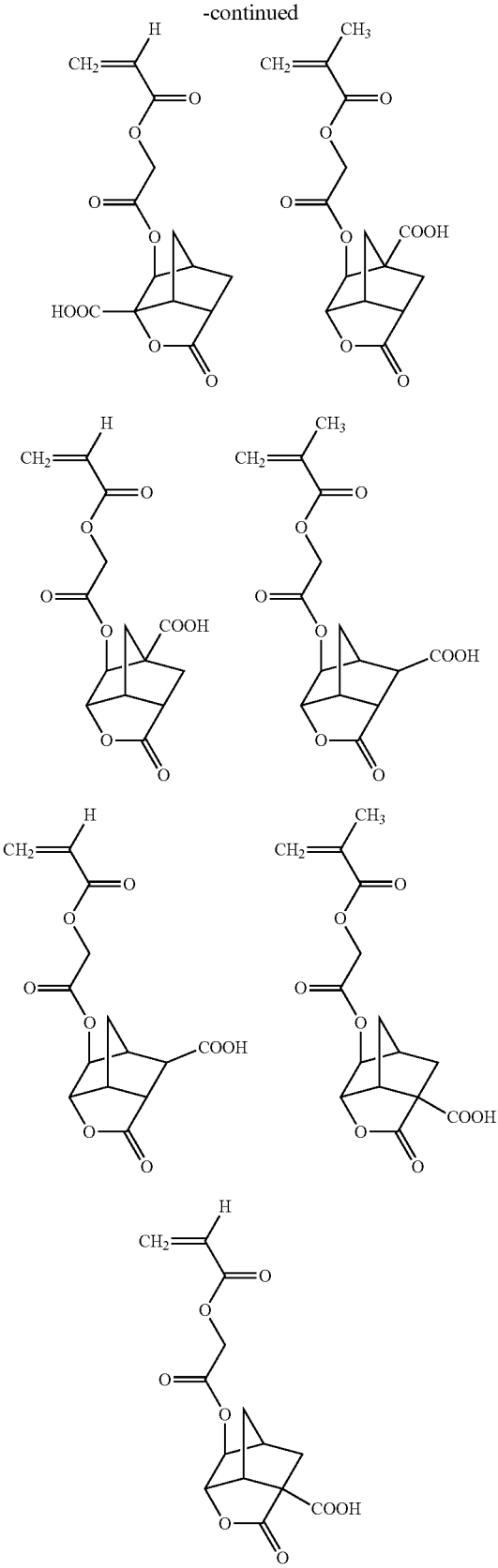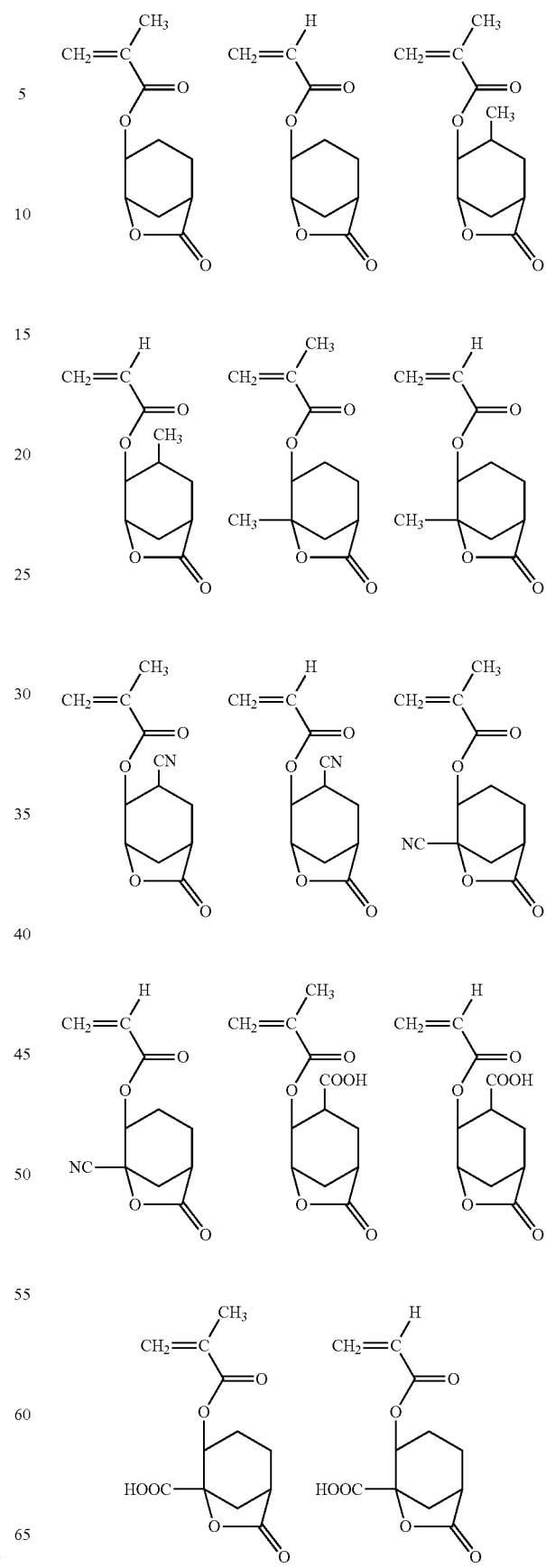
Examples of the monomer represented by the formula (a3-3) include the followings.

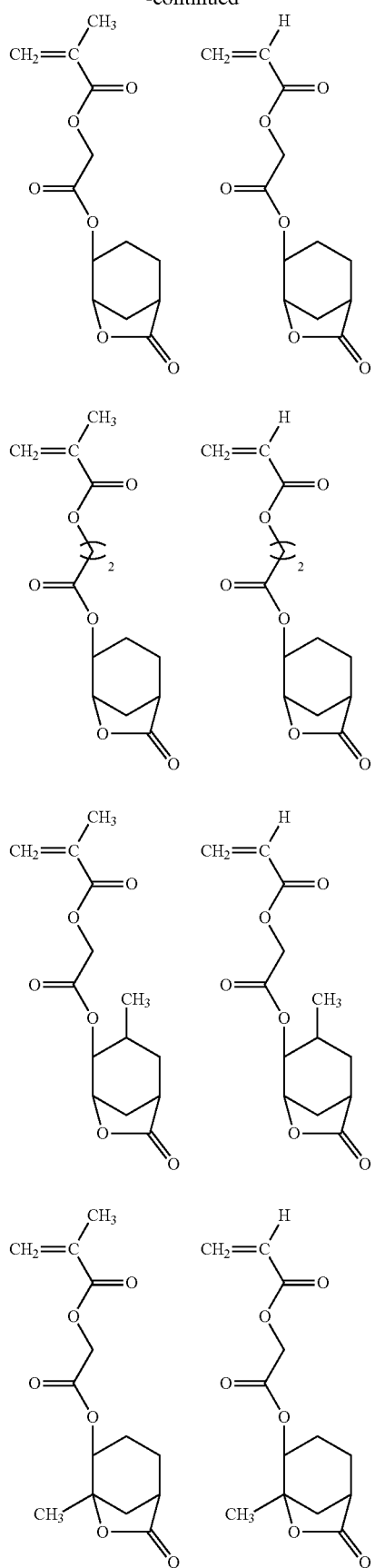
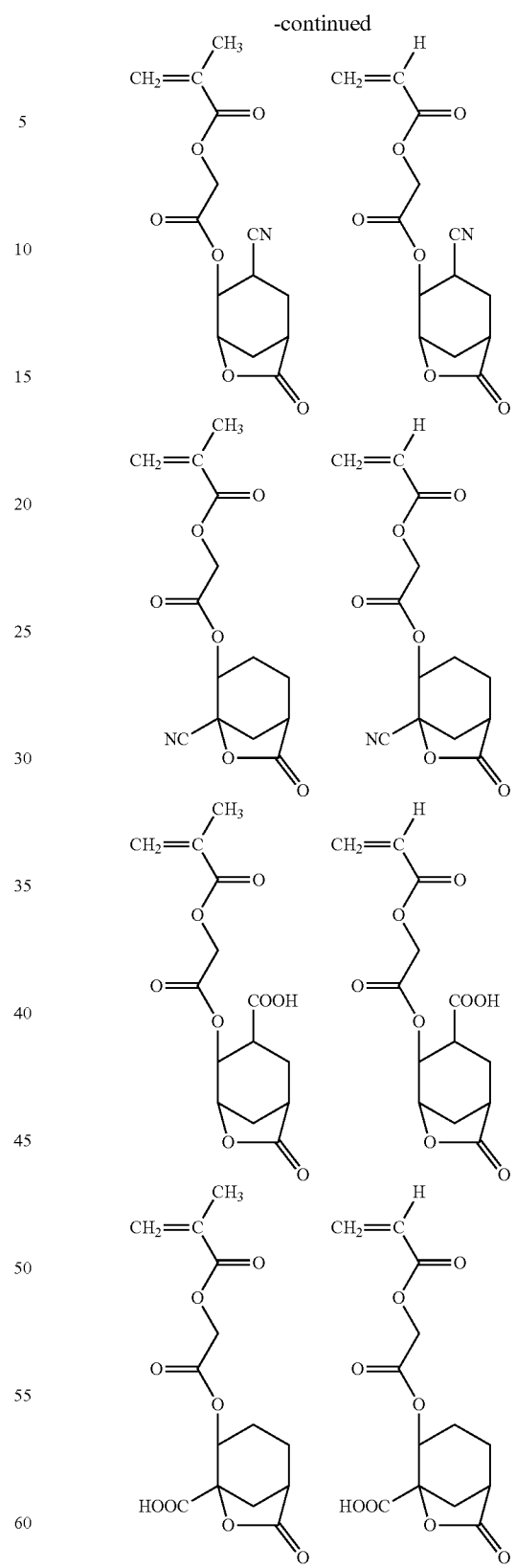
Among them, preferred are 5-oxo-4-oxatricyclo[4.2.1.0³,⁷]nonan-2-yl acrylate, 5-oxo-4-oxatricyclo[4.2.1.0³,⁷]nonan-2-yl methacrylate, tetrahydro-2-oxo-3-furyl acrylate, tetrahydro-2-oxo-3-furyl methacrylate, 2-(5-oxo-4-oxatricyclo

[4.2.1.0³,⁷]nonan-2-yloxy)-2-oxoethyl acrylate and 2-(5-oxo-4-oxatricyclo[4.2.1.0³,⁷]nonan-2-yloxy)-2-oxoethyl methacrylate, and more preferred are 5-oxo-4-oxatricyclo [4.2.1.0³,⁷]nonan-2-yl methacrylate, tetrahydro-2-oxo-3-furyl methacrylate and 2-(5-oxo-4-oxatricyclo[4.2.1.0³,⁷] nonan-2-yloxy)-2-oxoethyl methacrylate.

When the resin contains the structural unit derived from the monomer having no acid-labile group and having a lactone ring, the content thereof is usually 5 to 70% by mole and preferably 10 to 65% by mole and more preferably 10 to 60% by mole based on total molar of all the structural units of the resin.

The resin can contain a structural unit derived from a monomer having an acid labile group containing a lactone ring. Examples of the monomer having an acid labile group containing a lactone ring include the followings.

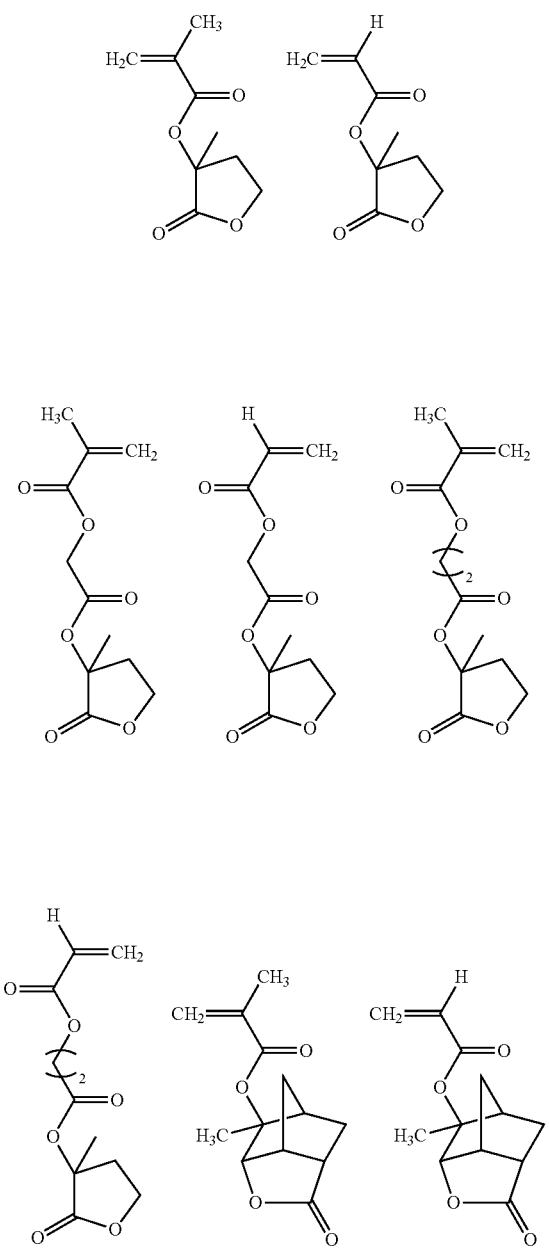

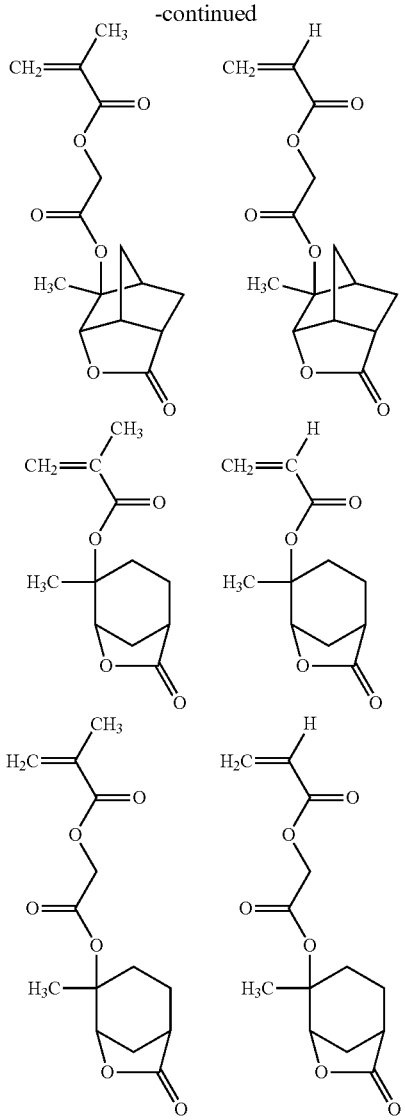

Examples of the other monomer having no acid-labile group include the monomers represented by the formulae (a4-1), (a4-2) and (a4-3):

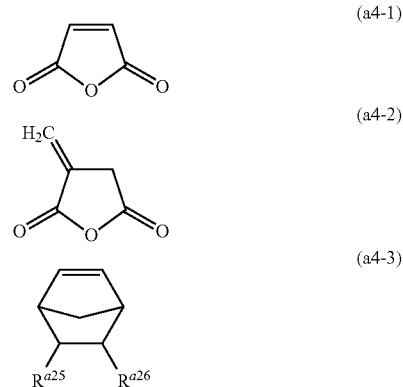

wherein $R^{a25}$ and $R^{a26}$ each independently represents a hydrogen atom, a C1-C3 aliphatic hydrocarbon group which can have one or more substituents, a carboxyl group, a cyano group or a —COOR$^{a27}$ group in which R$^{a27}$ represents a C1-C36 aliphatic hydrocarbon group or a C3-C36 saturated cyclic hydrocarbon group, and one or more —CH$_2$— in the C1-C36 aliphatic hydrocarbon group and the C3-C36 saturated cyclic hydrocarbon group can be replaced by —O— or —CO—, with the proviso that the carbon atom bonded to —O— of —COO— of R$^{a27}$ is not a tertiary carbon atom, or R$^{a25}$ and R$^{a26}$ are bonded together to form a carboxylic anhydride residue represented by —C(=O)OC(=O)—.

Examples of the substituent of the C1-C3 aliphatic hydrocarbon group include a hydroxyl group. Examples of the C1-C3 aliphatic hydrocarbon group which can have one or more substituents include a C1-C3 alkyl group such as a methyl group, an ethyl group and a propyl group, and a C1-C3 hydroxyalkyl group such a hydroxymethyl group and a 2-hydroxyethyl group. The C1-C36 aliphatic hydrocarbon group represented by R$^{a27}$ is preferably a C1-C8 aliphatic hydrocarbon group and is more preferably a C1-C6 aliphatic hydrocarbon group. The C3-C36 saturated cyclic hydrocarbon group represented by R$^{a27}$ is preferably a C4-C36 saturated cyclic hydrocarbon group, and is more preferably C4-C12 saturated cyclic hydrocarbon group. Examples of R$^{a27}$ include a methyl group, an ethyl group, a propyl group, a 2-oxo-oxolan-3-yl group and a 2-oxo-oxolan-4-yl group.

Examples of the monomer represented by the formula (a4-3) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When the resin contains a structural unit derived from a monomer represented by the formula (a4-1), (a4-2) or (a4-3), the content thereof is usually 2 to 40% by mole and preferably 3 to 30% by mole and more preferably 5 to 20% by mole based on total molar of all the structural units of the resin.

Preferable resin is a resin containing the structural units derived from the monomer having an acid-labile group, and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1). The monomer having one or more hydroxyl groups is preferably the monomer represented by the formula (a2-1), and the monomer having a lactone ring is preferably the monomer represented by the formula (a3-1) or (a3-2).

The resin can be produced according to known polymerization methods such as radical polymerization.

The resin usually has 2,500 or more of the weight-average molecular weight, and preferably 3,000 or more of the weight-average molecular weight. The resin usually has 50,000 or less of the weight-average molecular weight, and preferably has 30,000 or less of the weight-average molecular weight. The weight-average molecular weight can be measured with gel permeation chromatography.

The content of the resin is usually 80% by weight or more in the solid component. In this specification, "solid component" means components other than solvents in the photoresist composition. The content of the solid component can be analyzed with conventional means such as liquid chromatography and gas chromatography.

The photoresist composition of the present invention can contain a basic compound as a quencher.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

(C2)

wherein Ar$^{c1}$ represents an aromatic hydrocarbon group, and R$^{c5}$ and R$^{c6}$ each independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

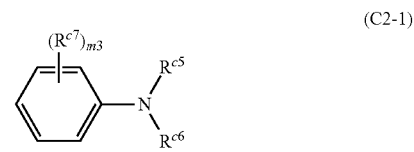

(C2-1)

wherein R$^{c5}$ and R$^{c6}$ are the same as defined above, and R$^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline.

Other examples of the basic compound include amines represented by the formulae (C3) to (C11):

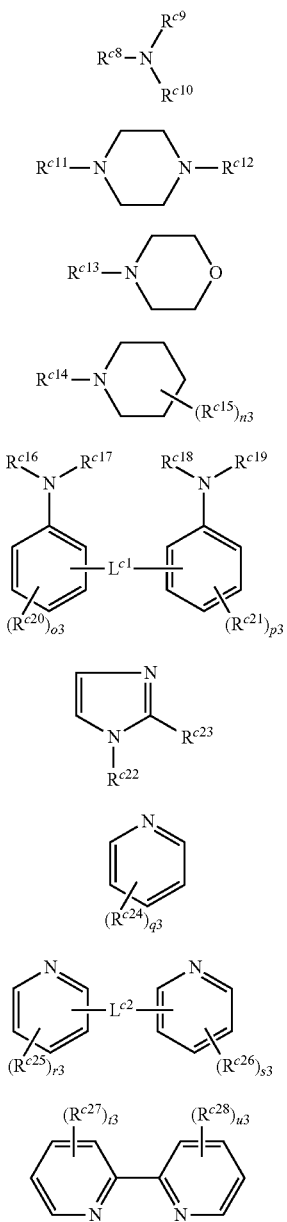

wherein $R^{c8}$, $R^{c20}$, $R^{c21}$, and $R^{c23}$ to $R^{c28}$ each independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c22}$ each independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an aliphatic hydrocarbon group, a saturated cyclic hydrocarbon group or an alkanoyl group, $L^{c1}$ and $L^{c2}$ each independently represents a divalent aliphatic hydrocarbon group, —CO—, —C(=NH)—, —C(=NR$^{c3}$)—, —S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

When the basic compound is used, the amount of the basic compound is usually 0.01 to 1 parts by weight per 100 parts by weight of solid component.

The photoresist composition of the present invention usually contains one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The photoresist composition of the present invention can contain, if necessary, a small amount of various additives such as a sensitizer, a dissolution inhibitor, other polymers, a surfactant, a stabilizer and a dye as long as the effect of the present invention is not prevented.

The photoresist composition of the present invention is useful for a chemically amplified photoresist composition.

A photoresist pattern can be produced by the following steps (1) to (5):

(1) a step of applying the photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having 0.2 μm of a pore size before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammoniumhydroxide (commonly known as "choline") is often used. After development, the photoresist pattern formed is preferably washed with ultrapure water, and the remained water on the photoresist pattern and the substrate is preferably removed.

The photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for ArF immersion lithography, EUV lithography and EB lithography. Furthermore, the photoresist composition of the present invention can also be used in double imaging.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns with guard column): TSKgel Multipore HXL-M, manufactured by TOSOH CORPORATION, Solvent: Tetrahydrofuran, Flow rate: 1.0 mL/min., Detector: RI detector, Column temperature: 40° C., Injection volume: 100 μL] using standard polystyrene as a standard reference material. Mass spectrometry (Liquid Chromatography: 1100 Type, manufactured by AGILENT TECHNOLOGIES LTD., Mass Spectrometry: LC/MSD Type or LC/MSD TOE Type, manufactured by AGILENT TECHNOLOGIES LTD.).

Example 1

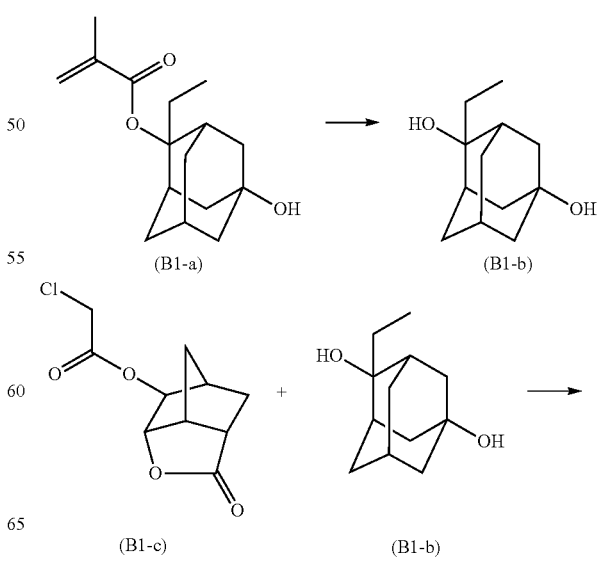

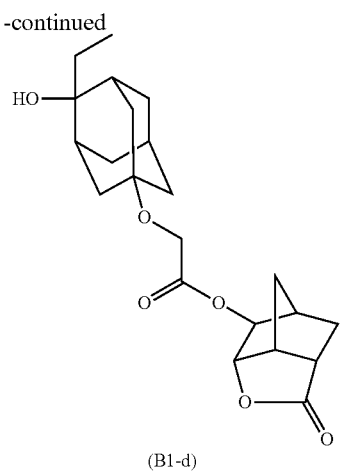

(B1-d)

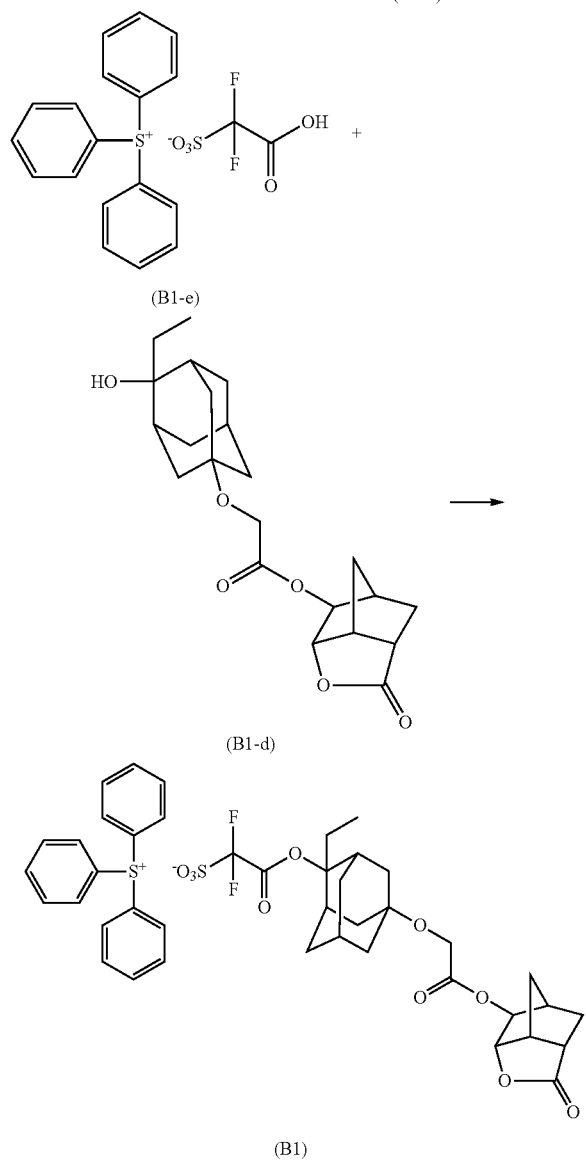

Eighty parts of 1,4-dioxane was mixed with 26.44 parts of a compound represented by the formula (B1-a) which is available from Idemitsu Kosan Co., Ltd. and of which commodity name is HADM. To the resultant mixture, an aqueous solution prepared by dissolving 4.40 parts of sodium hydroxide in 80.00 parts of ion-exchanged water was added dropwise at 23° C. over 30 minutes. The obtained mixture was stirred at 90° C. for 36 hours. The reaction mixture obtained was cooled and then, 400 parts of ion-exchanged water, 500 parts of ethyl acetate and 200 parts of sodium chloride were added thereto to conduct separation. The organic layer obtained was washed three times with 400 parts of ion-exchanged water. The organic layer was concentrated and the residue obtained was purified with silica gel column chromatography (silica gel: silica gel 60-200 mesh available from Merck KGaA, solvent: heptane/ethyl acetate=1/1 (volume ratio)) to obtain 7.89 parts of a compound represented by the formula (B1-b).

A mixture of 4.61 parts of a compound represented by the formula (B1-c) which is available from KURARAY CO., LTD and of which commodity name is CANL, and 25 parts of N,N-dimethylformamide was stirred at 23° C. for 30 minutes. To the mixture, 1.66 parts of potassium carbonate and 0.84 part of potassium iodide were added and the resultant mixture was stirred at 50° C. for 1 hour. The obtained mixture was cooled down to 40° C., and a solution prepared by dissolving 3.93 parts of a compound represented by the formula (B1-b) in 25 parts of N,N-dimethylformamide was added dropwise over 1 hour. The resultant mixture was stirred at 75° C. for 5 hours. The obtained mixture was cooled down to 23° C., and 60 parts of chloroform and 60 parts of 1N hydrochloric acid were added thereto to conduct separation. The organic layer obtained was repeated to wash with 60 parts of ion-exchanged water until the obtained aqueous layer was neutralized. The obtained organic layer was concentrated and the residue obtained was purified with silica gel column chromatography (silica gel: silica gel 60-200 mesh available from Merck KGaA, solvent: ethyl acetate) to obtain 2.24 parts of a compound represented by the formula (B1-d).

A salt represented by the formula (B1-e) was prepared according to the method described in Examples 1 of JP 2008-127367 A1. A mixture of 1.75 parts of the salt represented by the formula (B1-e), 40 parts of monochlorobenzene and 1.87 parts of a compound represented by the formula (B1-d) was stirred at 23° C. for 30 minutes. To the mixture, 0.16 part of sulfuric acid and 10 parts of molecular sieves (Molecular Sieves 4A available from Wako Pure Chemical Industries, Ltd.) were added, and the resultant mixture was refluxed at 130° C. for 3 hours to conduct dehydration. The reaction mixture obtained was concentrated to obtain a residue and to the residue, 100 parts of chloroform and 50 parts of ion-exchanged water to conduct separation. The obtained organic layer was washed three times with ion-exchanged water. To the organic layer, 1 parts of active carbon was added to stir at 23° C. for 30 minutes followed by filtration. The filtrate obtained was concentrated, and to the residue obtained, 20 parts of acetonitrile was added to prepare a solution. The obtained solution was concentrated, and 20 parts of ethyl acetate was added to the obtained residue. The resultant mixture was stirred and then, the supernatant solution was removed from the mixture. The obtained residue was dissolved in chloroform, and the obtained solution was concentrated to obtain 0.44 part of a salt represented by the formula (B1) in the form of oil. This is called as Salt B1.

MS (ESI(+) Spectrum): $M^+$ 263.1

MS (ESI(−) Spectrum): $M^-$ 547.2

Example 2

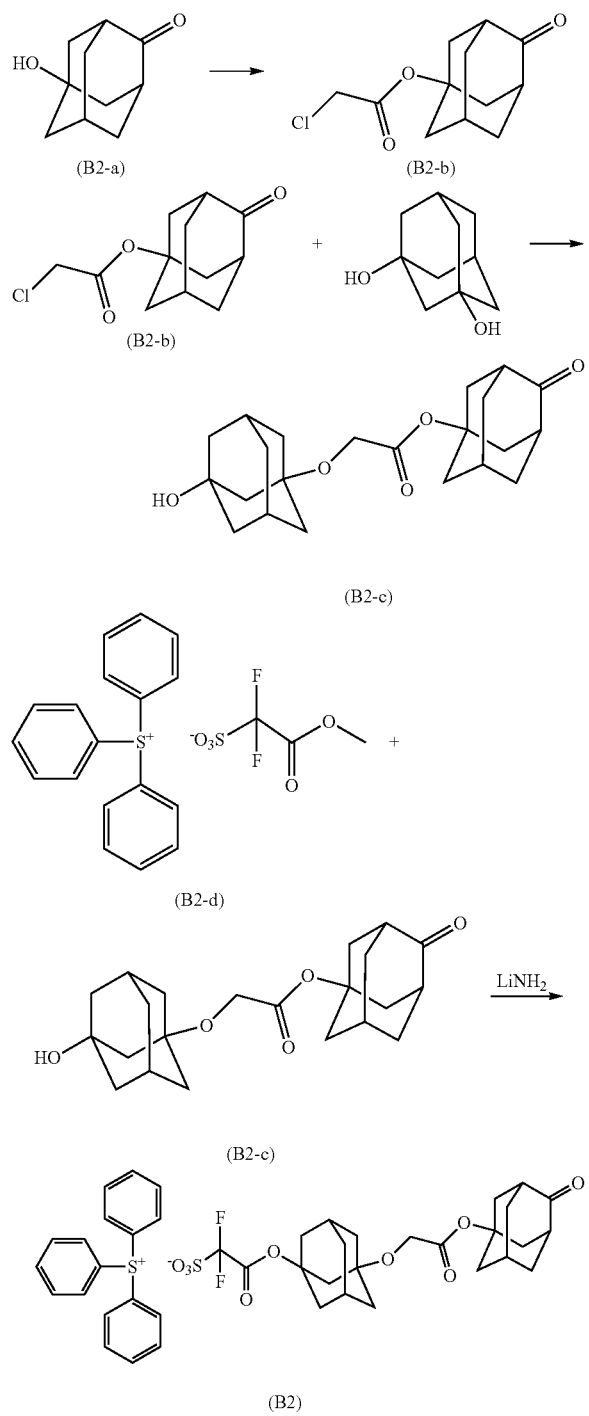

The mixture of 200 parts of tetrahydrofuran and 25.00 parts of a compound represented by the formula (B2-a) was stirred at room temperature. After confirming the dissolution of the compound represented by the formula (B2-a) in tetrahydrofuran, 14.27 parts of pyridine was added thereto. The resultant mixture was heated up to 40° C., and then, a mixture of 25.47 parts of chloroacetyl chloride and 50 parts of tetrahydrofuran was added dropwise thereto over 1 hour. The resultant mixture was stirred at 40° C. for 8 hours, and then, cooled down to 5° C. To the mixture obtained, 100 parts of ion-exchanged water at 0° C. was added to conduct separation. The obtained aqueous layer was extracted with 65 parts of ethyl acetate, and the obtained organic layer was washed with 65 parts of aqueous 10% potassium carbonate solution. The obtained organic layer was further washed three times with 65 parts of ion-exchanged water. The organic layer was concentrated and the residue obtained was purified with silica gel column chromatography (silica gel: silica gel 60-200 mesh available from Merck KGaA, solvent: heptane/ethyl acetate=2/1) to obtain 16.91 parts of a compound represented by the formula (B2-b).

A mixture of 4.84 parts of a compound represented by the formula (B2-b) and 25 parts of N,N-dimethylformamide was stirred at 23° C. for 30 minutes. To the mixture, 1.66 parts of potassium carbonate and 0.84 part of potassium iodide were added, and the resultant mixture was stirred at 50° C. for 1 hour. The obtained mixture was cooled down to 40° C., and a solution prepared by dissolving 3.31 parts of 1,3-adamantanediol in 25 parts of N,N-dimethylformamide was added dropwise over 1 hour. The resultant mixture was stirred at 75° C. for 5 hours. The obtained mixture was cooled down to 23° C., and 60 parts of chloroform and 60 parts of 1N hydrochloric acid were added thereto to conduct separation. The organic layer obtained was repeated to wash with 60 parts of ion-exchanged water until the obtained aqueous layer was neutralized. The obtained organic layer was concentrated and the residue obtained was purified with silica gel column chromatography (silica gel: silica gel 60-200 mesh available from Merck KGaA, solvent: ethyl acetate) to obtain 2.85 parts of a compound represented by the formula (B2-c).

A salt represented by the formula (B2-d) was prepared according to the method described in JP 2008-13551 A1. A mixture of 2.26 parts of the salt represented by the formula (B2-d), 15 parts of chloroform, 2.25 parts of a compound represented by the formula (B2-c), 2.5 parts of molecular sieves (Molecular Sieves 5A available from Wako Pure Chemical Industries, Ltd.) and 0.07 part of lithium amide was stirred at 80° C. for 24 hours. The obtained mixture was filtrated, and 0.14 part of oxalic acid and 5 parts of ion-exchanged water were added to the filtrate obtained to conduct separation. The obtained organic layer was washed six times with ion-exchanged water. To the organic layer, 1 parts of active carbon was added to stir at 23° C. for 30 minutes followed by filtration. The filtrate obtained was concentrated, and to the residue obtained, 5 parts of acetonitrile was added to prepare a solution. The obtained solution was concentrated, and 10 parts of ethyl acetate was added to the obtained residue. The resultant mixture was stirred and then, the supernatant solution was removed from the mixture. To the obtained residue, 10 parts of tert-butyl methyl ether was added. The resultant mixture was stirred and then, the supernatant solution was removed from the mixture. The obtained residue was dissolved in chloroform, and the obtained solution was concentrated to obtain a residue. The residue was purified with silica gel column chromatography (silica gel: silica gel 60-200 mesh available from Merck KGaA, solvent: chloroform/methanol=5/1) to obtain 0.11 part of a salt represented by the formula (B2). This is called as Salt B2.

MS (ESI(+) Spectrum): $M^+$ 263.1
MS (ESI(−) Spectrum): $M^-$ 531.2

Example 3

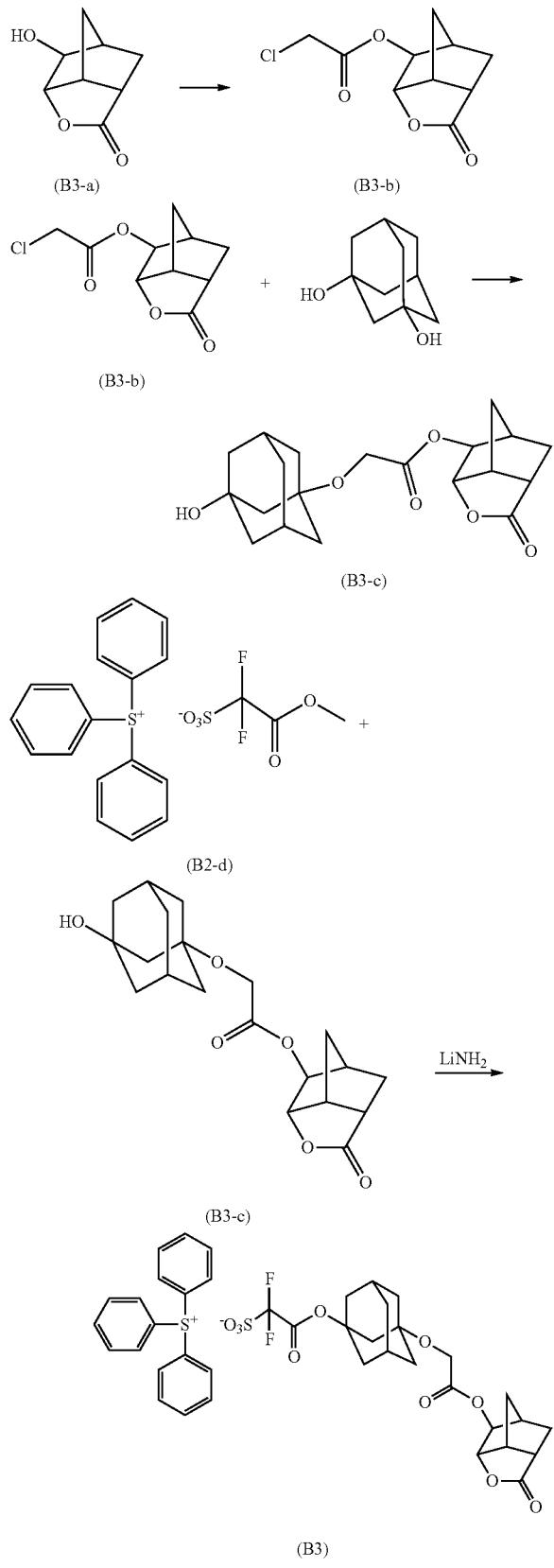

The mixture of 200 parts of tetrahydrofuran and 23.19 parts of a compound represented by the formula (B3-a) was stirred at room temperature. After confirming the dissolution of the compound represented by the formula (B3-a) in tetrahydrofuran, 14.27 parts of pyridine was added thereto. The resultant mixture was heated up to 40° C., and then, a mixture of 25.47 parts of chloroacetyl chloride and 50 parts of tetrahydrofuran was added dropwise thereto over 1 hour. The resultant mixture was stirred at 40° C. for 8 hours, and then, cooled down to 5° C. To the mixture obtained, 100 parts of ion-exchanged water at 0° C. was added to conduct separation. The obtained aqueous layer was extracted with 65 parts of ethyl acetate, and the obtained organic layer was washed with 65 parts of aqueous 10% potassium carbonate solution at 5° C. The obtained organic layer was further washed three times with 65 parts of ion-exchanged water. The organic layer was concentrated and the residue obtained was purified with silica gel column chromatography (silica gel: silica gel 60-200 mesh available from Merck KGaA, solvent: heptane/ethyl acetate=2/1) to obtain 14.69 parts of a compound represented by the formula (B3-b).

A mixture of 4.60 parts of a compound represented by the formula (B3-b) and 25 parts of N,N-dimethylformamide was stirred at 23° C. for 30 minutes. To the mixture, 1.66 parts of potassium carbonate and 0.84 part of potassium iodide were added, and the resultant mixture was stirred at 50° C. for 1 hour. The obtained mixture was cooled down to 40° C., and a solution prepared by dissolving 3.31 parts of 1,3-adamantanediol in 25 parts of N,N-dimethylformamide was added dropwise over 1 hour. The resultant mixture was stirred at 75° C. for 5 hours. The obtained mixture was cooled down to 23° C., and 60 parts of chloroform and 60 parts of 1N hydrochloric acid were added thereto to conduct separation. The organic layer obtained was repeated to wash with 60 parts of ion-exchanged water until the obtained aqueous layer was neutralized. The obtained organic layer was concentrated and the residue obtained was purified with silica gel column chromatography (silica gel: silica gel 60-200 mesh available from Merck KGaA, solvent: ethyl acetate) to obtain 2.21 parts of a compound represented by the formula (B3-c).

A salt represented by the formula (B2-d) was prepared according to the method described in JP 2008-13551 A1. A mixture of 2.26 parts of the salt represented by the formula (B2-d), 15 parts of chloroform, 2.18 parts of a compound represented by the formula (B3-c), 2.5 parts of molecular sieves (Molecular Sieves 5A available from Wako Pure Chemical Industries, Ltd.) and 0.07 part of lithium amide was stirred at 80° C. for 24 hours. The obtained mixture was filtrated, and 0.14 part of oxalic acid and 5 parts of ion-exchanged water were added to the filtrate obtained to conduct separation. The obtained organic layer was washed six times with ion-exchanged water. To the organic layer, 1 parts of active carbon was added to stir at 23° C. for 30 minutes followed by filtration. The filtrate obtained was concentrated, and to the residue obtained, 5 parts of acetonitrile was added to prepare a solution. The obtained solution was concentrated, and 10 parts of ethyl acetate was added to the obtained residue. The resultant mixture was stirred and then, the supernatant solution was removed from the mixture. To the obtained residue, 10 parts of tert-butyl methyl ether was added. The resultant mixture was stirred and then, the supernatant solution was removed from the mixture. The obtained residue was dissolved in chloroform, and the obtained solution was concentrated to obtain a residue. The residue was purified with silica gel column chromatography (silica gel: silica gel 60-200 mesh available from Merck KGaA, solvent: chloroform/methanol=5/1) to obtain 0.11 part of a salt represented by the formula (B3). This is called as Salt B3.

MS (ESI(+) Spectrum): M$^+$ 263.1
MS (ESI(−) Spectrum): M$^-$ 519.1

Example 4

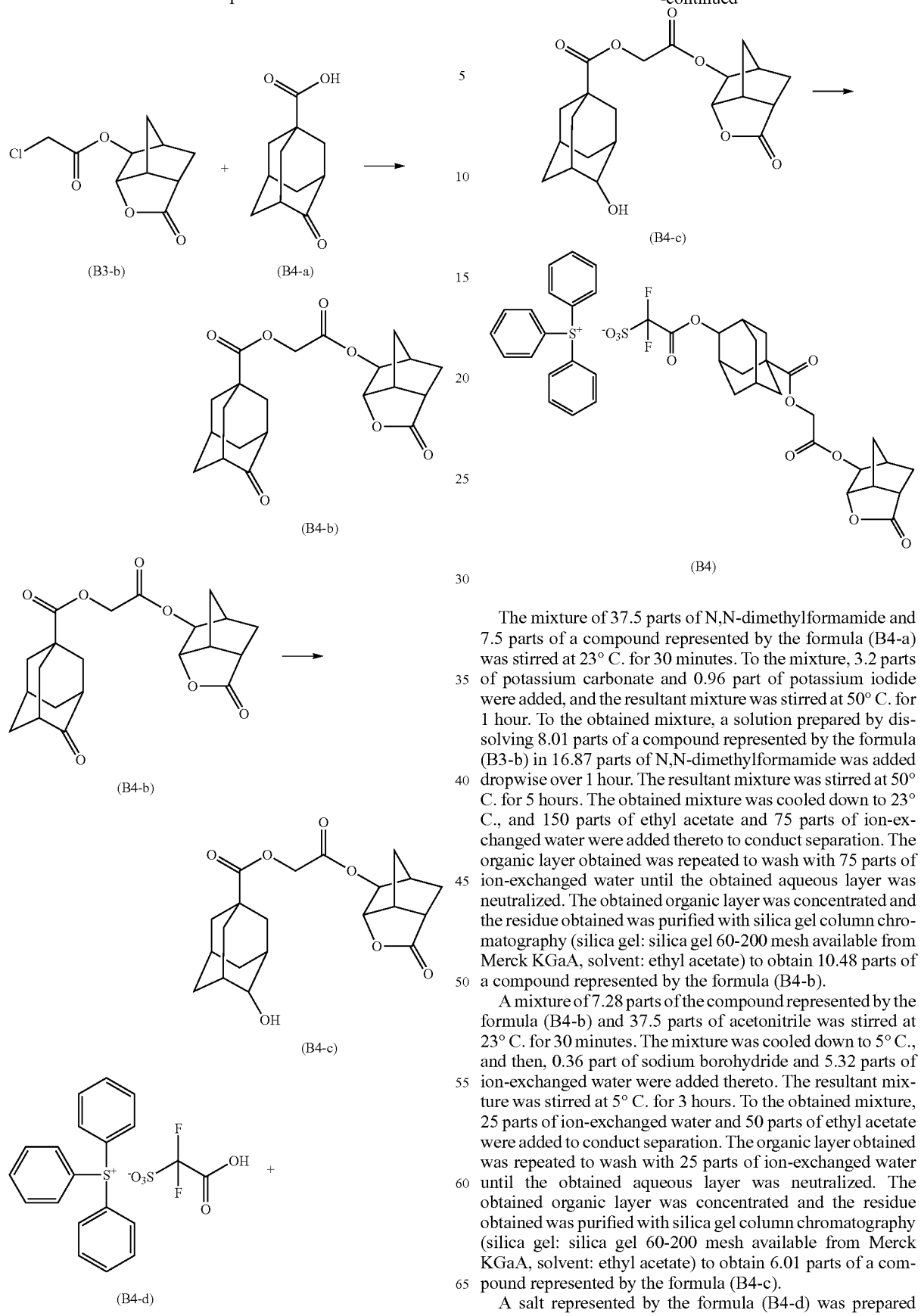

The mixture of 37.5 parts of N,N-dimethylformamide and 7.5 parts of a compound represented by the formula (B4-a) was stirred at 23° C. for 30 minutes. To the mixture, 3.2 parts of potassium carbonate and 0.96 part of potassium iodide were added, and the resultant mixture was stirred at 50° C. for 1 hour. To the obtained mixture, a solution prepared by dissolving 8.01 parts of a compound represented by the formula (B3-b) in 16.87 parts of N,N-dimethylformamide was added dropwise over 1 hour. The resultant mixture was stirred at 50° C. for 5 hours. The obtained mixture was cooled down to 23° C., and 150 parts of ethyl acetate and 75 parts of ion-exchanged water were added thereto to conduct separation. The organic layer obtained was repeated to wash with 75 parts of ion-exchanged water until the obtained aqueous layer was neutralized. The obtained organic layer was concentrated and the residue obtained was purified with silica gel column chromatography (silica gel: silica gel 60-200 mesh available from Merck KGaA, solvent: ethyl acetate) to obtain 10.48 parts of a compound represented by the formula (B4-b).

A mixture of 7.28 parts of the compound represented by the formula (B4-b) and 37.5 parts of acetonitrile was stirred at 23° C. for 30 minutes. The mixture was cooled down to 5° C., and then, 0.36 part of sodium borohydride and 5.32 parts of ion-exchanged water were added thereto. The resultant mixture was stirred at 5° C. for 3 hours. To the obtained mixture, 25 parts of ion-exchanged water and 50 parts of ethyl acetate were added to conduct separation. The organic layer obtained was repeated to wash with 25 parts of ion-exchanged water until the obtained aqueous layer was neutralized. The obtained organic layer was concentrated and the residue obtained was purified with silica gel column chromatography (silica gel: silica gel 60-200 mesh available from Merck KGaA, solvent: ethyl acetate) to obtain 6.01 parts of a compound represented by the formula (B4-c).

A salt represented by the formula (B4-d) was prepared according to the method described in JP 2008-127367 A1. A mixture of 2.19 parts of the salt represented by the formula (B4-d), 50 parts of monochlorobenzene and 2.34 parts of a compound represented by the formula (B4-c) was stirred at 23° C. for 30 minutes. To the obtained mixture, 0.2 part of sulfuric acid and 10 parts of molecular sieves (Molecular Sieves 4A available from Wako Pure Chemical Industries, Ltd.) were added thereto. The obtained mixture was refluxed at 130° C. for 3 hours to conduct dehydration. The obtained mixture was concentrated, and 50 parts of ion-exchanged water and 100 parts of chloroform were added thereto to conduct separation. The organic layer obtained was washed five times with ion-exchanged water, and then, 1 parts of active carbon was added thereto to stir at 23° C. for 30 minutes followed by filtration. The filtrate obtained was concentrated, and to the residue obtained, 25 parts of acetonitrile was added to prepare a solution. The obtained solution was concentrated, and 25 parts of ethyl acetate was added to the obtained residue. The resultant mixture was stirred and then, the supernatant solution was removed from the mixture. To the obtained residue, 25 parts of tert-butyl methyl ether was added. The resultant mixture was stirred and then, the supernatant solution was removed from the mixture. The obtained residue was dissolved in chloroform, and the obtained solution was concentrated to obtain a residue. The residue was purified with silica gel column chromatography (silica gel: silica gel 60-200 mesh available from Merck KGaA, solvent: chloroform/methanol=5/1) to obtain 1.84 part of a salt represented by the formula (B4). This is called as Salt B4.

MS (ESI(+) Spectrum): M⁺ 263.1
MS (ESI(−) Spectrum): M⁻ 547.1

Example 5

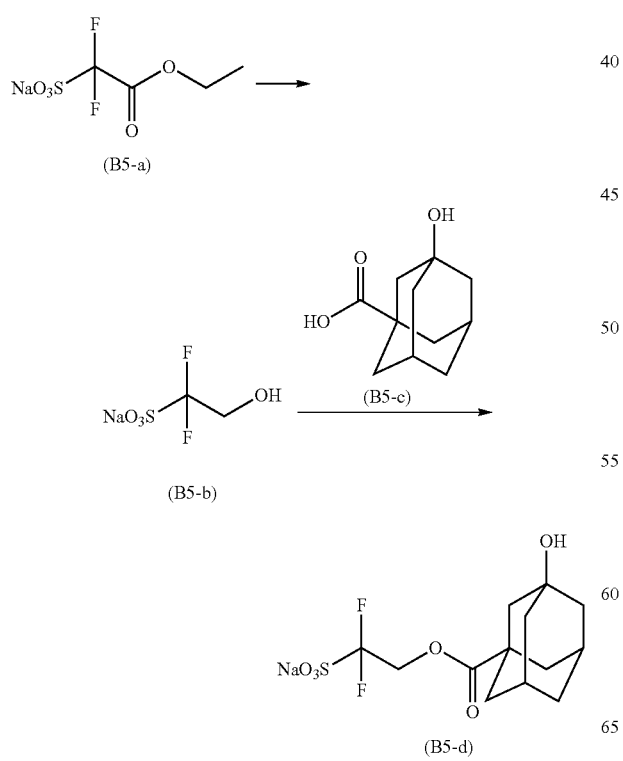
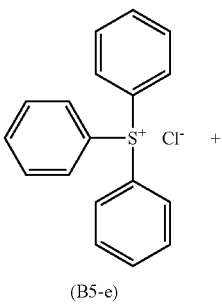
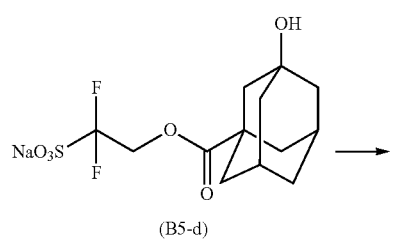
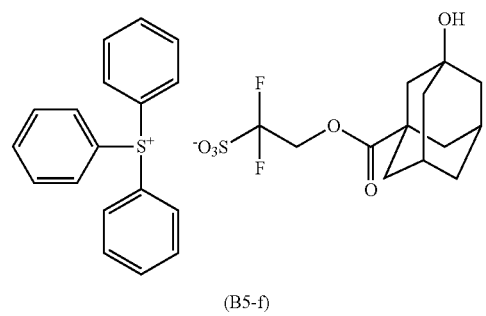
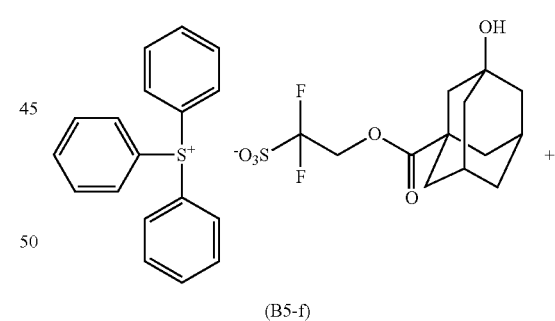
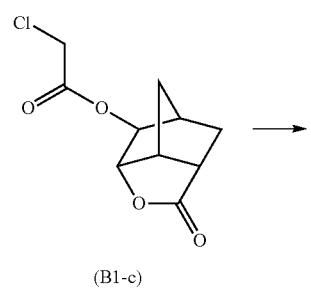

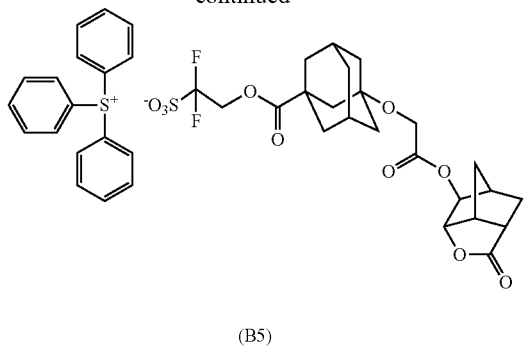

(B5)

The mixture of 10.4 parts of lithium aluminum hydride and 120 parts of anhydrous tetrahydrofuran was stirred at 23° C. for 30 minutes. To the mixture, a solution prepared by dissolving 62.2 parts of a compound represented by the formula (B5-a) in 900 parts of tetrahydrofuran was added dropwise under cooling with ice-bath, and the resultant mixture was stirred at 23° C. for 5 hours. To the obtained reaction mixture, 50 parts of ethyl acetate and 50 parts of 6N hydrochloric acid were added to conduct separation. The organic layer obtained was concentrated and the residue obtained was purified with silica gel column chromatography (silica gel: silica gel 60-200 mesh available from Merck KGaA, solvent: chloroform/methanol=5/1) to obtain 84.7 parts of a compound represented by the formula (B5-b) of which purity was 60%.

A mixture of 3.51 parts of a compound represented by the formula (B5-c) and 75 parts of anhydrous tetrahydrofuran was stirred at 23° C. for 30 minutes. To the mixture, a solution prepared by dissolving 2.89 parts of carbonyldiimidazole in 50 parts of anhydrous tetrahydrofuran was added dropwise at 23° C., and then, the resultant mixture was stirred at 23° C. for 4 hours. The obtained mixture was added dropwise into a mixture of 6.04 parts of the compound represented by the formula (B5-b) of which purity was 60% and 50 parts of anhydrous tetrahydrofuran, at 54 to 60° C. over 25 minutes. The resultant mixture was stirred at 65° C. for 18 hours, and then, cooled followed by filtration. The filtrate was concentrated and the residue obtained was purified with silica gel column chromatography (silica gel: silica gel 60-200 mesh available from Merck KGaA, solvent: chloroform/methanol=5/1) to obtain 2.99 parts of a compound represented by the formula (B5-d).

A mixture of 1 part of the compound represented by the formula (B5-d) and 30 parts of chloroform was stirred at 23° C. for 30 minutes. To the mixture, 0.83 parts of a salt represented by the formula (B5-e) was added, and then, the resultant mixture was stirred at 23° C. for 12 hours followed by conducting separation. The obtained organic layer was washed three times with 10 parts of ion-exchanged water, and then, 1 parts of active carbon was added thereto to stir at 23° C. for 30 minutes followed by filtration. The filtrate obtained was concentrated, and to the residue obtained, 20 parts of acetonitrile was added to prepare a solution. The obtained solution was concentrated, and 20 parts of ethyl acetate was added to the obtained residue. The resultant mixture was stirred and then, the supernatant solution was removed from the mixture. To the obtained residue, 20 parts of tert-butyl methyl ether was added. The resultant mixture was stirred and then, the supernatant solution was removed from the mixture. The obtained residue was dissolved in chloroform, and the obtained solution was concentrated to obtain a residue. The residue was purified with silica gel column chromatography (silica gel: silica gel 60-200 mesh available from Merck KGaA, solvent: chloroform/methanol=5/1) to obtain 0.69 part of a salt represented by the formula (B5-f).

A mixture of 0.69 part of the salt represented by the formula (B5-f) and 10 parts of N,N-dimethylformamide was stirred at 23° C. for 30 minutes. To the obtained mixture, 0.09 part of potassium carbonate and 0.05 part of potassium iodide were added. The obtained mixture was stirred at 50° C. for 1 hour. The resultant mixture was cooled down to 40° C., and then, a solution prepared by dissolving 0.26 part of a compound represented by the formula (B1-c) in 5 parts of N,N-dimethylformamide was added dropwise thereto over 1 hour. The obtained mixture was stirred at 75° C. for 3 hours and then, cooled down to 23° C. To the obtained reaction mixture, 30 parts of chloroform and 10 parts of ion-exchanged water were added to conduct separation. The organic layer obtained was repeated to wash until the obtained aqueous layer was neutralized. The obtained organic layer was concentrated, and the residue obtained was purified with silica gel column chromatography (silica gel: silica gel 60-200 mesh available from Merck KGaA, solvent: chloroform/methanol=5/1) to obtain 0.22 part of a salt represented by the formula (B5). This is called as Salt B5.

MS (ESI(+) Spectrum): M+ 263.1
MS (ESI(−) Spectrum): M− 533.1

Examples 6

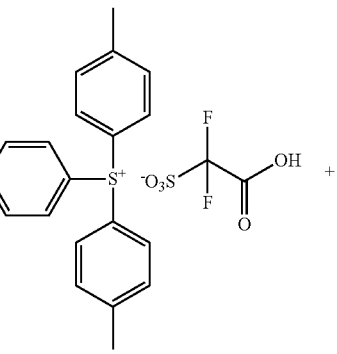

(B6-a)

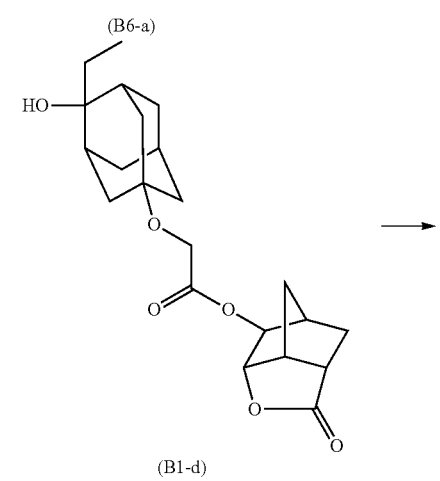

(B1-d)

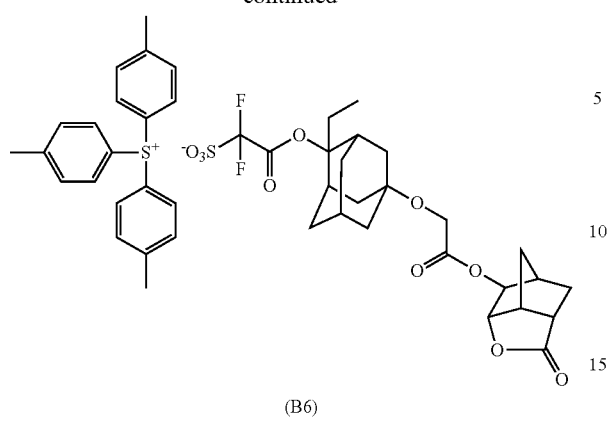

(B6)

A mixture of 2.40 parts of a salt represented by the formula (B6-a), 50 parts of monochlorobenzene and 2.34 parts of a compound represented by the formula (B1-d) was stirred at 23° C. for 30 minutes. To the obtained mixture, 0.2 part of sulfuric acid and 10 parts of molecular sieves (Molecular Sieves 4A available from Wako Pure Chemical Industries, Ltd.) were added thereto. The obtained mixture was refluxed at 130° C. for 3 hours to conduct dehydration. The obtained mixture was concentrated, and 50 parts of ion-exchanged water and 100 parts of chloroform were added thereto to conduct separation. The organic layer obtained was washed three times with ion-exchanged water, and then, 1 parts of active carbon was added thereto to stir at 23° C. for 30 minutes followed by filtration. The filtrate obtained was concentrated, and to the residue obtained, 20 parts of acetonitrile was added to prepare a solution. The obtained solution was concentrated, and 20 parts of ethyl acetate was added to the obtained residue. The resultant mixture was stirred and then, the supernatant solution was removed from the mixture. To the obtained residue, 20 parts of tert-butyl methyl ether was added. The resultant mixture was stirred and then, the supernatant solution was removed from the mixture. The obtained residue was dissolved in chloroform, and the obtained solution was concentrated to obtain 1.21 part of a salt represented by the formula (B6). This is called as Salt B6.

MS (ESI(+) Spectrum): M$^+$ 305.1

MS (ESI(−) Spectrum): M$^-$ 547.2

Example 7

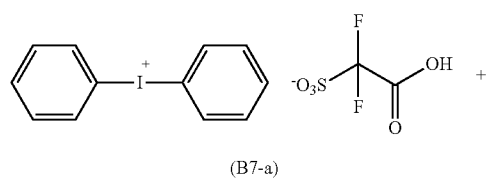

(B7-a)

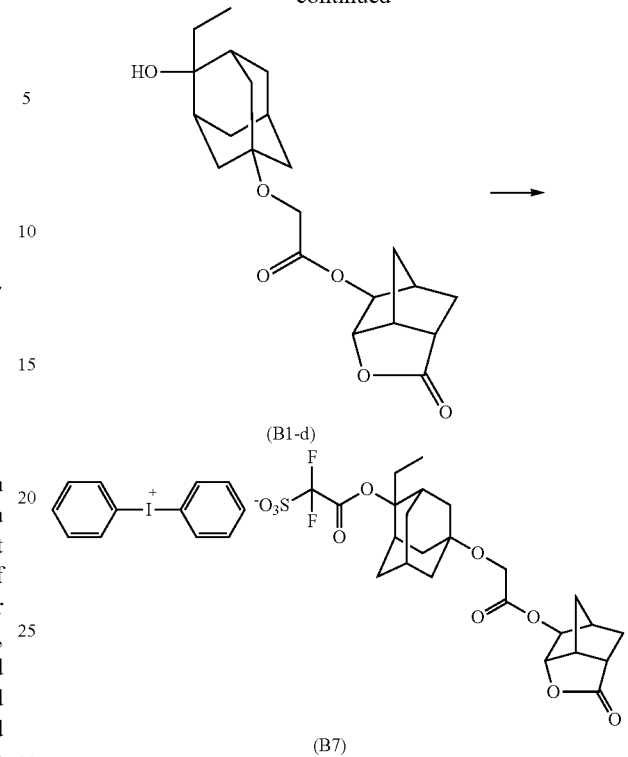

(B1-d)

(B7)

A mixture of 2.28 parts of a salt represented by the formula (B7-a), 50 parts of monochlorobenzene and 2.34 parts of a compound represented by the formula (B1-d) was stirred at 23° C. for 30 minutes. To the obtained mixture, 0.2 part of sulfuric acid and 10 parts of molecular sieves (Molecular Sieves 4A available from Wako Pure Chemical Industries, Ltd.) were added thereto. The obtained mixture was refluxed at 130° C. for 3 hours to conduct dehydration. The obtained mixture was concentrated, and 50 parts of ion-exchanged water and 100 parts of chloroform were added thereto to conduct separation. The organic layer obtained was washed three times with ion-exchanged water, and then, 1 parts of active carbon was added thereto to stir at 23° C. for 30 minutes followed by filtration. The filtrate obtained was concentrated, and the obtained residue was purified with silica gel column chromatography (silica gel: silica gel 60-200 mesh available from Merck KGaA, solvent: chloroform/methanol=5/1) to obtain 0.29 part of a salt represented by the formula (B7). This is called as Salt B7.

MS (ESI(+) Spectrum): M$^+$ 281.0

MS (ESI(−) Spectrum): M$^-$ 547.2

Example 8

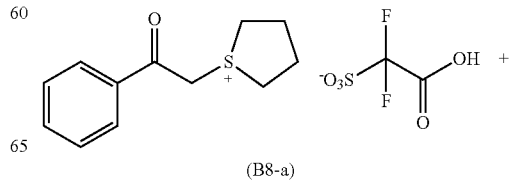

(B8-a)

-continued

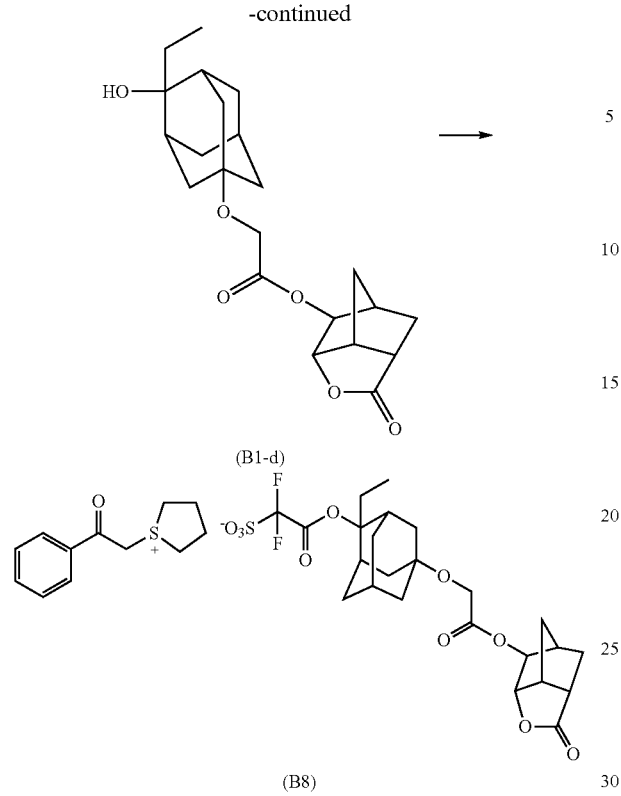

A mixture of 1.91 parts of a salt represented by the formula (B8-a), 50 parts of monochlorobenzene and 2.34 parts of a compound represented by the formula (B1-d) was stirred at 23° C. for 30 minutes. To the obtained mixture, 0.2 part of sulfuric acid and 10 parts of molecular sieves (Molecular Sieves 4A available from Wako Pure Chemical Industries, Ltd.) were added thereto. The obtained mixture was refluxed at 130° C. for 3 hours to conduct dehydration. The obtained mixture was concentrated, and 50 parts of ion-exchanged water and 100 parts of chloroform were added thereto to conduct separation. The organic layer obtained was washed three times with ion-exchanged water, and then, 1 parts of active carbon was added thereto to stir at 23° C. for 30 minutes followed by filtration. The filtrate obtained was concentrated, and the obtained residue was purified with silica gel column chromatography (silica gel: silica gel 60-200 mesh available from Merck KGaA, solvent: chloroform/methanol=5/1) to obtain 0.14 part of a salt represented by the formula (B8). This is called as Salt B8.

MS (ESI(+) Spectrum): M$^+$ 207.1

MS (ESI(−) Spectrum): M$^-$ 547.2

Example 9

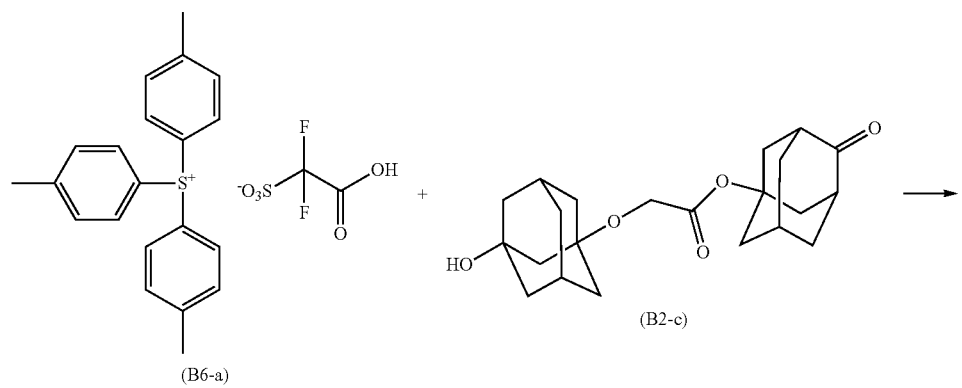

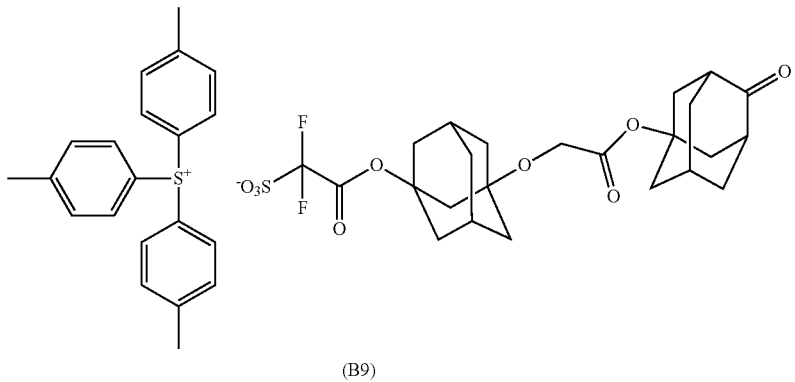

A mixture of 2.40 parts of a salt represented by the formula (B6-a), 50 parts of monochlorobenzene and 2.24 parts of a compound represented by the formula (B2-c) was stirred at 23° C. for 30 minutes. To the obtained mixture, 0.2 part of sulfuric acid and 10 parts of molecular sieves (Molecular Sieves 4A available from Wako Pure Chemical Industries, Ltd.) were added thereto. The obtained mixture was refluxed at 130° C. for 3 hours to conduct dehydration. The obtained mixture was concentrated, and 50 parts of ion-exchanged water and 100 parts of chloroform were added thereto to conduct separation. The organic layer obtained was washed three times with ion-exchanged water, and then, 1 parts of active carbon was added thereto to stir at 23° C. for 30 minutes followed by filtration. The filtrate obtained was concentrated. To the residue obtained, 20 parts of acetonitrile was added to prepare a solution. The obtained solution was concentrated, and 20 parts of ethyl acetate was added to the obtained residue. The resultant mixture was stirred and then, the supernatant solution was removed from the mixture. To the obtained residue, 20 parts of tert-butyl methyl ether was added. The resultant mixture was stirred and then, the supernatant solution was removed from the mixture. The obtained residue was dissolved in chloroform, and the obtained solution was concentrated to obtain 0.89 part of a salt represented by the formula (B9). This is called as Salt B9.

MS (ESI(+) Spectrum): M$^+$ 305.1
MS (ESI(−) Spectrum): M$^-$ 531.2

Example 10

A mixture of 2.28 parts of a salt represented by the formula (B7-a), 50 parts of monochlorobenzene and 2.24 parts of a compound represented by the formula (B2-c) was stirred at 23° C. for 30 minutes. To the obtained mixture, 0.2 part of sulfuric acid and 10 parts of molecular sieves (Molecular Sieves 4A available from Wako Pure Chemical Industries, Ltd.) were added thereto. The obtained mixture was refluxed at 130° C. for 3 hours to conduct dehydration. The obtained mixture was concentrated, and 50 parts of ion-exchanged water and 100 parts of chloroform were added thereto to conduct separation. The organic layer obtained was washed three times with ion-exchanged water, and then, 1 parts of active carbon was added thereto to stir at 23° C. for 30 minutes followed by filtration. The filtrate obtained was concentrated, and the obtained residue was purified with silica gel column chromatography (silica gel: silica gel 60-200 mesh available from Merck KGaA, solvent: chloroform/methanol=5/1) to obtain 0.25 part of a salt represented by the formula (B10). This is called as Salt B10.

MS (ESI(+) Spectrum): M$^+$ 281.0

MS (ESI(−) Spectrum): M$^-$ 531.2

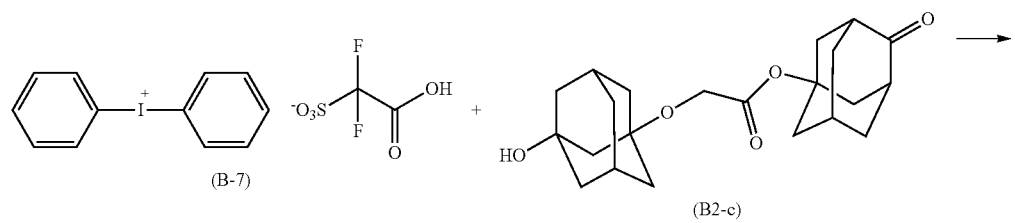

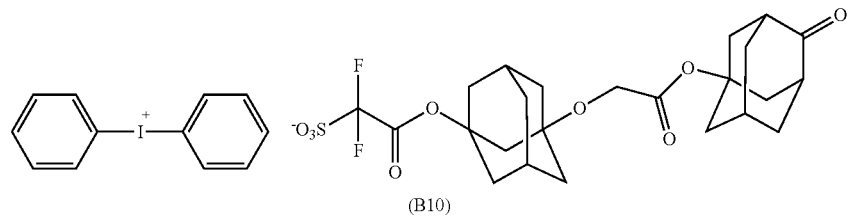

Example 11

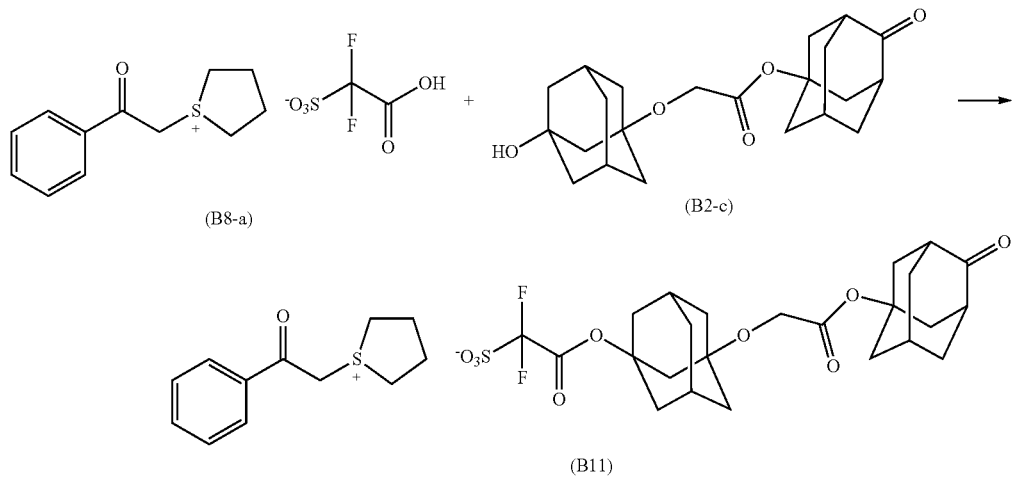

A mixture of 1.91 parts of a salt represented by the formula (B8-a), 50 parts of monochlorobenzene and 2.24 parts of a compound represented by the formula (B2-c) was stirred at 23° C. for 30 minutes. To the obtained mixture, 0.2 part of sulfuric acid and 10 parts of molecular sieves (Molecular Sieves 4A available from Wako Pure Chemical Industries, Ltd.) were added thereto. The obtained mixture was refluxed at 130° C. for 3 hours to conduct dehydration. The obtained mixture was concentrated, and 50 parts of ion-exchanged water and 100 parts of chloroform were added thereto to conduct separation. The organic layer obtained was washed three times with ion-exchanged water, and then, 1 parts of active carbon was added thereto to stir at 23° C. for 30 minutes followed by filtration. The filtrate obtained was concentrated, and the obtained residue was purified with silica gel column chromatography (silica gel: silica gel 60-200 mesh available from Merck KGaA, solvent: chloroform/methanol=5/1) to obtain 0.12 part of a salt represented by the formula (B11). This is called as Salt B11.

MS (ESI(+) Spectrum): $M^+$ 207.1
MS (ESI(−) Spectrum): $M^-$ 531.2

Example 12

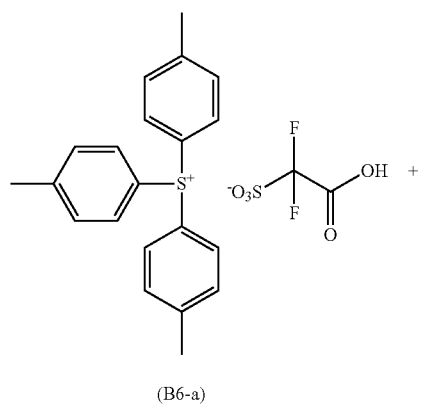

-continued

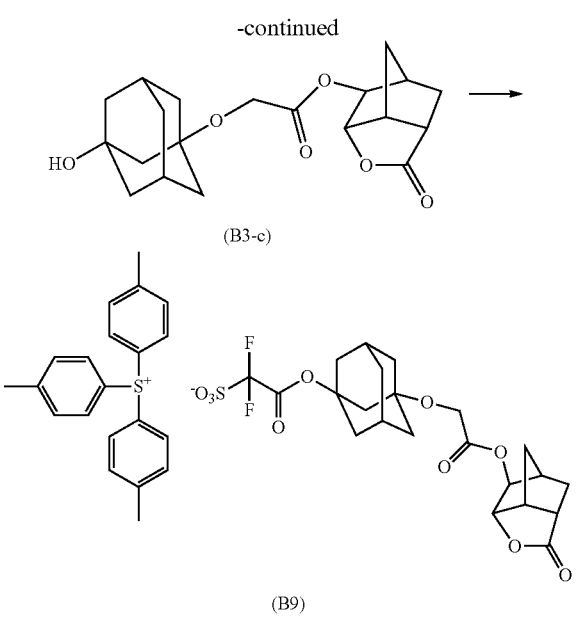

A mixture of 2.40 parts of a salt represented by the formula (B6-a), 50 parts of monochlorobenzene and 2.17 parts of a compound represented by the formula (B3-c) was stirred at 23° C. for 30 minutes. To the obtained mixture, 0.2 part of sulfuric acid and 10 parts of molecular sieves (Molecular Sieves 4A available from Wako Pure Chemical Industries, Ltd.) were added thereto. The obtained mixture was refluxed at 130° C. for 3 hours to conduct dehydration. The obtained mixture was concentrated, and 50 parts of ion-exchanged water and 100 parts of chloroform were added thereto to conduct separation. The organic layer obtained was washed three times with ion-exchanged water, and then, 1 parts of active carbon was added thereto to stir at 23° C. for 30 minutes followed by filtration. The filtrate obtained was concentrated. To the residue obtained, 20 parts of acetonitrile was added to prepare a solution. The obtained solution was concentrated, and 20 parts of ethyl acetate was added to the obtained residue. The resultant mixture was stirred and then, the supernatant solution was removed from the mixture. To the obtained residue, 20 parts of tert-butyl methyl ether was added. The resultant mixture was stirred and then, the supernatant solution was removed from the mixture. The obtained residue was dissolved in chloroform, and the obtained solution was concentrated to obtain 1.01 part of a salt represented by the formula (B12). This is called as Salt B12.

MS (ESI(+) Spectrum): M+ 305.1

MS (ESI(−) Spectrum): M− 519.1

Example 13

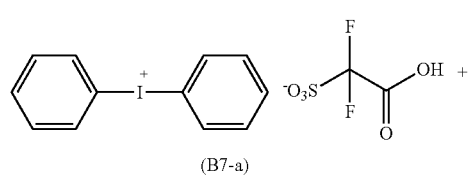

(B7-a)

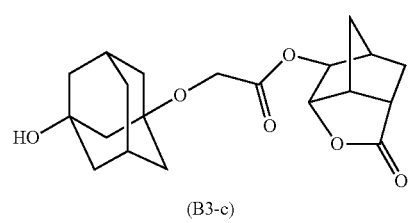

(B3-c)

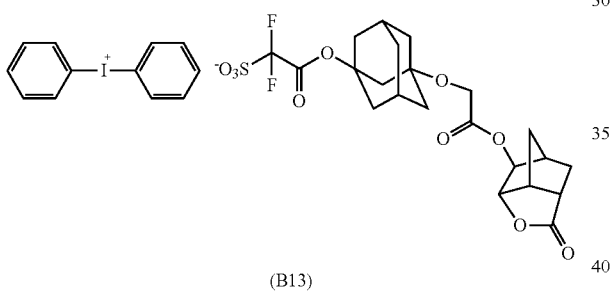

(B13)

Example 14

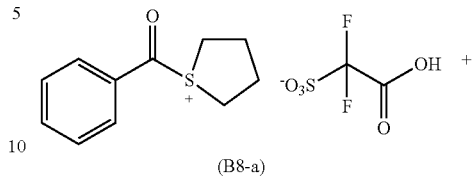

(B8-a)

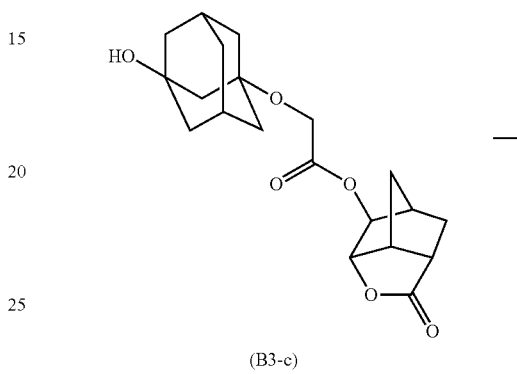

(B3-c)

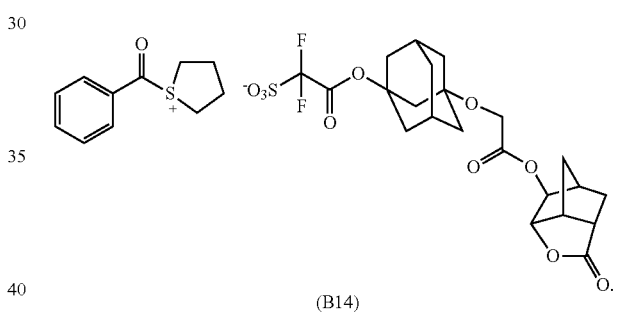

(B14)

A mixture of 2.28 parts of a salt represented by the formula (B7-a), 50 parts of monochlorobenzene and 2.17 parts of a compound represented by the formula (B3-c) was stirred at 23° C. for 30 minutes. To the obtained mixture, 0.2 part of sulfuric acid and 10 parts of molecular sieves (Molecular Sieves 4A available from Wako Pure Chemical Industries, Ltd.) were added thereto. The obtained mixture was refluxed at 130° C. for 3 hours to conduct dehydration. The obtained mixture was concentrated, and 50 parts of ion-exchanged water and 100 parts of chloroform were added thereto to conduct separation. The organic layer obtained was washed three times with ion-exchanged water, and then, 1 parts of active carbon was added thereto to stir at 23° C. for 30 minutes followed by filtration. The filtrate obtained was concentrated, and the obtained residue was purified with silica gel column chromatography (silica gel: silica gel 60-200 mesh available from Merck KGaA, solvent: chloroform/methanol=5/1) to obtain 0.42 part of a salt represented by the formula (B13). This is called as Salt B13.

MS (ESI(+) Spectrum): M+ 281.0

MS (ESI(−) Spectrum): M− 519.1

A mixture of 1.91 parts of a salt represented by the formula (B8-a), 50 parts of monochlorobenzene and 2.17 parts of a compound represented by the formula (B3-c) was stirred at 23° C. for 30 minutes. To the obtained mixture, 0.2 part of sulfuric acid and 10 parts of molecular sieves (Molecular Sieves 4A available from Wako Pure Chemical Industries, Ltd.) were added thereto. The obtained mixture was refluxed at 130° C. for 3 hours to conduct dehydration. The obtained mixture was concentrated, and 50 parts of ion-exchanged water and 100 parts of chloroform were added thereto to conduct separation. The organic layer obtained was washed three times with ion-exchanged water, and then, 1 parts of active carbon was added thereto to stir at 23° C. for 30 minutes followed by filtration. The filtrate obtained was concentrated, and the obtained residue was purified with silica gel column chromatography (silica gel: silica gel 60-200 mesh available from Merck KGaA, solvent: chloroform/methanol=5/1) to obtain 0.28 part of a salt represented by the formula (B14). This is called as Salt B14.

MS (ESI(+) Spectrum): M+ 207.1

MS (ESI(−) Spectrum): M− 519.1

Example 15

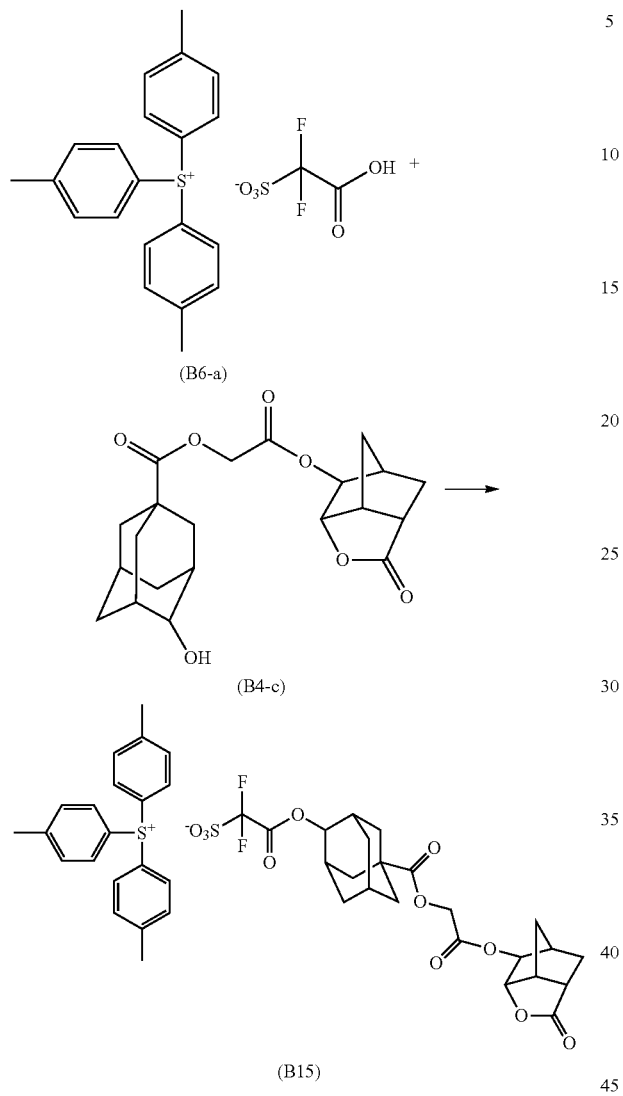

A mixture of 2.40 parts of a salt represented by the formula (B6-a), 50 parts of monochlorobenzene and 2.34 parts of a compound represented by the formula (B4-c) was stirred at 23° C. for 30 minutes. To the obtained mixture, 0.2 part of sulfuric acid and 10 parts of molecular sieves (Molecular Sieves 4A available from Wako Pure Chemical Industries, Ltd.) were added thereto. The obtained mixture was refluxed at 130° C. for 3 hours to conduct dehydration. The obtained mixture was concentrated, and 50 parts of ion-exchanged water and 100 parts of chloroform were added thereto to conduct separation. The organic layer obtained was washed three times with ion-exchanged water, and then, 1 parts of active carbon was added thereto to stir at 23° C. for 30 minutes followed by filtration. The filtrate obtained was concentrated. To the residue obtained, 20 parts of acetonitrile was added to prepare a solution. The obtained solution was concentrated, and 20 parts of ethyl acetate was added to the obtained residue. The resultant mixture was stirred and then, the supernatant solution was removed from the mixture. To the obtained residue, 20 parts of tert-butyl methyl ether was added. The resultant mixture was stirred and then, the supernatant solution was removed from the mixture. The obtained residue was dissolved in chloroform, and the obtained solution was concentrated to obtain 1.29 parts of a salt represented by the formula (B15). This is called as Salt B15.

MS (ESI(+) Spectrum): M⁺ 305.1
MS (ESI(−) Spectrum): M⁻ 547.1

Example 16

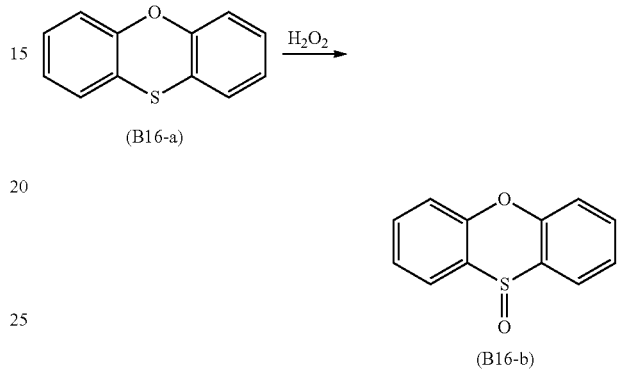

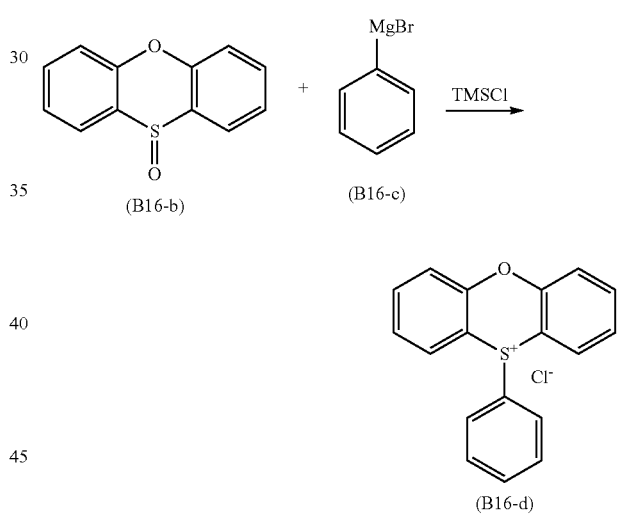

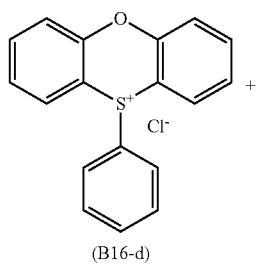

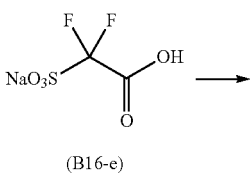

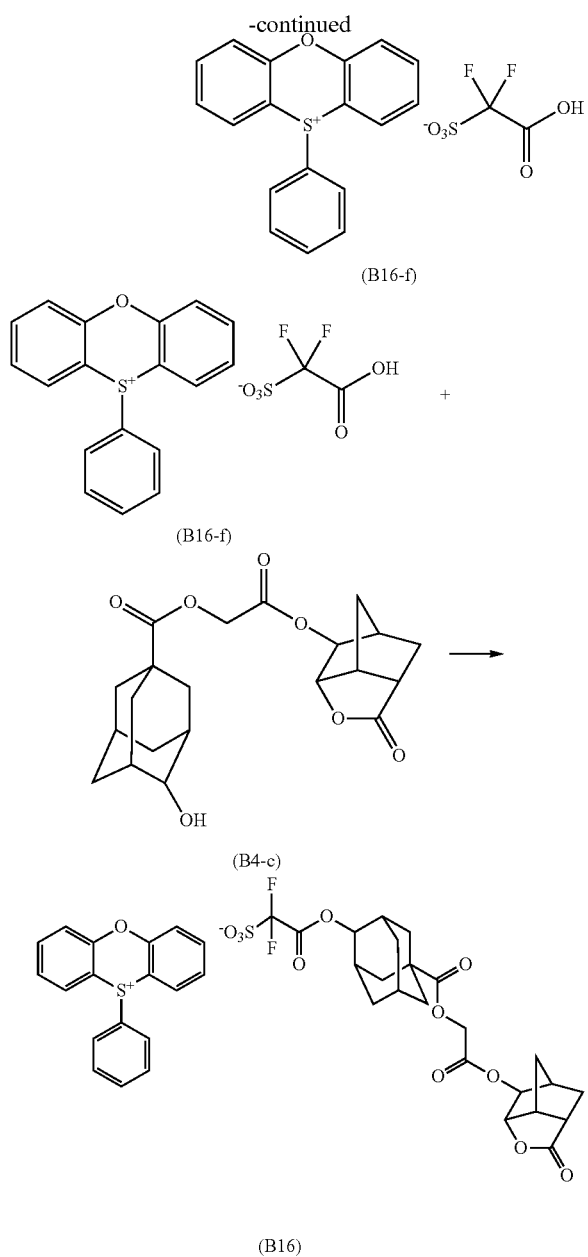

A mixture of 101.5 parts of a compound represented by the formula (B16-a) and 253.75 parts of acetic acid was stirred at room temperature. To the mixture, 61.17 parts of 31% aqueous hydrogen peroxide was added dropwise over 10 minutes, and then, the resultant mixture was stirred at 23° C. for 6 hours. To the obtained reaction mixture, 253.75 parts of ion-exchanged water was added to filtrate to obtain 96.93 parts of a compound represented by the formula (B16-b).

A mixture of 28 parts of the compound represented by the formula (B16-b) and 140 parts of tetrahydrofuran was stirred at room temperature, and then, 28.13 parts of trimethylsilyl chloride was added dropwise thereto over 10 minutes. To the resultant mixture, 73.36 parts of a compound represented by the formula (B16-c) of which purity was 32% was added dropwise over 25 minutes while keeping at 40° C. or less. The resultant mixture was stirred at 23° C. for 1 hour, and then, 70 parts of 1N hydrochloric acid was dropwise followed by separation. The obtained aqueous layer was washed with 70 parts of tert-butyl methyl ether, and then, was extracted with 210 parts of chloroform. The obtained organic layer was filtrated, and the filtrate was concentrated. The residue was dissolved in 16.06 parts of acetonitrile to prepare a solution, and 200.78 parts of tert-butyl methyl ether was added thereto followed by filtrating obtain 27.84 parts of a salt represented by the formula (B16-d).

A mixture of 5.91 parts of a salt represented by the formula (B16-d), 16.26 parts of ion-exchanged water and 3.74 parts of a compound represented by the formula (B16-e) was stirred at room temperature. To the mixture, 1.97 parts of 35% hydrochloric acid was added, and then, the obtained mixture was stirred at 23° C. for 5 hours. From the obtained mixture, the supernatant solution was removed. To the obtained residue, 20 parts of acetonitrile was added. The obtained solution was concentrated, and 24.81 parts of tert-butyl methyl ether was added to the obtained residue. The resultant mixture was stirred and then, the supernatant solution was removed from the mixture. The obtained residue was dissolved in acetonitrile, and the obtained solution was concentrated to obtain 5.17 parts of a salt represented by the formula (B16-f).

A mixture of 2.26 parts of a salt represented by the formula (B16-f), 50 parts of monochlorobenzene and 2.34 parts of a compound represented by the formula (B4-c) was stirred at 23° C. for 30 minutes. To the obtained mixture, 0.2 part of sulfuric acid and 10 parts of molecular sieves (Molecular Sieves 4A available from Wako Pure Chemical Industries, Ltd.) were added thereto. The obtained mixture was refluxed at 130° C. for 3 hours to conduct dehydration. The obtained mixture was concentrated, and 50 parts of ion-exchanged water and 100 parts of chloroform were added thereto to conduct separation. The organic layer obtained was washed three times with ion-exchanged water, and then, 1 parts of active carbon was added thereto to stir at 23° C. for 30 minutes followed by filtration. The filtrate obtained was concentrated. To the residue obtained, 20 parts of acetonitrile was added to prepare a solution. The obtained solution was concentrated, and 20 parts of ethyl acetate was added to the obtained residue. The resultant mixture was stirred and then, the supernatant solution was removed from the mixture. To the obtained residue, 20 parts of tert-butyl methyl ether was added. The resultant mixture was stirred and then, the supernatant solution was removed from the mixture. The obtained residue was dissolved in chloroform, and the obtained solution was concentrated to obtain 1.48 parts of a salt represented by the formula (B16). This is called as Salt B16.

MS (ESI(+) Spectrum): $M^+$ 277.1

MS (ESI(−) Spectrum): $M^-$ 547.1

Monomers used in the following Resin Synthesis Example 1 are following monomers E, F, B, C and D.

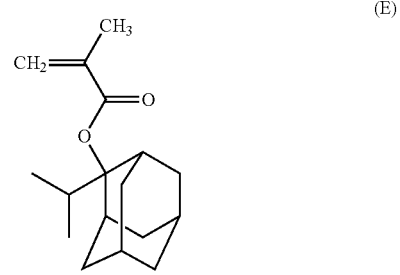

Monomers used in the following Resin Synthesis Example 2 are following monomers A, B and C.

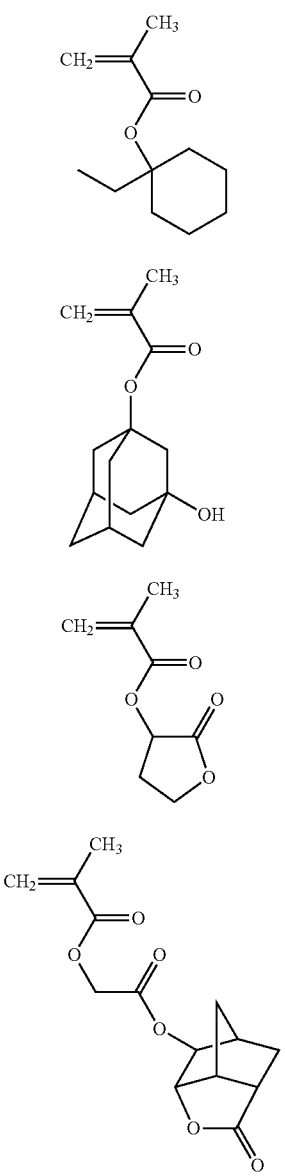

(F)

(B)

(C)

(D)

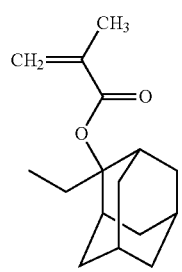

A

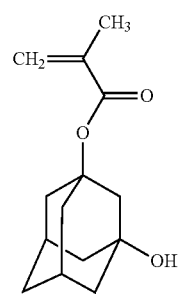

B

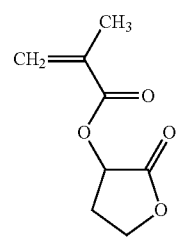

C

Resin Synthesis Example 1

The monomers E, F, B, C and D were mixed in a molar ratio of 30/14/6/20/30 (monomer E/monomer F/monomer B/monomer C/monomer D), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a mixture of a large amount of methanol and water (4/1) to cause precipitation, and this operation was repeated three times for purification. As a result, a resin having a weight-average molecular weight of about $8.1 \times 10^3$ was obtained in a yield of 65%. This resin is called as resin A1.

Resin Synthesis Example 2

The monomers A, B and C were mixed in a molar ratio of 50/25/25 (monomer A/monomer B/monomer C), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 77° C. for about 5 hours. The reaction mixture obtained was poured into a mixture of a large amount of methanol and water to cause precipitation, and this operation was repeated three times for purification. As a result, a resin having a weight-average molecular weight of about $8.0 \times 10^3$ was obtained in a yield of 60%. This resin is called as resin A2.

Monomers used in the following Resin Synthesis Example 3 are following monomers A, F, B, C and D.

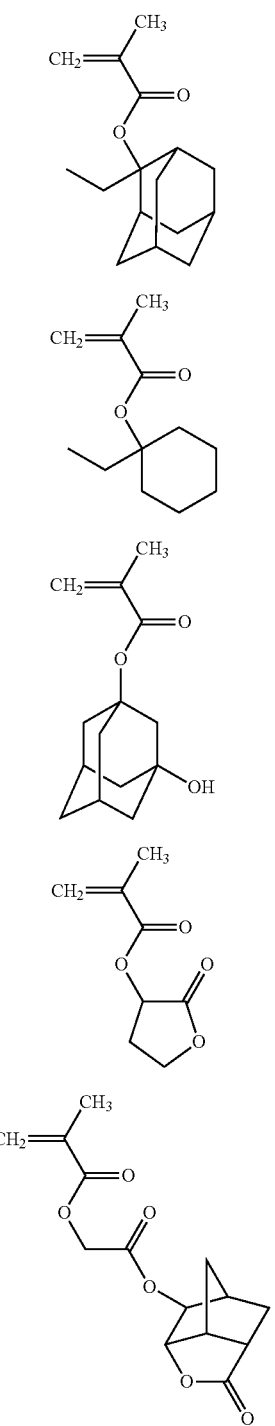

(A)
(F)
(B)
(C)
(D)

Resin Synthesis Example 3

The monomers A, F, B, C and D were mixed in a molar ratio of 30/14/6/20/30 (monomer A/monomer F/monomer B/monomer C/monomer D), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a mixture of a large amount of methanol and water (4/1) to cause precipitation, and this operation was repeated three times for purification. As a result, a resin having a weight-average molecular weight of about $7.8 \times 10^3$ was obtained in a yield of 68%. This resin is called as resin A3.

Examples 17 to 36 and Comparative Example 1

<Resin>
Resin A1, A2, A3
<Acid Generator>
Salt B1, B2, B3, B4, B5, B6, B7, B8, B9, B10, B11, B12, B13, B14, B15, B16
H1:

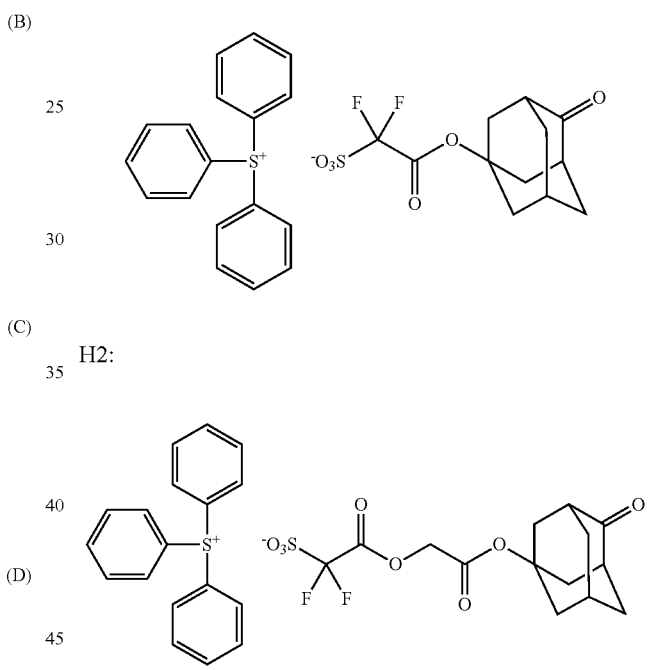

H2:

<Quencher>
C1: 2,6-diisopropylaniline
<Solvent>

| Y1: | propylene glycol monomethyl ether acetate | 265 parts |
|---|---|---|
|  | propylene glycol monomethyl ether | 20 parts |
|  | 2-heptanone | 20 parts |
|  | γ-butyrolactone | 3.5 parts |

The following components were mixed and dissolved, further, filtrated through a fluorine resin filter having pore diameter of 0.2 μm, to prepare photoresist compositions.

Resin (kind and amount are described in Table 1)
Acid Generator (kind and amount are described in Table 1)
Quencher (kind and amount are described in Table 1)
Solvent Y1

TABLE 1

| Ex. No. | Resin (kind/ amount (part)) | Acid Generator (kind/ amount (part)) | Quencher (kind/ amount (part)) | PB (° C.) | PEB (° C.) |
|---|---|---|---|---|---|
| Ex. 17 | A1/10 | B1/0.7 | C1/0.075 | 100 | 100 |
| Ex. 18 | A2/10 | B1/0.7 | C1/0.075 | 110 | 110 |
| Ex. 19 | A1/10 | B2/1.0 | C1/0.07 | 95 | 95 |
| Ex. 20 | A3/10 | B2/1.0 | C1/0.07 | 105 | 105 |
| Ex. 21 | A3/10 | B3/1.0 | C1/0.07 | 105 | 105 |
| Ex. 22 | A3/10 | B4/1.0 | C1/0.07 | 105 | 105 |
| Ex. 23 | A3/10 | B2/0.8 H1/0.2 | C1/0.07 | 105 | 105 |
| Ex. 24 | A2/10 | B2/1.0 | C1/0.07 | 105 | 105 |
| Ex. 25 | A3/10 | B5/1.0 | C1/0.07 | 105 | 105 |
| Ex. 26 | A1/10 | B6/0.7 | C1/0.075 | 100 | 100 |
| Ex. 27 | A1/10 | B7/0.7 | C1/0.075 | 100 | 100 |
| Ex. 28 | A1/10 | B1/0.5 B8/0.5 | C1/0.07 | 100 | 100 |
| Ex. 29 | A3/10 | B9/1.0 | C1/0.07 | 105 | 105 |
| Ex. 30 | A3/10 | B10/1.0 | C1/0.07 | 105 | 105 |
| Ex. 31 | A3/10 | B2/0.5 B11/0.5 | C1/0.07 | 105 | 105 |
| Ex. 32 | A3/10 | B12/1.0 | C1/0.07 | 105 | 105 |
| Ex. 33 | A3/10 | B13/1.0 | C1/0.07 | 105 | 105 |
| Ex. 34 | A3/10 | B3/0.5 B14/0.5 | C1/0.07 | 105 | 105 |
| Ex. 35 | A3/10 | B15/1.0 | C1/0.07 | 105 | 105 |
| Ex. 36 | A3/10 | B16/1.0 | C1/0.07 | 105 | 105 |
| Comp. Ex. 1 | A2/10 | H2/1.0 | C1/0.07 | 105 | 105 |

12-inch silicon wafers were each coated with "ARC-29", which is an organic anti-reflective coating composition available from Nissan Chemical Industries, Ltd., and then baked at 205° C. for 60 seconds, to form a 780 Å-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in the column "PB" in Table 1 for 60 seconds. Using an ArF excimer stepper for immersion exposure ("XT: 1900Gi" manufactured by ASML, NA=1.35, ¾ Annular, X-Y deflection), each wafer thus formed with the respective resist film was subjected to line and space pattern exposure, with the exposure quantity being varied stepwise.

After the exposure, each wafer was subjected to post-exposure baking on a hotplate at a temperature shown in the column "PEB" in Table 1 for 60 seconds and then to paddle development for 60 seconds with an aqueous solution of 2.38 wt % tetramethylammonium hydroxide.

Each of patterns developed on the organic anti-reflective coating substrate after the development was observed with a scanning electron microscope, the results of which are shown in Tables 2 and 3.

Effective Sensitivity (ES): It was expressed as the amount of exposure that the line pattern and the space pattern of 50 nm become 1:1 after exposure and development.

Focus margin (DOF): The photoresist patterns were obtained at ES, with the focal point distance being varied stepwise. Each of patterns developed on the organic anti-reflective coating substrate after the development were observed and the focal point distances when the patterns of which line width was 47.5 nm or more and 52.5 nm or less were obtained were measured and the difference between the max value of the focal point distance and the minimum value of the focal point distance was calculated. When the difference is 0.15 µm or more and less than 0.17 µm, DOF is good and its evaluation is marked by "○", when the difference is 0.17 µm or more, DOF is very good and its evaluation is marked by "⊚", and when the difference is less than 0.15 µm, DOF is bad and its evaluation is marked by "x". The bigger the difference is, the better the photoresist composition is. The difference obtained was also shown in parentheses in Table 2.

Pattern Collapse Margin (PCM): The photoresist patterns obtained with the amount of exposure being increased stepwise by 0.2 mJ/cm$^2$ based on the amount of exposure at which the line pattern and the space pattern of 45 nm became 1:1 were observed. Even though the line width of the photoresist pattern was less than 38 nm, a disappearance of the photoresist pattern by a collapse or peeling of the photoresist pattern was not observed, PCM is good, and its evaluation is marked by "○", and even though the line width of the photoresist pattern was 38 nm or more, a disappearance of the photoresist pattern by a collapse or peeling of the photoresist pattern was observed, PCM is bad, and its evaluation is marked by "x". Further, each of the minimum line widths of the photoresist pattern when a disappearance of the photoresist pattern by a collapse or peeling of the photoresist pattern was not observed was shown in parentheses in Table 3.

TABLE 2

| Ex. No. | DOF |
|---|---|
| Ex. 17 | ⊚ (0.21 µm) |
| Ex. 18 | ○ (0.15 µm) |
| Ex. 26 | ⊚ (0.24 µm) |
| Ex. 27 | ⊚ (0.18 µm) |
| Ex. 28 | ⊚ (0.21 µm) |
| Comp. Ex. 1 | X (0.09 µm) |

TABLE 3

| Ex. No. | PCM |
|---|---|
| Ex. 19 | ○ (36 nm) |
| Ex. 20 | ○ (35 nm) |
| Ex. 21 | ○ (34 nm) |
| Ex. 22 | ○ (34 nm) |
| Ex. 23 | ○ (35 nm) |
| Ex. 24 | ○ (37 nm) |
| Ex. 25 | ○ (36 nm) |
| Ex. 29 | ○ (34 nm) |
| Ex. 30 | ○ (35 nm) |
| Ex. 31 | ○ (34 nm) |
| Ex. 32 | ○ (33 nm) |
| Ex. 33 | ○ (34 nm) |
| Ex. 34 | ○ (34 nm) |
| Ex. 35 | ○ (34 nm) |
| Ex. 36 | ○ (34 nm) |
| Comp. Ex. 1 | X (40 nm) |

Example 37

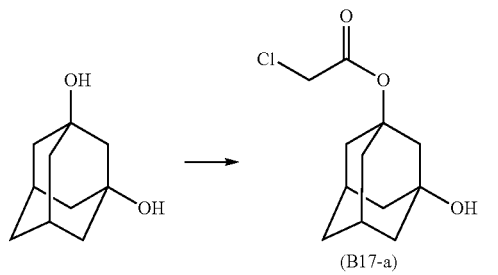

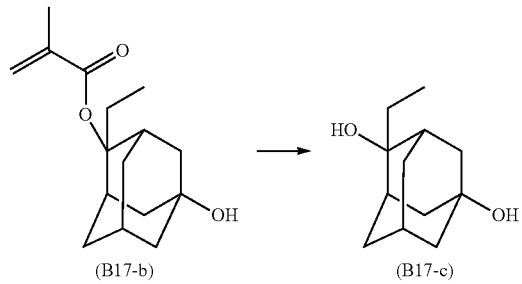

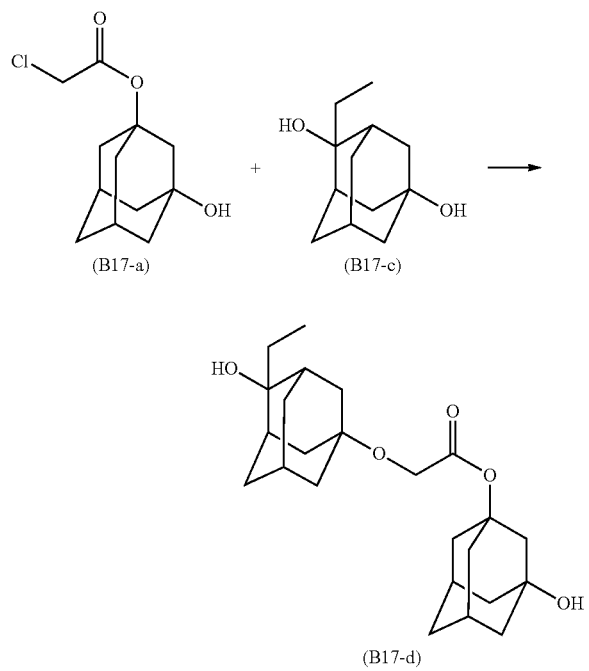

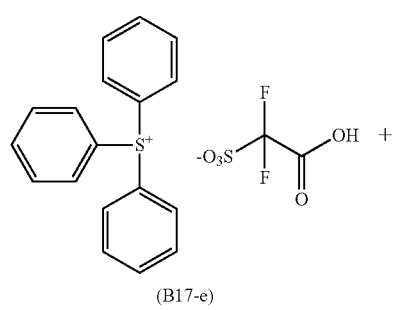

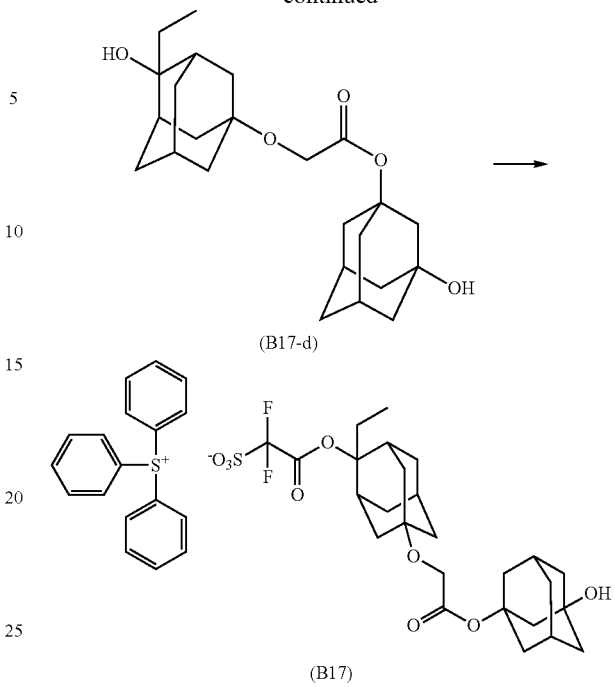

A mixture of 250 parts of 1,3-adamantanediol and 2000 parts of tetrahydrofuran was stirred at room temperature, and then, 142 parts of pyridine was added thereto. The resultant mixture was heated up to 40° C., and then, a solution prepared by dissolving 254 parts of chloroacetyl chloride in 500 parts of tetrahydrofuran was added dropwise thereto over 80 minutes. The resultant mixture was stirred at 40° C. for 8 hours, and then, cooled down to 5° C. To the obtained mixture, 1000 parts of ion-exchanged water at 5° C. was added to conduct separation. The obtained aqueous layer was extracted with 600 parts of ethyl acetate, and the obtained organic layer was washed with 600 parts of aqueous 10% potassium carbonate solution, and further washed three times with 600 parts of ion-exchanged water. The organic layer was concentrated and the residue obtained was purified with silica gel column chromatography (silica gel: silica gel 60-200 mesh available from Merck KGaA, solvent: heptane/ethyl acetate=1/1 (volume ratio)) to obtain 75 parts of a compound represented by the formula (B17-a).

Eighty parts of 1,4-dioxane was mixed with 26.44 parts of a compound represented by the formula (B17-b) which is available from Idemitsu Kosan Co., Ltd. and of which commodity name is HADM. To the resultant mixture, an aqueous solution prepared by dissolving 4.40 parts of sodium hydroxide in 80.00 parts of ion-exchanged water was added dropwise at 23° C. over 30 minutes. The obtained mixture was stirred at 90° C. for 36 hours. The reaction mixture obtained was cooled and then, 400 parts of ion-exchanged water, 500 parts of ethyl acetate and 200 parts of sodium chloride were added thereto to conduct separation. The organic layer obtained was washed three times with 400 parts of ion-exchanged water. The organic layer was concentrated and the residue obtained was purified with silica gel column chromatography (silica gel: silica gel 60-200 mesh available from Merck KGaA, solvent: heptane/ethyl acetate=1/1 (volume ratio)) to obtain 7.89 parts of a compound represented by the formula (B17-c).

A mixture of 4.88 parts of a compound represented by the formula (B17-a) and 25 parts of N,N-dimethylformamide was stirred at 23° C. for 30 minutes. To the mixture, 1.66 parts of potassium carbonate and 0.84 part of potassium iodide were added and the resultant mixture was stirred at 50° C. for 1 hour. The obtained mixture was cooled down to 40° C., and a solution prepared by dissolving 3.93 parts of a compound represented by the formula (B17-c) in 25 parts of N,N-dimethylformamide was added dropwise over 1 hour. The resultant mixture was stirred at 75° C. for 5 hours. The obtained mixture was cooled down to 23° C., and 60 parts of chloroform and 60 parts of 1N hydrochloric acid were added thereto to conduct separation. The organic layer obtained was repeated to wash with 60 parts of ion-exchanged water until the obtained aqueous layer was neutralized. The obtained organic layer was concentrated and the residue obtained was purified with silica gel column chromatography (silica gel: silica gel 60-200 mesh available from Merck KGaA, solvent: ethyl acetate) to obtain 2.54 parts of a compound represented by the formula (B17-d).

A salt represented by the formula (B17-e) was prepared according to the method described in Examples 1 of JP 2008-127367 A1. A mixture of 2.19 parts of the salt represented by the formula (B17-e), 50 parts of monochlorobenzene and 2.43 parts of a compound represented by the formula (B17-d) was stirred at 23° C. for 30 minutes. To the mixture, 0.2 part of sulfuric acid and 10 parts of molecular sieves (Molecular Sieves 4A available from Wako Pure Chemical Industries, Ltd.) were added, and the resultant mixture was refluxed at 130° C. for 3 hours to conduct dehydration. The reaction mixture obtained was concentrated to obtain a residue and to the residue, 100 parts of chloroform and 50 parts of ion-exchanged water to conduct separation. The obtained organic layer was washed three times with ion-exchanged water. To the organic layer, 1 parts of active carbon was added to stir at 23° C. for 30 minutes followed by filtration. The filtrate obtained was concentrated, and to the residue obtained, 20 parts of acetonitrile was added to prepare a solution. The obtained solution was concentrated, and 20 parts of ethyl acetate was added to the obtained residue. The resultant mixture was stirred and then, the supernatant solution was removed from the mixture. The obtained residue was dissolved in chloroform, and the obtained solution was concentrated to obtain 0.62 part of a salt represented by the formula (B17) in the form of oil. This is called as Salt B17.

MS (ESI(+) Spectrum): M$^+$ 263.1
MS (ESI(−) Spectrum): M$^-$ 561.2

Example 38

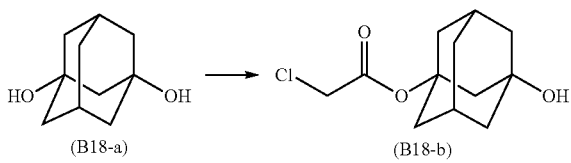

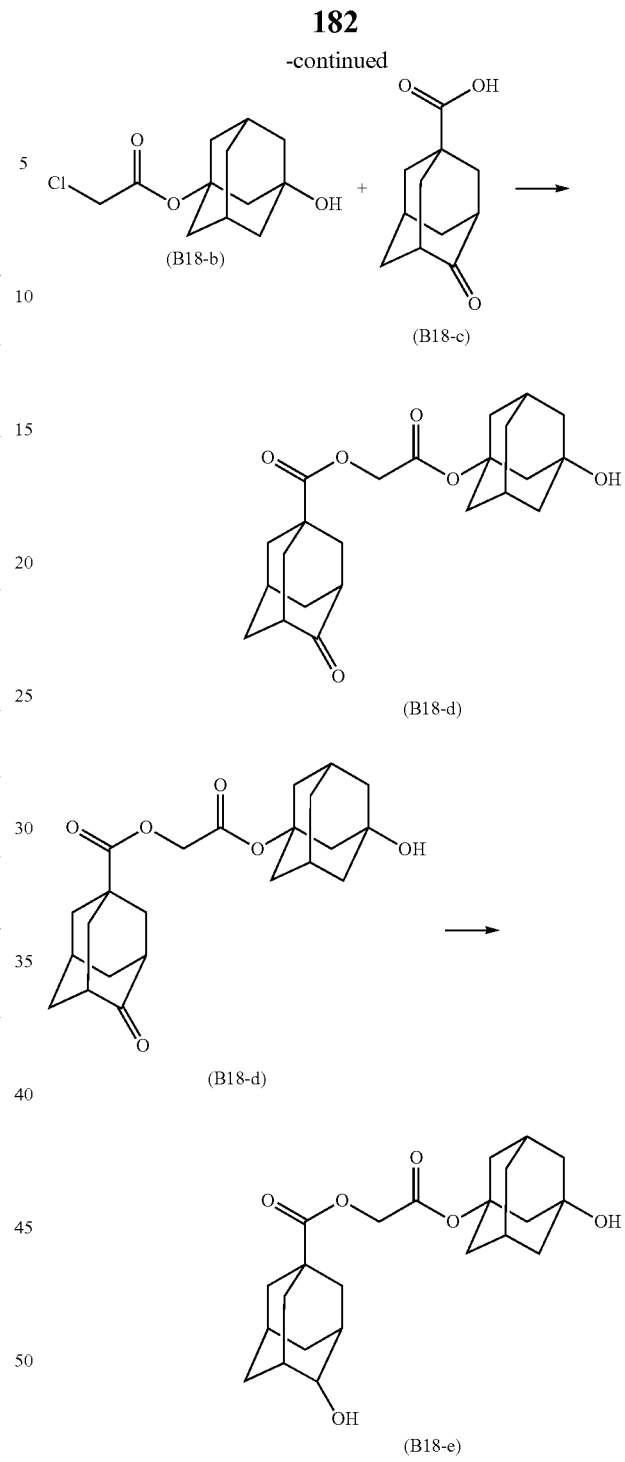

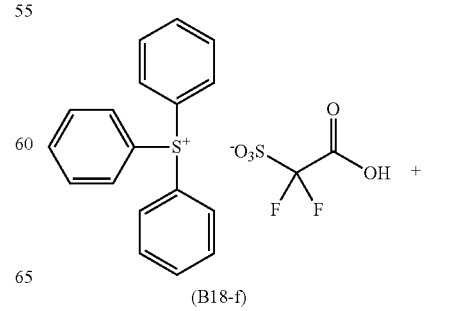

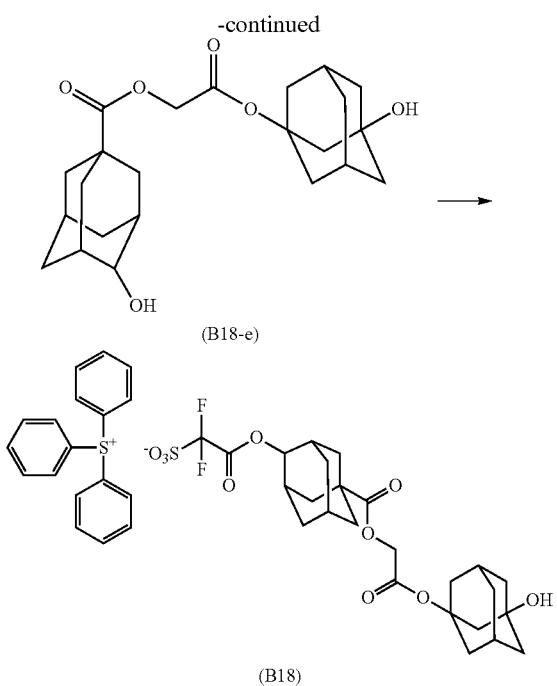

(B18-e)

(B18)

A mixture of 25.31 parts of a compound represented by the formula (B18-a) and 200 parts of tetrahydrofuran was stirred at room temperature, and then, 14.27 parts of pyridine was added thereto. The resultant mixture was heated up to 40° C., and then, a solution prepared by dissolving 25.47 parts of chloroacetyl chloride in 50 parts of tetrahydrofuran was added dropwise thereto over 1 hour. The resultant mixture was stirred at 40° C. for 8 hours, and then, cooled down to 5° C. To the obtained mixture, 100 parts of ion-exchanged water at 5° C. was added to conduct separation. The obtained aqueous layer was extracted with 65 parts of ethyl acetate, and the obtained organic layer was washed with 65 parts of aqueous 10% potassium carbonate solution at 5° C., and further washed three times with 65 parts of ion-exchanged water. The organic layer was concentrated and the residue obtained was purified with silica gel column chromatography (silica gel: silica gel 60-200 mesh available from Merck KGaA, solvent: ethyl acetate) to obtain 22.24 parts of a compound represented by the formula (B18-b).

A mixture of 7.5 parts of a compound represented by the formula (B18-c) and 37.5 parts of N,N-dimethylformamide was stirred at 23° C. for 30 minutes. To the mixture, 3.2 parts of potassium carbonate and 0.96 part of potassium iodide were added and the resultant mixture was stirred at 50° C. for 1 hour. To the obtained mixture, a solution prepared by dissolving 8.5 parts of a compound represented by the formula (B18-b) in 16.87 parts of N,N-dimethylformamide was added dropwise over 1 hour. The resultant mixture was stirred at 50° C. for 5 hours. The obtained mixture was cooled down to 23° C., and 150 parts of ethyl acetate and 75 parts of ion-exchanged water were added thereto to conduct separation. The organic layer obtained was repeated to wash with 75 parts of ion-exchanged water until the obtained aqueous layer was neutralized. The obtained organic layer was concentrated and the residue obtained was purified with silica gel column chromatography (silica gel: silica gel 60-200 mesh available from Merck KGaA, solvent: ethyl acetate) to obtain 10.29 parts of a compound represented by the formula (B18-d).

A mixture of 7.54 parts of the compound represented by the formula (B18-d) and 37.5 parts of acetonitrile was stirred at 23° C. for 30 minutes. The mixture was cooled down to 5° C., and then, 0.36 part of sodium borohydride and 5.32 parts of ion-exchanged water were added thereto. The resultant mixture was stirred at 5° C. for 3 hours. To the obtained mixture, 25 parts of ion-exchanged water and 50 parts of ethyl acetate were added to conduct separation. The organic layer obtained was repeated to wash with 25 parts of ion-exchanged water until the obtained aqueous layer was neutralized. The obtained organic layer was concentrated and the residue obtained was purified with silica gel column chromatography (silica gel: silica gel 60-200 mesh available from Merck KGaA, solvent: ethyl acetate) to obtain 6.33 parts of a compound represented by the formula (B18-e).

A salt represented by the formula (B18-f) was prepared according to the method described in Examples 1 of JP 2008-127367 A1. A mixture of 2.19 parts of the salt represented by the formula (B18-f), 50 parts of monochlorobenzene and 2.43 parts of a compound represented by the formula (B18-e) was stirred at 23° C. for 30 minutes. To the mixture, 0.2 part of sulfuric acid and 10 parts of molecular sieves (Molecular Sieves 4A available from Wako Pure Chemical Industries, Ltd.) were added, and the resultant mixture was refluxed at 130° C. for 3 hours to conduct dehydration. The reaction mixture obtained was concentrated to obtain a residue and to the residue, 100 parts of chloroform and 50 parts of ion-exchanged water to conduct separation. The obtained organic layer was washed five times with ion-exchanged water. To the organic layer, 1 parts of active carbon was added to stir at 23° C. for 30 minutes followed by filtration. The filtrate obtained was concentrated, and to the residue obtained, 25 parts of acetonitrile was added to prepare a solution. The obtained solution was concentrated, and 25 parts of ethyl acetate was added to the obtained residue. The resultant mixture was stirred and then, the supernatant solution was removed from the mixture. To the obtained residue, 25 parts of tert-butyl methyl ether was added. The resultant mixture was stirred and then, the supernatant solution was removed from the mixture. The obtained residue was dissolved in chloroform, and the obtained solution was concentrated to obtain a residue. The residue obtained was purified with silica gel column chromatography (silica gel: silica gel 60-200 mesh available from Merck KGaA, solvent: chloroform/methanol=5/1) to obtain 1.48 parts of a salt represented by the formula (B18). This is called as Salt B18.

MS (ESI(+) Spectrum): M$^+$ 263.1
MS (ESI(−) Spectrum): M$^-$ 561.2

Example 39

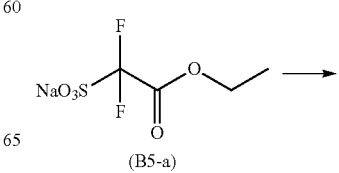

(B5-a)

-continued

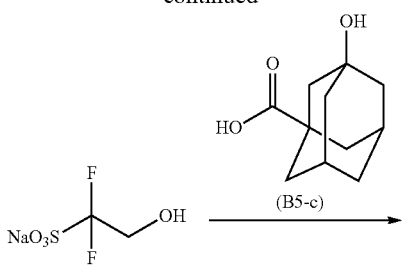

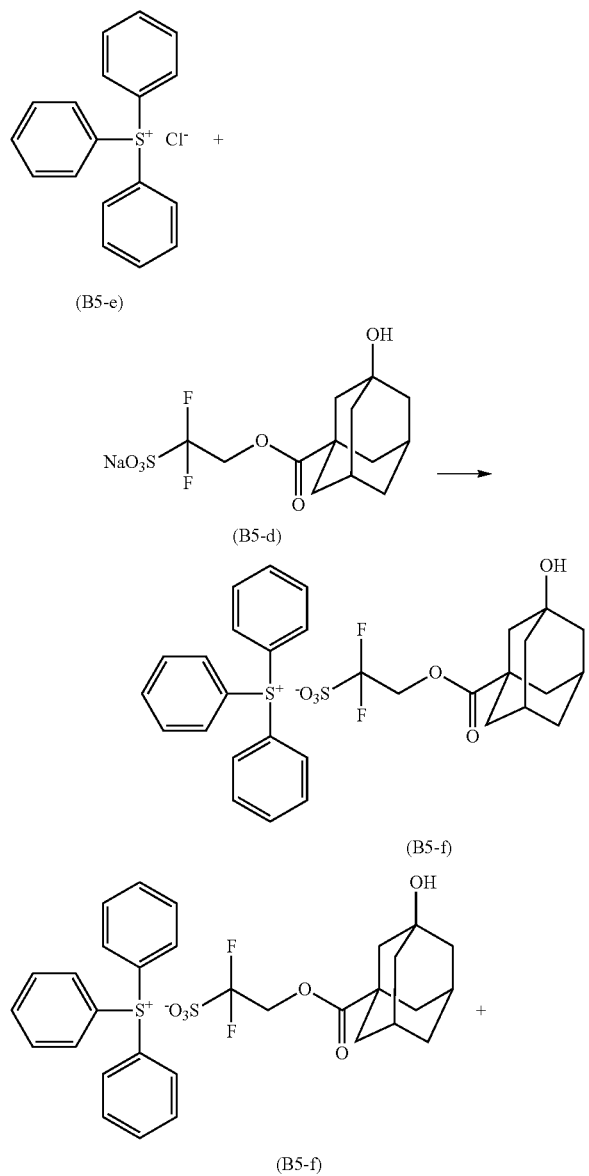

-continued

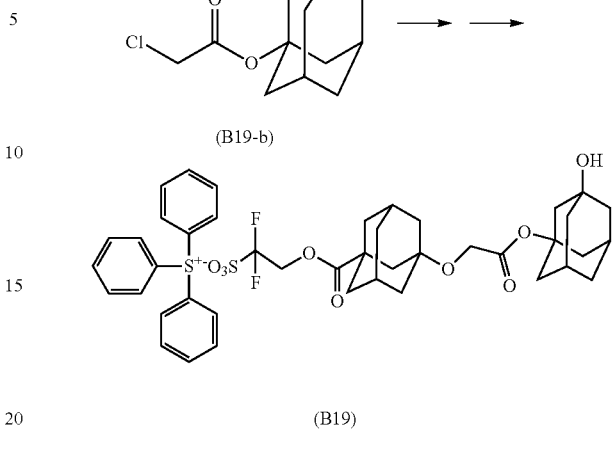

The mixture of 10.4 parts of lithium aluminum hydride and 120 parts of anhydrous tetrahydrofuran was stirred at 23° C. for 30 minutes. To the mixture, a solution prepared by dissolving 62.2 parts of a compound represented by the formula (B5-a) in 900 parts of tetrahydrofuran was added dropwise under cooling with ice-bath, and the resultant mixture was stirred at 23° C. for 5 hours. To the obtained reaction mixture, 50 parts of ethyl acetate and 50 parts of 6N hydrochloric acid were added to conduct separation. The organic layer obtained was concentrated and the residue obtained was purified with silica gel column chromatography (silica gel: silica gel 60-200 mesh available from Merck KGaA, solvent: chloroform/methanol=5/1) to obtain 84.7 parts of a compound represented by the formula (B5-b) of which purity was 60%.

A mixture of 3.51 parts of a compound represented by the formula (B5-c) and 75 parts of anhydrous tetrahydrofuran was stirred at 23° C. for 30 minutes. To the mixture, a solution prepared by dissolving 2.89 parts of carbonyldiimidazole in 50 parts of anhydrous tetrahydrofuran was added dropwise at 23° C., and then, the resultant mixture was stirred at 23° C. for 4 hours. The obtained mixture was added dropwise into a mixture of 6.04 parts of the compound represented by the formula (B5-b) of which purity was 60% and 50 parts of anhydrous tetrahydrofuran, at 54 to 60° C. over 25 minutes. The resultant mixture was stirred at 65° C. for 18 hours, and then, cooled followed by filtration. The filtrate was concentrated and the residue obtained was purified with silica gel column chromatography (silica gel: silica gel 60-200 mesh available from Merck KGaA, solvent: chloroform/methanol=5/1) to obtain 2.99 parts of a compound represented by the formula (B5-d).

A mixture of 1 part of the compound represented by the formula (B5-d) and 30 parts of chloroform was stirred at 23° C. for 30 minutes. To the mixture, 0.83 parts of a salt represented by the formula (B5-e) was added, and then, the resultant mixture was stirred at 23° C. for 12 hours followed by conducting separation. The obtained organic layer was washed three times with 10 parts of ion-exchanged water, and then, 1 parts of active carbon was added thereto to stir at 23° C. for 30 minutes followed by filtration. The filtrate obtained was concentrated, and to the residue obtained, 20 parts of acetonitrile was added to prepare a solution. The obtained solution was concentrated, and 20 parts of ethyl acetate was added to the obtained residue. The resultant mixture was stirred and then, the supernatant solution was removed from the mixture. To the obtained residue, 20 parts of tert-butyl methyl ether was added. The resultant mixture was stirred and then, the supernatant solution was removed from the mixture. The obtained residue was dissolved in chloroform, and the obtained solution was concentrated to obtain a residue. The residue was purified with silica gel column chromatography (silica gel: silica gel 60-200 mesh available from Merck KGaA, solvent: chloroform/methanol=5/1) to obtain 0.69 part of a salt represented by the formula (B5-f).

A mixture of 0.69 part of the salt represented by the formula (B5-f) and 10 parts of N,N-dimethylformamide was stirred at 23° C. for 30 minutes. To the obtained mixture, 0.09 part of potassium carbonate and 0.05 part of potassium iodide were added. The obtained mixture was stirred at 50° C. for 1 hour. The resultant mixture was cooled down to 40° C., and then, a solution prepared by dissolving 0.28 part of a compound represented by the formula (B19-b) in 5 parts of N,N-dimethylformamide was added dropwise thereto over 1 hour. The obtained mixture was stirred at 75° C. for 3 hours and then, cooled down to 23° C. To the obtained reaction mixture, 30 parts of chloroform and 10 parts of 1N hydrochloric acid were added to conduct separation. The organic layer obtained was repeated to wash with 10 parts of ion-exchanged water until the obtained aqueous layer was neutralized. The obtained organic layer was concentrated, and the residue obtained was purified with silica gel column chromatography (silica gel: silica gel 60-200 mesh available from Merck KGaA, solvent: chloroform/methanol=5/1) to obtain 0.12 part of a salt represented by the formula (B19). This is called as Salt B19.

MS (ESI(+) Spectrum): $M^+$ 263.1
MS (ESI(−) Spectrum): $M^−$ 547.2

Example 40

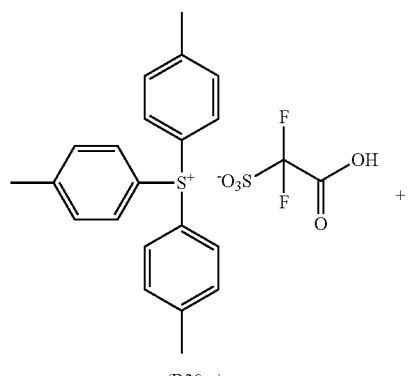

(B20-a)

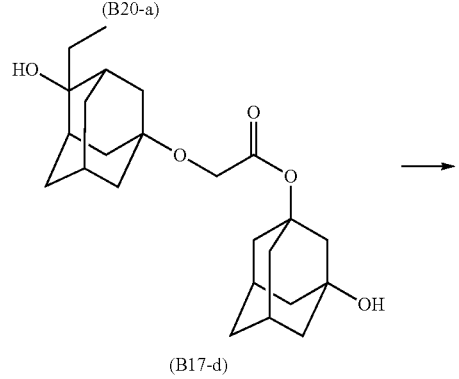

(B17-d)

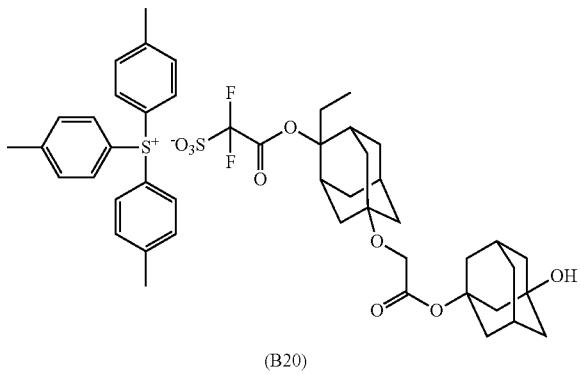

(B20)

A mixture of 2.40 parts of the salt represented by the formula (B20-a), 50 parts of monochlorobenzene and 2.43 parts of a compound represented by the formula (B17-d) was stirred at 23° C. for 30 minutes. To the mixture, 0.2 part of sulfuric acid and 10 parts of molecular sieves (Molecular Sieves 4A available from Wako Pure Chemical Industries, Ltd.) were added, and the resultant mixture was refluxed at 130° C. for 3 hours to conduct dehydration. The reaction mixture obtained was concentrated to obtain a residue and to the residue, 100 parts of chloroform and 50 parts of ion-exchanged water to conduct separation. The obtained organic layer was washed three times with ion-exchanged water. To the organic layer, 1 parts of active carbon was added to stir at 23° C. for 30 minutes followed by filtration. The filtrate obtained was concentrated, and to the residue obtained, 20 parts of acetonitrile was added to prepare a solution. The obtained solution was concentrated, and 20 parts of ethyl acetate was added to the obtained residue. The resultant mixture was stirred and then, the supernatant solution was removed from the mixture. To the obtained residue, 20 parts of tert-butyl methyl ether was added. The resultant mixture was stirred and then, the supernatant solution was removed from the mixture. The obtained residue was dissolved in chloroform, and the obtained solution was concentrated to obtain 0.88 parts of a salt represented by the formula (B20). This is called as Salt B20.

MS (ESI(+) Spectrum): $M^+$ 305.1
MS (ESI(−) Spectrum): $M^−$ 561.2

Example 41

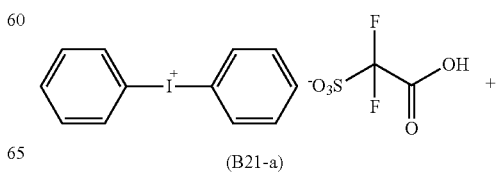

(B21-a)

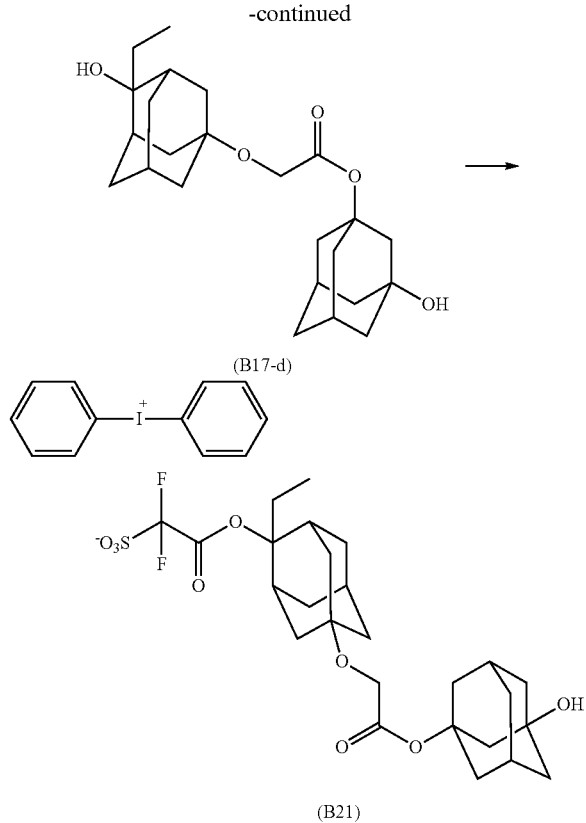

(B17-d)

(B21)

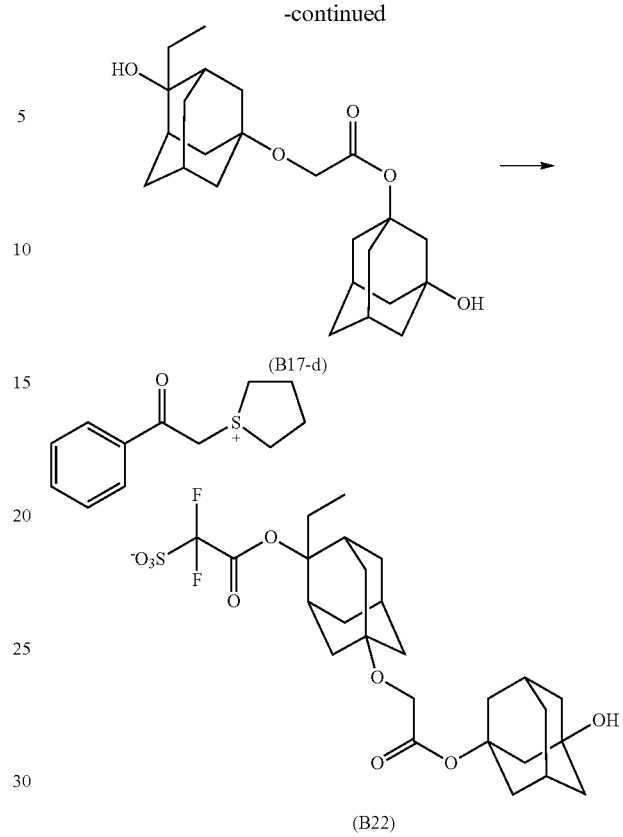

(B17-d)

(B22)

A mixture of 2.28 parts of the salt represented by the formula (B21-a), 50 parts of monochlorobenzene and 2.43 parts of a compound represented by the formula (B17-d) was stirred at 23° C. for 30 minutes. To the mixture, 0.2 part of sulfuric acid and 10 parts of molecular sieves (Molecular Sieves 4A available from Wako Pure Chemical Industries, Ltd.) were added, and the resultant mixture was refluxed at 130° C. for 3 hours to conduct dehydration. The reaction mixture obtained was concentrated to obtain a residue and to the residue, 100 parts of chloroform and 50 parts of ion-exchanged water to conduct separation. The obtained organic layer was washed three times with ion-exchanged water. To the organic layer, 1 parts of active carbon was added to stir at 23° C. for 30 minutes followed by filtration. The filtrate obtained was concentrated, and the residue obtained was purified with silica gel column chromatography (silica gel: silica gel 60-200 mesh available from Merck KGaA, solvent: chloroform/methanol=5/1) to obtain 0.52 part of a salt represented by the formula (B21). This is called as Salt B21.

MS (ESI(+) Spectrum): M$^+$ 281.0
MS (ESI(−) Spectrum): M$^-$ 561.2

Example 42

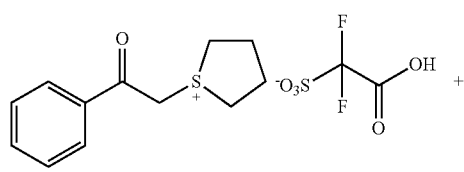

(B22-a)

A mixture of 1.91 parts of the salt represented by the formula (B22-a), 50 parts of monochlorobenzene and 2.43 parts of a compound represented by the formula (B17-d) was stirred at 23° C. for 30 minutes. To the mixture, 0.2 part of sulfuric acid and 10 parts of molecular sieves (Molecular Sieves 4A available from Wako Pure Chemical Industries, Ltd.) were added, and the resultant mixture was refluxed at 130° C. for 3 hours to conduct dehydration. The reaction mixture obtained was concentrated to obtain a residue and to the residue, 100 parts of chloroform and 50 parts of ion-exchanged water to conduct separation. The obtained organic layer was washed three times with ion-exchanged water. To the organic layer, 1 parts of active carbon was added to stir at 23° C. for 30 minutes followed by filtration. The filtrate obtained was concentrated, and the residue obtained was purified with silica gel column chromatography (silica gel: silica gel 60-200 mesh available from Merck KGaA, solvent: chloroform/methanol=5/1) to obtain 0.28 part of a salt represented by the formula (B22). This is called as Salt B22.

MS (ESI(+) Spectrum): M$^+$ 207.1
MS (ESI(−) Spectrum): M$^-$ 561.2

Example 43

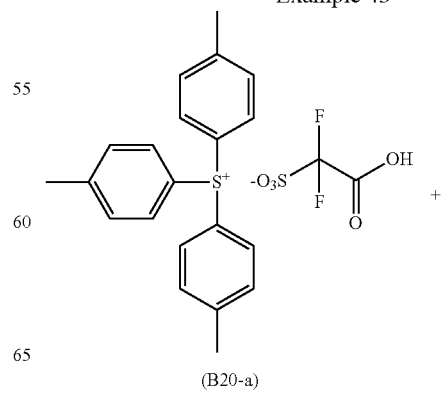

(B20-a)

-continued

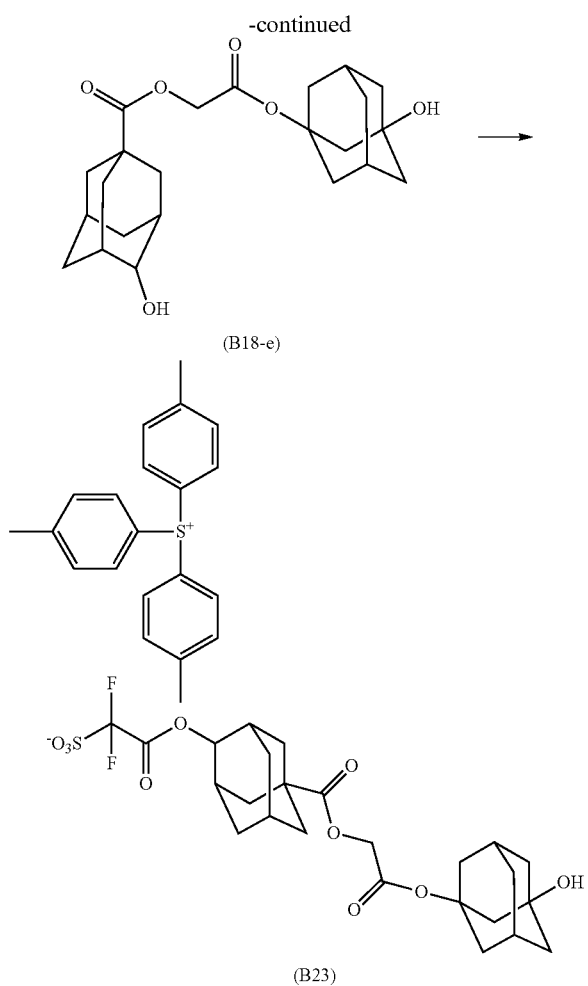

(B18-e)

(B23)

A mixture of 2.40 parts of the salt represented by the formula (B20-a), 50 parts of monochlorobenzene and 2.43 parts of a compound represented by the formula (B18-e) was stirred at 23° C. for 30 minutes. To the mixture, 0.2 part of sulfuric acid and 10 parts of molecular sieves (Molecular Sieves 4A available from Wako Pure Chemical Industries, Ltd.) were added, and the resultant mixture was refluxed at 130° C. for 3 hours to conduct dehydration. The reaction mixture obtained was concentrated to obtain a residue and to the residue, 100 parts of chloroform and 50 parts of ion-exchanged water to conduct separation. The obtained organic layer was washed three times with ion-exchanged water. To the organic layer, 1 parts of active carbon was added to stir at 23° C. for 30 minutes followed by filtration. The filtrate obtained was concentrated, and to the residue obtained, 20 parts of acetonitrile was added to prepare a solution. The obtained solution was concentrated, and 20 parts of ethyl acetate was added to the obtained residue. The resultant mixture was stirred and then, the supernatant solution was removed from the mixture. To the obtained residue, 20 parts of tert-butyl methyl ether was added. The resultant mixture was stirred and then, the supernatant solution was removed from the mixture. The obtained residue was dissolved in chloroform, and the obtained solution was concentrated to obtain 1.49 parts of a salt represented by the formula (B23). This is called as Salt B23.

MS (ESI(+) Spectrum): $M^+$ 305.1

MS (ESI(−) Spectrum): $M^-$ 561.2

Example 44

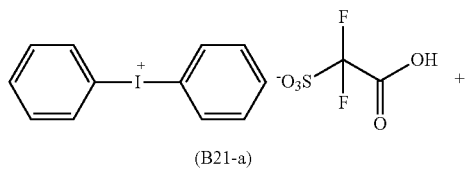

(B21-a)

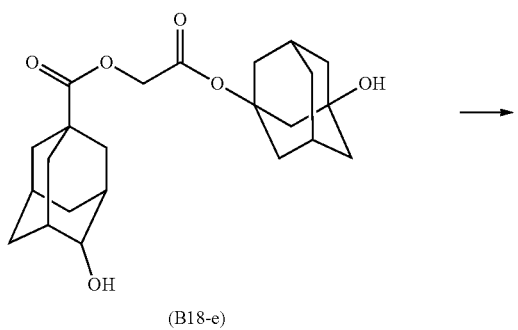

(B18-e)

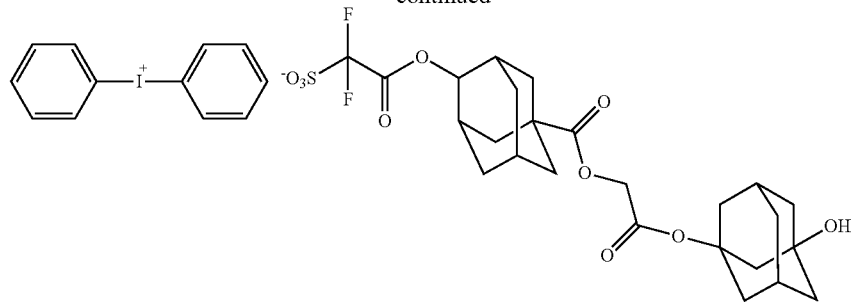

(B24)

A mixture of 2.28 parts of the salt represented by the formula (B21-a), 50 parts of monochlorobenzene and 2.43 parts of a compound represented by the formula (B18-e) was stirred at 23° C. for 30 minutes. To the mixture, 0.2 part of sulfuric acid and 10 parts of molecular sieves (Molecular Sieves 4A available from Wako Pure Chemical Industries, Ltd.) were added, and the resultant mixture was refluxed at 130° C. for 3 hours to conduct dehydration. The reaction mixture obtained was concentrated to obtain a residue and to the residue, 100 parts of chloroform and 50 parts of ion-exchanged water to conduct separation. The obtained organic layer was washed three times with ion-exchanged water. To the organic layer, 1 parts of active carbon was added to stir at 23° C. for 30 minutes followed by filtration. The filtrate obtained was concentrated, and the residue obtained was purified with silica gel column chromatography (silica gel: silica gel 60-200 mesh available from Merck KGaA, solvent: chloroform/methanol=5/1) to obtain 1.21 part of a salt represented by the formula (B24). This is called as Salt B24.

MS (ESI(+) Spectrum): $M^+$ 281.0
MS (ESI(−) Spectrum): $M^-$ 561.2

Example 45

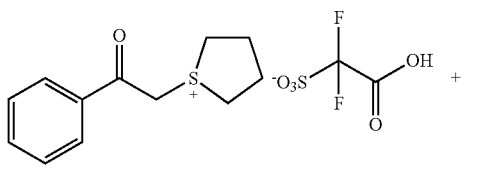

(B22-a)

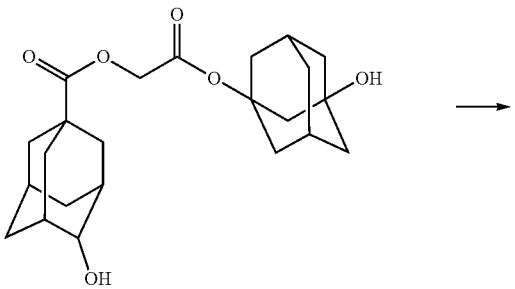

(B18-e)

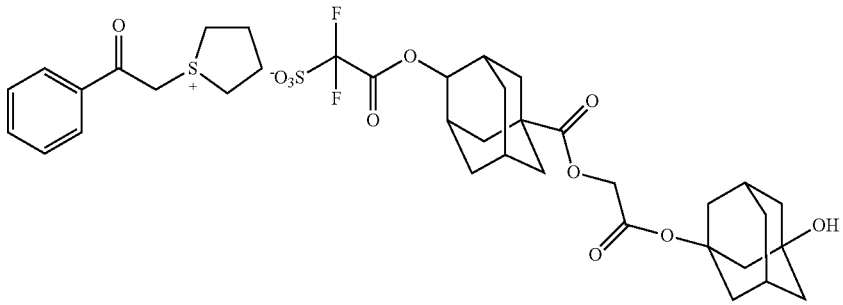

(B25)

A mixture of 1.91 parts of the salt represented by the formula (B22-a), 50 parts of monochlorobenzene and 2.43 parts of a compound represented by the formula (B18-e) was stirred at 23° C. for 30 minutes. To the mixture, 0.2 part of sulfuric acid and 10 parts of molecular sieves (Molecular Sieves 4A available from Wako Pure Chemical Industries, Ltd.) were added, and the resultant mixture was refluxed at 130° C. for 3 hours to conduct dehydration. The reaction mixture obtained was concentrated to obtain a residue and to the residue, 100 parts of chloroform and 50 parts of ion-exchanged water to conduct separation. The obtained organic layer was washed three times with ion-exchanged water. To the organic layer, 1 parts of active carbon was added to stir at 23° C. for 30 minutes followed by filtration. The filtrate obtained was concentrated, and the residue obtained was purified with silica gel column chromatography (silica gel: silica gel 60-200 mesh available from Merck KGaA, solvent: chloroform/methanol=5/1) to obtain 0.58 part of a salt represented by the formula (B25). This is called as Salt B25.

MS (ESI(+) Spectrum): $M^+$ 207.1

MS (ESI(−) Spectrum): $M^-$ 561.2

Example 46

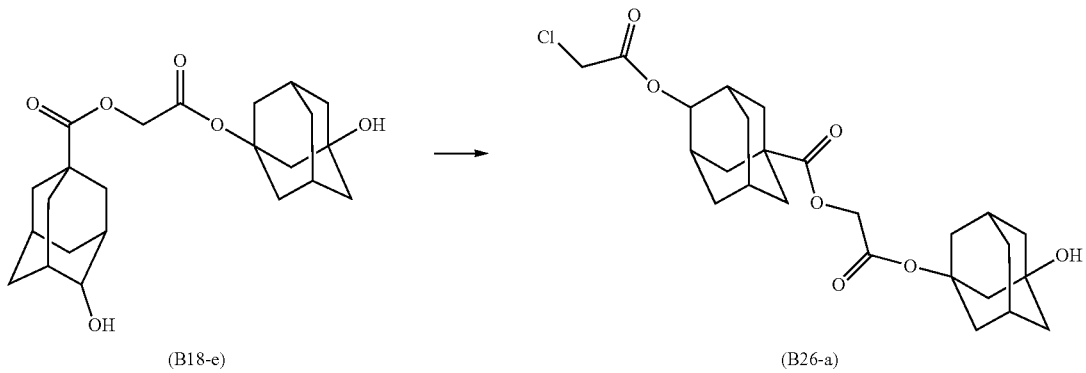

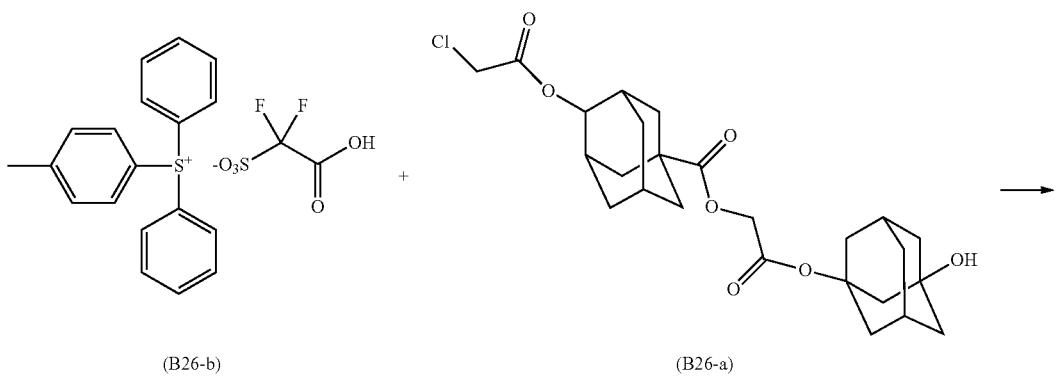

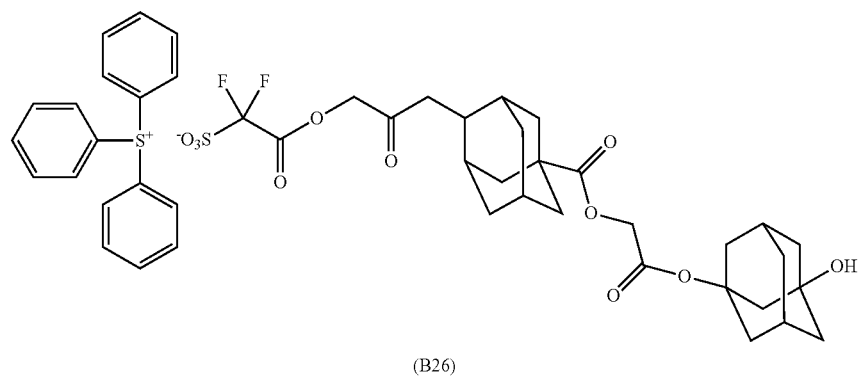

A mixture of 6.08 parts of a compound represented by the formula (B18-e) and 25 parts of tetrahydrofuran was stirred at room temperature, and then, 1.43 parts of pyridine was added thereto. The resultant mixture was heated up to 40° C., and then, a solution prepared by dissolving 2.55 parts of chloroacetyl chloride in 5 parts of tetrahydrofuran was added dropwise thereto over 1 hour. The resultant mixture was stirred at 40° C. for 5 hours, and then, cooled down to 5° C. To the obtained mixture, 10 parts of ion-exchanged water at 5° C. and 40 parts of ethyl acetate were added to conduct separation. The obtained organic layer was washed with 10 parts of aqueous 10% potassium carbonate solution at 5° C., and further washed five times with 10 parts of ion-exchanged water. The organic layer was concentrated and the residue obtained was purified with silica gel column chromatography (silica gel: silica gel 60-200 mesh available from Merck KGaA, solvent: ethyl acetate) to obtain 5.88 parts of a compound represented by the formula (B26-a).

A mixture of 2.5 parts of a compound represented by the formula (B26-b) and 12.96 parts of N,N-dimethylformamide was stirred at 23° C. for 30 minutes. To the mixture, 0.79 part of potassium carbonate and 0.24 part of potassium iodide were added and the resultant mixture was stirred at 40° C. for 1 hour. To the obtained mixture, a solution prepared by dissolving 2.28 parts of a compound represented by the formula (B26-a) in 4.56 parts of N,N-dimethylformamide was added dropwise over 1 hour. The resultant mixture was stirred at 40° C. for 6 hours. The obtained mixture was cooled down to 23° C., and 94.02 parts of chloroform, 14.38 parts of aqueous 5% oxalic acid solution and 8.64 parts of ion-exchanged water were added thereto to conduct separation. The organic layer obtained was washed seven times with 38.02 parts of ion-exchanged water. To the obtained organic layer, 1 parts of active carbon was added to stir at 23° C. for 30 minutes followed by filtration. The filtrate obtained was concentrated, 10 parts of acetonitrile was added to the obtained residue to prepare a solution. The obtained solution was concentrated, and 10 parts of ethyl acetate was added to the obtained residue. The resultant mixture was stirred and then, the supernatant solution was removed from the mixture. To the obtained residue, 10 parts of tert-butyl methyl ether was added. The resultant mixture was stirred and then, the supernatant solution was removed from the mixture. The obtained residue was dissolved in chloroform, and the obtained solution was concentrated and the residue obtained was purified with silica gel column chromatography (silica gel: silica gel 60-200 mesh available from Merck KGaA, solvent: chloroform/methanol=5/1) to obtain 0.74 parts of a salt represented by the formula (B26). This is called as Salt B26.

MS (ESI(+) Spectrum): $M^+$ 263.1
MS (ESI(−) Spectrum): $M^-$ 619.2

Example 47

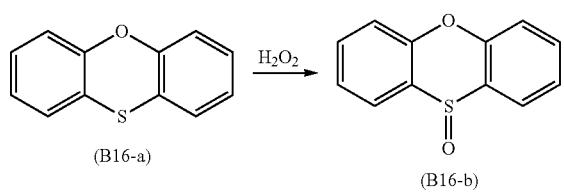

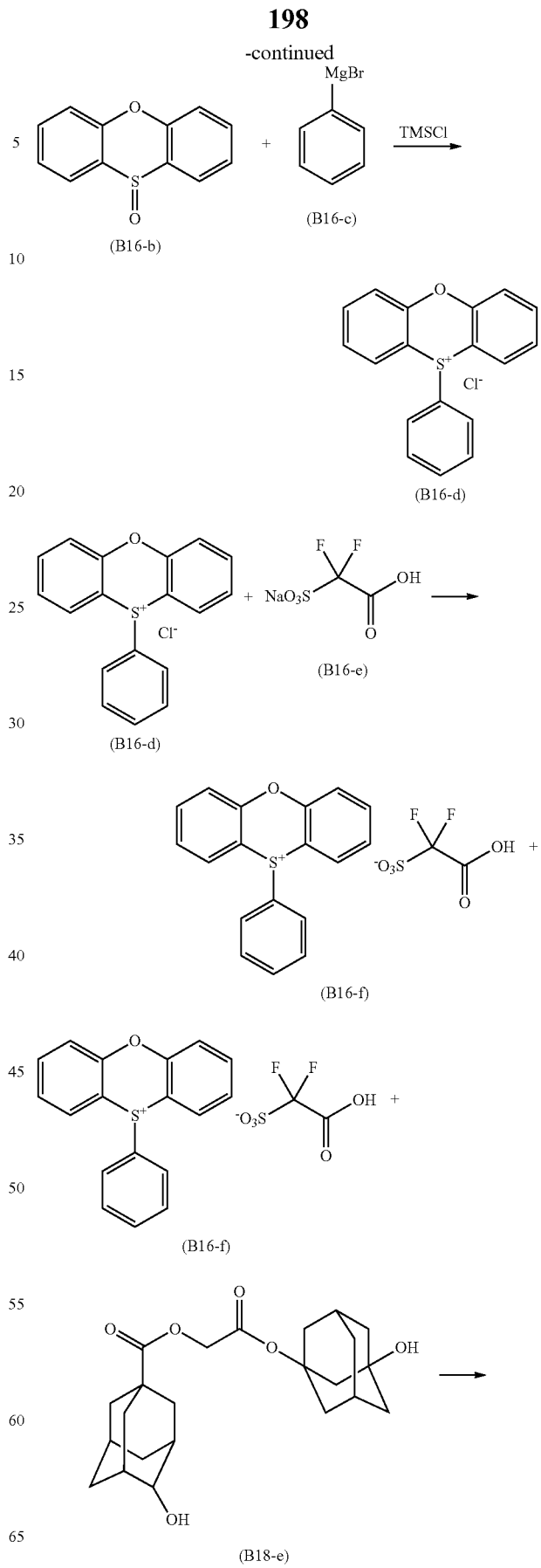

-continued

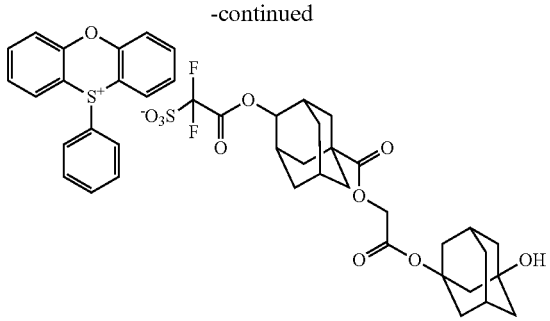

(B27)

A mixture of 101.5 parts of a compound represented by the formula (B16-a) and 253.75 parts of acetic acid was stirred at room temperature. To the mixture, 61.17 parts of 31% aqueous hydrogen peroxide was added dropwise over 10 minutes, and then, the resultant mixture was stirred at 23° C. for 6 hours. To the obtained reaction mixture, 253.75 parts of ion-exchanged water was added to filtrate to obtain 96.93 parts of a compound represented by the formula (B16-b).

A mixture of 28 parts of the compound represented by the formula (B16-b) and 140 parts of tetrahydrofuran was stirred at room temperature, and then, 28.13 parts of trimethylsilyl chloride was added dropwise thereto over 10 minutes. To the resultant mixture, 73.36 parts of a compound represented by the formula (B16-c) of which purity was 32% was added dropwise over 25 minutes while keeping at 40° C. or less. The resultant mixture was stirred at 23° C. for 1 hour, and then, 70 parts of 1N hydrochloric acid was dropwise followed by separation. The obtained aqueous layer was washed with 70 parts of tert-butyl methyl ether, and then, was extracted with 210 parts of chloroform. The obtained organic layer was filtrated, and the filtrate was concentrated. The residue was dissolved in 16.06 parts of acetonitrile to prepare a solution, and 200.78 parts of tert-butyl methyl ether was added thereto followed by filtrating obtain 27.84 parts of a salt represented by the formula (B16-d).

A mixture of 5.91 parts of a salt represented by the formula (B16-d), 16.26 parts of ion-exchanged water and 3.74 parts of a compound represented by the formula (B16-e) was stirred at room temperature. To the mixture, 1.97 parts of 35% hydrochloric acid was added, and then, the obtained mixture was stirred at 23° C. for 5 hours. From the obtained mixture, the supernatant solution was removed. To the obtained residue, 20 parts of acetonitrile was added. The obtained solution was concentrated, and 24.81 parts of tert-butyl methyl ether was added to the obtained residue. The resultant mixture was stirred and then, the supernatant solution was removed from the mixture. The obtained residue was dissolved in acetonitrile, and the obtained solution was concentrated to obtain 5.17 parts of a salt represented by the formula (B16-f).

A mixture of 2.26 parts of a salt represented by the formula (B16-f), 50 parts of monochlorobenzene and 2.43 parts of a compound represented by the formula (B18-e) was stirred at 23° C. for 30 minutes. To the obtained mixture, 0.2 part of sulfuric acid and 10 parts of molecular sieves (Molecular Sieves 4A available from Wako Pure Chemical Industries, Ltd.) were added thereto. The obtained mixture was refluxed at 130° C. for 3 hours to conduct dehydration. The obtained mixture was concentrated, and 50 parts of ion-exchanged water and 100 parts of chloroform were added thereto to conduct separation. The organic layer obtained was washed three times with ion-exchanged water, and then, 1 parts of active carbon was added thereto to stir at 23° C. for 30 minutes followed by filtration. The filtrate obtained was concentrated. To the residue obtained, 20 parts of acetonitrile was added to prepare a solution. The obtained solution was concentrated, and 20 parts of ethyl acetate was added to the obtained residue. The resultant mixture was stirred and then, the supernatant solution was removed from the mixture. To the obtained residue, 20 parts of tert-butyl methyl ether was added. The resultant mixture was stirred and then, the supernatant solution was removed from the mixture. The obtained residue was dissolved in chloroform, and the obtained solution was concentrated to obtain 1.18 parts of a salt represented by the formula (B27). This is called as Salt B27.

MS (ESI(+) Spectrum): M$^+$ 277.1
MS (ESI(−) Spectrum): M$^−$ 561.2

Examples 48 to 62 and Comparative Example 2

<Resin>
Resin A1, A2, A3
<Acid Generator>
Salt B17, B18, B19, B20, B21, B22, B23, B24, B25, B26, B27
H3:

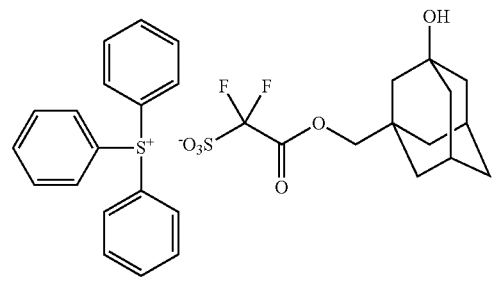

H4:

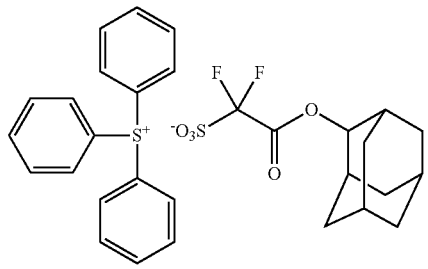

<Quencher>
C1: 2,6-diisopropylaniline
<Solvent>

| Y1: | propylene glycol monomethyl ether acetate | 265 parts |
| --- | --- | --- |
| | propylene glycol monomethyl ether | 20 parts |
| | 2-heptanone | 20 parts |
| | γ-butyrolactone | 3.5 parts |

The following components were mixed and dissolved, further, filtrated through a fluorine resin filter having pore diameter of 0.2 μm, to prepare photoresist compositions.

Resin (kind and amount are described in Table 4)
Acid Generator (kind and amount are described in Table 4)
Quencher (kind and amount are described in Table 4)
Solvent Y1

TABLE 4

| Ex. No. | Resin (kind/ amount (part)) | Acid Generator (kind/ amount (part)) | Quencher (kind/ amount (part)) | PB (° C.) | PEB (° C.) |
|---|---|---|---|---|---|
| Ex. 48 | A1/10 | B17/0.7 | C1/0.075 | 100 | 100 |
| Ex. 49 | A2/10 | B17/0.7 | C1/0.075 | 110 | 110 |
| Ex. 50 | A1/10 | B18/1.0 | C1/0.07 | 95 | 95 |
| Ex. 51 | A3/10 | B18/1.0 | C1/0.07 | 105 | 105 |
| Ex. 52 | A3/10 | B18/0.7 H3/0.3 | C1/0.07 | 105 | 105 |
| Ex. 53 | A2/10 | B18/1.0 | C1/0.07 | 105 | 105 |
| Ex. 54 | A3/10 | B19/1.0 | C1/0.07 | 105 | 105 |
| Ex. 55 | A1/10 | B20/0.7 | C1/0.075 | 100 | 100 |
| Ex. 56 | A1/10 | B21/0.7 | C1/0.075 | 100 | 100 |
| Ex. 57 | A1/10 | B17/0.5 B22/0.5 | C1/0.075 | 100 | 100 |
| Ex. 58 | A3/10 | B23/1.0 | C1/0.07 | 105 | 105 |
| Ex. 59 | A3/10 | B24/1.0 | C1/0.07 | 105 | 105 |
| Ex. 60 | A3/10 | B18/0.5 B25/0.5 | C1/0.07 | 105 | 105 |
| Ex. 61 | A3/10 | B26/1.0 | C1/0.07 | 105 | 105 |
| Ex. 62 | A3/10 | B27/1.0 | C1/0.07 | 105 | 105 |
| Comp. Ex. 2 | A2/10 | H4/1.0 | C1/0.07 | 105 | 105 |

12-inch silicon wafers were each coated with "ARC-29", which is an organic anti-reflective coating composition available from Nissan Chemical Industries, Ltd., and then baked at 205° C. for 60 seconds, to form a 780 Å-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in the column "PB" in Table 4 for 60 seconds. Using an ArF excimer stepper for immersion exposure ("XT: 1900Gi" manufactured by ASML, NA=1.35, ¾ Annular, X-Y deflection), each wafer thus formed with the respective resist film was subjected to line and space pattern exposure, with the exposure quantity being varied stepwise.

After the exposure, each wafer was subjected to post-exposure baking on a hotplate at a temperature shown in the column "PEB" in Table 4 for 60 seconds and then to paddle development for 60 seconds with an aqueous solution of 2.38 wt % tetramethylammonium hydroxide.

Each of patterns developed on the organic anti-reflective coating substrate after the development was observed with a scanning electron microscope, the results of which are shown in Tables 5 and 6.

Effective Sensitivity (ES): It was expressed as the amount of exposure that the line pattern and the space pattern of 50 nm become 1:1 after exposure and development.

Resolution: The photoresist pattern at ES was observed with a scanning electron microscope. When the resolution at ES was 43 nm or less, the resolution is very good and its evaluation is marked by "⊚", when the resolution at ES was more than 43 nm and 45 nm or less, the resolution is good and its evaluation is marked by "○", and when the resolution at ES was more than 45 nm, the resolution is bad and its evaluation is marked by "x". The resolution was shown in parentheses in Table 5 and 6.

Pattern profile: The line and space pattern of 50 nm was observed with a scanning electron microscope, and when a cross-section of the pattern is a rectangle or nearly a rectangle, pattern profile is good and its evaluation is marked by "○", when upper of a cross-section of the pattern is round or length of the upper of a cross-section of the pattern is longer than that of bottom of a cross-section of the pattern, or a cross-section of the pattern is a tapered shape, pattern profile is bad, and its evaluation is marked by "x".

Line Edge Roughness (LER): The photoresist pattern at ES was observed with a scanning electron microscope. The difference between the height of the highest point and height of the lowest point of the scabrous wall surface of the photoresist pattern was measured. When the difference is 5 nm or less, LER is good and its evaluation is marked by "○", and when the difference is more than 5 nm, LER is bad and its evaluation is marked by "x". The smaller the difference is, the better the pattern is. The difference was shown in parentheses in Table 5.

TABLE 5

| Ex. No. | Resolution | Pattern Profile | LER |
|---|---|---|---|
| Ex. 48 | ⊚ (43 nm) | ○ | ○ (4.4 nm) |
| Ex. 49 | ○ (45 nm) | ○ | ○ (4.9 nm) |
| Ex. 55 | ⊚ (43 nm) | ○ | ○ (4.2 nm) |
| Ex. 56 | ○ (45 nm) | ○ | ○ (4.7 nm) |
| Ex. 57 | ⊚ (43 nm) | ○ | ○ (4.1 nm) |
| Comp. Ex. 2 | X (50 nm) | X | X (6.3 nm) |

TABLE 6

| Ex. No. | Resolution |
|---|---|
| Ex. 50 | ⊚ (43 nm) |
| Ex. 51 | ⊚ (43 nm) |
| Ex. 52 | ⊚ (43 nm) |
| Ex. 53 | ○ (45 nm) |
| Ex. 54 | ⊚ (43 nm) |
| Ex. 58 | ⊚ (43 nm) |
| Ex. 59 | ○ (45 nm) |
| Ex. 60 | ⊚ (43 nm) |
| Ex. 61 | ⊚ (43 nm) |
| Ex. 62 | ⊚ (43 nm) |
| Comp. Ex. 2 | X (50 nm) |

The salt of the present invention is novel and is useful as a component of a photoresist composition, and the photoresist composition containing the salt of the present invention provides a photoresist pattern having good resolution, good LER, good focus margin and good PCM, and is especially suitable for ArF excimer laser lithography, KrF excimer laser lithography, ArF immersion lithography, EUV (extreme ultraviolet) lithography, EUV immersion lithography and EB (electron beam) lithography.

What is claimed is:

1. A salt represented by the formula (X):

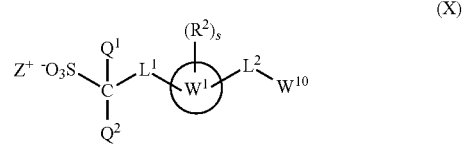

wherein $Q^1$ and $Q^2$ each independently represent a fluorine atom or a C1-C6 perfluoroalkyl group, $L^1$ represents

*—CO—O-L³-, *—CO—O-L⁴-O—, *-L⁵-O—CO— or *—CO—O-L⁶-CO—O— wherein L³ represents a single bond, L⁴, L⁵ and L⁶ independently each represent a C1-C6 alkylene group and * represents a binding position to —C(Q¹)(Q²)-, $L_2$ represents a C1-C17 divalent saturated hydrocarbon group in which one or more —CH₂— can be replaced by —O— or —CO—, ring $W^1$ represents a C3-C36 saturated hydrocarbon ring, $R^2$ is independently in each occurrence a hydroxyl group, a C1-C6 alkyl group or a C1-C6 alkoxy group, s represents an integer of 0 to 2, $Z^+$ represents an organic counter ion, and $W^{10}$ represents a group represented by the formula (X-1):

(X-1)

wherein ring $W^2$ represents a C4-C36 saturated hydrocarbon ring in which one or more —CH₂— can be replaced by —O— or —CO—, with the proviso that at least one —CH₂— in the C4-C36 saturated hydrocarbon ring is replaced by —CO—, $R^3$ is independently in each occurrence a C1-C6 alkyl group, a C1-C6 alkoxy group or a C1-C6 alkoxycarbonyl group, and t represents an integer of 0 to 2, or a group represented by the formula (X-2):

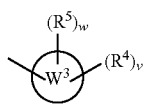
(X-2)

wherein ring $W^3$ represents a C3-C36 saturated hydrocarbon ring, $R^4$ is independently in each occurrence a hydroxyl group, a C1-C6 hydroxyalkyl group which can have one or more halogen atoms or a C1-C6 hydroxyalkoxy group which can have one or more halogen atoms, $R^5$ is independently in each occurrence a C1-C6 alkyl group or a C1-C6 alkoxy group, v represents an integer of 1 to 3, and w represents an integer of 0 to 2.

2. The salt according to claim 1, wherein $W^{10}$ is the group represented by the formula (X-1).

3. The salt according to claim 1, wherein $W^{10}$ is the group represented by the formula (X-2).

4. The salt according to claim 1, wherein $L^2$ is *—O-L⁷-CO—O—, *—O-L⁸-CO—O-L⁹-O—, *—CO—O-L¹⁰-CO—O—, *—O—CO-L¹¹-O— or *—O-L¹²-O— wherein L⁷, L⁸, L⁹, L¹⁰, L¹¹ and L¹² independently each represent a C1-C6 alkylene group and * represents a binding position to ring $W^1$.

5. The salt according to claim 1, wherein ring $W^1$ is an adamantane ring.

6. The salt according to claim 1, wherein ring $W^2$ is a ring represented by the formula (I-Ba) or (I-Bb)

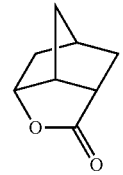
(I-Ba)

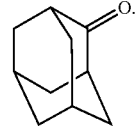
(I-Bb)

7. The salt according to claim 1, wherein ring $W^3$ is an adamantane ring.

8. The salt according to claim 1, wherein $Z^+$ is a triarylsulfonium cation.

9. An acid generator comprising the salt according to claim 1.

10. A photoresist composition comprising the acid generator according to claim 9 and a resin comprising a structural unit having an acid-labile group, being insoluble or poorly soluble in an aqueous alkali solution but becoming soluble in an aqueous alkali solution by the action of an acid.

11. The photoresist composition according to claim 10, which further contains a basic compound.

12. A process for producing a photoresist pattern comprising the following steps (1) to (5):
    (1) a step of applying the photoresist composition according to claim 10 or 11 on a substrate,
    (2) a step of forming a photoresist film by conducting drying,
    (3) a step of exposing the photoresist film to radiation,
    (4) a step of baking the exposed photoresist film, and
    (5) a step of developing the baked photoresist film with an alkaline developer, thereby forming a photoresist pattern.

* * * * *